(12) United States Patent
Castillo et al.

(10) Patent No.: US 7,384,910 B2
(45) Date of Patent: Jun. 10, 2008

(54) SMALL PEPTIDES FOR THE TREATMENT OF ALZHEIMER'S DISEASE AND OTHER BETA-AMYLOID PROTEIN FIBRILLOGENESIS DISORDERS

(76) Inventors: Gerardo M. Castillo, 20716 37th Ave. SE., Bothell, WA (US) 98021; Thomas P. Lake, 7732 Interurban Blvd., Snohomish, WA (US) 98296; Beth P. Nguyen, 1219 Vineyard Dr., Gurnee, IL (US) 60031; Virginia J. Sanders, 1588 Indiana St., Apt. #6, San Francisco, CA (US) 94107; Alan D. Snow, 3812 - 167th Place SW., Lynnwood, WA (US) 98037

( * ) Notice: Subject to any disclaimer, the term of this patent is extended or adjusted under 35 U.S.C. 154(b) by 170 days.

(21) Appl. No.: 11/016,706

(22) Filed: Dec. 16, 2004

(65) Prior Publication Data

US 2005/0244334 A1  Nov. 3, 2005

Related U.S. Application Data

(63) Continuation-in-part of application No. 09/962,955, filed on Sep. 24, 2001, now Pat. No. 6,933,280, which is a continuation-in-part of application No. 09/938,275, filed on Aug. 22, 2001, now Pat. No. 7,314,724, which is a continuation of application No. 08/947,057, filed on Oct. 8, 1997, now abandoned.

(60) Provisional application No. 60/615,614, filed on Sep. 30, 2004, provisional application No. 60/554,342, filed on Mar. 17, 2004, provisional application No. 60/531,406, filed on Dec. 18, 2003.

(51) Int. Cl.
    *A61K 38/08* (2006.01)
(52) U.S. Cl. .......................................... 514/2
(58) Field of Classification Search ...................... None
    See application file for complete search history.

(56) References Cited

OTHER PUBLICATIONS

Koo et al. "Amyloid β-Protein as a Substrate Interacts with Extracellular Matrix to Promote Neurite Outgrowth," Proc. Natl. Acad. Science, vol. 90, pp. 4748-4752, May 1993.
Narindrasorsak et al. "Characterization of High Affinity Binding between Laminin and Alzheimer's Disease Amyloid Precursor Proteins," Laboratory Investigation, vol. 67, No. 5, pp. 643-652, 1992.
Narindrasorsak et al. "An Interaction between Basement Membrane and Alzheimer Amyloid Precursor Proteins Suggests a Role in the Pathogenesis of Alzheimer's Disease," Laboratory Investigation, vol. 72, No. 3, pp. 272-282, 1995.
Mann. "Cerebral Amyloidosis, Ageing and Alzheimer's Disease; A Contribution From Studies on Down's Syndrome," Neurobiology of Aging, vol. 10, pp. 397-399, 1989.
Gajdusek. "Unconventional viruses and the Origen and Disappearance of Kuru," Science, vol. 197, No. 4307, Sep. 2, 1977.

Prusiner et al. "Purification and Structural Studies of a Major Scrapie Prion Protein," Cell, vol. 38, 127-134, Aug. 1984.
Prusiner. "Prions," [publication date unknown].
Tateishi et al. "Gerstmann-Straussler-Scheinker Disease: Immunohistological and Experimental Studies," Annals of Nuerology, vol. 24, No. 1, Jul. 1988.
Foidart et al. "Distribution and Immunoelectron Microscopic Localization of Laminin, A Non collagenous Basement Membrane Glycoprotein," Laboratory Investigation, vol. 42, No. 3, p. 336, 1980.
Burgeson et al. "A New Nomencalture for the Laminins," Matrix Biology, vol. 14, pp. 209-211, 1994.
Yurchenco et al. "Laminin Polymerization in Vitro: Evidence for a two step assembly with Domain Specificity," The Journal of Biological Chemistry, vol. 260, No. 12, pp. 7636-7644, Jun. 25, 1985.
Yurchenco et al. "Laminin Forms an Independent Network in Basement Membranes," The journal of Cell Biology, vol. 117, No. 5, pp. 1119-1133, Jun. 1993.
Newgreen et al. "Fibronectin in Early Avian Embryos: Synthesis and Distribution Along the Migration Pathways of Neural Crest Cells," Cell tissues res. vol. 211, pp. 211-269, 1980.
Rovasio et al. "Neural Crest Cell Migration: Requirements for Exogenous Fibronectin and High Cell Density," The Journal of Cell Biology, vol. 96, pp. 462-473, Feb. 1983.
Lander et al. "Laminin is associated with the 'nuerite outgrowth-promotion factors' found in conditioned media," Proc. Natl. Acad. Sci. USA, vol. 82, pp. 2183-2187, Apr. 1985.
Fraser et al. "A monoclonal antibody against a laminin-heparan sulfate proteoglycan complex perturbs cranial neural crest migration in vivo," The Journal of Cell Biology, vol. 106, pp. 1321-1329, Apr. 1988.
Kleinman et al. "Formation of a Supramolecular Complex Is Involved the Reconstitution of Basement Membrane Composets," Biochemistry, vol. 22, pp. 4969-4974, 1983.
Engvall et al. "Mapping of Domains in Human Laminin Using Monoclonal Antibodies: Localization of the Neurite-promotion Site," The Journal of Cell Biology, vol. 103, No. 6, Pt. 1, pp. 2457-2465, 1986.
Liesi et al. "Laminin is induced in astrocytes of adult brain by injury," The EMBO Journal, vol. 3, No. 3, pp. 683-686, 1984.
Terranova et al. "Role of laminin in the attachment of PAM 212 (epithelial) Cells to Basement Membrane Collagen," Cell, vol. 22, pp. 719-726, Dec. 1980.
Rao et al. "Binding domain for laminin of type IV collagen," Biochemical and biophysical research communications, vol. 128, No. 1, Apr. 16, 1985.
Charonis et al. "Binding of laminin to type IV collagen: A morphological study," The Journal of Cell Biology, vol. 100, pp. 1848-1853, 1985.

(Continued)

*Primary Examiner*—Christina Bradley
(74) *Attorney, Agent, or Firm*—Rebecca Eagen

(57) ABSTRACT

A pharmaceutical composition comprising peptide Leu-Ala-Phe-Val-Leu-Arg-Lys-amide having at least one D-amino acid.

3 Claims, 91 Drawing Sheets

OTHER PUBLICATIONS

Laurie et al. "Localization of Binding Sites for Laminin, Heparan Sulfate Proteoglycan and Fibronectin on Basement Membrane (Tyoe IV) Collagen," J. Mol. Biol., vol. 189, pp. 205-216, 1986.

Riopelle et al. Functional interactions of neuronal heparan sulphate proteoglycans with laminin, Brain Research, vol. 525, pp. 92-100, 1990.

Battaglia et al. "Basement-membrane heparan sulfate proteoglycan binds to laminin by its heparan sulfate chains and to nidogen by sites in the protein core," Eur. J. Biochem., vol. 208, pp. 359-366, 1992.

Sakashita et al. "Basement membrane glycoprotein laminin binds to heparin," FEBS letters, vol. 116, No. 2, Jul. 1980.

Del Rosso et al. "Binding of the basement-membrane glycoprotein laminin to glycosaminoglycans," Biochem. J., vol. 199, pp. 699-704, 1981.

Skubitz et al. "Localization of three distinct heparin-hinding Domains of Laminin by Monoclonal antibodies," The Journal of Biological Chemistry, vol. 263, No. 10, pp. 4861-4868, Apr. 5, 1988.

Hall et al. "The $\alpha_1/\beta_1$ and $\alpha_6/\beta_1$ integrin heterodimers mediate cell attachment to distinct sites on laminin," The Journal of Cell Biology, vol. 110, pp. 2175-2184, Jun. 1990.

Goodman et al. "Multiple cell surface receptors for the short arms of laminin: $\alpha 1/\beta 1$ integrin and RGD-dependent proteins mediate cell attachment only to domains III in Murine Tumor Laminin," The Journal of Cell Biology, vol. 113, No. 4, pp. 931-941, May 1991.

Yurchenco et al. "Heparin modulation of laminin polymerization," The Journal of Biological Chemistry, vol. 265, No. 7, pp. 3981-3991, Mar. 5, 1990.

Fox et al. "Recombinant nidogen consists of three globular domains and mediates binding of laminin to collagen type IV," The EMBO Journal, vol. 10, No. 11, pp. 3137-3146, 1991.

Sung et al. "Cell and Heparin Binding in the Distal Long Arm of Laminin: Identification of Active and Cryptic Sites with Recombinant and Hybrid Glycoprotein," The Journal of Cell Biology, vol. 123, No. 5, pp. 1255-1268, Dec. 1993.

Shimomura et al. "Studies on Marcomolecular Components of human glomerular basement membrane and alterations in diabetes," Diabetes. vol. 36, Mar. 1987.

Lyon et al. "Co-deposition of basement membrane components during the induction of murine splenic AA amyloid," Laboratory investigation, vol. 64, No. 6, p. 785, 1991.

Perlmutter et al. "Microangiopathy, the Vascular Basement Membrane and Alzheimer's Disease: A Review," Brain Research Bulletin, vol. 24, pp. 677-686, 1990.

Murtomaki et al. "Laminin and its neurite outgrowth-promotion domain in the brain in alzheimer's disease and down's syndrome patients," Journal of Neuroscience Research, vol. 32, pp. 261-273, 1992.

Perlmutter et al. "Vascular basement membrane components and the lesions of Alzheimer's Disease: light and electron microscopy analyses," Microscopy research and technique, vol. 28, pp. 204-215, 1994.

Naiki et al. "Kinetic analysis of amyloid fibril polymerization in vitro," Laboratory investigation, vol. 65, No. 1, p. 104, 1991.

Levine, III et al. "Thioflavine T interaction with synthetic Alzheimer's Disease β-amyloid peptides: detection of amyloid aggregation in solution," Protein Science, vol. 2, pp. 404-410, 1993.

Naiki et al. "First-order kinetic model of Alzheimer's β-amyloid fibril extension in vitro," Laboratory investigation, vol. 74, No. 2, p. 374, 1996.

Westermark et al. "Islet amyloid in type 2 human diabetes mellitus and adult diabitic ats cantains a novel putative polypeptide hormone," American Journal of Pathology, vol. 127, No. 3, Jun. 1987.

Cooper et al. "Purification and charactericity of a peptide from amyloid-rich pancreases of type 2 diabetic patients," Proc. Natl. Acad. Sci. USA, vol. 84, pp. 8628-8632, Dec. 1987.

Levine, III et al. "Thioflavine T interaction with amyloid β-sheet structures," int. j. exp. clin. invest. vol. 2, pp. 1-6, 1995.

Laemmli. "Cleavage of structural proteins during the assembly of the head of bacteriophage T4," Nature, vol. 227, Aug. 15, 1970.

Schagger et al. "Tricine-sodium dodecyl sulfate-polyacrylamide gel electrophoresis for the separation of proteins i8ng the range from 1 to 100kDa," analytical biochemistry, vol. 166, pp. 368-379, 1987.

Sasaki et al. "The laminin B2 chain has a multidomain structure homologous to the B1 chain," The journal of biological chemistry, vol. 262, No. 35, pp. 17111-17117, Dec. 15, 1987.

Sasaki et al. "Sequence of the cDNA encoding the laminin B1 chain reveals a multidomain protein containing cysteine-rich repeats," Proc. natl. Acad. Sci. USA, vol. 84, pp. 935-939, Feb. 1987.

Durkin et al. "Primary structure of the mouse laminin B2 chain and Comparison with Laminin B1," Biochemistry, vol. 27, pp. 5198-5204, 1988.

Sasaki et al. "Laminin, a multidomain protein," The journal of Biological Chemistry, vol. 263, No. 32, pp. 16536-16544, Nov. 15, 1988.

Colognato-Pyke et al. "Mapping of Network-forming, heparin-hinding, and $\alpha 1\beta 1$ integrin-recognition sites within the $\alpha$-chain short arm of Laminin-1," The journal of biological chemistry, vol. 270, No. 16, pp. 9398-9406, Apr. 21, 1995.

Mandybur. "Cerebral amyloid angiopathy: the vascular pathology and complications," Journal of Neuropathology and Experimental neurology, vol. 45, No. 1, pp. 79-90, Jan. 1986.

Pardridge et al. "Amyloid angiopathy and Alzheimer's Disease: amino acid composition and partial sequence of a 4,200-dalton peptid isolated from cortical microvessels," Journal of Neurochemistry, vol. 49, No. 5, 1987.

Pike et al. "In vitro aging of β-amyloid protein causes peptide aggregation and neurotoxicity," Brain research, vol. 563, pp. 311-314, 1991.

Pike et al. "Structure-activity analyses of β-amyloid peptides: contributions of the β25-35 region to aggregation and neurotoxicity," Journal of neurochemistry, vol. 64, No. 1, 1995.

Harrigan et al. "Beta amyloid is neurotixic in hippocampal slice cultures," Neurobiology of aging, vol. 16, No. 5, pp. 779-789, 1995.

Games et al. "Alzheimer-type neuropatholofy in transgenic mice overexpressing V717F β-amyloid precursor protein," Nature, vol. 373, Feb. 9, 1995.

Hsiao et al. "Age related CNS disorder and early death in transgenic FVB/N mice overexpressing Alzheimer amyloid precursor proteins," Neuron, vol. 15, pp. 1203-1218, Nov. 1995.

Flood et al. "An amyloid β-protein fragment, Aβ[12-28], equipotently impairs post-training memory processing when infcted into different limbic system structures," Brain research, vol. 663, pp. 271-276, 1994.

Flood et al. "Amnestic effects in mice of four synthetic peptides homologous to amyloid β-protein from patients with Alzheimer's Disease," proc. natl. acad. sci. USA, vol. 88, pp. 3363-3366, Apr. 1991.

Puchtler et al. "On the Binding of Congo Red by Amyloid," [publication data unknown].

Harada et al. "Human amyloid protein: chemical variability and homogeneity," The Journal of histochemistry and cytochemistry, vol. 19, No. 1, 1971.

Metaxas et al. "Familial mediterranean fever and amyloidosis," Kidney International, vol. 20, pp. 676-685, 1981.

Skinner et al. "The prealbumin nature of the amloid protein in familial amyloid polyneuropathy (Fap) swedish variety," Biochimical and Biophysical Research Communications, vol. 99, No. 4, pp. 1326-1332, 1981.

Saraiva et al. "Amyloid Fibril Protein in Familial Amyloidotic Polyneuropathy, Portuguese Type," J. Clin. Invest., vol. 74, pp. 104-119, Jul. 1984.

Saraiva et al. "Studies on plasma trasthyretin (prealbumin) in familial amyloidotic polyneuropathy, portuguese type," J. Lab. Clin. Med., vol. 102, No. 4, Oct. 1983.

Tawara et al. "Amyloid fibril protein in type 1 familial amyloiditic polyneuropathy in Japanese," J. Lab. Clin. Med., vol. 96, No. 6, Dec. 1981.

Jensson et al. "The saga of cystatin C gene mutation cousing amyloid angiopathy and brain hemorrhage-clenical genetics in iceland," Clinical Genetics, vol. 36, pp. 368-377, 1989.

Wright et al. "Relationship of amyloid deposits int eh human aorta to aortic atherosclerosis," Laboratory Investigation, vol. 30, No. 6, p. 767, 1974.

Pitkanen et al. "Senile systemic amyloidosis," AJP, vol. 117, No. 3, Dec. 1984.

Johnson et al. "Biology of disease," Laboratory Investigation, vol. 66, No. 5, p. 522, 1992.

Butler et al. "Immunoreactive calcitonin in amyloid fibrils of medullary carcinoma of the thyroid gland," Arch Pathol Lab Med, vol. 110, Jul. 1986.

Berger et al. "Calcitonin-like immunoireactivity of amyloid fibrils in medullarry thyroid carcinomas," Virchows archiv a pathol anat histopathol, vol. 412, pp. 543-551, 1988.

Gejyo et al. "A new form of amyloid protein associated with chronic hemodialysis was identified as $\beta_2$- microglobulin," Biochemical and Biophysical Research Communications, vol. 129, No. 3, pp. 701-706, Jun. 28, 1985.

Gejyo et al. "$\beta_2$-microglobulin: a mew form of amyloid protein associated with chronic hemodialysis," Kidney International, vol. 30, pp. 385-390, 1986.

Glenner et al. "Alzheimer's Disease: initial report of the purification and characterization of a novel cerebrovascular amyloid protein," Biochemical and Biophysical Research Communications, vol. 120, No. 3, pp. 885-890, May 16, 1984.

Masters et al. "Amyloid plaque core protein in Alzheimer's Disease and Down Syndrome," Proc. Natl. Acad. Sci. USA vol. 82, pp. 4245-4249, Jun. 1985.

Rumble et al. "Amyloid A4 protein and its precursor in down's syndrome and Alzheimer's Disease," The New England Journal of Medicine, vol. 320, No. 22, Jun. 1, 1989.

PEPTIDES

| | Structure | Formula | MW |
|---|---|---|---|
| DP-001 | Arg-Lys-Arg-Leu-Gln-Val-Gln-Leu-Ser-Ile-Arg-Thr | $C_{64}H_{120}N_{24}O_{17}$ | 1497.82 |
| DP-002 | Arg-Gln-Val-Phe-Gln-Val-Ala-Tyr-Ile-Ile-Ile-Lys-Ala | $C_{74}H_{121}N_{19}O_{17}$ | 1548.90 |
| DP-003 | Tyr-Leu-Ser-Lys-Gly-Arg-Leu-Val-Phe-Ala-Leu-Gly | $C_{63}H_{102}N_{16}O_{15}$ | 1323.61 |
| DP-004 | Thr-Leu-Phe-Leu-Ala-His-Gly-Arg-Leu-Val-Phe-Met | $C_{67}H_{105}N_{17}O_{14}S$ | 1404.75 |
| DP-005 | Ala-Gly-Gln-Trp-His-Arg-Val-Ser-Val-Arg-Trp-Gly | $C_{65}H_{95}N_{23}O_{15}$ | 1438.62 |
| DP-006 | Asp-Gly-Arg-Trp-His-Arg-Val-Ala-Val-Ile-Met-Gly | $C_{61}H_{97}N_{21}O_{15}S$ | 1396.65 |
| DP-007 | His-Gln-Thr-Trp-Thr-Arg-Asn-Leu-Gln-Val-Thr-Leu | $C_{66}H_{105}N_{21}O_{19}$ | 1496.70 |
| DP-008 | Ile-Ser-Asn-Val-Phe-Val-Gln-Arg-Leu-Ser-Leu-Ser | $C_{61}H_{103}N_{17}O_{18}$ | 1362.60 |

Figure 1A

PEPTIDES

| | Structure | Formula | MW |
|---|---|---|---|
| DP-009 | Arg-Gly-Leu-Val-Phe-His-Thr-Gly-Thr-Lys-Asn-Ser-Phe | $C_{66}H_{102}N_{20}O_{18}$ | 1463.67 |
| DP-010 | Gly-Asn-Ser-Thr-Ile-Ser-Ile-Arg-Ala-Pro-Val-Tyr | $C_{56}H_{92}N_{16}O_{18}$ | 1277.45 |
| DP-011 | Val-Arg-Trp-Gly-Met-Gln-Gln-Ile-Gln-Leu-Val-Val | $C_{66}H_{109}N_{19}O_{16}S$ | 1456.78 |
| DP-012 | Ala-Pro-Val-Asn-Val-Thr-Ala-Ser-Val-Gln-Ile-Gln | $C_{53}H_{91}N_{15}O_{18}$ | 1226.40 |
| DP-013 | Thr-Arg-Ile-Ser-Leu-Gln-Val-Gln-Leu-Arg-Lys-Arg | $C_{64}H_{120}N_{24}O_{17}$ | 1497.82 |
| DP-014 | Ala-Lys-Ile-Ile-Ile-Tyr-Ala-Val-Gln-Phe-Val-Gln-Arg | $C_{74}H_{121}N_{19}O_{17}$ | 1547.92 |
| DP-015 | Gly-Leu-Ala-Phe-Val-Leu-Arg-Gly-Lys-Ser-Leu-Tyr | $C_{63}H_{102}N_{16}O_{15}$ | 1323.61 |
| DP-016 | Met-Phe-Val-Leu-Arg-Gly-His-Ala-Leu-Phe-Leu-Thr | $C_{67}H_{105}N_{17}O_{14}S$ | 1404.75 |

Figure 1B

PEPTIDES

| | Structure | Formula | MW |
|---|---|---|---|
| DP-017 | Gly-Trp-Arg-Val-Ser-Val-Arg-His-Trp-Gln-Gly-Ala | $C_{65}H_{95}N_{23}O_{15}$ | 1438.62 |
| DP-018 | Gly-Met-Ile-Val-Ala-Val-Arg-His-Trp-Arg-Gly-Asp | $C_{61}H_{97}N_{21}O_{15}S$ | 1396.65 |
| LP-019 | Arg-Lys-Arg-Leu-Gln-Val-Gln-Leu-Ser-Ile-Arg-Thr | $C_{64}H_{120}N_{24}O_{17}$ | 1497.82 |
| LP-020 | Arg-Gln-Val-Phe-Gln-Val-Ala-Tyr-Ile-Ile-Ile-Lys-Ala | $C_{74}H_{121}N_{19}O_{17}$ | 1548.90 |
| LP-021 | Tyr-Leu-Ser-Lys-Gly-Arg-Leu-Val-Phe-Ala-Leu-Gly | $C_{63}H_{102}N_{16}O_{15}$ | 1323.61 |
| LP-022 | Thr-Leu-Phe-Phe-Met-Arg-Leu-Val-His-Ala-Leu-Gly | $C_{67}H_{105}N_{17}O_{14}S$ | 1404.75 |
| LP-023 | Ala-Gly-Gln-Trp-His-Arg-Val-Ser-Val-Arg-Trp-Gly | $C_{65}H_{95}N_{23}O_{15}$ | 1438.62 |
| LP-024 | Asp-Gly-Arg-Trp-His-Arg-Val-Ala-Val-Ile-Met-Gly | $C_{61}H_{97}N_{21}O_{15}S$ | 1396.65 |

Figure 1C

PEPTIDES

| PTI- | Structure | Formula | MW |
|---|---|---|---|
| LP-025 | Leu-Pro-Phe-Phe-Asp | $C_{33}H_{43}N_5O_8$ | 637.74 |
| DP-026 | Ala-Gly-Gln-Trp-His-Arg-Val | $C_{38}H_{56}N_{14}O_9$ | 852.95 |
| DP-027 | Gly-Gln-Trp-His-Arg-Val-Ser | $C_{38}H_{56}N_{14}O_{10}$ | 868.95 |
| DP-028 | Gln-Trp-His-Arg-Val-Ser-Val | $C_{41}H_{62}N_{14}O_{10}$ | 911.04 |
| DP-029 | Trp-His-Arg-Val-Ser-Val-Arg | $C_{42}H_{66}N_{16}O_9$ | 939.09 |
| DP-030 | His-Arg-Val-Ser-Val-Arg-Trp | $C_{42}H_{66}N_{16}O_9$ | 939.09 |
| DP-031 | Arg-Val-Ser-Val-Arg-Trp-Gly | $C_{38}H_{62}N_{14}O_9$ | 859.00 |
| DP-032 | Asp-Gly-Arg-Trp-His-Arg-Val | $C_{40}H_{60}N_{16}O_{10}$ | 925.02 |

Figure 1D

PEPTIDES

| | Structure | Formula | MW |
|---|---|---|---|
| DP-033 | Gly-Arg-Trp-His-Arg-Val-Ala | $C_{39}H_{60}N_{16}O_8$ | 881.01 |
| DP-034 | Arg-Trp-His-Arg-Val-Ala-Val | $C_{42}H_{66}N_{16}O_8$ | 923.09 |
| DP-035 | Trp-His-Arg-Val-Ala-Val-Ile | $C_{42}H_{65}N_{13}O_8$ | 880.07 |
| DP-036 | His-Arg-Val-Ala-Val-Ile-Met | $C_{36}H_{64}N_{12}O_8S$ | 825.05 |
| DP-037 | Arg-Val-Ala-Val-Ile-Met-Gly | $C_{32}H_{60}N_{10}O_8S$ | 744.96 |
| DP-038 | Thr-Leu-Phe-Leu-Ala-His-Gly | $C_{36}H_{55}N_9O_9$ | 757.89 |
| DP-039 | Leu-Phe-Leu-Ala-His-Gly-Arg | $C_{38}H_{60}N_{12}O_8$ | 812.97 |
| DP-040 | Phe-Leu-Ala-His-Gly-Arg-Leu | $C_{38}H_{60}N_{12}O_8$ | 812.98 |

Figure 1E

PEPTIDES

| | Structure | Formula | MW |
|---|---|---|---|
| DP-041 | Leu-Ala-His-Gly-Arg-Leu-Val | $C_{34}H_{60}N_{12}O_8$ | 764.93 |
| DP-042 | Ala-His-Gly-Arg-Leu-Val-Phe | $C_{37}H_{58}N_{12}O_8$ | 798.95 |
| DP-043 | His-Gly-Arg-Leu-Val-Phe-Met | $C_{39}H_{62}N_{12}O_8S$ | 859.07 |
| DP-044 | Gly-Leu-Ala-Phe-Val-Leu-Arg | $C_{37}H_{62}N_{10}O_8$ | 774.97 |
| DP-045 | Leu-Ala-Phe-Val-Leu-Arg-Gly | $C_{37}H_{62}N_{10}O_8$ | 774.97 |
| DP-046 | Ala-Phe-Val-Leu-Arg-Gly-Lys | $C_{37}H_{63}N_{11}O_8$ | 789.98 |
| DP-047 | Phe-Val-Leu-Arg-Gly-Lys-Ser | $C_{37}H_{63}N_{11}O_9$ | 805.98 |
| DP-048 | Val-Leu-Arg-Gly-Lys-Ser-Leu | $C_{34}H_{65}N_{11}O_9$ | 771.96 |

Figure 1F

PEPTIDES

| | Structure | Formula | MW |
|---|---|---|---|
| DP-049 | Leu-Arg-Gly-Lys-Ser-Leu-Tyr | $C_{38}H_{65}N_{11}O_{10}$ | 836.01 |
| DP-050 | Arg-Val-Ala-Val-Ile-Met-Pro-Arg-Val-Ala-Val-Ile-Met | $C_{65}H_{119}N_{19}O_{14}S_2$ | 1454.92 |
| DP-051 | Trp-His-Arg-Val-Ala-Val-Ile-Met | $C_{47}H_{74}N_{14}O_9S$ | 1011.27 |
| DP-052 | Arg-Val-Ala-Val-Ile-Met | $C_{30}H_{57}N_9O_7S$ | 687.91 |
| DP-053 | His-Arg-Pro-Ala-Val-Ile-Met | $C_{36}H_{62}N_{12}O_8S$ | 823.04 |
| DP-054 | His-Arg-Val-Pro-Val-Ile-Met | $C_{38}H_{66}N_{12}O_8S$ | 851.09 |
| DP-055 | His-Arg-Val-Ala-Val-Pro-Met | $C_{35}H_{60}N_{12}O_8S$ | 809.01 |
| DP-056 | Leu-Ala-Phe-Val-Leu-Arg | $C_{35}H_{59}N_9O_7$ | 717.91 |

Figure 1G

PEPTIDES
| | Structure | Formula | MW |
|---|---|---|---|
| DP-057 | Leu-Pro-Phe-Val-Leu-Arg 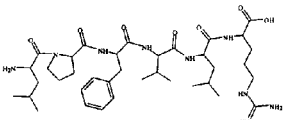 | $C_{37}H_{61}N_9O_7$ | 743.95 |
| DP-058 | Arg-Arg-Pro-Ala-Phe-Val-Leu-Arg 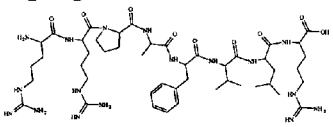 | $C_{46}H_{79}N_{17}O_9$ | 1014.25 |
| DP-059 | Thr-Arg-Ile-Ser-Leu-Gln-Val 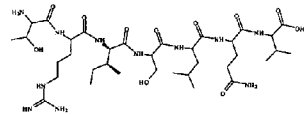 | $C_{35}H_{65}N_{11}O_{11}$ | 815.97 |
| DP-060 | Ser-Leu-Gln-Val-Gln-Leu-Arg 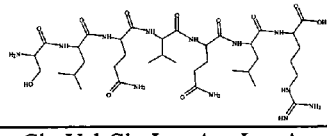 | $C_{36}H_{66}N_{12}O_{11}$ | 843.00 |
| DP-061 | Gln-Val-Gln-Leu-Arg-Lys-Arg 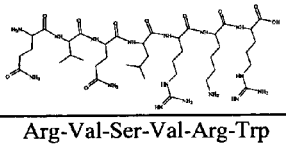 | $C_{39}H_{74}N_{16}O_{10}$ | 927.12 |
| DP-062 | Arg-Val-Ser-Val-Arg-Trp 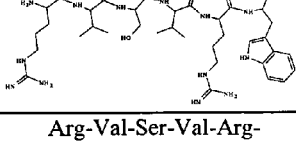 | $C_{36}H_{59}N_{13}O_8$ | 801.95 |
| DP-063 | Arg-Val-Ser-Val-Arg- 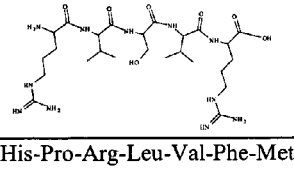 | $C_{25}H_{49}N_{11}O_7$ | 615.74 |
| DP-064 | His-Pro-Arg-Leu-Val-Phe-Met 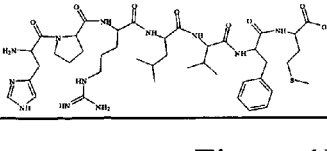 | $C_{42}H_{66}N_{12}O_8S$ | 899.13 |
Figure 1H PEPTIDES
| | Structure | Formula | MW |
|---|---|---|---|
| DP-065 | Trp-His-Arg-Val-Ala-Val-Ile-Met-amide 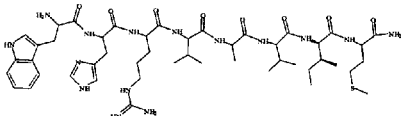 | $C_{47}H_{75}N_{15}O_8S$ | 1010.28 |
| DP-066 | Trp-His-Arg-Val-Ala-Val-Ile-amide 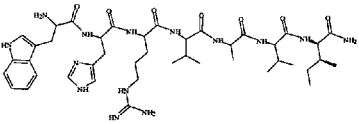 | $C_{42}H_{66}N_{14}O_7$ | 879.08 |
| DP-067 | Arg-Val-Ala-Val-Ile-Met-amide 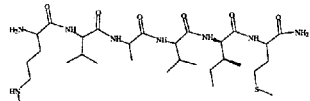 | $C_{30}H_{58}N_{10}O_6S$ | 686.92 |
| DP-068 | Arg-Val-Ala-Val-Ile-Met-Gly-amide 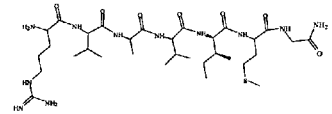 | $C_{32}H_{61}N_{11}O_7S$ | 743.98 |
| DP-069 | Leu-Ala-Phe-Val-Leu-Arg-amide 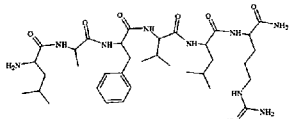 | $C_{35}H_{60}N_{10}O_6$ | 716.93 |
| DP-070 | His-Gly-Arg-Leu-Val-Phe-Met-amide 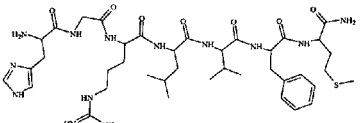 | $C_{39}H_{63}N_{13}O_7S$ | 858.08 |
| DP-071 | Thr-Leu-Phe-Leu-Ala-Arg 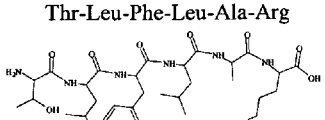 | $C_{34}H_{57}N_9O_8$ | 719.89 |
| DP-072 | Trp-His-Leu-Ala-Phe-Val-Leu-Arg 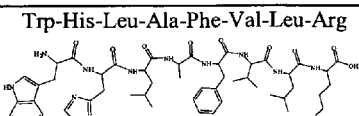 | $C_{52}H_{76}N_{14}O_9$ | 1041.27 |
Figure 1I

PEPTIDES

| | Structure | Formula | MW |
|---|---|---|---|
| DP-073 | Acetyl-Leu-Ala-Phe-Val-Leu-Arg-amide 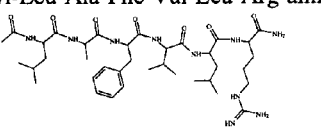 | $C_{37}H_{62}N_{10}O_7$ | 759.00 |
| DP-074 | Leu-Ala-Phe-Val-Leu-Arg-Lys-amide 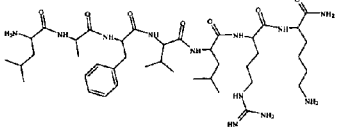 | $C_{41}H_{72}N_{12}O_7$ | 845.10 |
| DP-075 | Thr-Leu-Phe-Leu-Ala-Arg-amide 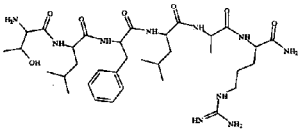 | $C_{34}H_{58}N_{10}O_7$ | 718.90 |
| DP-076 | Acetyl-Thr-Leu-Phe-Leu-Ala-Arg-amide 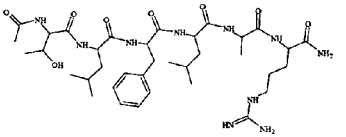 | $C_{36}H_{60}N_{10}O_8$ | 760.94 |
| DP-077 | Thr-Leu-Phe-Leu-Ala-Arg-Lys 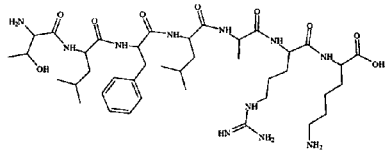 | $C_{40}H_{69}N_{11}O_9$ | 848.06 |
| DP-078 | Thr-Leu-Phe-Leu-Ala-Arg-Lys-amide 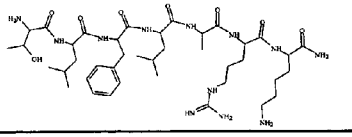 | $C_{40}H_{70}N_{12}O_8$ | 847.07 |
| DP-079 | Trp-His-Leu-Ala-Phe-Val-Leu-Arg-amide 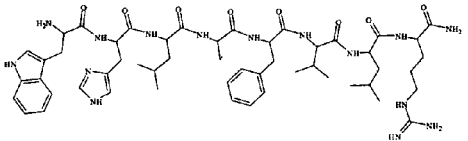 | $C_{52}H_{77}N_{15}O_8$ | 1040.28 |
| DP-080 | Trp-His-Leu-Ala-Phe-Val-Leu-Arg-Lys-amide 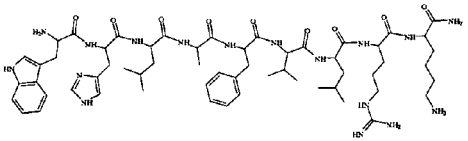 | $C_{58}H_{89}N_{17}O_9$ | 1168.46 |

Figure 1J

PEPTIDES

| PTI- | Structure | Formula | MW |
|---|---|---|---|
| LP-081 SEQ. ID. NO. 8 | Acetyl-Leu-Pro-Phe-Phe-Asp-amide  | $C_{35}H_{46}N_6O_8$ | 678.79 |

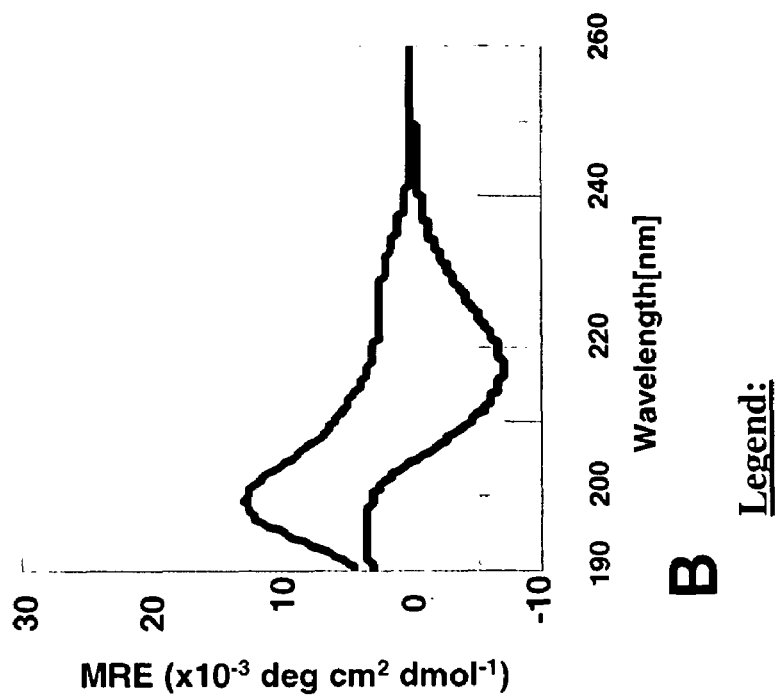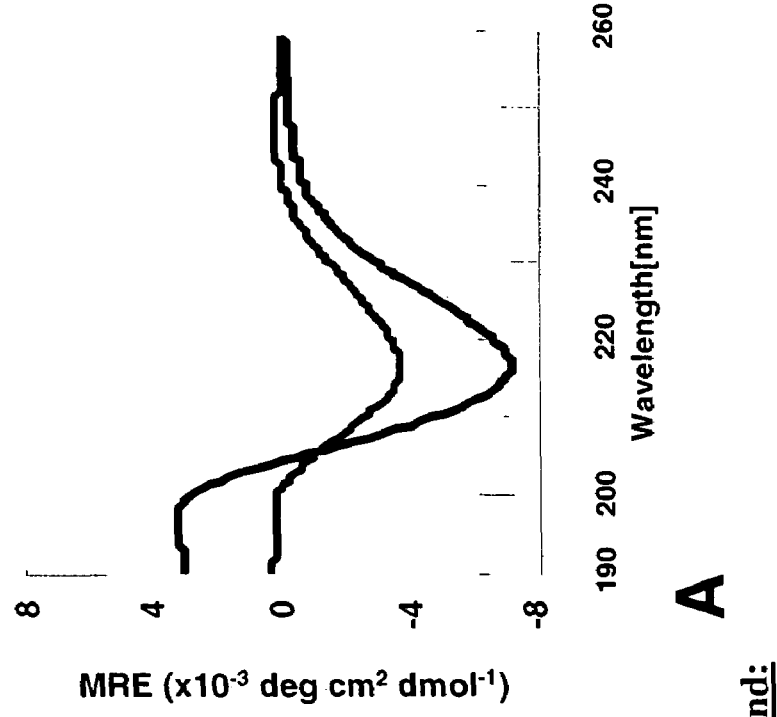
Figure 12

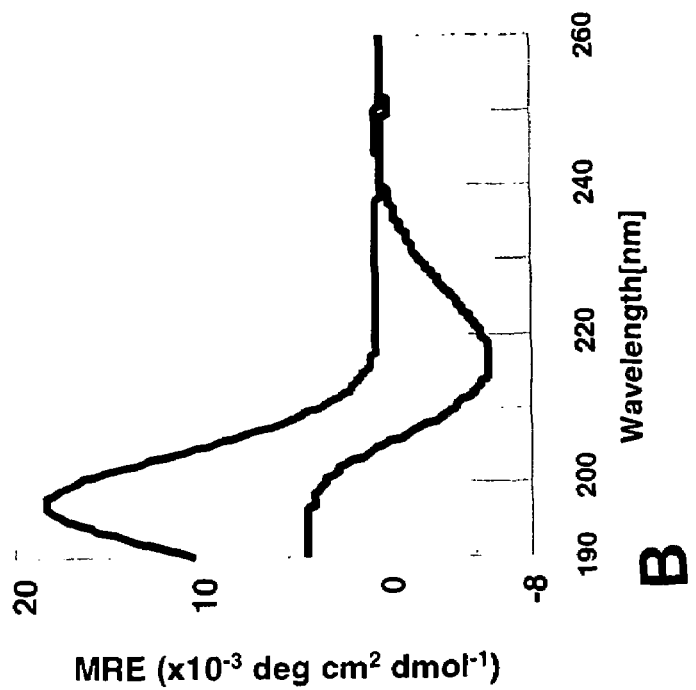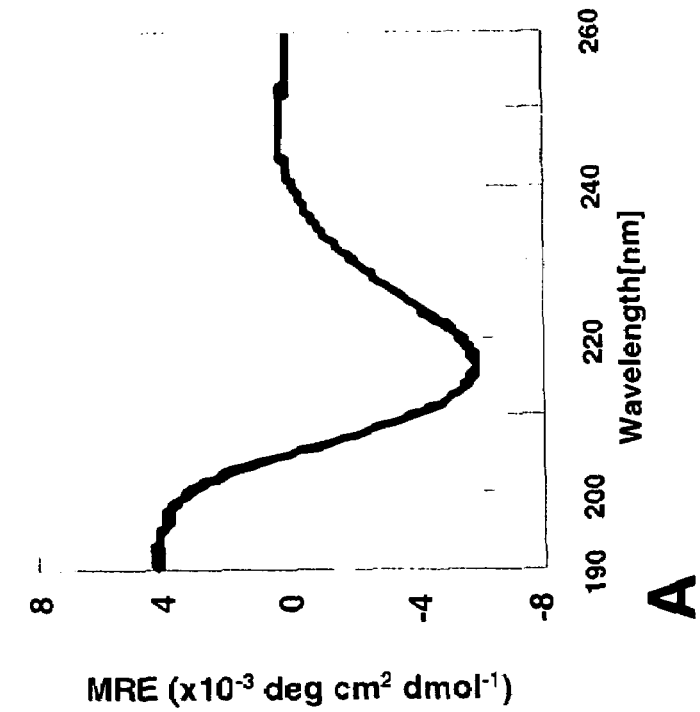
Figure 17

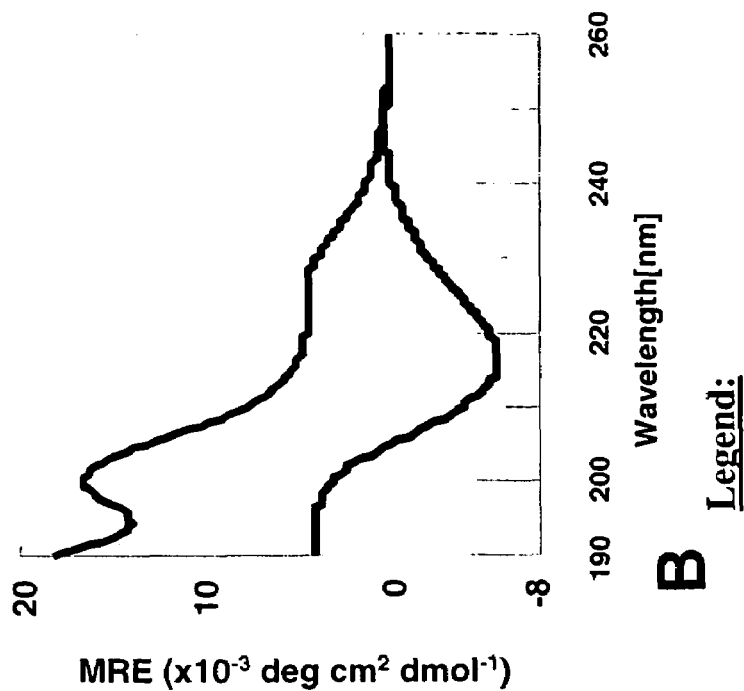
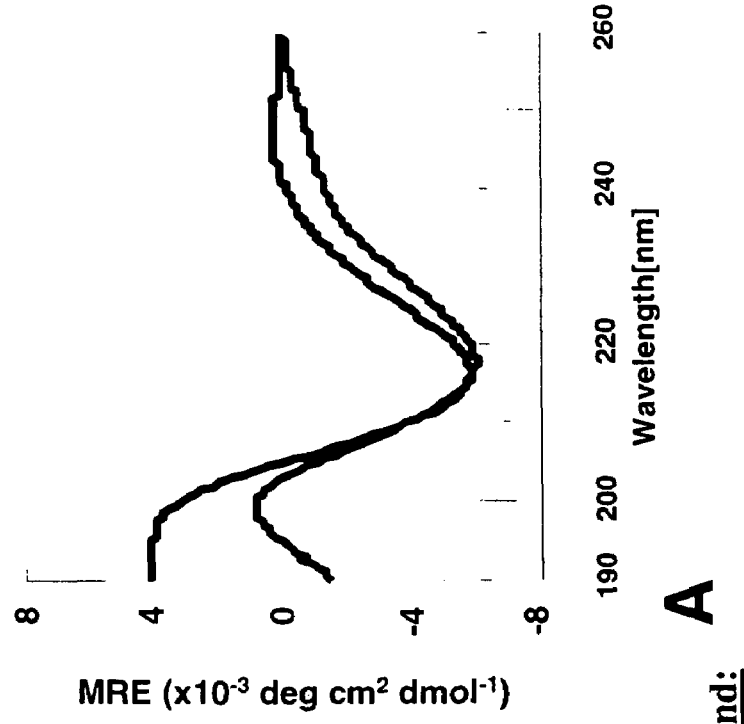
Figure 20

Figure 21 RVAVIMPRVAVIM from DP-06

WHRVAVIM from DP-06

RVAVIM from DP-06

LAFVLR from DP-015

Figure 25. LPFVLR from DP-015

RRPAFVLR from DP-015

TRISLQV from DP-013

SLQVQLR from DP-013

QVQLRKR from DP-013

HPRLVFM from DP-004

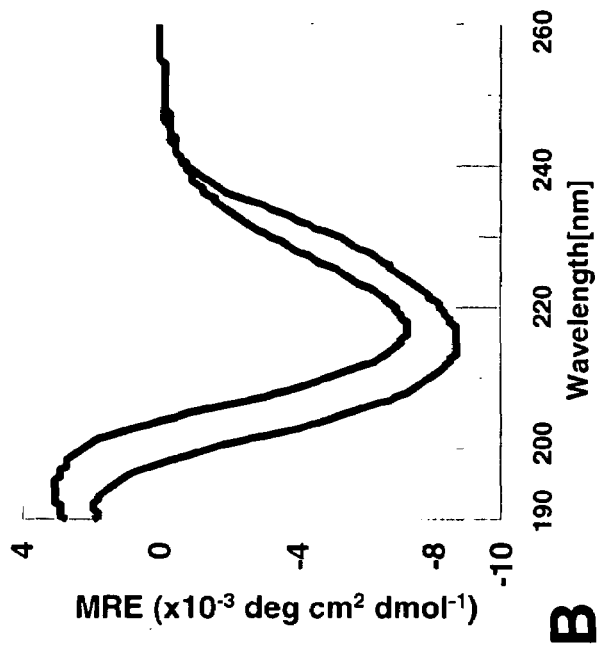
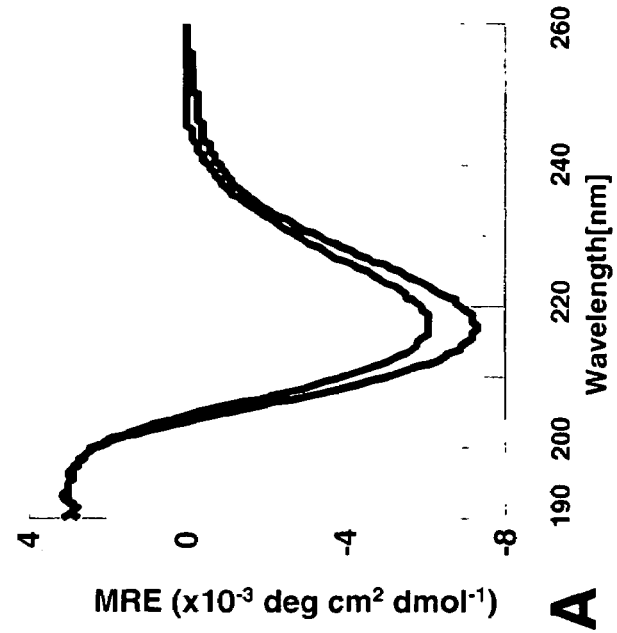
Aβ42 only (0.1mg/ml)
Aβ42+DP-065 (1:2) wt/wt
DP-065　　WHRVAVIM-amide
Aβ42 only (0.1mg/ml)
Aβ42+low molecular weight polylysine (1:2) wt/wt
KKKKKKKKKK
(average MW 5 kDa)
Figure 37

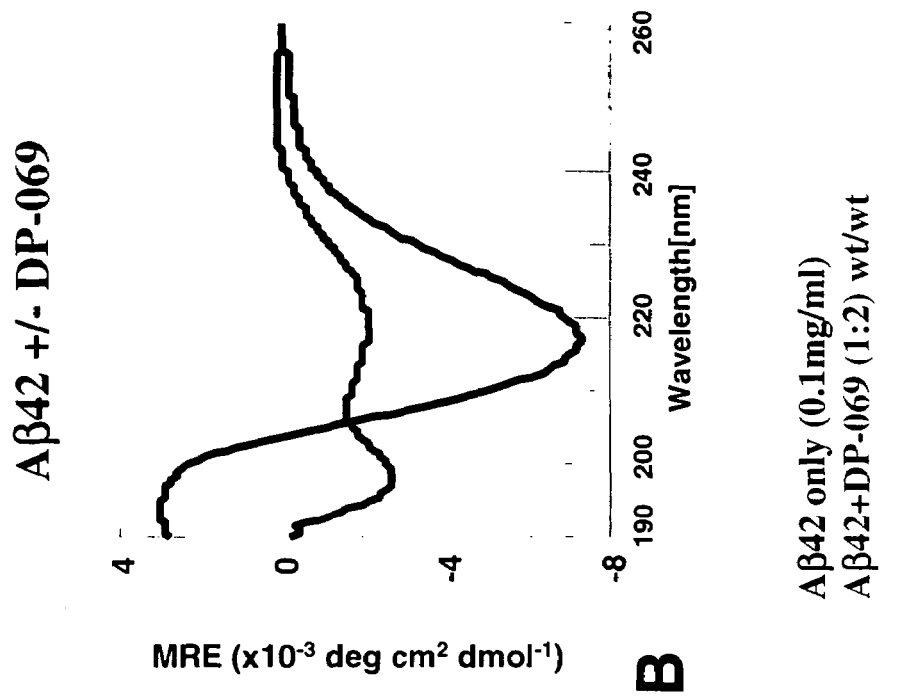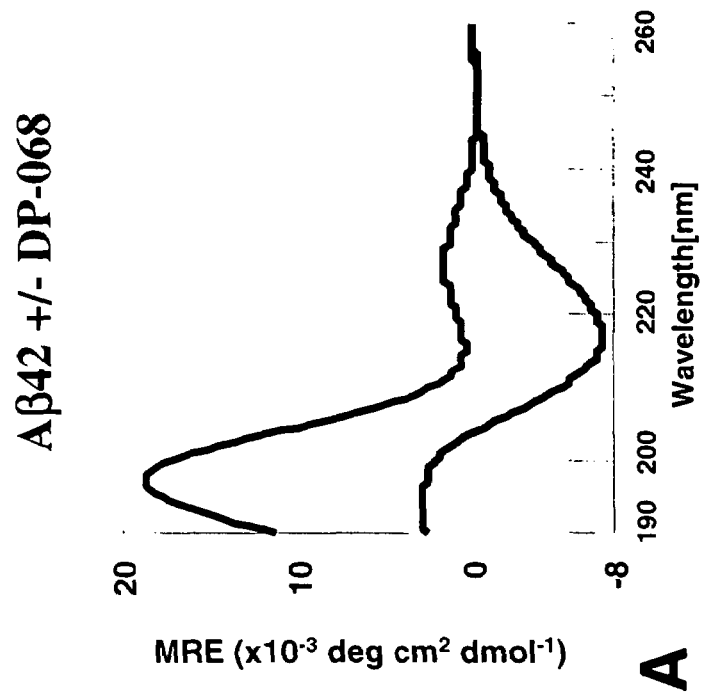
Figure 39

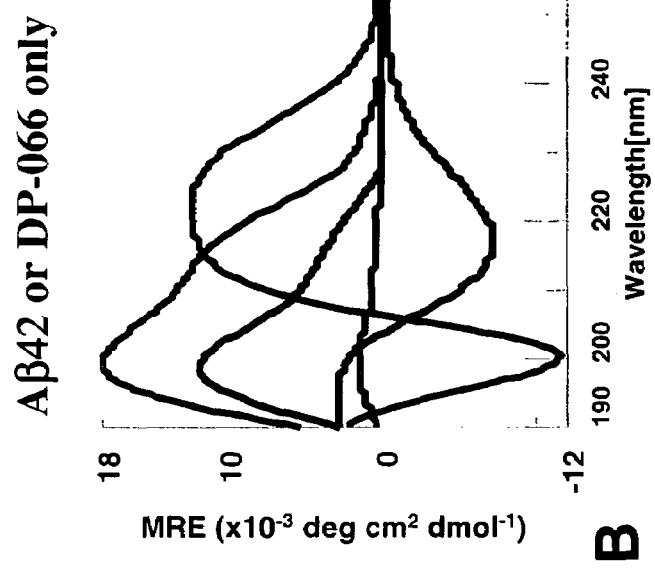
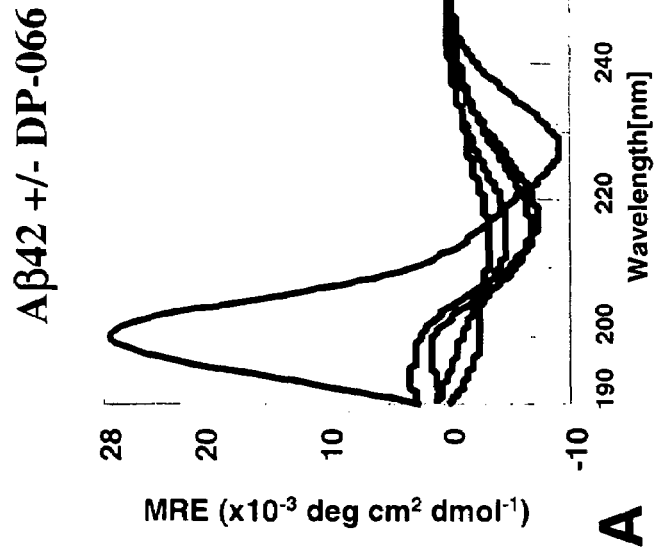
Figure 43

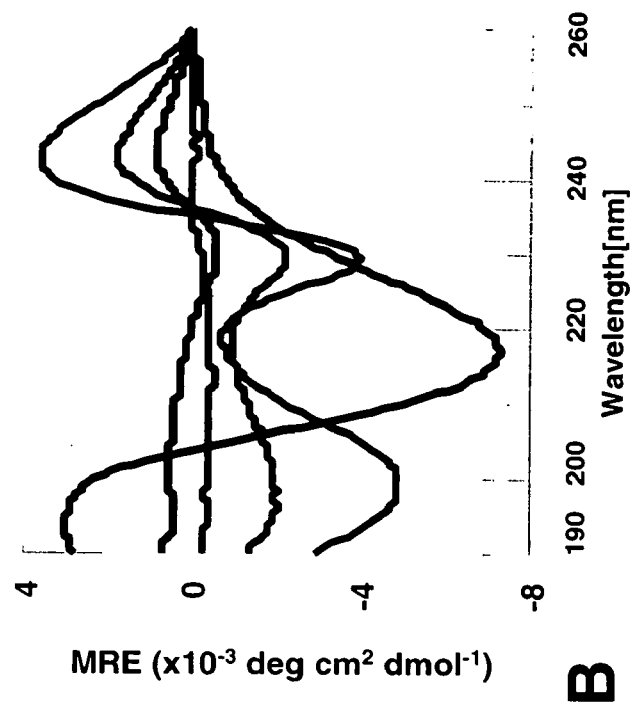
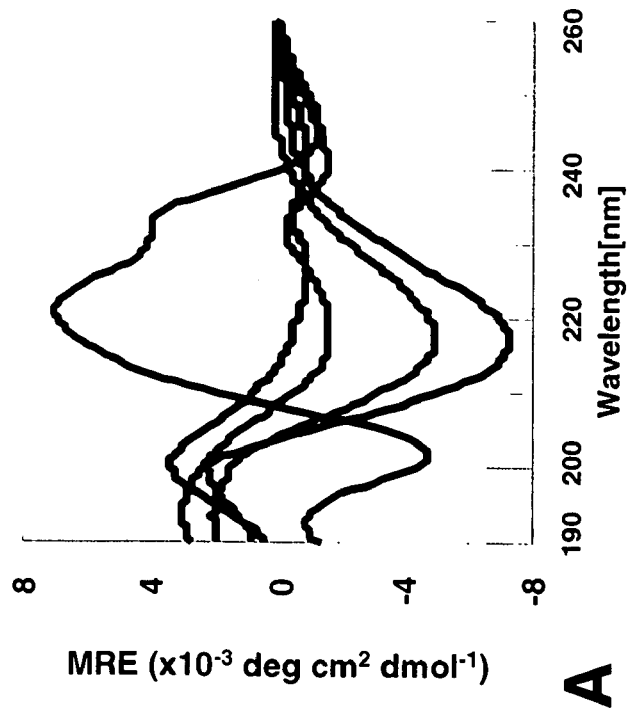
Figure 49

Ranking Order of Laminin Peptides to Aβ42 based on Thio T % Inhibition

| | Thio T | |
|---|---|---|
| | 1:2 w/w | 1:1 w/w |
| DP-072 (WHLAFVLR) | 32.6 | 32.2 |
| DP-071 (TLFLAR) | 15.3 | 14.6 |
| DP-070 (HGRLVFM-amide) | 18.7 | 0.0 |
| DP-067 (RVAVIM-amide) | 19.2 | 12.2 |
| DP-069 (LAFVLR-amide) | 18.2 | 11.1 |
| DP-066 (WHRVAVI-amide) | 13.5 | 13.0 |
| DP-068 (RVAVIMG-amide) | 11.5 | 12.8 |
| DP-065 (WHRVAVIM-amide) | 9.6 | 14.0 |

Figure 52

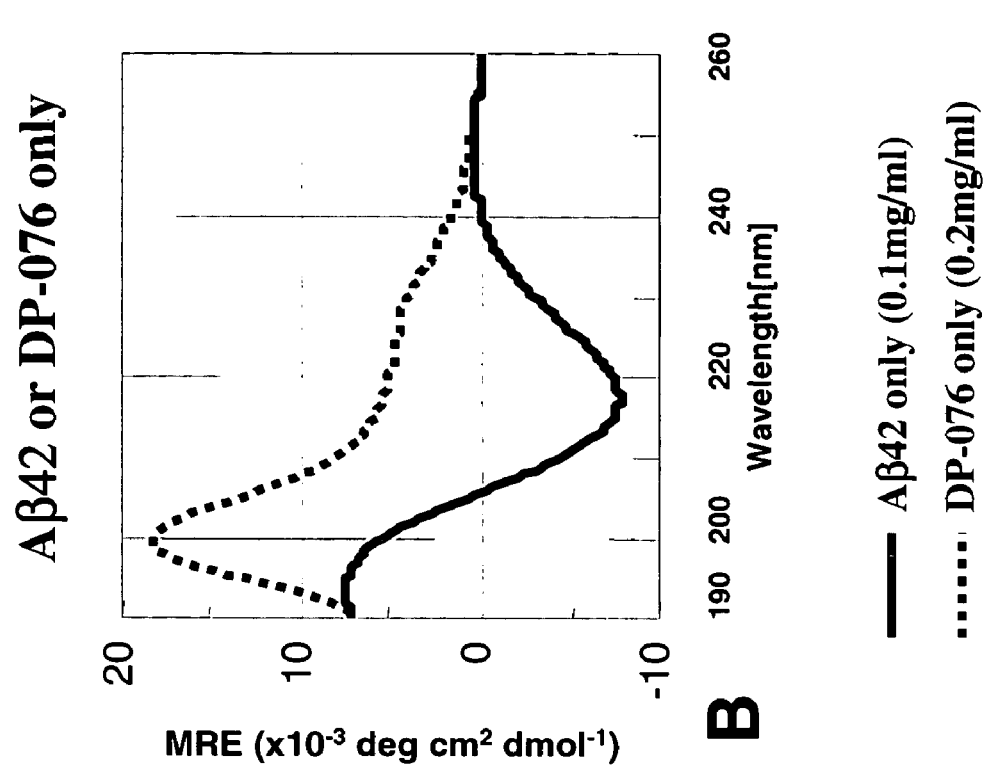
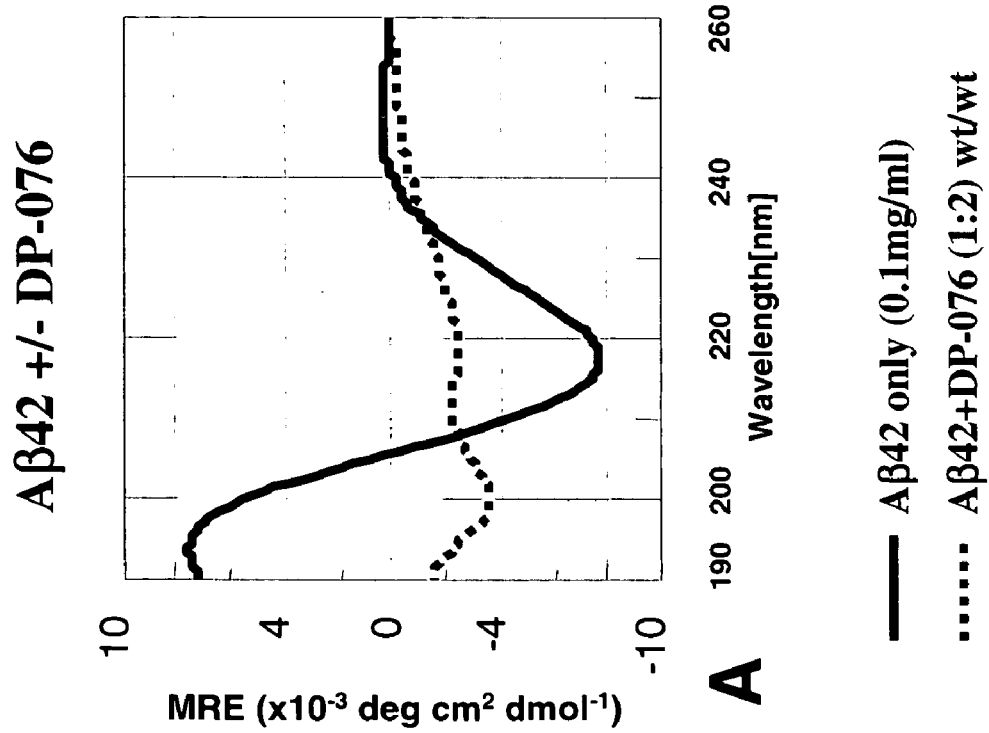
Figure 56

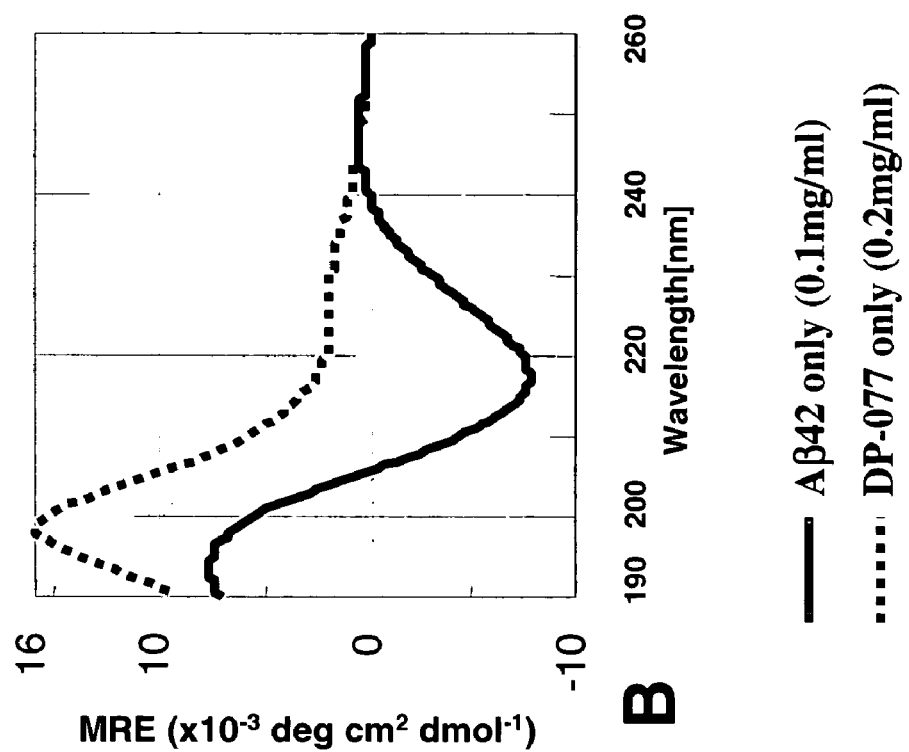
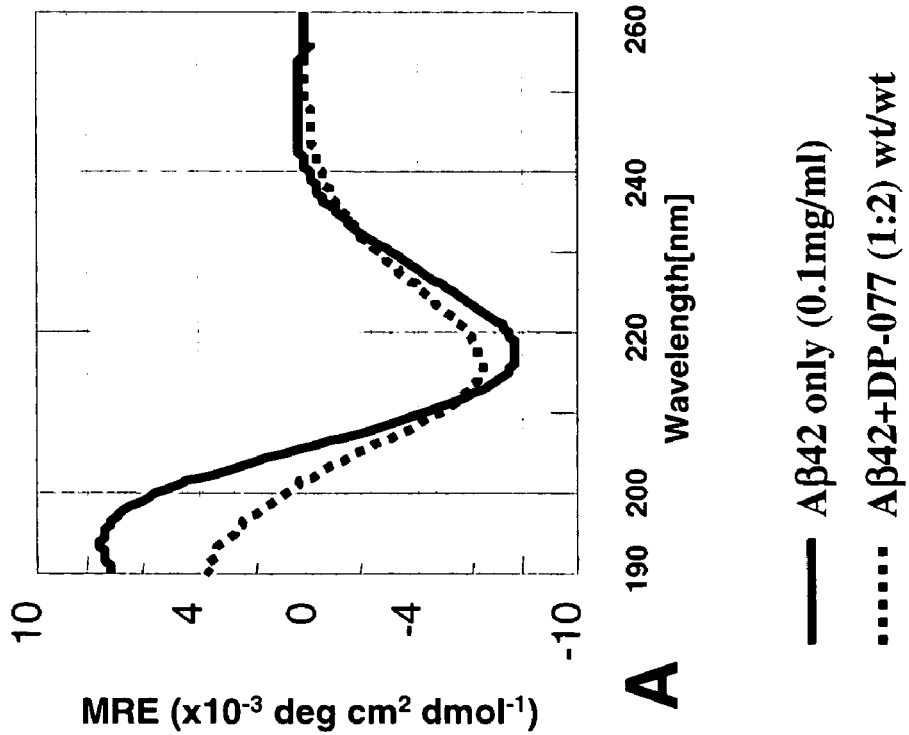
Figure 57

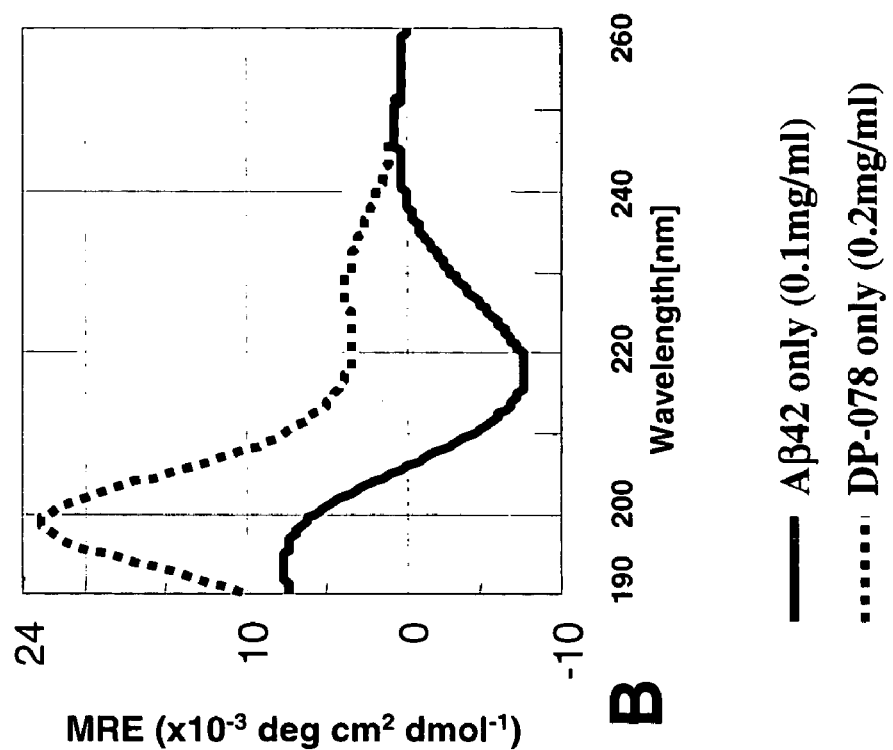
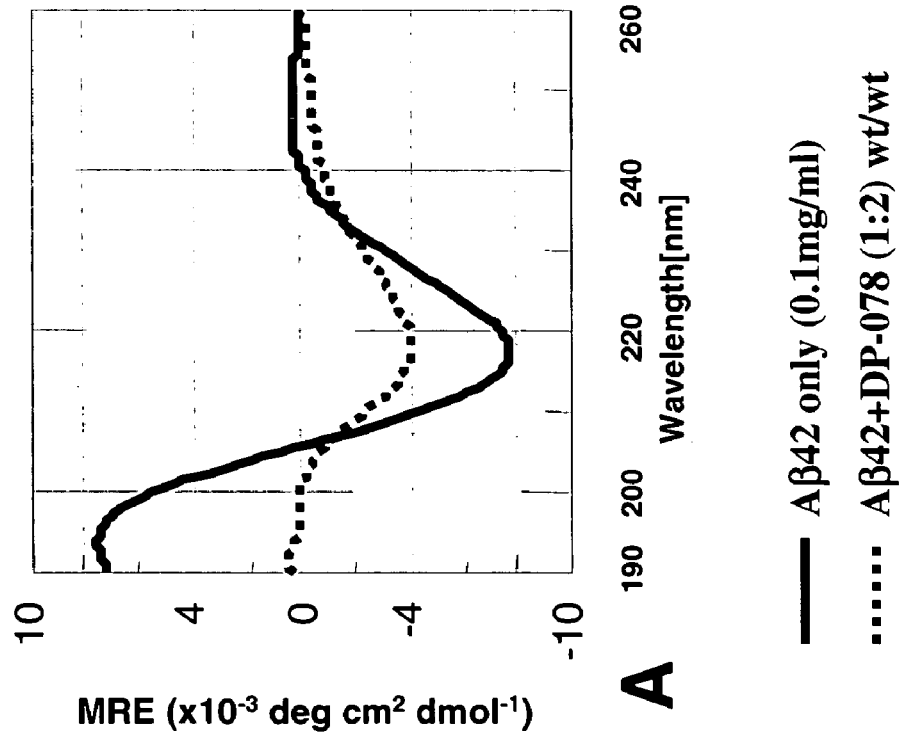
Figure 58

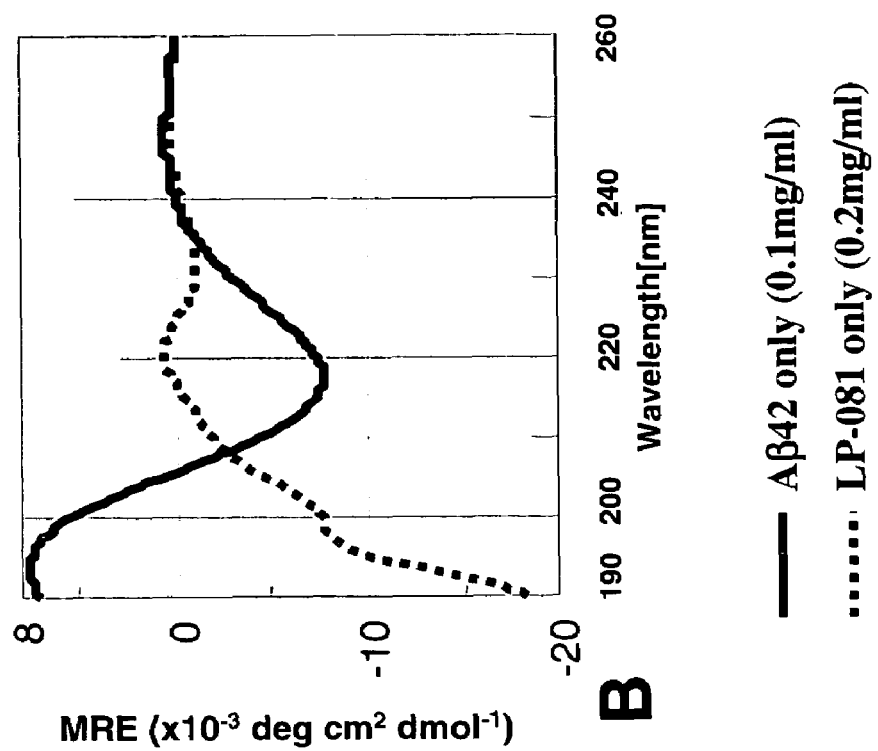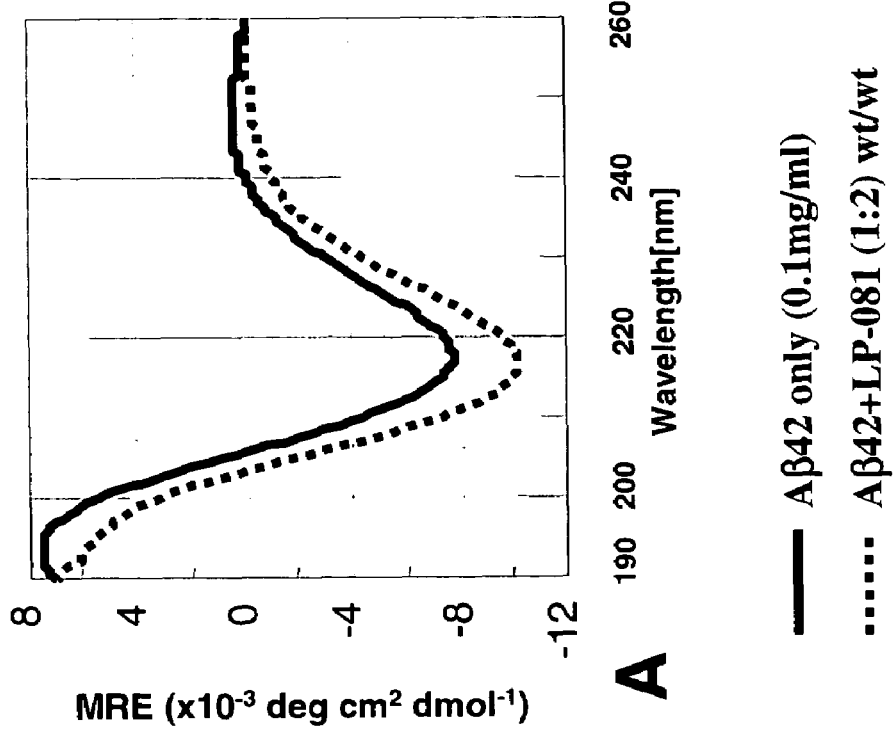
Figure 61

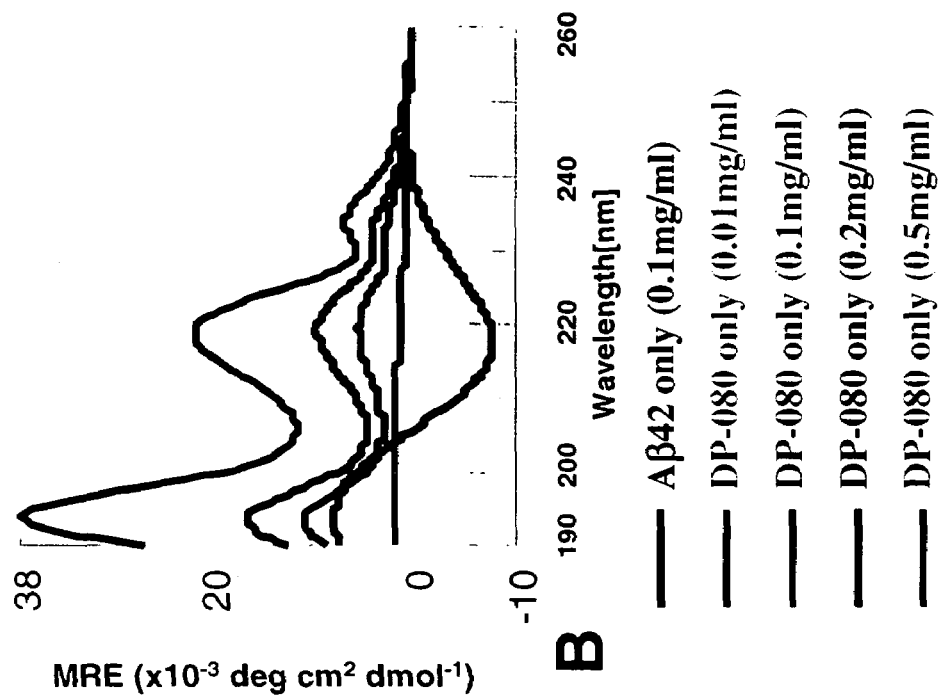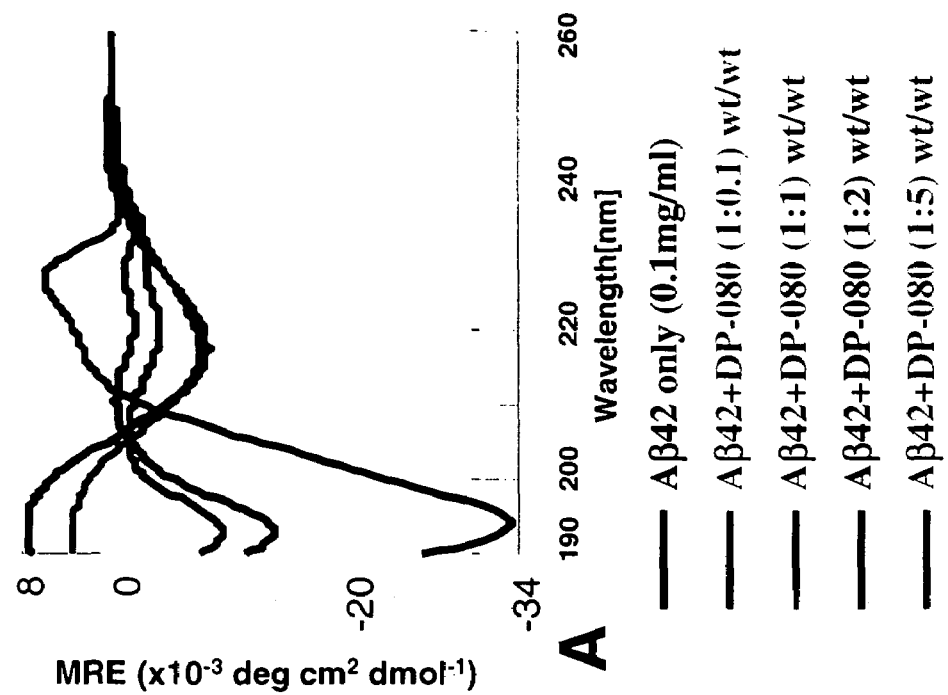
Figure 70

SEQUENCE LISTING

<160> NUMBER OF SEQ ID NOS: 89

<210> SEQ ID NO 1
<211> LENGTH: 12
<212> TYPE: PRT
<213> ORGANISM: Mus musculus

<400> SEQUENCE: 1

Arg Lys Arg Leu Gln Val Gln Leu Ser Ile Arg Thr
1               5                   10

<210> SEQ ID NO 2
<211> LENGTH: 12
<212> TYPE: PRT
<213> ORGANISM: Mus musculus

<400> SEQUENCE: 2

Lys Ala Phe Asp Ile Thr Tyr Val Arg Leu Lys Phe
1               5                   10

<210> SEQ ID NO 3
<211> LENGTH: 13
<212> TYPE: PRT
<213> ORGANISM: Mus musculus

<400> SEQUENCE: 3

Arg Gln Val Phe Gln Val Ala Tyr Ile Ile Ile Lys Ala
1               5                   10

<210> SEQ ID NO 4
<211> LENGTH: 12
<212> TYPE: PRT
<213> ORGANISM: Homo sapiens

<400> SEQUENCE: 4

His Gln Thr Trp Thr Arg Asn Leu Gln Val Thr Leu
1               5                   10

<210> SEQ ID NO 5
<211> LENGTH: 12
<212> TYPE: PRT
<213> ORGANISM: Homo sapiens

<400> SEQUENCE: 5

Ile Ser Asn Val Phe Val Gln Arg Leu Ser Leu Ser
1               5                   10

<210> SEQ ID NO 6
<211> LENGTH: 12

<212> TYPE: PRT
<213> ORGANISM: Homo sapiens

<400> SEQUENCE: 6

Ala Ser Pro Pro Ser Val Lys Val Trp Gln Asp Ala
 1               5                  10

<210> SEQ ID NO 7
<211> LENGTH: 13
<212> TYPE: PRT
<213> ORGANISM: Homo sapiens

<400> SEQUENCE: 7

Arg Gly Leu Val Phe His Thr Gly Thr Lys Asn Ser Phe
 1               5                  10

<210> SEQ ID NO 8
<211> LENGTH: 12
<212> TYPE: PRT
<213> ORGANISM: Homo sapiens

<400> SEQUENCE: 8

Tyr Leu Ser Lys Gly Arg Leu Val Phe Ala Leu Gly
 1               5                  10

<210> SEQ ID NO 9
<211> LENGTH: 12
<212> TYPE: PRT
<213> ORGANISM: Homo sapiens

<400> SEQUENCE: 9

Asn Asp Gly Lys Trp His Thr Val Val Phe Gly His
 1               5                  10

<210> SEQ ID NO 10
<211> LENGTH: 12
<212> TYPE: PRT
<213> ORGANISM: Homo sapiens

<400> SEQUENCE: 10

Gly Asn Ser Thr Ile Ser Ile Arg Ala Pro Val Tyr
 1               5                  10

<210> SEQ ID NO 11
<211> LENGTH: 12
<212> TYPE: PRT
<213> ORGANISM: Mus musculus

<400> SEQUENCE: 11

Thr Leu Phe Leu Ala His Gly Arg Leu Val Phe Met
 1               5                  10

<210> SEQ ID NO 12
<211> LENGTH: 12
<212> TYPE: PRT
<213> ORGANISM: Mus musculus

<400> SEQUENCE: 12

His Pro Asp Asp Phe Val Phe Tyr Val Gly Gly Tyr
 1               5                  10

<210> SEQ ID NO 13
<211> LENGTH: 12
<212> TYPE: PRT
<213> ORGANISM: Mus musculus

```
<400> SEQUENCE: 13

Trp Leu Tyr Val Asp Asp Gln Leu Gln Leu Val Lys
 1               5                  10

<210> SEQ ID NO 14
<211> LENGTH: 12
<212> TYPE: PRT
<213> ORGANISM: Mus musculus

<400> SEQUENCE: 14

Val Gln Ser Arg Gln His Ser Arg Ala Gly Gln Trp
 1               5                  10

<210> SEQ ID NO 15
<211> LENGTH: 12
<212> TYPE: PRT
<213> ORGANISM: Mus musculus

<400> SEQUENCE: 15

Ala Gly Gln Trp His Arg Val Ser Val Arg Trp Gly
 1               5                  10

<210> SEQ ID NO 16
<211> LENGTH: 12
<212> TYPE: PRT
<213> ORGANISM: Mus musculus

<400> SEQUENCE: 16

Val Arg Trp Gly Met Gln Gln Ile Gln Leu Val Val
 1               5                  10

<210> SEQ ID NO 17
<211> LENGTH: 12
<212> TYPE: PRT
<213> ORGANISM: Mus musculus

<400> SEQUENCE: 17

Thr Trp Ser Gln Lys Ala Leu His His Arg Val Pro
 1               5                  10

<210> SEQ ID NO 18
<211> LENGTH: 12
<212> TYPE: PRT
<213> ORGANISM: Mus musculus

<400> SEQUENCE: 18

Asp Gly Arg Trp His Arg Val Ala Val Ile Met Gly
 1               5                  10

<210> SEQ ID NO 19
<211> LENGTH: 12
<212> TYPE: PRT
<213> ORGANISM: Mus musculus

<400> SEQUENCE: 19

Ala Pro Val Asn Val Thr Ala Ser Val Gln Ile Gln
 1               5                  10

<210> SEQ ID NO 20
<211> LENGTH: 12
<212> TYPE: PRT
<213> ORGANISM: Mus musculus

<400> SEQUENCE: 20
```

Ala Ala Ser Ile Lys Val Ala Val Ser Ala Asp Arg
1               5                   10

<210> SEQ ID NO 21
<211> LENGTH: 12
<212> TYPE: PRT
<213> ORGANISM: Mus musculus

<400> SEQUENCE: 21

Ala Tyr Ser Phe Ile Val Lys Ile Glu Arg Val Gly
1               5                   10

<210> SEQ ID NO 22
<211> LENGTH: 12
<212> TYPE: PRT
<213> ORGANISM: Mus musculus

<400> SEQUENCE: 22

Glu Asp Ser Leu Ile Ser Arg Arg Ala Tyr Phe Asn
1               5                   10

<210> SEQ ID NO 23
<211> LENGTH: 12
<212> TYPE: PRT
<213> ORGANISM: Mus musculus

<400> SEQUENCE: 23

Arg Ala Tyr Phe Asn Gly Gln Ser Phe Ile Ala Ser
1               5                   10

<210> SEQ ID NO 24
<211> LENGTH: 12
<212> TYPE: PRT
<213> ORGANISM: Mus musculus

<400> SEQUENCE: 24

His Lys Lys Leu Lys Ile Arg Ser Gln Glu Lys Tyr
1               5                   10

<210> SEQ ID NO 25
<211> LENGTH: 12
<212> TYPE: PRT
<213> ORGANISM: Mus musculus

<400> SEQUENCE: 25

Ala Pro Gly Arg Ala Val Lys Asn Val Gln Ile Thr
1               5                   10

<210> SEQ ID NO 26
<211> LENGTH: 12
<212> TYPE: PRT
<213> ORGANISM: Mus musculus

<400> SEQUENCE: 26

Val Ile Arg Asp Ser Asn Val Val Gln Leu Asp Val
1               5                   10

<210> SEQ ID NO 27
<211> LENGTH: 12
<212> TYPE: PRT
<213> ORGANISM: Mus musculus

<400> SEQUENCE: 27

Gly Lys Asn Thr Gly Asp His Phe Val Leu Tyr Met

```
                   1               5                  10

<210> SEQ ID NO 28
<211> LENGTH: 12
<212> TYPE: PRT
<213> ORGANISM: Mus musculus

<400> SEQUENCE: 28

Ala Val Ser Ile Asp Arg Thr Leu Gln Phe Gly His
  1               5                  10

<210> SEQ ID NO 29
<211> LENGTH: 13
<212> TYPE: PRT
<213> ORGANISM: Mus musculus

<400> SEQUENCE: 29

Arg Leu Val Ser Tyr Asn Gly Ile Ile Phe Phe Leu Lys
  1               5                  10

<210> SEQ ID NO 30
<211> LENGTH: 12
<212> TYPE: PRT
<213> ORGANISM: Mus musculus

<400> SEQUENCE: 30

Ala Ser Lys Ala Ile Gln Val Phe Leu Leu Ala Gly
  1               5                  10

<210> SEQ ID NO 31
<211> LENGTH: 12
<212> TYPE: PRT
<213> ORGANISM: Mus musculus

<400> SEQUENCE: 31

His Gln Asn Met Gly Ser Val Asn Val Ser Val Gly
  1               5                  10

<210> SEQ ID NO 32
<211> LENGTH: 12
<212> TYPE: PRT
<213> ORGANISM: Mus musculus

<400> SEQUENCE: 32

Leu Val Leu Phe Leu Asn His Gly His Phe Val Ala
  1               5                  10

<210> SEQ ID NO 33
<211> LENGTH: 12
<212> TYPE: PRT
<213> ORGANISM: Mus musculus

<400> SEQUENCE: 33

Gly Gly Leu Pro Ala Ser Ser Tyr Ser Ser Lys Leu
  1               5                  10

<210> SEQ ID NO 34
<211> LENGTH: 12
<212> TYPE: PRT
<213> ORGANISM: Mus musculus

<400> SEQUENCE: 34

Leu Arg Thr Pro Thr Gln Met Val Gly Val Thr Pro
  1               5                  10
```

<210> SEQ ID NO 35
<211> LENGTH: 12
<212> TYPE: PRT
<213> ORGANISM: Mus musculus

<400> SEQUENCE: 35

Ser Gly Thr Leu Ala Leu Ser Lys Gln Gly Lys Ala
 1               5                  10

<210> SEQ ID NO 36
<211> LENGTH: 40
<212> TYPE: PRT
<213> ORGANISM: Mus musculus

<400> SEQUENCE: 36

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 37
<211> LENGTH: 42
<212> TYPE: PRT
<213> ORGANISM: Mus musculus

<400> SEQUENCE: 37

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 38
<211> LENGTH: 416
<212> TYPE: PRT
<213> ORGANISM: Homo sapiens

<400> SEQUENCE: 38

Val Val Arg Leu Asn Asp Thr Val Gly Val Thr Lys Lys Cys Ser Glu
 1               5                  10                  15

Asp Trp Lys Leu Val Arg Ser Ala Ser Phe Ser Arg Gly Gly Gln Leu
            20                  25                  30

Ser Phe Thr Asp Leu Gly Leu Pro Pro Thr Asp His Leu Gln Ala Ser
        35                  40                  45

Phe Gly Phe Gln Thr Phe Gln Pro Ser Gly Ile Leu Leu Asp His Gln
    50                  55                  60

Thr Trp Thr Arg Asn Leu Gln Val Thr Leu Glu Asp Gly Tyr Ile Glu
65                  70                  75                  80

Leu Ser Thr Ser Asp Ser Gly Gly Pro Ile Phe Lys Ser Pro Gln Thr
                85                  90                  95

Tyr Met Asp Gly Leu Leu His Tyr Val Ser Val Ile Ser Asp Asn Ser
            100                 105                 110

Gly Leu Arg Leu Leu Ile Asp Asp Gln Leu Leu Arg Asn Ser Lys Arg
        115                 120                 125

Leu Lys His Ile Ser Ser Ser Arg Gln Ser Leu Arg Leu Gly Gly Ser
    130                 135                 140

```
Asn Phe Glu Gly Cys Ile Ser Asn Val Phe Val Gln Arg Leu Ser Leu
145                 150                 155                 160

Ser Pro Glu Val Leu Asp Leu Thr Ser Asn Ser Leu Lys Arg Asp Val
                165                 170                 175

Ser Leu Gly Gly Cys Ser Leu Asn Lys Pro Pro Phe Leu Met Leu Leu
            180                 185                 190

Lys Gly Ser Thr Arg Phe Asn Lys Thr Lys Thr Phe Arg Ile Asn Gln
        195                 200                 205

Leu Leu Gln Asp Thr Pro Val Ala Ser Pro Arg Ser Val Lys Val Trp
210                 215                 220

Gln Asp Ala Cys Ser Pro Leu Pro Lys Thr Gln Ala Asn His Gly Ala
225                 230                 235                 240

Leu Gln Phe Gly Asp Ile Pro Thr Ser His Leu Leu Phe Lys Leu Pro
                245                 250                 255

Gln Glu Leu Leu Lys Pro Arg Ser Gln Phe Ala Val Asp Met Gln Thr
            260                 265                 270

Thr Ser Ser Arg Gly Leu Val Phe His Thr Gly Thr Lys Asn Ser Phe
        275                 280                 285

Met Ala Leu Tyr Leu Ser Lys Gly Arg Leu Val Phe Ala Leu Gly Thr
290                 295                 300

Asp Gly Lys Lys Leu Arg Ile Lys Ser Lys Glu Lys Cys Asn Asp Gly
305                 310                 315                 320

Lys Trp His Thr Val Val Phe Gly His Asp Gly Glu Lys Gly Arg Leu
                325                 330                 335

Val Val Asp Gly Leu Arg Ala Arg Glu Gly Ser Leu Pro Gly Asn Ser
            340                 345                 350

Thr Ile Ser Ile Arg Ala Pro Val Tyr Leu Gly Ser Pro Ser Gly
        355                 360                 365

Lys Pro Lys Ser Leu Pro Thr Asn Ser Phe Val Gly Cys Leu Lys Asn
370                 375                 380

Phe Gln Leu Asp Ser Lys Pro Leu Tyr Thr Pro Ser Ser Ser Phe Gly
385                 390                 395                 400

Val Ser Ser Cys Leu Gly Gly Pro Leu Glu Lys Gly Ile Tyr Phe Ser
                405                 410                 415

<210> SEQ ID NO 39
<211> LENGTH: 964
<212> TYPE: PRT
<213> ORGANISM: Mus musculus

<400> SEQUENCE: 39

Thr Ser Ile Ser Leu Tyr Met Lys Pro Pro Lys Pro Gln Thr Thr
1               5                   10                  15

Gly Ala Trp Val Ala Asp Gln Phe Val Leu Tyr Leu Gly Ser Lys Asn
                20                  25                  30

Ala Lys Lys Glu Tyr Met Gly Leu Ala Ile Lys Asn Asp Asn Leu Val
            35                  40                  45

Tyr Val Tyr Asn Leu Gly Met Lys Asp Val Glu Ile Leu Leu Asp Ser
        50                  55                  60

Lys Pro Val Ser Ser Trp Pro Ala Tyr Phe Ser Ile Val Lys Ile Glu
65                  70                  75                  80

Arg Val Gly Lys His Gly Lys Val Phe Leu Thr Val Pro Ser Ser Ser
                85                  90                  95

Ser Thr Ala Glu Glu Lys Phe Ile Lys Lys Gly Glu Phe Ala Gly Asp
```

-continued

```
              100                 105                 110
Asp Ser Leu Leu Asp Leu Thr Pro Glu Asp Thr Val Phe Tyr Val Gly
            115                 120                 125

Gly Val Pro Ala Asn Phe Lys Leu Pro Ala Ser Leu Asn Leu Pro Ser
        130                 135                 140

Tyr Ser Gly Cys Leu Glu Leu Ala Thr Leu Asn Asn Asp Val Ile Ser
145                 150                 155                 160

Leu Tyr Asn Phe Lys His Ile Tyr Asn Met Asp Pro Ser Lys Ser Val
                165                 170                 175

Pro Cys Ala Arg Asp Lys Leu Ala Phe Thr Gln Ser Arg Ala Ala Ser
            180                 185                 190

Tyr Phe Phe Asp Gly Ser Ser Tyr Ala Val Val Arg Asp Ile Thr Arg
        195                 200                 205

Arg Gly Lys Phe Gly Gln Val Thr Arg Phe Asp Ile Glu Ile Arg Thr
    210                 215                 220

Pro Ala Asp Asn Gly Leu Val Leu Leu Met Val Asn Gly Ser Met Phe
225                 230                 235                 240

Phe Ser Leu Glu Met Arg Asn Gly Tyr Leu His Val Phe Tyr Asp Phe
                245                 250                 255

Gly Phe Ser Asn Gly Pro Val His Leu Glu Asp Thr Leu Lys Lys Ala
            260                 265                 270

Gln Ile Asn Asp Ala Lys Tyr Arg Glu Ile Ser Ile Ile Tyr His Asn
        275                 280                 285

Asp Lys Lys Met Ile Leu Val Val Asp Arg Arg His Val Lys Ser Thr
    290                 295                 300

Asp Asn Glu Lys Lys Lys Ile Pro Phe Thr Asp Ile Tyr Ile Gly Gly
305                 310                 315                 320

Ala Pro Gln Glu Val Leu Gln Ser Arg Thr Leu Arg Ala His Leu Pro
                325                 330                 335

Leu Asp Ile Asn Phe Arg Gly Cys Met Lys Gly Ile Gln Phe Gln Lys
            340                 345                 350

Lys Asp Phe Asn Leu Leu Glu Gln Thr Glu Thr Leu Gly Val Gly Tyr
        355                 360                 365

Gly Cys Pro Glu Asp Ser Leu Ile Ser Arg Arg Ala Tyr Phe Asn Gly
    370                 375                 380

Gln Ser Phe Ile Ala Ser Ile Gln Lys Ile Ser Phe Phe Asp Gly Phe
385                 390                 395                 400

Glu Gly Gly Phe Asn Phe Arg Thr Leu Gln Pro Asn Gly Leu Leu Phe
                405                 410                 415

Tyr Tyr Thr Ser Gly Ser Asp Val Phe Ser Ile Ser Leu Asp Asn Gly
            420                 425                 430

Thr Val Val Met Asp Val Lys Gly Ile Lys Val Met Ser Thr Asp Lys
        435                 440                 445

Gln Tyr His Asp Gly Leu Pro His Phe Val Val Thr Ser Ile Ser Asp
    450                 455                 460

Thr Arg Tyr Glu Leu Val Val Asp Lys Ser Arg Leu Arg Gly Lys Asn
465                 470                 475                 480

Pro Thr Lys Gly Lys Ala Glu Gln Thr Gln Thr Thr Glu Lys Lys Phe
                485                 490                 495

Tyr Phe Gly Gly Ser Pro Ile Ser Pro Gln Tyr Ala Asn Phe Thr Gly
            500                 505                 510

Cys Ile Ser Asn Ala Tyr Phe Thr Arg Leu Asp Arg Asp Val Glu Val
        515                 520                 525
```

```
Glu Ala Phe Gln Arg Tyr Ser Glu Lys Val His Thr Ser Leu Tyr Glu
    530                 535                 540

Cys Pro Ile Glu Ser Ser Pro Leu Phe Leu His Lys Lys Gly Lys
545                 550                 555                 560

Asn Ser Ser Lys Pro Lys Thr Asn Lys Gln Gly Glu Lys Ser Lys Asp
                565                 570                 575

Ala Pro Ser Trp Asp Pro Ile Gly Leu Lys Phe Leu Glu Gln Lys Ala
            580                 585                 590

Pro Arg Asp Ser His Cys His Leu Phe Ser Ser Pro Arg Ala Ile Glu
        595                 600                 605

His Ala Tyr Gln Tyr Gly Gly Thr Ala Asn Ser Arg Gln Glu Phe Glu
    610                 615                 620

His Glu Gln Gly Asp Phe Gly Glu Lys Ser Gln Phe Ser Ile Arg Leu
625                 630                 635                 640

Lys Thr Arg Ser Ser His Gly Met Ile Phe Tyr Val Ser Asp Gln Glu
                645                 650                 655

Glu Asn Asp Phe Met Thr Leu Phe Leu Ala His Gly Arg Leu Val Phe
            660                 665                 670

Met Phe Asn Val Gly His Lys Lys Leu Lys Ile Arg Ser Gln Glu Lys
        675                 680                 685

Tyr Asn Asp Gly Leu Trp His Asp Val Ile Phe Ile Arg Glu Lys Ser
    690                 695                 700

Ser Gly Arg Leu Val Ile Asp Gly Leu Arg Val Leu Glu Glu Arg Leu
705                 710                 715                 720

Pro Pro Ser Gly Ala Ala Trp Lys Ile Lys Gly Pro Ile Tyr Leu Gly
                725                 730                 735

Gly Val Ala Pro Gly Arg Ala Val Lys Asn Val Gln Ile Thr Ser Val
            740                 745                 750

Tyr Ser Phe Ser Gly Cys Leu Gly Asn Leu Gln Leu Asn Gly Ala Ser
        755                 760                 765

Ile Thr Ser Ala Ser Gln Thr Phe Ser Val Thr Pro Cys Phe Glu Gly
    770                 775                 780

Pro Met Glu Thr Gly Thr Tyr Phe Ser Thr Glu Gly Gly Tyr Val Val
785                 790                 795                 800

Leu Asp Glu Ser Phe Asn Ile Gly Leu Lys Phe Glu Ile Ala Phe Glu
                805                 810                 815

Val Arg Pro Arg Ser Ser Ser Gly Thr Leu Val His Gly His Ser Val
            820                 825                 830

Asn Gly Glu Tyr Leu Asn Val His Met Arg Asn Gly Gln Val Ile Val
        835                 840                 845

Lys Val Asn Asn Gly Val Arg Asp Phe Ser Thr Ser Val Thr Pro Lys
    850                 855                 860

Gln Asn Leu Cys Asp Gly Arg Trp His Arg Ile Thr Val Ile Arg Asp
865                 870                 875                 880

Ser Asn Val Val Gln Leu Asp Val Asp Ser Glu Val Asn His Val Val
                885                 890                 895

Gly Pro Leu Asn Pro Lys Pro Val Asp His Arg Glu Pro Val Phe Val
            900                 905                 910

Gly Gly Val Pro Glu Ser Leu Leu Thr Pro Arg Leu Ala Pro Ser Lys
        915                 920                 925

Pro Phe Thr Gly Cys Ile Arg His Phe Val Ile Asp Ser Arg Pro Val
    930                 935                 940
```

```
Ser Phe Ser Lys Ala Ala Leu Val Ser Gly Ala Val Ser Ile Asn Ser
945                 950                 955                 960

Cys Pro Thr Ala
```

<210> SEQ ID NO 40
<211> LENGTH: 956
<212> TYPE: PRT
<213> ORGANISM: Mus musculus

<400> SEQUENCE: 40

```
Thr Ala Leu Lys Phe His Ile Gln Ser Pro Val Pro Ala Pro Glu Pro
  1               5                  10                  15

Gly Lys Asn Thr Gly Asp His Phe Val Leu Tyr Met Gly Ser Arg Gln
                 20                  25                  30

Ala Thr Gly Asp Tyr Met Gly Val Ser Leu Arg Asn Gln Lys Val His
             35                  40                  45

Trp Val Tyr Arg Leu Gly Lys Ala Gly Pro Thr Thr Leu Ser Ile Asp
 50                  55                  60

Glu Asn Ile Gly Glu Gln Phe Ala Ala Val Ser Ile Asp Arg Thr Leu
 65                  70                  75                  80

Gln Phe Gly His Met Ser Val Thr Val Glu Lys Gln Met Val His Glu
                 85                  90                  95

Ile Lys Gly Asp Thr Val Ala Pro Gly Ser Glu Gly Leu Leu Asn Leu
            100                 105                 110

His Pro Asp Asp Phe Val Phe Tyr Val Gly Gly Tyr Pro Ser Asn Phe
        115                 120                 125

Thr Pro Pro Glu Pro Leu Arg Phe Pro Gly Tyr Leu Gly Cys Ile Glu
    130                 135                 140

Met Glu Thr Leu Asn Glu Glu Val Val Ser Leu Tyr Asn Phe Glu Gln
145                 150                 155                 160

Thr Phe Met Leu Asp Thr Ala Val Asp Lys Pro Cys Ala Arg Ser Lys
                165                 170                 175

Ala Thr Gly Asp Pro Trp Leu Thr Asp Gly Ser Tyr Leu Asp Gly Ser
            180                 185                 190

Gly Phe Ala Arg Ile Ser Phe Glu Lys Gln Phe Ser Asn Thr Lys Arg
        195                 200                 205

Phe Asp Gln Glu Leu Arg Leu Val Ser Tyr Asn Gly Ile Ile Phe Phe
    210                 215                 220

Leu Lys Gln Glu Ser Gln Phe Leu Cys Leu Ala Val Gln Glu Gly Thr
225                 230                 235                 240

Leu Val Leu Phe Tyr Asp Phe Gly Ser Gly Leu Lys Lys Ala Asp Pro
                245                 250                 255

Leu Gln Pro Pro Gln Ala Leu Thr Ala Ala Ser Lys Ala Ile Gln Val
            260                 265                 270

Phe Leu Leu Ala Gly Asn Arg Lys Arg Val Leu Val Arg Val Glu Arg
        275                 280                 285

Ala Thr Val Phe Ser Val Asp Gln Asp Asn Met Leu Glu Met Ala Asp
    290                 295                 300

Ala Tyr Tyr Leu Gly Gly Val Pro Pro Glu Gln Leu Pro Leu Ser Leu
305                 310                 315                 320

Arg Gln Leu Phe Pro Ser Gly Gly Ser Val Arg Gly Cys Ile Lys Gly
                325                 330                 335

Ile Lys Ala Leu Gly Lys Tyr Val Asp Leu Lys Arg Leu Asn Thr Thr
            340                 345                 350
```

```
Gly Ile Ser Phe Gly Cys Thr Ala Asp Leu Leu Val Gly Arg Thr Met
        355                 360                 365

Thr Phe His Gly His Gly Phe Leu Pro Leu Ala Leu Pro Asp Val Ala
        370                 375                 380

Pro Ile Thr Glu Val Val Tyr Ser Gly Phe Gly Phe Arg Gly Thr Gln
385                 390                 395                 400

Asp Asn Asn Leu Leu Tyr Tyr Arg Thr Ser Pro Asp Gly Pro Tyr Gln
                405                 410                 415

Val Ser Leu Arg Glu Gly His Val Thr Leu Arg Phe Met Asn Gln Glu
                420                 425                 430

Val Glu Thr Gln Arg Val Phe Ala Asp Gly Ala Pro His Tyr Val Ala
                435                 440                 445

Phe Tyr Ser Asn Val Thr Gly Val Trp Leu Tyr Val Asp Asp Gln Leu
        450                 455                 460

Gln Leu Val Lys Ser His Glu Arg Thr Thr Pro Met Leu Gln Leu Gln
465                 470                 475                 480

Pro Glu Glu Pro Ser Arg Leu Leu Gly Leu Pro Val Ser Gly
                485                 490                 495

Thr Phe His Asn Phe Ser Gly Cys Ile Ser Asn Val Phe Val Gln Arg
        500                 505                 510

Leu Arg Gly Pro Gln Arg Val Phe Asp Leu His Gln Asn Met Gly Ser
        515                 520                 525

Val Asn Val Ser Val Gly Cys Thr Pro Ala Gln Leu Ile Glu Thr Ser
        530                 535                 540

Arg Ala Thr Ala Gln Lys Val Ser Arg Arg Ser Arg Gln Pro Ser Gln
545                 550                 555                 560

Asp Leu Ala Cys Thr Thr Pro Trp Leu Pro Gly Thr Ile Gln Asp Ala
                565                 570                 575

Tyr Gln Phe Gly Gly Pro Leu Pro Ser Tyr Leu Gln Phe Val Gly Ile
                580                 585                 590

Ser Pro Ser His Arg Asn Arg Leu His Leu Ser Met Leu Val Arg Pro
        595                 600                 605

His Ala Ala Ser Gln Gly Leu Leu Ser Thr Ala Pro Met Ser Gly
        610                 615                 620

Arg Ser Pro Ser Leu Val Leu Phe Leu Asn His Gly His Phe Val Ala
625                 630                 635                 640

Gln Thr Glu Gly Pro Gly Pro Arg Leu Gln Val Gln Ser Arg Gln His
                645                 650                 655

Ser Arg Ala Gly Gln Trp His Arg Val Ser Val Arg Trp Gly Met Gln
                660                 665                 670

Gln Ile Gln Leu Val Val Asp Gly Ser Gln Thr Trp Ser Gln Lys Ala
                675                 680                 685

Leu His His Arg Val Pro Arg Ala Glu Arg Pro Gln Pro Tyr Thr Leu
        690                 695                 700

Ser Val Gly Gly Leu Pro Ala Ser Ser Tyr Ser Ser Lys Leu Pro Val
705                 710                 715                 720

Ser Val Gly Phe Ser Gly Cys Leu Lys Lys Leu Gln Leu Asp Lys Gln
                725                 730                 735

Pro Leu Arg Thr Pro Thr Gln Met Val Gly Val Thr Pro Cys Val Ser
                740                 745                 750

Gly Pro Leu Glu Asp Gly Leu Phe Phe Pro Gly Ser Glu Gly Val Val
        755                 760                 765

Thr Leu Glu Leu Pro Lys Ala Lys Met Pro Tyr Val Ser Leu Glu Leu
```

```
                  770                 775                 780
Glu Met Arg Pro Leu Ala Ala Gly Leu Ile Phe His Leu Gly Gln
785                 790                 795                 800

Ala Leu Ala Thr Pro Tyr Met Gln Leu Lys Val Leu Thr Glu Gln Val
                805                 810                 815

Leu Leu Gln Ala Asn Asp Gly Ala Gly Glu Phe Ser Thr Trp Val Thr
                820                 825                 830

Tyr Pro Lys Leu Cys Asp Gly Arg Trp His Arg Val Ala Val Ile Met
                835                 840                 845

Gly Arg Asp Thr Leu Arg Leu Glu Val Asp Thr Gln Ser Asn His Thr
850                 855                 860

Thr Gly Arg Leu Pro Glu Ser Leu Ala Gly Ser Pro Ala Leu Leu His
865                 870                 875                 880

Leu Gly Ser Leu Pro Lys Ser Ser Thr Ala Arg Pro Glu Leu Pro Ala
                885                 890                 895

Tyr Arg Gly Cys Leu Arg Lys Leu Leu Ile Asn Gly Ala Pro Val Asn
                900                 905                 910

Val Thr Ala Ser Val Gln Ile Gln Gly Ala Val Gly Met Arg Gly Cys
                915                 920                 925

Pro Ser Gly Thr Leu Ala Leu Ser Lys Gln Gly Lys Ala Leu Thr Gln
                930                 935                 940

Arg His Ala Lys Pro Ser Val Ser Pro Leu Leu His
945                 950                 955

<210> SEQ ID NO 41
<211> LENGTH: 12
<212> TYPE: PRT
<213> ORGANISM: Mus musculus

<400> SEQUENCE: 41

Lys Pro Arg Leu Gln Phe Ser Leu Asp Ile Gln Thr
 1               5                  10

<210> SEQ ID NO 42
<211> LENGTH: 12
<212> TYPE: PRT
<213> ORGANISM: Mus musculus

<400> SEQUENCE: 42

Arg Asn Arg Leu His Leu Ser Met Leu Val Arg Pro
 1               5                  10

<210> SEQ ID NO 43
<211> LENGTH: 12
<212> TYPE: PRT
<213> ORGANISM: Homo sapiens

<400> SEQUENCE: 43

Ala Ser Phe Gly Phe Gln Thr Phe Gln Pro Ser Gly
 1               5                  10

<210> SEQ ID NO 44
<211> LENGTH: 12
<212> TYPE: PRT
<213> ORGANISM: Homo sapiens

<400> SEQUENCE: 44

Phe Lys Leu Pro Gln Glu Leu Leu Lys Pro Arg Ser
 1               5                  10
```

```
<210> SEQ ID NO 45
<211> LENGTH: 12
<212> TYPE: PRT
<213> ORGANISM: Homo sapiens

<400> SEQUENCE: 45

Lys Asn Ser Phe Met Ala Leu Tyr Leu Ser Lys Gly
  1               5                  10

<210> SEQ ID NO 46
<211> LENGTH: 12
<212> TYPE: PRT
<213> ORGANISM: Mus musculus

<400> SEQUENCE: 46

Leu His Val Phe Tyr Asp Phe Gly Phe Ser Asn Gly
  1               5                  10

<210> SEQ ID NO 47
<211> LENGTH: 12
<212> TYPE: PRT
<213> ORGANISM: Mus musculus

<400> SEQUENCE: 47

Val Leu Val Arg Val Glu Arg Ala Thr Val Phe Ser
  1               5                  10

<210> SEQ ID NO 48
<211> LENGTH: 12
<212> TYPE: PRT
<213> ORGANISM: Mus musculus

<400> SEQUENCE: 48

Phe Leu Pro Leu Ala Leu Pro Asp Val Ala Pro Ile
  1               5                  10

<210> SEQ ID NO 49
<211> LENGTH: 12
<212> TYPE: PRT
<213> ORGANISM: Mus musculus

<400> SEQUENCE: 49

Gly Pro Leu Pro Ser Tyr Leu Gln Phe Val Gly Ile
  1               5                  10

<210> SEQ ID NO 50
<211> LENGTH: 12
<212> TYPE: PRT
<213> ORGANISM: Mus musculus

<400> SEQUENCE: 50

Asp Gly Arg Trp His Arg Val Ala Val Ile Met Gly
  1               5                  10

<210> SEQ ID NO 51
<211> LENGTH: 12
<212> TYPE: PRT
<213> ORGANISM: Mus musculus

<400> SEQUENCE: 51

Ser Val Gln Ile Gln Gly Ala Val Gly Met Arg Gly
  1               5                  10

<210> SEQ ID NO 52
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Pro Phe Phe Asp
  1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 53

Arg Lys Arg Leu Gln Val Gln Xaa
  1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 54

Lys Arg Leu Gln Val Gln Leu Xaa
  1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 55

Arg Leu Gln Val Gln Leu Ser Xaa
  1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present
```

```
<400> SEQUENCE: 56

Leu Gln Val Gln Leu Ser Ile Xaa
  1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 57

Gln Val Gln Leu Ser Ile Arg Xaa
  1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 58

Val Gln Leu Ser Ile Arg Thr Xaa
  1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Gln Val Phe Gln Val Ala
  1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gln Val Phe Gln Val Ala Tyr
  1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61
```

```
Val Phe Gln Val Ala Tyr Ile
  1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Phe Gln Val Ala Tyr Ile Ile
  1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Val Ala Tyr Ile Ile Ile
  1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Val Ala Tyr Ile Ile Ile Lys
  1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Tyr Ile Ile Ile Lys Ala
  1               5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 66

Tyr Leu Ser Lys Gly Arg Leu Xaa
  1               5
```

```
<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 67

Leu Ser Lys Gly Arg Leu Val Xaa
 1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 68

Ser Lys Gly Arg Leu Val Phe Xaa
 1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 69

Lys Gly Arg Leu Val Phe Ala Xaa
 1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 70

Gly Arg Leu Val Phe Ala Leu Xaa
 1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (8)
<223> OTHER INFORMATION: Tyr or not present

<400> SEQUENCE: 71

Arg Leu Val Phe Ala Leu Gly Xaa
 1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 72

Thr Leu Phe Leu Ala His Gly Xaa
 1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 73

Leu Phe Leu Ala His Gly Arg Xaa
 1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 74

Phe Leu Ala His Gly Arg Leu Xaa
 1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 75
```

Leu Ala His Gly Arg Leu Val Xaa
 1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 76

Ala His Gly Arg Leu Val Phe Xaa
 1               5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 77

His Gly Arg Leu Val Phe Met Xaa
 1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 78

Ala Gly Gln Trp His Arg Val Xaa
 1               5

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 79

Gly Gln Trp His Arg Val Ser Xaa
 1               5

<210> SEQ ID NO 80
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 80

Gln Trp His Arg Val Ser Val Xaa
  1               5

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 81

Trp His Arg Val Ser Val Arg Xaa
  1               5

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 82

His Arg Val Ser Val Arg Trp Xaa
  1               5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 83

Arg Val Ser Val Arg Trp Gly Xaa
  1               5

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
```

<223> OTHER INFORMATION: Tyr or not present

<400> SEQUENCE: 84

Asp Gly Arg Trp His Arg Val Xaa
 1               5

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 85

Gly Arg Trp His Arg Val Ala Xaa
 1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 86

Arg Trp His Arg Val Ala Val Xaa
 1               5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 87

Trp His Arg Val Ala Val Ile Xaa
 1               5

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 88

His Arg Val Ala Val Ile Met Xaa
 1               5

```
<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr or not present

<400> SEQUENCE: 89

Arg Val Ala Val Ile Met Gly Xaa
 1               5
```

SMALL PEPTIDES FOR THE TREATMENT OF ALZHEIMER'S DISEASE AND OTHER BETA-AMYLOID PROTEIN FIBRILLOGENESIS DISORDERS

This application is a continuation-in-part of U.S. patent application Ser. No. 09/962,955 filed Sep. 24, 2001 which is a continuation-in-part of U.S. patent application Ser. No. 09/938,275 filed Aug. 22, 2001, which is a continuation of U.S. patent application Ser. No. 08/947,057 filed Oct. 8, 1997 now abandoned; This application also claims priority to U.S. Provisional Application 60/531,406 filed Dec. 18, 2003 and to U.S. Provisional Application 60/554,342 filed Mar. 17, 2004 and to U.S. Provisional Application 60/615,614 filed Sep. 30, 2004.

TECHNICAL FIELD

This invention relates to the use of 5 to 13 mer peptides and peptide derivatives for the treatment of Alzheimer's disease and other beta-amyloid protein fibrillogenesis disorders.

BACKGROUND OF THE INVENTION

Additional background for therapeutic use of peptide fragments in the treatment of Alzheimer's disease and other amyloidoses can be found in U.S. patent application Ser. No. 09/938,275 filed Aug. 22, 2001, and in U.S. patent application Ser. No. 09/962,955 filed Sep. 24, 2001, the text and drawings of each of which are hereby incorporated by reference into the present application as if fully set forth herein.

Beta-Amyloid Protein as a Therapeutic Target for Alzheimer's disease

Alzheimer's disease (AD) is characterized by the deposition and accumulation of a 39-43 amino acid peptide termed the beta-amyloid protein, Aβ or β/A4 (Glenner and Wong, *Biochem. Biophys. Res. Comm.* 120:885-890.1984; Masters et al, *Proc. Nat. Acad. Sci. U.S.A.* 82:4245-4249, 1985; Husby et al, *Bull. WHO* 71:105-108, 1993). Aβ is derived from larger precursor proteins termed beta amyloid precursor proteins (or APPs) of which there are several alternatively spliced variants. The most abundant forms of the APPs include proteins consisting of 695, 751 and 770 amino acids (Kitaguchi et al, *Nature* 331:530-532, 1988; Ponte et al, *Nature* 331:525-527, 1988; Tanzi et al, *Nature* 331:528-530, 1988). The small Aβ peptide is a major component that makes up the core of amyloid deposits called "plaques" in the brains of patients with AD. In addition, AD is characterized by the presence of numerous neurofibrillary "tangles", consisting of paired helical filaments which abnormally accumulate in the neuronal cytoplasm (Grundke-Iqbal et al *Proc. Natl. Acad. Sci. U.S.A.* 83:4913-4917, 1986; Kosik et al, *Proc. Natl. Acad. Sci. U.S.A.* 83:4044-4048, 1986; Lee et al, *Science* 251:675-678, 1991). The other major type of lesion found in AD brain is the accumulation of amyloid in the walls of blood vessels, both within the brain parenchyma and meningeal vessels that lie outside the brain. The amyloid deposits localized to the walls of blood vessels are referred to as cerebrovascular amyloid or congophilic angiopathy (Mandybur, *J. Neuropath. Exp. Neurol.* 45:79-90, 1986; Pardridge et al, *J. Neurochem.* 49:1394-1401, 1987). The pathological hallmarks of AD therefore are the presence of "plaques", "tangles", and cerebrovascular amyloid deposits.

For many years there has been an ongoing scientific debate as to the importance of "amyloid" in AD and whether the "plaques" and "tangles" characteristic of this disease, were a cause or merely the consequences of the disease. Recent studies indicate that amyloid is indeed a causative factor for AD and should not be regarded merely as a consequence. The Alzheimer's Aβ protein in cell culture has been shown to cause degeneration of nerve cells within a short time period (Pike et al, *Br. Res.* 563:311-314, 1991; *J. Neurochem.* 64:253-265, 1995). Studies suggest that it is the fibrillar structure, characteristic of all amyloids, that is mainly responsible for the neurologic effects. Aβ has also been found to be neurologic in slice cultures of hippocampus (Hadrian et al, *Neurobiol. Aging* 16:779-789, 1995) and induces nerve cell death in transgenic mice (Games et al, *Nature* 373:523-527, 1995; Hsiao et al, *Science* 274:99-102, 1996). Injection of Aβ into rat brain also causes memory impairment and neuronal dysfunction (Flood et al, *Proc. Natl. Acad. Sci. U.S.A.* 88:3363-3366, 1991; *Br. Res.* 663:271-276, 1994). Convincing evidence that Aβ amyloid is directly involved in the pathogenesis of AD comes from genetic studies. It was discovered that the increased production of Aβ could result from mutations in the gene encoding, its precursor, APP (Van Broeckhoven et al, *Science* 248:1120-1122, 1990; Murrell et al, *Science* 254:97-99, 1991; Haass et al, *Nature Med.* 1:1291-1296, 1995). The identification of mutations in the APP gene which causes early onset familial AD is a strong argument that Aβ and amyloid are central to the pathogenetic process underlying this disease. Four reported disease-causing mutations have now been discovered which demonstrate the importance of Aβ in causing familial AD (reviewed in Hardy, *Nature Gen.* 1:233-234, 1992). Lastly, recent studies suggest that a reduction in amyloid plaque load in APP transgenic mice lead to improvements in behavioral impairment and memory loss (Chen et al, *Nature* 408:978-982, 2000; Janus et al, *Nature* 408:979-982, 2000; Morgan et al, *Nature* 408:982-985, 2000). This is the strongest argument to date that implicates that reduction of Aβ amyloid load in brain should be a central target for the development of new and effective treatments of AD and related disorders.

Alzheimer's Disease and the Aging Population

Alzheimer's disease is a leading cause of dementia in the elderly, affecting 5-10% of the population over the age of 65 years (Jorm, *A Guide to Understanding of Alzheimer's Disease and Related Disorders*, New York University Press, New York, 1987). In AD, the parts of the brain essential for cognitive processes such as memory, attention, language, and reasoning degenerate. In some inherited forms of AD, onset is in middle age, but more commonly, symptoms appear from the mid-60's onward. AD today affects 4-5 million Americans, with slightly more than half of these people receiving care in many different health care institutions. The prevalence of AD and other dementias doubles every 5 years beyond the age of 65, and recent studies indicate that nearly 50% of all people age 85 and older have symptoms of AD (NIH Progress Report on AD, National Institute on Aging, 2000). Thirty-three million people of the total population of the United States are age 65 and older, and this will climb to 51 million people by the year 2025 (NIH Progress Report on AD, National Institute on Aging, 2000). The annual economic toll of AD in the United States in terms of health care expenses and lost wages of both patients and their caregivers is estimated at $80 to $100 billion (NIH Progress Report on AD, National Institute on Aging, 2000).

DISCLOSURE OF THE INVENTION

This application is a continuation-in-part of U.S. patent application Ser. No. 09/962,955 filed Sep. 24, 2001, which is a continuation-in-part of U.S. patent application Ser. No. 09/938, 275 filed Aug. 22, 2001, the text and drawings of each of which are hereby incorporated by reference into the present application as if fully set forth herein.

Small peptides are disclosed which demonstrate great efficacy in inhibiting and/or disrupting amyloid fibrils. Also disclosed is the use of the same peptides for imaging the location of Aβ in the body for the purpose of diagnosis of Alzheimer's disease and other beta-amyloid protein (Aβ) fibrillogenesis disorders, as well as the use of the same peptides for detecting Aβ in biological samples for the purpose of diagnosis of Alzheimer's disease and other beta-amyloid protein (Aβ) fibrillogenesis disorders. "Fibrillogenesis" as used herein means the clinical or pathological binding of beta-amyloid to itself to form fibrils, and sometimes beta sheets, as known to those skilled in the art.

This disclosure pertains to compounds and pharmaceutical compositions thereof, that can bind to beta-amyloid protein (Aβ) and modulate or moderate the aggregation and/or fibrillogenisis of Aβ, for the treatment and diagnosis of Aβ diseases such as Alzheimer's disease and other disorders that involve the accumulation and persistence of Aβ. These Aβ diseases include, but are not limited to, the amyloid associated with Alzheimer's disease and Down's syndrome, and various forms of cerebral amyloidosis, such as will be familiar to those knowledgeable in the art.

The disclosure relates to the novel and surprising discovery that certain peptides are binders and disruptors of Aβ amyloid fibrils, and are therefore useful for the therapeutic intervention of Alzheimer's disease and related Aβ disorders. Selected peptides are binders of Alzheimer's disease Aβ amyloid, and are therefore useful for the imaging and diagnosis of Alzheimer's disease and related Aβ disorders. Methods are disclosed for treating Alzheimer's disease and other Aβ disorders, comprising administering to a subject or patient a therapeutically effective dose of a selected 6-9mer peptide.

In one embodiment, in which preferably all amino acids indicated are D-amino acids, except where otherwise indicated (such as by designating L-form peptides with "LP" number codes, or prefixing selected amino acid codes with "L-"),.pharmaceutical compositions preferably contain at least one 1 peptide selected from the group of peptides comprising Ala-Gly-Gln-Trp-His-Arg-Val (DP-026), Gly-Gln-Trp-His-Arg-Val-Ser (DP-027), Gln-Trp-His-Arg-Val-Ser-Val (DP-028), Trp-His-Arg-Val-Ser-Val-Arg (DP-029), His-Arg-Val-Ser-Val-Arg-Trp (DP-03 0), Arg-Val-Ser-Val-Arg-Trp-Gly (DP-03 1), Asp-Gly-Arg-Trp-His-Arg-Val (DP-03 2), Gly-Arg-Trp-His-Arg-Val-Ala (DP-033), Arg-Trp-His-Arg-Val-Ala-Val (DP-034), Trp-His-Arg-Val-Ala-Val-Ile (DP-035), His-Arg-Val-Ala-Val-Ile-Met (DP-036), Arg-Val-Ala-Val-Ile-Met-Gly (DP-03 7), Thr-Leu-Phe-Leu-Ala-His-Gly (DP-03 8), Leu-Phe-Leu-Ala-His-Gly-Arg (DP-03 9), Phe-Leu-Ala-His-Gly-Arg-Leu (DP-040), Leu-Ala-His-Gly-Arg-Leu-Val (DP-04 1), Ala-His-Gly-Arg-Leu-Val-Phe (DP-042), His-Gly-Arg-Leu-Val-Phe-Met (DP-043), Gly-Leu-Ala-Phe-Val-Leu-Arg (DP-044), Leu-Ala-Phe-Val-Leu-Arg-Gly (DP-045), Ala-Phe-Val-Leu-Arg-Gly-Lys (DP-046), Phe-Val-Leu-Arg-Gly-Lys-Ser (DP-047), Val-Leu-Arg-Gly-Lys-Ser-Leu (DP-048), Leu-Arg-Gly-Lys-Ser-Leu-Tyr (DP-049), Arg-Val-Ala- Val-Ille-Met-Pro-Arg-Val-Ala-Val-Ile-Met (DP-050), Trp-His-Arg-Val-Ala-Val-Ile-Met (DP-05 1), Arg-Val-Ala-Val-Ile-Met (DP-052), His-Arg-Pro-Ala-Val-Ile-Met (DP-05 3), His-Arg-Val-Pro-Val-Ile-Met (DP-054), His-Arg-Val-Ala-Val-Pro-Met (DP-05 5), Leu-Ala-Phe-Val-Leu-Arg (DP-056), Leu-Pro-Phe-Val-Leu-Arg (DP-05 7), Arg-Arg-Pro-Ala-Phe-Val-Leu-Arg (DP-05 8), Thr-Arg-Ile-Ser-Leu-Gln-Val (DP-059), Ser-Leu-Gln-Val-Gln-Leu-Arg (DP-060), Gln-Val-Gln-Leu-Arg-Lys-Arg (DP-06 1), Arg-Val-Ser-Val-Arg-Trp (DP-062), Arg-Val-Ser-Val-Arg (DP-063), His-Pro-Arg-Leu-Val-Phe-Met (DP-064), Trp-His-Arg-Val-Ala-Val-Ile-Met-amide (DP-065), Trp-I-Iis-Arg-Val-Ala-Val-Ile-amide (DP-066), Arg-Val-Ala-Val-Ile-Met-amide (DP-067), Arg-Val-Ala-Val-Ile-Met-Gly-amide (DP-068), Leu-Ala-Phe-Val-Leu-Arg-amide (DP-069), His-Gly-Arg-Leu-Val-Phe-Met-amide (DP-070), Thr-Leu-Phe-Leu-Ala-Arg (DP-07 1), Trp-His-Leu-Ala-Phe-Val-Leu-Arg (DP-072), Acetyl-Leu-Ala-Phe-Val-Leu-Arg-amide (DP-073), Leu-Ala-Phe-Val-Leu-Arg-Lys-amide (DP-074), Thr-Leu-Phe-Leu-Ala-Arg-amide (DP-075), Acetyl-Thr-Leu-Phe-Leu-Ala-Arg-amide (DP-076), Thr-Leu-Phe-Leu-Ala-Arg-Lys (DP-077), Thr-Leu-Phe-Leu-Ala-Arg-Lys-amide (DP-078), Trp-His-Leu-Ala-Phe-Val-Leu-Arg-amide (DP-079), Trp-His-Leu-Ala-Phe-Val-Leu-Arg-Lys-amide (DP-080). The group also includes certain analogs, derivatives, enantiomers, or fragments of the disclosed sequences herein as further discussed herein, and all hereafter referred to for easy reference as Sequence Group A.

In certain preferred embodiments, a compound has the general formula, or structure: Y-(Xaa)-Z wherein (Xaa) is essentially a peptide containing D-amino acids selected from the group consisting of -Arg-Val-Ser-Val-Arg-Trp-, -Arg-Val-Ala-Val-Ile-, -His-Gly-Arg-Leu-Val-Phe-, -Leu-Ala-Phe-Val-Leu-Arg-or-Thr-Leu-Phe-Leu-Ala-Arg-; and wherein Y-is an amino terminal (N-terminal) modifying group which can be another amino acid, a N-acylated amino acid, a peptide, a N-acylated peptide, of hydrogen, or other known N-terminus modifying compounds, and wherein Z is carboxyl-terminal (C-terminal) modifying group selected from the group consisting of hydrogen, an amino acid, a C-amidated amino acid, a peptide, a C-amindated peptide, or other known C-terminal modifying groups.

Examples of peptides from Sequence Group A that work in the Y—(X-aa)-Z model, hereafter referred to as Sequence Group B, include, His-Arg-Val-Ser-Val-Arg-Trp (DP-030) Arg-Val-Ser-Val-Arg-Trp-Gly (DP-031), Trp-His-Arg-Val-Ala-Val-Ile (DP-035), His-Arg-Val-Ala-Val-Ile-Met (DP-036), Arg-Val-Ala-Val-Ile-Met-Gly (DP-037), Ala-His-Gly-Arg-Leu-Val-Phe (DP-042), His-Gly-Arg-Leu-Val-Phe-Met (DP-043), Trp-His-Arg-Val-Ala-Val-Ile-Met (DP-051), Leu-Ala-Phe-Val-Leu-Arg (DP-056), Trp-His-Arg-Val-Ala-Val-Ile-amide (DP-066), Arg-Val-Ala-Val-Ile-Met-Gly-amide (DP-068), Leu-Ala-Phe-Val-Leu-Arg-amide (DP-069), His-Gly-Arg-Leu-Val-Phe-Met-amide (DP-070), Thr-Leu-Phe-Leu-Ala-Arg (DP-071), Trp-His-Leu-Ala-Phe-Val-Leu-Arg (DP-072), Acetyl-Leu-Ala-Phe-Val-Leu-Arg-amide (DP-073), Leu-Ala-Phe-Val-Leu-Arg-Lys-amide (DP-074), Acetyl-Thr-Leu-Phe-Leu-Ala-Arg-amide (DP-076), Trp-His-Leu-Ala-Phe-Val-Leu-Arg-amide (DP-079), Trp-His-Leu-Ala-Phe-Val-Leu-Arg-Lys-amide (DP-080).

It is preferable to select a peptide Y—(X-aa)-Z as defined above but containing (X-aa) peptides selected from -Arg-Val-Ala-Val-Ile-, -Leu-Ala-Phe-Val-Leu-Arg-, Thr-Leu-Phe-Leu-Ala-Arg-. Examples of these preferred structures hereafter referred to as Sequence Group C include Trp-His-Arg-Val-Ala-Val-Ile (DP-035), His-Arg-Val-Ala-Val-Ile-Met (DP-036), Arg-Val-Ala-Val-Ile-Met-Gly (DP-037), Trp-His-Arg-Val-Ala-Val-Ile-Met (DP-051), Trp-His-Arg-Val-Ala-Val-Ile-amide (DP-066), Arg-Val-Ala-Val-Ile-Met-Glyamide (DP-068), Leu-Ala-Phe-Val-Leu-Arg (DP-056), Leu-Ala-Phe-Val-Leu-Arg-amide (DP-069), Trp-His-Leu-Ala-Phe-Val-Leu-Arg (DP-072), Acetyl-Leu-Ala-Phe-Val-Leu-Arg-amide (DP-073), Leu-Ala-Phe-Val-Leu-Arg-Lys-amide (DP-074), Trp-His-Leu-Ala-Phe-Val-Leu-Arg-amide (DP-079), Trp-His-Leu-Ala-Phe-Val-Leu-Arg-Lys-amide (DP-080), Thr-Leu-Phe-Leu-Ala-Arg (DP-071), Acetyl-Thr-Leu-Phe-Leu-Ala-Arg-amide (DP-076).

Preferred efficacious peptide fragments containing D-amino acids in this disclosure are-Arg-Val-Ser-Val-Arg-Trp-, -Arg-Val-Ala-Val-Ile-, -His-Gly-Arg-Leu-Val-Phe-, -Leu-Ala-Phe-Val-Leu-Arg-and-Thr-Leu-Phe-Leu-Ala-Arg-. These preferred fragments may be therapeutically employed either alone, in combination with each other, as foundations for further synthesis, or as otherwise disclosed herein.

Also disclosed is the use of N-methylated analogs of Sequence Group A, B, or C, including the use of αN-methylation or L-amino acids (preferably methylated amino acids) exclusively or partially during synthesis such that the resulting peptides will have purely αN-methylated amide bonds or partially αN-methylated or alternating αN-methylated and non-αN-methylated amide bonds. Preferred compounds are selected from Sequence Group A, B, or C with modified amide bonds such that at least one of the amide bonds in the peptide back-bone is N-methylated, preventing the peptide itself from beta-sheet formation.

Mimetic (peptidomimetic) compounds are also disclosed as modeled from other peptides disclosed herein, including the peptides of Sequence Group A, B, or C. The term "mimetic" generally includes "isosteres", such as modifications of the peptide backbones (i.e. amide bond mimetics) with amide nitrogen, amide carbonyl, or complete replacement of the amide bond. The amide bond can advantageously be replaced by similar length bridges known to those skilled in the art, such as: —$CH_2S$—, —CH=CH—, —$CH_2NH$—, —$CSNH_2$—, or $COCH_2$.

Mimetics can be generated using software that can derive a virtual peptide model from several of the peptide structures disclosed herein. This can be done using the software derived from SLATE algorithm. See, Perkin, Mills and Dean, 1995 *Journal of Computer Aided Molecular Design* 9 (6) p 479-490; Mills et al. 2001 *Journal of Computer Aided Molecular Design* 15 (1) p 81-96; De Esch, I J, et al 2001 *Journal of Med. Chem.* 44 (11) p 1666-74; Mills Perkins and Dean 1997 *Journal of Computer Aided Molecular Design* 11 (2) p 175-92). One example of the program derived from SLATE algorithm is Quasi by De Novo Pharmaceutical. This program superimposes several active but apparently dissimilar peptide molecules that are active to arrive at the most probable structures essential for activity (with minimum energy constraint). This can be used to generate a mold or target binding site with predicted position of hydrogen binding atoms in three dimensional space. This can then be used to generate a non-peptide mimic of the original ligand peptides. These molecule generator softwares are now commercially available (example Skelgen and Skelgen II).

A "mimetic" of a compound also refers to a compound in which chemical structures of the compound that are necessary for functional activity have been replaced with other chemical structures which mimic the conformation of the compound or peptides thereof. The term "mimetic" as used herein is also intended to include molecules which mimic the chemical structure of a L or D-peptidic structure, and retain the functional properties of a L-or D-peptidic structure. Other approaches to designing peptide analogs, derivatives and mimetics are also well known in the art. For example, see P. S. Farmer, in *Drug Design*, E. J. Ariens, ed., Academic Press, New York, 1980, v. 10, pp. 119-143; Ball and Alewood, *J. Mol. Recognition* 3:55, 1990; Morgan and Gainor, *Ann. Rep. Med. Chem.* 24:243, 1989; and Freidinger, *Trends Pharmacol. Sci.* 10:270, 1989. See also Sawyer, "Peptidomimetic design and chemical approaches to peptide metabolism", in MD Taylor and GL Amidon, eds., in *Peptide-Based Drug Design: Controlling Transport and Metabolism*, Ch. 17, 1995; Smith et al, *J. Am. Chem. Soc.* 117:11113-11123, 1995; Smith et al, *J. Am. Chem. Soc.* 116:9947-9962, 1994; and Hirschman et al, *J. Am. Chem. Soc.* 115:12550-12568, 1993.

The term "analogs" includes variants of the peptide molecule brought about by, for example, homologous substitution of one or more amino acid residues as will be appreciated by those skilled in the art, reversal of the sequence, or partial or complete replacement of component amino acids with compositionally identical enantiomers (D-vs L-amino acids). Analogs also include "conservative amino acid substitutions" in which one amino acid is substituted with an amino acid having a similar side chain. Examples of similar side chain amino acids, are basic side chain amino acids (e.g., lysine, arginine, histidine), acidic side chain amino acids (e.g., aspartic acid, glutamic acid), non polar side chain amino acids (e.g., glycine, alanine, valine, leucine, isoleucine, proline, phenylalanine, methionine, tryptophan), uncharged polar side chain amino acids (e.g., aspargine, glutamine, serine, threonine, tyrosine, cystine), branched side chain amino acids (e.g., threonine, leucine, valine, isoleucine) and aromatic side chain amino acids (e.g., tyrosine, phenylalanine, tryptophan, histidine). Analogs also include "homolougous amino acid substitutions" in which an amino acid is substituted with homologous amino acids, such as replacement of phenyalanine with tyrosine, pyridylalanine, or homophenylalanine, and replacement of leucine with valine, or vice versa.

The term "derivative" includes minor chemical changes familiar to those skilled in the art in which one or more reactive groups on Sequence Group A, B, or C peptides have been "peptide derivatized" such that there are peptides in which an amino acid side chain, peptide backbone, or amino-or carboxy-terminus has been derivatized as further discussed herein.

In any of the above structures or sequences, the nomenclature or symbolic representation of any or all of the individual amino acids are given by the standard 3-letter abbreviation for the amino acids preceded optionally by either D-or L-representing the 2 enatiomeric forms (mirror images of each other) of individual amino acids making up the sequence. Acetyl-and -amide at the N-and C-terminal respectively are optionally included when present or indicated as preferred.

Also disclosed are compounds that include Sequence Group A, B, or C peptides, portions of Sequence Group A, B, or C peptides and their novel analogs and derivatives thereof, the administration of which comprises a method for treating Alzheimer's disease and other Aβ amyloidoses. A method is thus provided for treating Alzheimer's disease and other disorders involving the formation and persistence of Aβ, comprising the administration to the subject a therapeutically effective amount of a compound such that the subject is treated for disorder associated with Aβ amyloidosis. Preferably, the disorders are Alzheimer's disease, Down's syndrome and other Aβ amyloidoses. Typically, the pharmaceutical composition includes a therapeutically effective amount of a disclosed compound or pharmaceutically acceptable salts of a compound, with optional pharmaceutically acceptable carrier, diluent or excipient.

Also disclosed is the use of pills, tablets, caplets, soft and hard gelatin capsules, lozenges, sachets, cachets, vegicaps, liquid drops, elixers, suspensions, emulsions, solutions, syrups, tea bags, aerosols (as a solid or in a liquid medium), suppositories, sterile injectable solutions, and sterile packaged powders, which contain a disclosed compound to treat patients with Alzheimer's disease and other Aβ amyloidoses. Therefore, the use of a disclosed compound for therapy or for the manufacture of a medicament for the treatment of a disorder associated with Aβ amyloidoses is also contemplated.

Compositions and methods involving administering to a subject a therapeutic dose of a selected disclosed compound that inhibits Aβ amyloid deposition, or Aβ amyloidosis in disorders in which Aβ amyloid deposition occurs are provided. Disclosed compounds can be used therapeutically to treat amyloidosis or can be used prophylactically in a subject susceptible to Aβ amyloidosis. The methods are based, at least in part, on directly binding Aβ amyloid either in the brain or in peripheral circulation, inhibiting Aβ amyloid fibril formation, and/or causing dissolution of pre-formed Aβ amyloid fibrils. Peripheral sequestration of Aβ by Sequence Group A, B, or C compounds is believed to result in movement of Aβ from the brain to the peripheral circulation, thereby inhibiting brain Aβ amyloid fibril formation, and/or causing dissolution of pre-formed brain Aβ amyloid fibrils.

Methods for detecting the presence or absence of Aβ peptides in a biological sample are provided. These methods include contacting a biological sample with a selected compound, wherein the compound is labeled with a detectable substance, for example, with a radionucleotide, phosphorescent compound, fluorescent compound, fluorescent protein, paramagnetic compound, metal chelators, or enzyme, all of which are readily detectable in various assays and diagnostics know to those skilled in the art, and then detecting the detectable substance bound to Aβ peptides in the biological sample.

Methods for imaging the presence or absence of Aβ peptides in the body or biological tissues are provided. These methods include contacting Aβ peptides in the body with a compound, wherein the compound is labeled with detectable substance, for example, with a radionucleotide, phosphorescent compound, fluorescent compound, fluorescent protein, paramagnetic compound, metal chelator, or enzyme, and detecting the detectable substance bound to Aβ peptides in the body or biological tissues.

Use of anti-idiotypic antibodies to Sequence Group A, B, or C peptides, analogs, derivatives or fragments thereof, as potent binders of Aβ, and inhibitors of Aβ amyloid formation, deposition, accumulation and/or persistence in Alzheimer's disease and other Aβ amyloidosis is presented. The term "anti-idiotypic antibodies" refers to the antibodies (A) raised against or that specifically recognize the Fab regions of other antibodies (B), and the Fab regions of antibodies B, recognize one of the peptides in Sequence Group A, B, or C. The result is that the anti-idiotypic antibodies A to Sequence Group A, B, or C peptides have Fab regions mimicking a Sequence Group A, B, or C peptide, in terms of reactivity, amyloid binding and amyloid disrupting properties.

Use of antibodies recognizing compounds for in vivo labeling is presented; for example, with a radionucleotide, for radioimaging to be utilized for in vivo diagnosis, and/or for in vitro diagnosis.

An important Aβ amyloidosis to which the disclosed therapeutics is addressed is Alzheimer's disease. A preferred therapeutically effective amount of disclosed compound is a dosage in the range of from about 10 μg to about 50 mg/kg body weight/per day, and more preferably in the range of from about 100 μg to about 10 mg/kg body weight per day.

A pharmaceutical agent containing a selected disclosed compound may advantageously be given by injection or infusion or nasal drop or nasal spray or oral administration. In any of the above structures or sequences, the nomenclature or symbolic representation of any or all of the individual amino acids may be given by either the standard 3-letter abbreviation for the amino acid, or the standard single letter code for the amino acid, and sometimes both in appropriate cases.

BRIEF DESCRIPTION OF THE DRAWINGS

The following drawings are illustrative of embodiments of the invention and are not meant to limit the scope of the invention.

FIGS. 1a-k are peptide sequences and drawings for 5-13 mer peptides DP1-18, LP19-25, DP 26-80 and LP81.

FIGS. 6-20 are CD spectra of Ab42 plus DP-50 through DP-064, respectively, at (1:2).

FIGS. 37-41 are CD spectra of Ab42 plus polylysine and DP-065 through DP-072 at (1:2).

FIGS. 42-49 are CD spectra of Ab42 plus DP-065 through DP-072 at (1:0.1, 1:1, 1:2, 1:5).

FIG. 52 is a summary of Thio T ranking 65-72.

FIG. 56A are CD spectra showing the effects of 0.2 mg/ml of peptide DP-076 on beta-sheet secondary structure of Aβ42 amyloid fibrils (i.e. Aβ 42+/−DP-076). FIG. 56B shows the CD spectra of Aβ 42 or DP-076 only.

FIG. 57A are CD spectra showing the effects of 0.2 mg/ml of peptide DP-077 on beta-sheet secondary structure of Aβ42 amyloid fibrils (i.e. Aβ 42+/−DP-077). FIG. 57B shows the CD spectra of Aβ 42 or DP-077 only.

FIG. 58A are CD spectra showing the effects of 0.2 mg/ml of peptide DP-078 on beta-sheet secondary structure of Aβ42 amyloid fibrils (i.e. Aβ 42+/−DP-078). FIG. 58B shows the CD spectra of Aβ 42 or DP-078 only.

FIG. 61A are CD spectra showing the effects of 0.2 mg/ml of peptide LP-081 on beta-sheet secondary structure of Aβ42 amyloid fibrils (i.e. Aβ 42+/−LP-081). FIG. 61B shows the CD spectra of Aβ 42 or LP-081 only.

FIG. 70A are CD spectra showing the dose-dependent effects of peptide DP-080 on beta-sheet secondary structure of Aβ42 amyloid fibrils (i.e. Aβ 42+/−DP-080). FIG. 70B shows the CD spectra of Aβ 42 or DP-080 only.

BEST MODE OF CARRYING OUT THE INVENTION

EXAMPLE 1

Preparation of Peptides

Figure 1K:
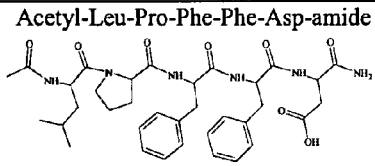

The peptides disclosed herein were produced in both the L-and D-amino acid forms. In addition, truncated peptides and peptide analogs were assembled for use as potential therapeutic peptides for the treatment of Aβ fibrillogenesis in Alzheimer's disease and related disorders. These peptides are preferably conventionally synthesized. For example, L-and D-peptides were synthesized on peptide synthesizers known to those skilled in the art, such as the Advanced ChemTech Model 396 multiple peptide synthesizer (Louisville, Ky.), using an automated protocol established by the manufacturer for 0.025 mmole scale synthesis. Double couplings were performed on all cycles using 2-(1H-benzotriazol-1-yl)-1,1,3,3-tetramethyluronium hexafluorophosphate (HBTU)/N,N-diisopropylethylamine (DIEA)/HOBt/FMOC-AA in four-fold excess for 30 minutes, followed by DIC/HOBt/FMOC-AA in fourfold excess for 45 minutes.

The peptide was then de-protected and removed from the resin by treatment with TFA/water (95%/5%) for 3 hours and then precipitated with cold ether. The resulting solid was then pelleted by centrifugation (2400 rpm ×10 min), and the ether was discarded. The solid was then be re-suspended in ether and re-centrifuged for the second time after which the ether was decanted for the second time. The solid was dissolved in 10% acetic acid and lyophilized to dryness (~30 mg for 12 amino acid peptides; 18 mg for 7 amino acid peptides). The crude peptide was purified by preparative HPLC using instruments known to those skilled in the art, such as a HP 1100 series with diode array detector, with a Vydac C18 column (21×250 mm) using a 15%-40% acetonitrile gradient over 80 minutes (at a flow rate of 5 ml/min). The primary fraction was then collected and re-analyzed for purity using analytical HPLC to ensure a single symmetrical peak at all wavelengths. The confirmation of structures and sequences was based on comparison of predicted molecular weights, to molecular weights obtained by ESI mass spectroscopy. These analyses were performed using instruments known to those skilled in the art, such as a Sciex API IIIE triple quadruple ion spray mass spectrometer or ESI Agilent MSD-SL. 12-13mer peptides were synthesized with the following sequences, preferably all employing D-amino acids, except where otherwise indicated:

Arg-Lys-Arg-Leu-Gln-Val-Gln-Leu-Ser-Ile-Arg-Thr (DP-00 1), Arg-Gln-Val-Phe-Gln-Val-Ala-Tyr-Ile-Ile-Ile-Lys-Ala (DP-002), Tyr-eu-Ser-Lys-Gly-Arg-Leu-Val-Phe-Ala-Leu-Gly (DP-003), Thr-Leu-Phe-Leu-Ala-His-Gly-Arg-Leu-Val-Phe-Met(DP-004), Ala-Gly-Gln-Trp-His-Arg-Val-Ser-Val-Arg-Trp-Gly (DP-005), Asp-Arg-Trp-His-Arg-Val-Ala-Val-Ile-Met-Gly (DP-006), His-Gln-Thr-Trp-Thr-Arg-Asn-Leu-Gln-Val-Thr-Leu (DP-007), Ile-Ser-Asn-Val-Phe-Val-Gln-Arg-Leu-Ser-Leu-Ser (DP-008), Arg-Gly-Leu-Val-Phe-His-Thr-Gly-Thr-Lys-Asn-Ser-Phe (DP-009), Gly-Asn-Ser-Thr-Ile-Ser-Ile-Arg-Ala-Pro-Val-Tyr (DP-010), Val-Arg-Trp-Gly-Met-Gln-Gln-Ile-Gln-Leu-Val-Val (DP-011), Ala-Pro-Val-Asn-Val-Thr-Ala-Ser-Val-Gln-Ile-Gln (DP-012), Thr-Arg-Ile-Ser-Leu-Gln-Val-Gln-Leu-Arg-Lys-Arg (DP-013), Ala-Lys-Ile-Ile-Ile-Tyr-Ala-Val-Gln-Phe-Val-Gln-Arg (DP-014), Gly-Leu-Ala-Phe-Val-Leu-Arg-Gly-Lys-Ser-Leu-Tyr (DP-015), Met-Phe-Val-Leu-Arg-Gly-His-Ala-Leu-Phe-Leu-Thr (DP-016), Gly-Trp-Arg-Val-Ser-Val-Arg-His-Trp-Gln-Gly-Ala (DP-017), Gly-Met-Ile-Val-Ala-Val-Arg His-Trp-Arg-Gly-Asp (DP-018), L-Arg-L-Lys-L-Arg-L-Leu-L-Gln-L-Val-L-Gln-L-Leu-L-Ser-L-Ile-L-Arg-L-Thr (LP-019), SEQ. ID. NO. 1, and Arg-Val-Ala-Val-Ile-Met-Pro-Arg-Val-Ala-Val-Ile-Met (DP-050).

In addition 6-9 mer peptides including, iAB5 (LP-025), SEQ. ID. NO. 7, and piAB5 (LP-081), SEQ. ID. NO. 8, were synthesized with the following sequences and/or modifications: L-Leu-L-Pro-L-Phe-L-Phe-L-Asp (LP-025), SEQ. ID. NO. 7, Ala-Gly-Gln-Trp-His-Arg-Val (DP-026), Gly-Gln-Trp-His-Arg-Val-Ser (DP-027), Gln-Trp-His-Arg-Val-Ser-Val (DP-028), Trp-His-Arg-Val-Ser-Val-Arg (DP-029), His-Arg-Val-Ser-Val-Arg-Trp (DP-030), Arg-Val-Ser-Val-Arg-Trp-Gly (DP-031), Asp-Gly-Arg-Trp-His-Arg-Val (DP-032), Gly-Arg-Trp-His-Arg-Val-Ala (DP-033), Arg-Trp-His-Arg-Val-Ala-Val (DP-034), Trp-His-Arg-Val-Ala-Val-Ile (DP-035), His-Arg-Val-Ala-Val-Ile-Met (DP-036), Arg-Val-Ala-Val-Ile-Met-Gly (DP-037), Thr-Leu-Phe-Leu-Ala-His-Gly (DP-038), Leu-Phe-Leu-Ala-His-Gly-Arg (DP-039), Phe-Leu-Ala-His-Gly-Arg-Leu (DP-040), Leu-Ala-His-Gly-Arg-Leu-Val (DP-04 1), Ala-His-Gly-Arg-Leu-Val-Phe (DP-042), His-Gly-Arg-Leu-Val-Phe-Met (DP-043), Gly-Leu-Ala-Phe-Val-Leu-Arg (DP-044), Leu-Ala-Phe-Val-Leu-Arg-Gly (DP-045), Ala-Phe-Val-Leu-Arg-Gly-Lys (DP-046), Phe-Val-Leu-Arg-Gly-Lys-Ser (DP-047), Val-Leu-Arg-Gly-Lys-Ser-Leu (DP-048), Leu-Arg-Gly-Lys-Ser-Leu-Tyr (DP-049), Trp-His-Arg-Val-Ala-Val-Ile-Met (DP-051), Arg-Val-Ala-Val-Ile-Met (DP-052), His-Arg-Pro-Ala-Val-Ile-Met (DP-053), His-Arg-Val-Pro-Val-Ile-Met (DP-054), His-Arg-Val-Ala-Val-Pro-Met (DP-055), Leu-Ala-Phe-Val-Leu-Arg (DP-056), Leu-Pro-Phe-Val-Leu-Arg (DP-057), Arg-Arg-Pro-Ala-Phe-Val-Leu-Arg (DP-058), Thr-Arg-Ile-Ser-Leu-Gln-Val (DP-059), Ser-Leu-Gln-Val-Gln-Leu-Arg (DP-060), Gln-Val-Gln-Leu-Arg-Lys-Arg (DP-061), Arg-Val-Ser-Val-Arg-Trp (DP-062), Arg-Val-Ser-Val-Arg (DP-063), His-Pro-Arg-Leu-Val-Phe-Met (DP-064), Trp-His-Arg-Val-Ala-Val-Ile-Met-amide (DP-065), Trp-His-Arg-Val-Ala-Val-Ile-amide (DP-066), Arg-Val-Ala-Val-Ile-Met-amide (DP-067), Arg-Val-Ala-Val-Ile-Met-Gly-amide (DP-068), Leu-Ala-Phe-Val-Leu-Arg-amide (DP-069), His-Gly-Arg-Leu-Val-Phe-Met-amide (DP-070), Thr-Leu-Phe-Leu-Ala-Arg (DP-071), Trp-His-Leu-Ala-Phe-Val-Leu-Arg (DP-072), Acetyl-Leu-Ala-Phe-Val-Leu-Arg-amide (DP-073), Leu-Ala-Phe-Val-Leu-Arg-Lys-amide (DP-074), Thr-Leu-Phe-Leu-Ala-Arg-amide (DP-075), Acetyl-Thr-Leu-Phe-Leu-Ala-Arg-amide (DP-076), Thr-Leu-Phe-Leu-Ala-Arg-Lys (DP-077), Thr-Leu-Phe-Leu-Ala-Arg-Lys-amide (DP-078), Trp-His-Leu-Ala-Phe-Val-Leu-Arg-amide (DP-079), Trp-His-Leu-Ala-Phe-Val-Leu-Arg-Lys-amide (DP-080), and Acetyl-L-Leu-L-Pro-L-Phe-L-Asp-L-amide (LP-08 1), SEQ. ID. NO. 1. D-indicates D-amino acids and L-indicates L-amino acids.

EXAMPLE 2

Disruption of Alzheimer Fibrils Beta-Sheet Secondary Structure by 12-13mer Peptides as Assessed by CD Spectropolarimetry Circular dichroism (CD) spectra of Aβ42 in the presence or absence of synthetic peptides outlined in Example 1 were recorded at 25° C. on a JASCO-810 Spectropolarimeter using a 0.5 mm path length quartz cuvette, and over the range of 190-260 nm. The instrument was calibrated with an aqueous solution of (+)camphorsulfonic acid. The instrument was then set to collect data at a bandwidth of 5 nm, response time of 32 seconds, data pitch of 0.5 nm, and a scan speed of 10 nm/min. Each CD spectrum was an average of 5 spectra, each taken from a separate replicate solution. The CD results were reported as Molar Residue Ellipticity (MRE) of Aβ42, after subtraction of the background solvent spectrum and/or test peptide spectrum. For this study, fibrillar Aβ42 (0.1 mg/ml) in TPBSF (10% TFE, 150 mM NaF, 50 mM HNaPO$_4$, pH 7.4) was incubated for 3 days at 37° C. in the presence and absence of various 12-13mer peptides at an Aβ42:peptide wt/wt ratio of 1:2, before recording the CD spectra. The percent disruption of beta-sheet structure was determined by the calculating the percent loss of negative ellipticity at 218 nm compared to Aβ42 alone, after the corresponding blanks were subtracted.

Figure 2:
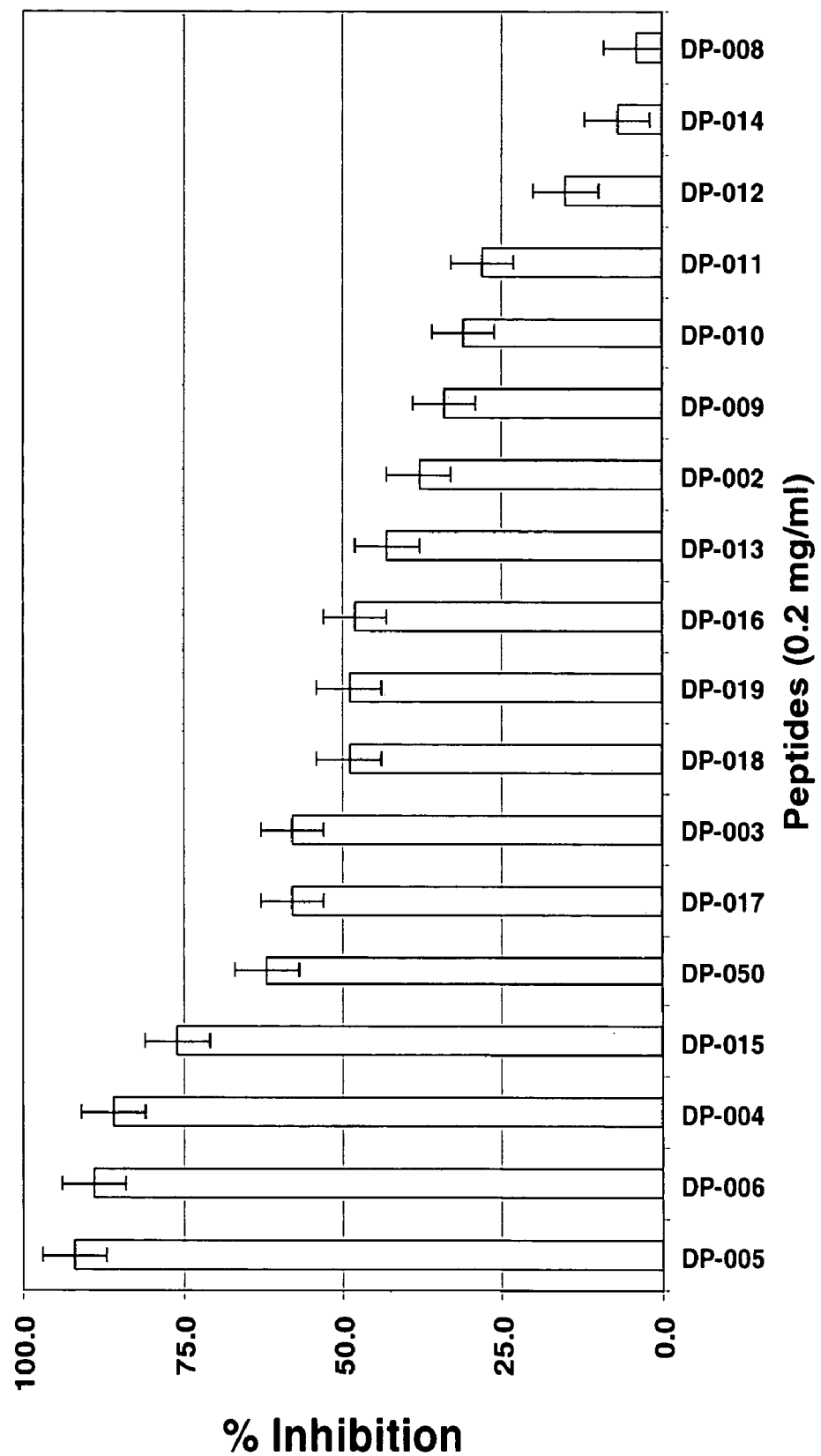
FIG. 2 is a graph showing an ordered summary comparison of the effect of various 12-13mer peptides on beta-sheet secondary structure of 25 μM Aβ42 amyloid fibrils as assessed by circular dichroism (CD) spectropolarimetry. Shown is the percent disruption of Aβ42 fibrils as assessed by loss of ellipticity at 218 nm, representing the signal that is inversely related to beta-sheet secondary structure.

FIG. 2 showing the disrupters of Aβ42 beta-sheet secondary structure among 12-13 mer peptide analogs, sorted in order of effectiveness, as assessed by CD spectropolarimetry. Other peptides that are also effective are not included in this list. The preferred peptides include in order of effectiveness as shown in FIG. 2 are Ala-Gly-Gln-Trp-His-Arg-Val-Ser-Val-Arg-Trp-Gly (DP-005), Asp-Gly-Arg-Trp-His-Arg-Val-Ala-Val-Ile-Met-Gly (DP-006), Thr-Leu-Phe-Leu-Ala-His-Gly-Arg-Leu-Val-Phe-Met (DP-004), Gly-Leu-Ala-Phe-Val-Leu-Arg-Gly-Lys-Ser-Leu-Tyr (DP-015), Arg-Val-Ala-Val-Ile-Met-Pro-Arg-Val-Ala-Val-Ile-Met (DP-050), Gly-Trp-Arg-Val-Ser-Val-Arg-His-Trp-Gln-Gly-Ala (DP-017), Tyr-eu-Ser-Lys-Gly-Arg-Leu-Val-Phe-Ala-Leu-Gly (DP-003), Gly-Met-Ile-Val-Ala-Val-Arg-His-Trp-Arg-Gly-Asp (DP-018), L-Arg-L-Lys-L-Arg-L-Leu-L-Gln-L-Val-L-Gln-L-Leu-L-Ser-L-Ile-L-Arg-L-Thr (DP-019), Met-Phe-Val-Leu-Arg-Gly-His-Ala-Leu-Phe-Leu-Thr (DP-016), Thr-Arg-Ile-Ser-Leu-Gln-Val-Gln-Leu-Arg-Lys-Arg (DP-013), Arg-Gln-Val-Phe-Gln-Val-Ala-Tyr-Ile-Ile-Ile-Lys-Ala (DP-002), Arg-Gly-Leu-Val-Phe-His-Thr-Gly-Thr-Lys-Asn-Ser-Phe (DP-009), Gly-Asn-Ser-Thr-Ile-Ser-Ile-Arg-Ala-Pro-Val-Tyr (DP-010), Val-Arg-Trp-Gly-Met-Gln-Gln-Ile-Gln-Leu-Val-Val (DP-011), Ala-Pro-Val-Asn-Val-Thr-Ala-Ser-Val-Gln-Ile-Gln (DP-012), Ala-Lys-Ile-Ile-Ile-Tyr-Ala-Val-Gln-Phe-Val-Gln-Arg (DP-014), and Ile-Ser-Asn-Val-Phe-Val-Gln-Arg-Leu-Ser-Leu-Ser (DP-008). DP-005, DP-006, DP-004 and DP-015 show >75% disruption of fibrillar Aβ42, whereas DP-050, DP-017 and DP-003, show >50% disruption of Aβ42 fibrils (FIG. 2).

EXAMPLE 3

Disruption of Alzheimer's Aβ Fibrils by 12-13mer Peptides as Assessed by Thioflavin T Fluorometry Various peptides synthesized as outlined in Example 1 were tested for potential Aβ amyloid disrupting activity using a variety of in vitro assays. One such assay, Thioflavin T fluorometry, which measures the amount of amyloid fibrils (LeVine III, *Protein Sci.* 2:404-410, 1993; *Amyloid: Int. J. Exp. Clin. Invest.* 2:1-6, 1995; Naiki and Nakakuki, *Lab. Invest.*, 74:374-383, 1996; Castillo et al, *J. Neurochem.* 69:2452-2465, 1997) was used to identify synthetic peptides capable of disrupting Aβ42 amyloid fibrils. For these studies, 0.1 mg/ml of Aβ42 (Bachem Inc) was incubated in microcentrifuge tubes at 37° C. for 3 days (in triplicate), either alone, or in the presence of 0.2 mg/ml peptide (at an Aβ:peptide weight ratio of 1:2) in TPBSF (10% TFE, 150 mM NaF, 50 mM HNaPO$_4$, pH 7.4). Fifty µl aliquots were taken for analysis at day 3, and 200 ul aliquots of 125 µM Thioflavin T in 62 mM NaPO4 (pH 6.0), were added to give a final Thioflavin T concentration of 100 µM and 62 mM of NaPO4. Fluorescence emission at 480 nm was measured on a microplate 96well-fluorometer (Labsystem) at an excitation wavelength of 450 nm. For all determinations any fluorescence given off by peptides in the presence of the Thioflavin T reagent was always subtracted from all pertinent readings. Previous studies have indicated that increasing concentrations of fibrillar Aβ42 gives a proportional increase in fluorescence in the presence of 100 µM Thioflavin T, ruling out the presence of any disproportionate inner filter effects at this Thioflavin T concentration (Castillo et al *J. Neurochem.* 69:2452-2465, 1997).

Figure 3:
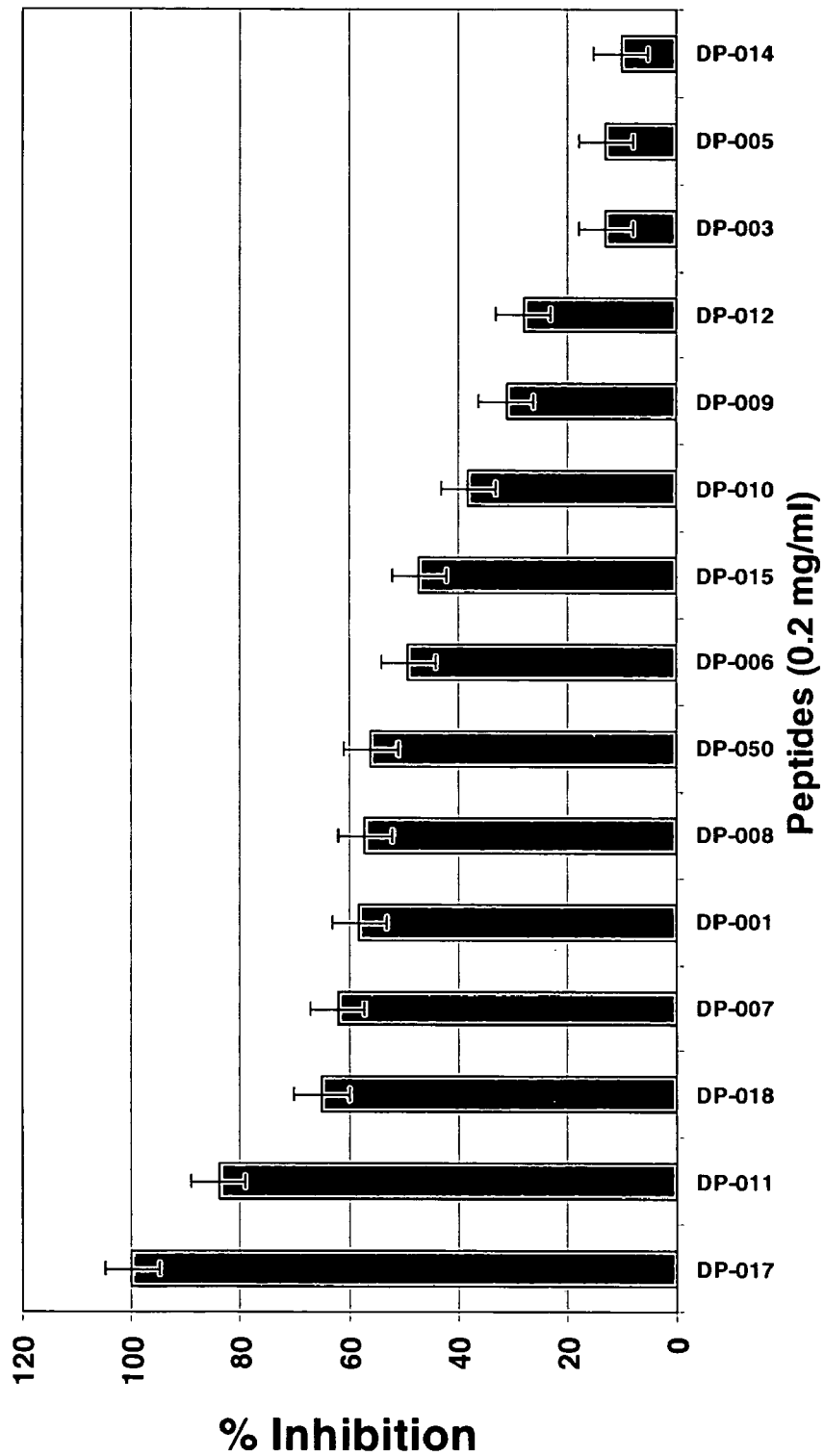
FIG. 3 is a graph showing an ordered summary comparison of the effect of 12-13mer peptides on beta-sheet secondary structure of 25 uM Aβ42 amyloid fibrils as assessed by Thioflavin T fluorometry. Shown is the percent disruption of Aβ42 fibrils by various 12-13mer peptides at an Aβ42: 12-13mer peptide weight ratio of 1:2.

FIG. 3 shows preferred disrupters of Thioflavin T binding to Aβ42 from among 12-13 amino acid peptide analogs, sorted in order of effectiveness. The peptides in order of effectiveness as determined by Thioflavin T fluorometry, include but are not limited to Gly-Trp-Arg-Val-Ser-Val-Arg-His-Trp-Gln-Gly-Ala (DP-017), Val-Arg-Trp-Gly-Met-Gln-Gln-Ile-Gln-Leu-Val-Val (DP-011), Gly-Met-Ile-Val-Ala-Val-Arg-His-Trp-Arg-Gly-Asp (DP-018), His-Gln-Thr-Trp-Thr-Arg-Asn-Leu-Gln-Val-Thr-Leu (DP-007), Arg-Lys-Arg-Leu-Gln-Val-Gln-Leu-Ser-Ile-Arg-Thr (DP-001), Ile-Ser-Asn-Val-Phe-Val-Gln-Arg-Leu-Ser-Leu-Ser (DP-008), Arg-Val-Ala-Val-Ile-Met-Pro-Arg-Val-Ala-Val-Ile-Met (DP-050), Asp-Gly-Arg-Trp-His-Arg-Val-Ala-Val-Ile-Met-Gly (DP-006), Gly-Leu-Ala-Phe-Val-Leu-Arg-Gly-Lys-Ser-Leu-Tyr (DP-015), Gly-Asn-Ser-Thr-Ile-Ser-Ile-Arg-Ala-Pro-Val-Tyr (DP-010), Arg-Gly-Leu-Val-Phe-His-Thr-Gly-Thr-Lys-Asn-Ser-Phe (DP-009), Ala-Pro-Val-Asn-Val-Thr-Ala-Ser-Val-Gln-Ile-Gln (DP-012), Tyr-eu-Ser-Lys-Gly-Arg-Leu-Val-Phe-Ala-Leu-Gly (DP-003), Ala-Gly-Gln-Trp-His-Arg-Val-Ser-Val-Arg-Trp-Gly (DP-005), and Ala-Lys-Ile-Ile-Ile-Tyr-Ala-Val-Gln-Phe-Val-Gln-Arg (DP-014). DP-017 and DP-011 demonstrate >80% disruption of Aβ42 fibrils, DP-018 and DP-007 demonstrate >60% disruption of Aβ42 fibrils, whereas DP-001, DP-008, DP-050, DP-006 and DP-015 demonstrate >40% disruption of Aβ42 fibrils (FIG. 3).

EXAMPLE 4

Disruption of Alzheimer Fibrils β-Sheet Secondary Structure by 6-9mer Peptides as Assessed by CD Spectropolarimetry Circular dichroism (CD) spectropolarimetry is another in vitro technique used to determine a given peptide's effectiveness in disrupting the b-sheet secondary structure of Aβ-fibrils. CD spectra of Aβ42 in the presence or absence of synthetic peptides were recorded at 25° C. on a JASCO-810 Spectropolarimeter using a 0.5 mm path length quartz cuvette, and over the range of 190-260 nm. The instrument was calibrated with an aqueous solution of (+)camphorsulfonic acid. The instrument was then set to collect data at a bandwidth of 5 nm, response time of 32 seconds, data pitch of 0.5 nm, and a scan speed of 10 nm/min. Each CD spectrum was an average of 5 spectra, each taken from a separate replicate solution. The CD results were reported as Molar Residue Ellipticity (MRE) of Aβ42, after subtraction of the background solvent spectrum and/or test peptide spectrum. For this study, fibrillar Aβ42 (0.1 mg/ml) in TPBSF (10% TFE, 150 mM NaF, 50 mM HNaPO$_4$, pH 7.4) was incubated for 3 days at 37° C. in the presence and absence of various peptides at an Aβ42:peptide wt/wt ratio of 1:2, before recording the CD spectra. The percent disruption of beta-sheet structure was determined by the calculating the percent loss of negative ellipticity at 218 nm compared to Aβ42 alone after the corresponding blanks were subtracted.

Figure 73:
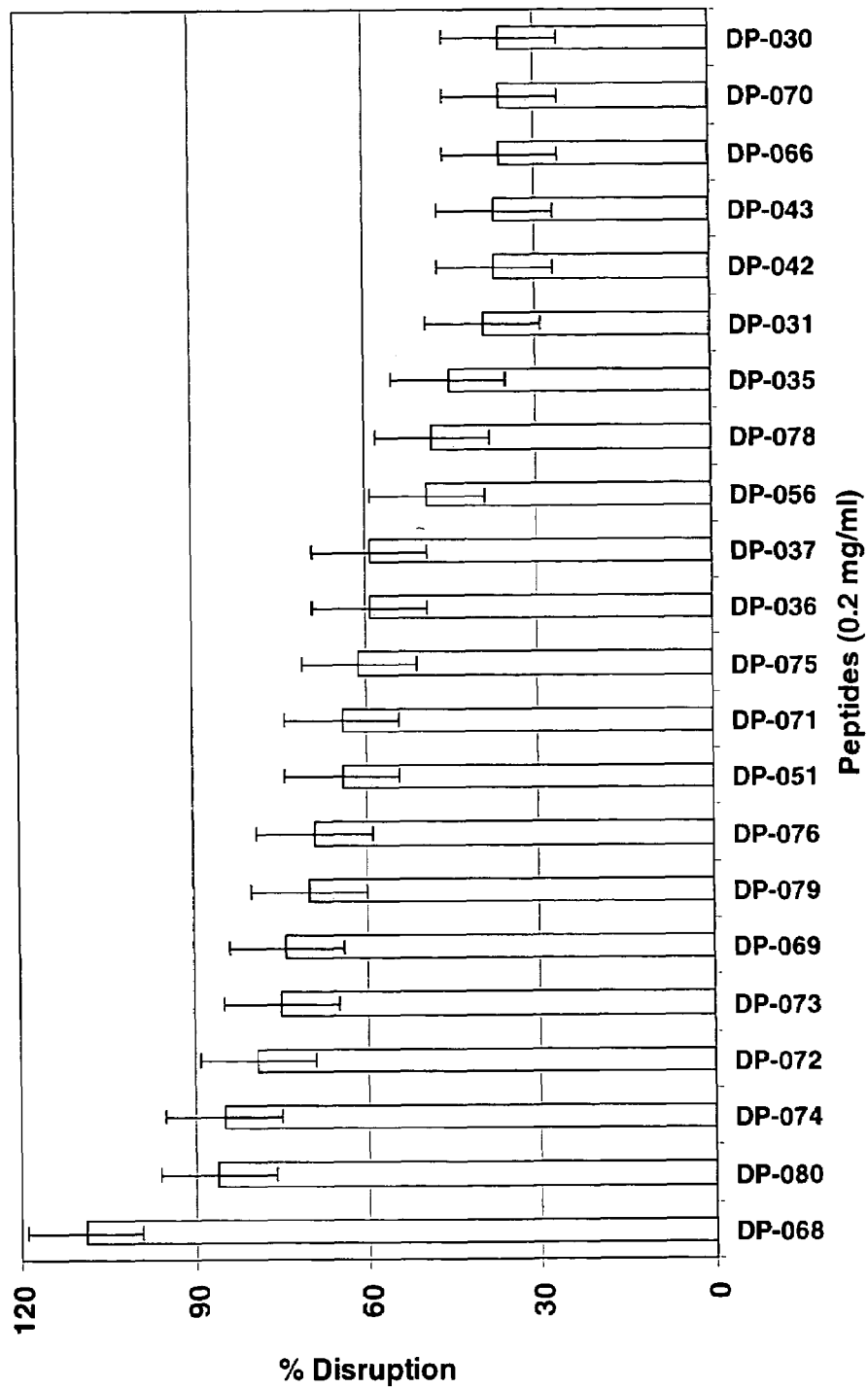
FIG. 73 is a graph showing an ordered summary comparison of the effect of 6-9mer peptides on beta-sheet secondary structure of 25 uM Aβ42 amyloid fibrils as assessed by CD spectropolarimetry. Shown is the percent disruption of Aβ42 fibrils as assessed by loss of ellipticity at 218 nm, representing the signal that is inversely related to beta-sheet secondary structure.

FIG. 73 showing the disrupters of Aβ42 beta-sheet structure among 6-9mer peptides and analogs, sorted in order of effectiveness as assessed by CD spectropolarimetry. The preferred peptides in order of effectiveness, include, but are not limited to Arg-Val-Ala-Val-He-Met-Gly-amide (DP-068), Trp-His-Leu-Ala-Phe-Val-Leu-Arg-Lys-amide (DP-080), Leu-Ala-Phe-Val-Leu-Arg-Lys-amide (DP-074), Trp-His-Leu-Ala-Phe-Val-Leu-Arg (DP-072), Acetyl-Leu-Ala-Phe-Val-Leu-Arg-amide (DP-073), Leu-Ala-Phe-Val-Leu-Arg-amide (DP-069), Trp-His-Leu-Ala-Phe-Val-Leu-Argamide (DP-079), Acetyl-Thr-Leu-Phe-Leu-Ala-Arg-amide (DP-076), Trp-His-Arg-Val-Ala-Val-Ile-Met (DP-051), Thr-Leu-Phe-Leu-Ala-Arg (DP-071), Thr-Leu-Phe-Leu-Ala-Arg-amide (DP-075), His-Arg-Val-Ala-Val-Ile-Met (DP-036), Arg-Val-Ala-Val-Ile-Met-Gly (DP-037), Leu-Ala-Phe-Val-Leu-Arg (DP-056), Thr-Leu-Phe-Leu-Ala-Arg-Lys-amide (DP-078), Trp-His-Arg-Val-Ala-Val-Ile (DP-035), Arg-Val-Ser-Val-Arg-Trp-Gly (DP-031), Ala, His-Gly-Arg-Leu-Val-Phe (DP-042), His-Gly-Arg-Leu-Val-Phe-Met (DP-043), Trp-His-Arg-Val-Ala-Val-Ile-amide (DP-066), His-Gly-Arg-Leu-Val-Phe-Met-amide (DP-070), and His-Arg-Val-Ser-Val-Arg-Trp (DP-030). DP-068 demonstrates >90% disrutpion of Aβ42 β-sheet structure, whereas DP-080, DP-074, DP-072, DP-073, DP-069, DP-079, DP-076, DP-051, DP-071 and DP-075 all demonstrate >60% disruption of Aβ42 β-sheet structure (FIG. 73).

EXAMPLE 5

Disruption of Alzheimer's Aβ3 Fibrils by 6-9mer Peptides as Assessed by Thioflavin T Fluorometry Thioflavin T fluorometry, which measures the amount of amyloid fibrils (LeVine III, *Protein Sci.* 2:404-410, 1993; *Amyloid: Int. J. Exp. Clin. Invest.* 2:1-6, 1995; Naiki and Nakakuki, *Lab. Invest.*, 74:374-383, 1996; Castillo et al, *J. Neurochem.* 69:2452-2465, 1997) was also used to determine the effectiveness of 6-9mer peptides on disrupting Aβ42 amyloid fibrils. For these studies, 0.1 mg/ml of Aβ42 (Bachem Inc) was incubated in microcentrifuge tubes at 37° C. for 3 days (in triplicate), either alone, or in the presence of 0.2 mg/ml peptide (at an Aβ:peptide weight ratio of 1:2) in TPBSF (10% TFE, 150 mM NaF, 50 mM HNaPO$_4$, pH 7.4). Fifty μl aliquots were taken for analysis at day 3 and 200 ul aliquots of 125 μM Thioflavin T in 62 mM NaPO4 (pH 6.0), were added giving a final Thioflavin T concentration of 100 μM and 62 mM of NaPO4. Fluorescence emission at 480 nm was measured on a microplate 96well fluorometer (Labsystem) at an excitation wavelength of 450 nm. For all determinations any fluorescence given off by peptides in the presence of the Thioflavin T reagent was always subtracted from all pertinent readings. Previous studies have indicated that increasing concentrations of fibrillar Aβ42 gives a proportional increase in fluorescence in the presence of 100 μM Thioflavin T, ruling out the presence of any disproportionate inner filter effects at this Thioflavin T concentration (Castillo et al *J. Neurochem.* 69:2452-2465, 1997).

Figure 74:
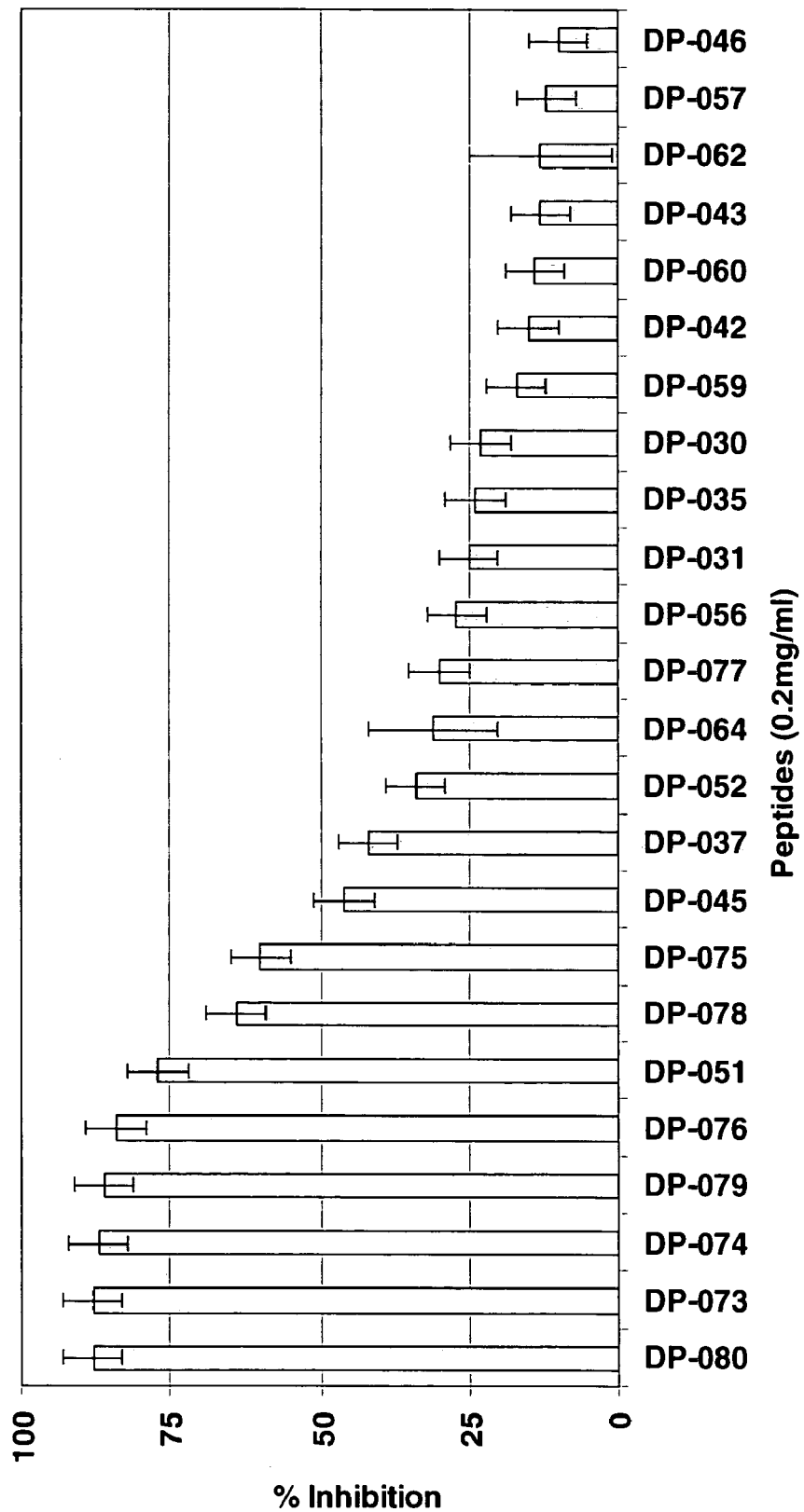
FIG. 74 is a graph showing an ordered summary comparison of the effect of the 6-9mer peptides on beta-sheet secondary structure of 25 uM Aβ42 amyloid fibrils as assessed by Thioflavin T fluorometry. Shown is the percent disruption of Aβ42 fibrils by various 6-9mer peptides at an Aβ42:6-9mer peptide weight ratio of 1:2.

FIG. 74 shows the disrupters of Thioflavin T binding to Aβ42 from among 6-9mer peptides and analogs, sorted in order of effectiveness. The preferred peptides in order of effectiveness, include but are not limited to, Trp-His-Leu-Ala-Phe-Val-Leu-Arg-Lys-amide (DP-080), Acetyl-Leu-Ala-Phe-Val-Leu-Arg-amide (DP-073), Leu-Ala-Phe-Val-Leu-Arg-Lys-amide (DP-074), Trp-His-Leu-Ala-Phe-Val-Leu-Arg-amide (DP-079), Acetyl-Thr-Leu-Phe-Leu-Ala-Arg-amide (DP-076), Trp-His-Arg-Val-Ala-Val-Ile-Met (DP-051), Thr-Leu-Phe-Leu-Ala-Arg-Lys-amide (DP-078), Thr-Leu-Phe-Leu-Ala-Arg-amide (DP-075), Leu-Ala-Phe-Val-Leu-Arg-Gly (DP-045), Arg-Val-Ala-Val-Ile-Met-Gly (DP-037), Arg-Val-Ala-Val-Ile-Met (DP-052), His-Pro-Arg-Leu-Val-Phe-Met (DP-064), Thr-Leu-Phe-Leu-Ala-Arg-Lys (DP-077), Leu-Ala-Phe-Val-Leu-Arg (DP-056), Arg-Val-Ser-Val-Arg-Trp-Gly (DP-031), Trp-His-Arg-Val-Ala-Val-Ile (DP-035), His-Arg-Val-Ser-Val-Arg-Trp (DP-030), Thr-Arg-Ile-Ser-Leu-Gln-Val (DP-059), Ala-His-Gly-Arg-Leu-Val-Phe (DP-042), Ser-Leu-Gln-Val-Gln-Leu-Arg (DP-060), His-Gly-Arg-Leu-Val-Phe-Met (DP-043), Arg-Val-Ser-Val-Arg-Trp (DP-062), Leu-Pro-Phe-Val-Leu-Arg (DP-057), and Ala-Phe-Val-Leu-Arg-Gly-Lys (DP-046). DP-080, DP-073, DP-074, DP-079, DP-076 and DP-051 all demonstrated >75% inhibition/disruption of Aβ42 fibrils, whereas DP-078 abd DP-075 demonstrated >50% inhibition/disruption of Aβ42 fibrils.

EXAMPLE 6

Binding of 6-9mer Peptides to Alzheimer's Aβ42 Fibrils

The ability of various peptides to bind to substrate bound Aβ42 was determined by a solid phase binding assay along with a determination of unbound peptide fractions using high pressure liquid chromatography attached to a mass selective detector (HPLC/MSD; Agilent 1100 HPLC system). The peptides were resolved in HPLC using a Synergi-Max RP (2×0.4 cm; 2 um) column from phenomenex with a flow rate of 1 ml/min and a gradient of 0-60% acetonitrile in water, containing 1% formic acid over 5.5 minutes. The peptides were detected as they come out from the column using MSD SL (Agilent). The MSD had the following settings: Positive ion monitoring in scan mode from 200-1200 Da; fragmentor voltage, 150; drying gas flow, 13 L/min N$_2$; nebuliser pressure, 45 psi; drying gas temperature, 350° C.; and capillary voltage, 3500 volts.

The solid phase binding assay was performed as follows: 10 ug aliquots of Aβ42 were bound to PVDF membrane at the bottom of a 96-well microplate (available from Millipore), according to the manufacturer's instructions. The plate was allowed to dry and aliquots of 150 ul of 0.1 mg/ml of 6-9mer peptides were applied in each well. Each 6-9mer peptide was applied in triplicate in the Aβ42-containing wells (test wells), and in triplicate in the non-Ab42 containing wells (blank wells). The plates containing 16 different 6-9mer peptides was incubated at 37° C. for 2 hrs. The unbound peptide in each well was then transferred to HPLC/MSD vials for analysis with the settings outlined above. The peptides recovered from wells without Aβ42 were taken as the total peptides, whereas the peptides recovered from wells with Aβ42, were taken as the total-bound peptides. The percentages of various peptides bound after 2 hrs of incubation were then plotted (FIG. 75)

Figure 75:
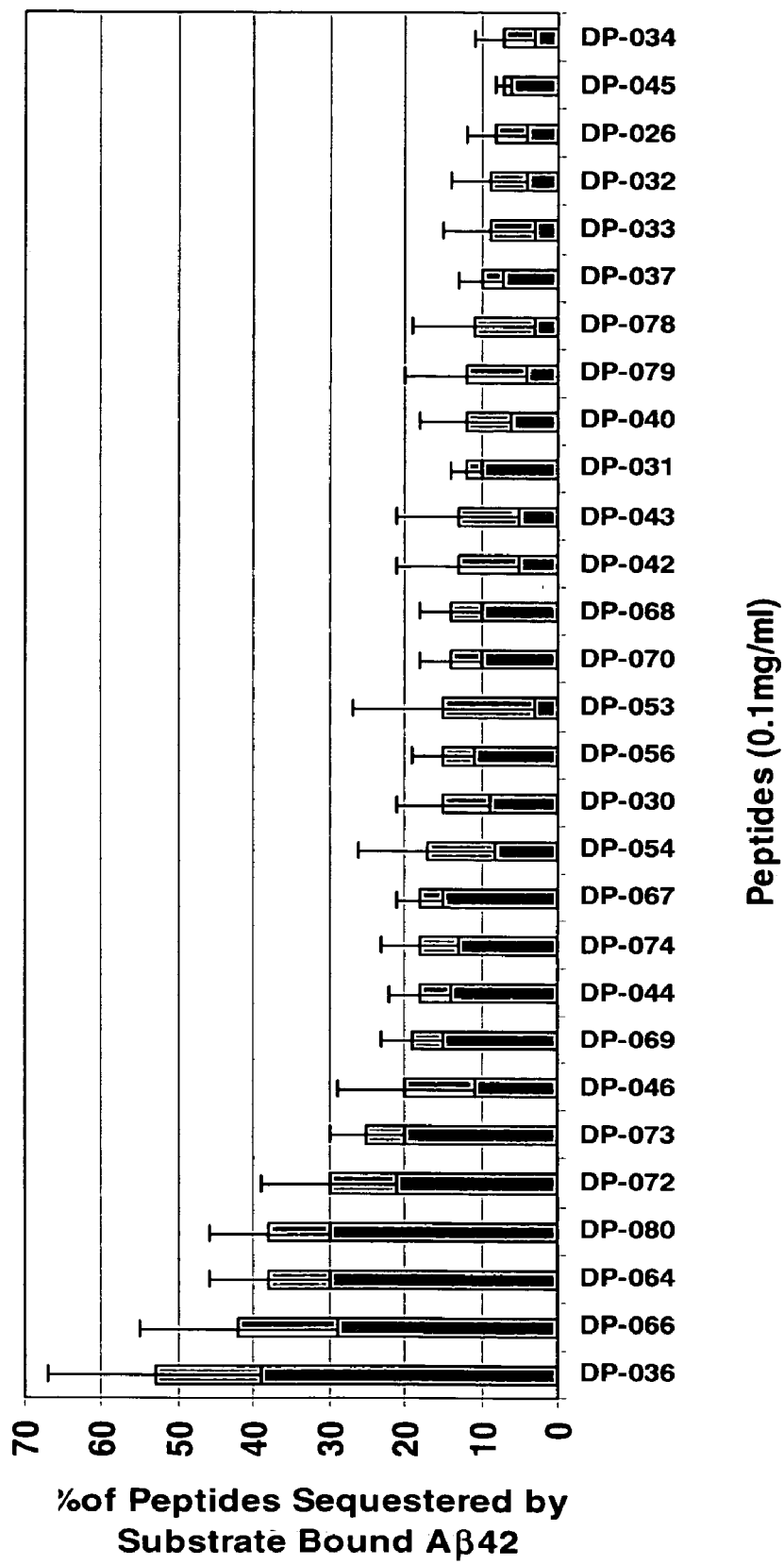
FIG. 75 is a graph showing an ordered summary comparison of the binding efficiency of 6-9mer peptides on substrate bound Aβ42 as assessed by LC/MS measurements of unbound peptides after a 2 hour equilibration period. Shown is the percent of various 6-9mer peptides unbound to Aβ42 fibrils after 2 hrs of incubation.

FIG. 75 shows the binders of Aβ42 from among the 6-9mer peptides and analogs, sorted in order of effectiveness. The preferred peptides in order of effectiveness, include, but are not limited to, His-Arg-Val-Ala-Val-Ile-Met (DP-036), Trp-His-Arg-Val-Ala-Val-Ile-amide (DP-066), His-Pro-Arg-Leu-Val-Phe-Met (DP-064), Trp-His-Leu-Ala-Phe-Val-Leu-Arg-Lys-amide (DP-080), Trp-His-Leu-Ala-Phe-Val-Leu-Arg (DP-072), Acetyl-Leu-Ala-Phe-Val-Leu-Arg-amide (DP-073), Ala-Phe-Val-Leu-Arg-Gly-Lys (DP-046), Leu-Ala-Phe-Val-Leu-Arg-amide (DP-069), Gly-Leu-Ala-Phe-Val-Leu-Arg (DP-044), Leu-Ala-Phe-Val-Leu-Arg-Lys-amide (DP-074), Arg-Val-Ala-Val-Ile-Met-amide (DP-067), His-Arg-Val-Pro-Val-Ile-Met (DP-054), His-Arg-Val-Ser-Val-Arg-Trp (DP-030), Leu-Ala-Phe-Val-Leu-Arg (DP-056), His-Arg-Pro-Ala-Val-Ile-Met (DP-053), His-Gly-Arg-Leu-Val-Phe-Met-amide (DP-070), Arg-Val-Ala-Val-Ile-Met-Gly-amide (DP-068), Ala-His-Gly-Arg-Leu-Val-Phe (DP-042), His-Gly-Arg-Leu-Val-Phe-Met (DP-043), Arg-Val-Ser-Val-Arg-Trp-Gly (DP-031), Phe-Leu-Ala-His-Gly-Arg-Leu (DP-040), Trp-His-Leu-Ala-Phe-Val-Leu-Arg-amide (DP-079), Thr-Leu-Phe-Leu-Ala-Arg-Lys-amide (DP-078), Arg-Val-Ala-Val-Ile-Met-Gly (DP-037), Gly- Arg-Trp-His-Arg-Val-Ala (DP-033), Asp-Gly-Arg-Trp-His-Arg-Val (DP-032), Ala-Gly-Gln-Trp-His-Arg-Val (DP-026), Leu-Ala-Phe-Val-Leu-Arg-Gly (DP-045), and Arg-Trp-His-Arg-Val-Ala-Val (DP-034). DP-036 and DP-066 demonstrated >40% binding to substrate bound Aβ42, whereas DP-064 and DP-080 demonstrated >30% binding, and DP-0072 and DP-073 demonstrated >20% binding (FIG. 75).

EXAMPLE 7

Disruption of Alzheimer Fibrils β-Sheet Secondary Structure by 6-9mer Peptides as Assessed by CD Spectropolarimetry Circular dichroism (CD) spectropolarimetry is another in vitro technique used to determine a given peptide's effectiveness in disrupting the b-sheet secondary structure of Aβ-fibrils. CD spectra of Aβ42 in the presence or absence of synthetic 6-9mer peptides were recorded at 25° C. on a JASCO-810 Spectropolarimeter using a 0.5 mm path length quartz cuvette, and over the range of 190-260 nm. The instrument was calibrated with an aqueous solution of (+)camphorsulfonic acid. The instrument was then set to collect data at a bandwidth of 5 nm, response time of 32 seconds, data pitch of 0.5 nm, and a scan speed of 10 nm/min. Each CD spectrum was an average of 5 spectra, each taken from a separate replicate solution. The CD results were reported as Molar Residue Ellipticity (MRE) of Aβ42, after subtraction of the background solvent spectrum and/or test peptide spectrum. For this study, fibrillar Aβ42 (0.1 mg/ml) in TPBSF (10% TFE, 150 mM NaF, 50 mM $HNaPO_4$, pH 7.4) was incubated for 3 days at 37° C. in the presence and absence of various 6-9mer peptides at an Aβ42:peptide wt/wt ratio of 1:2, before recording the CD spectra.

Figure 62:
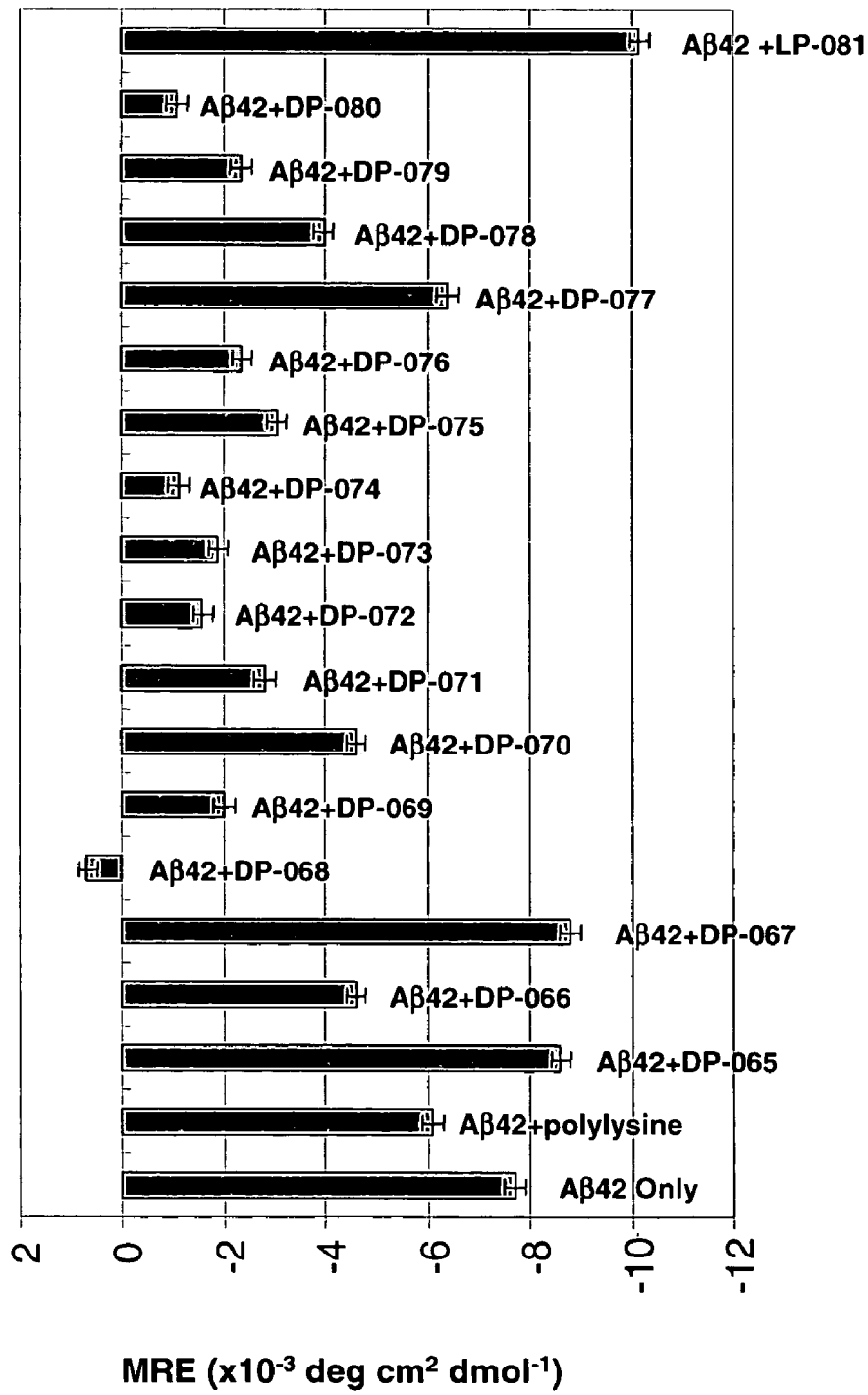
FIG. 62 is a graph showing a summary comparison of the effect of 0.2 mg/ml peptides DP-065 to LP-081, and polylysine, on beta-sheet secondary structure of 25 uM Aβ42 amyloid fibrils as assessed by CD. Shown is the molar residue ellipticity of Aβ42 at 218 nm in the y-axis, representing the signal associated with beta-sheet secondary structure. Loss of ellipticity at 218 nm compared to the signal of Aβ42 fibrils only, indicates the peptides ability to reduce beta-sheet secondary structure.
Figure 63:
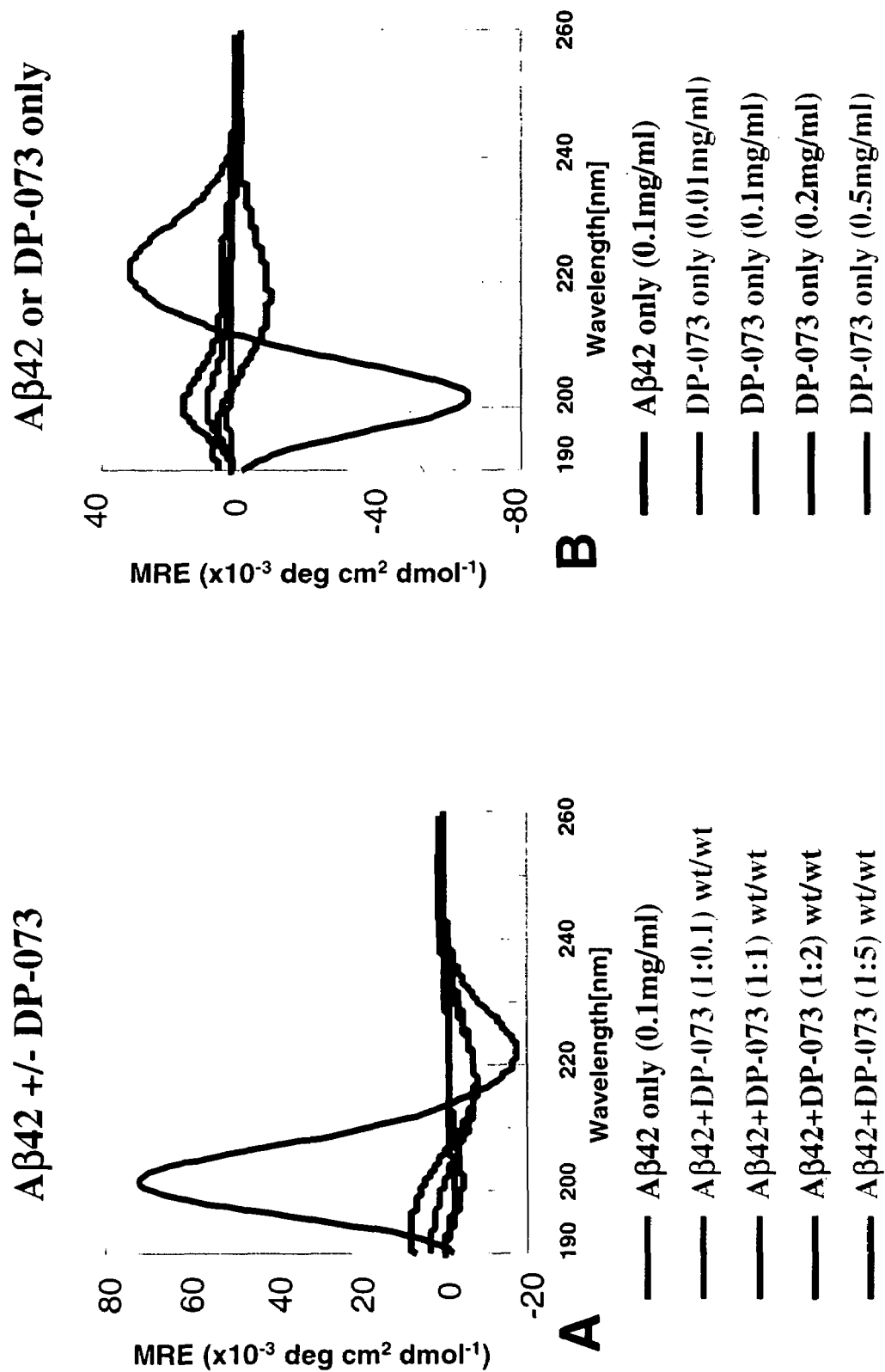
FIG. 63A are CD spectra showing the dose-dependent effects of peptide DP-073 on beta-sheet secondary structure of Aβ42 amyloid fibrils (i.e. Aβ 42+/−DP-073).
FIG. 63B shows the CD spectra of Aβ 42 or DP-073 only.
Figure 64:
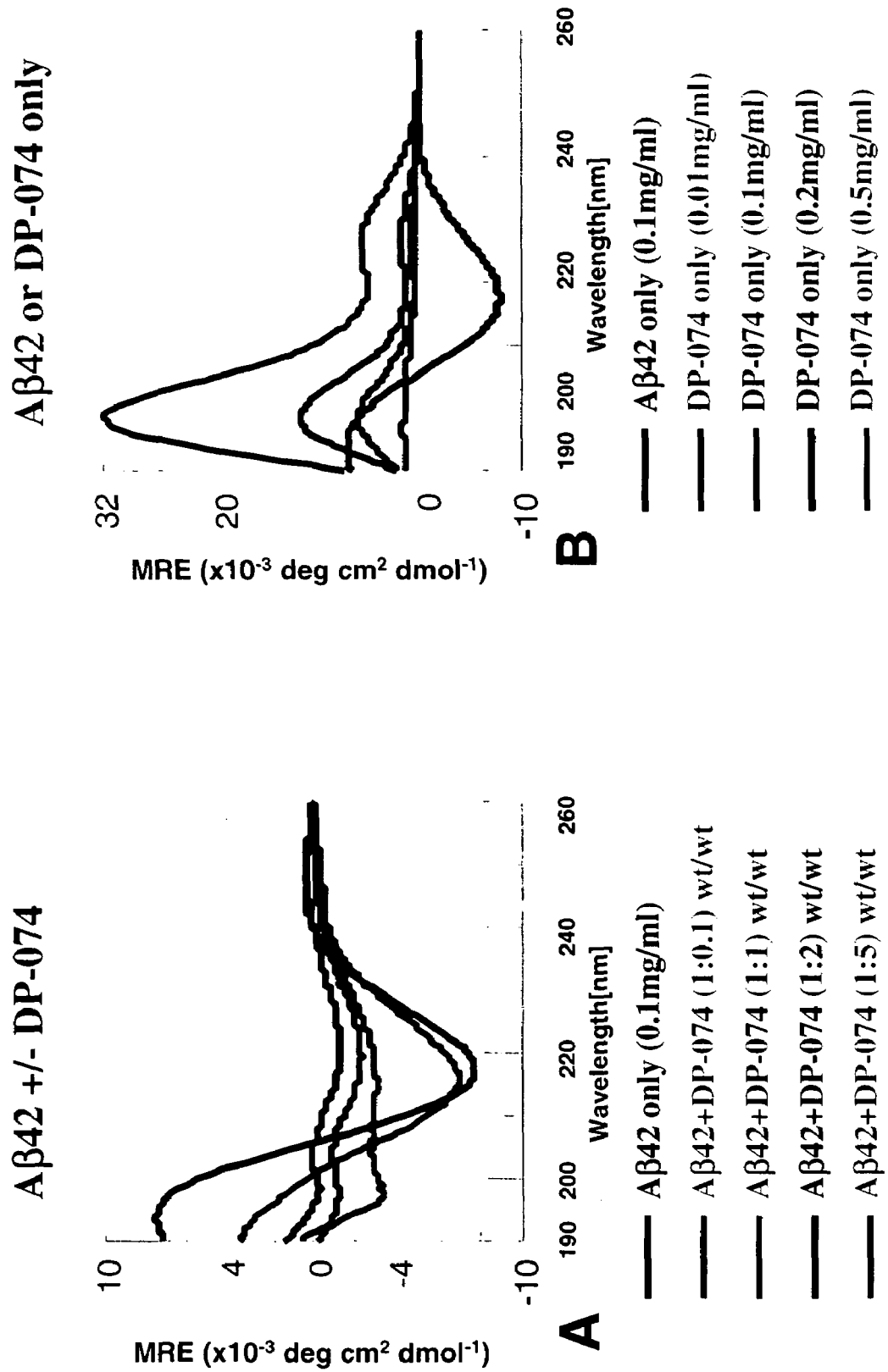
FIG. 64A are CD spectra showing the dose-dependent effects of peptide DP-074 on beta-sheet secondary structure of Aβ42 amyloid fibrils (i.e. Aβ 42+/−DP-074).
FIG. 64B shows the CD spectra of Aβ 42 or DP-074 only.
Figure 65:
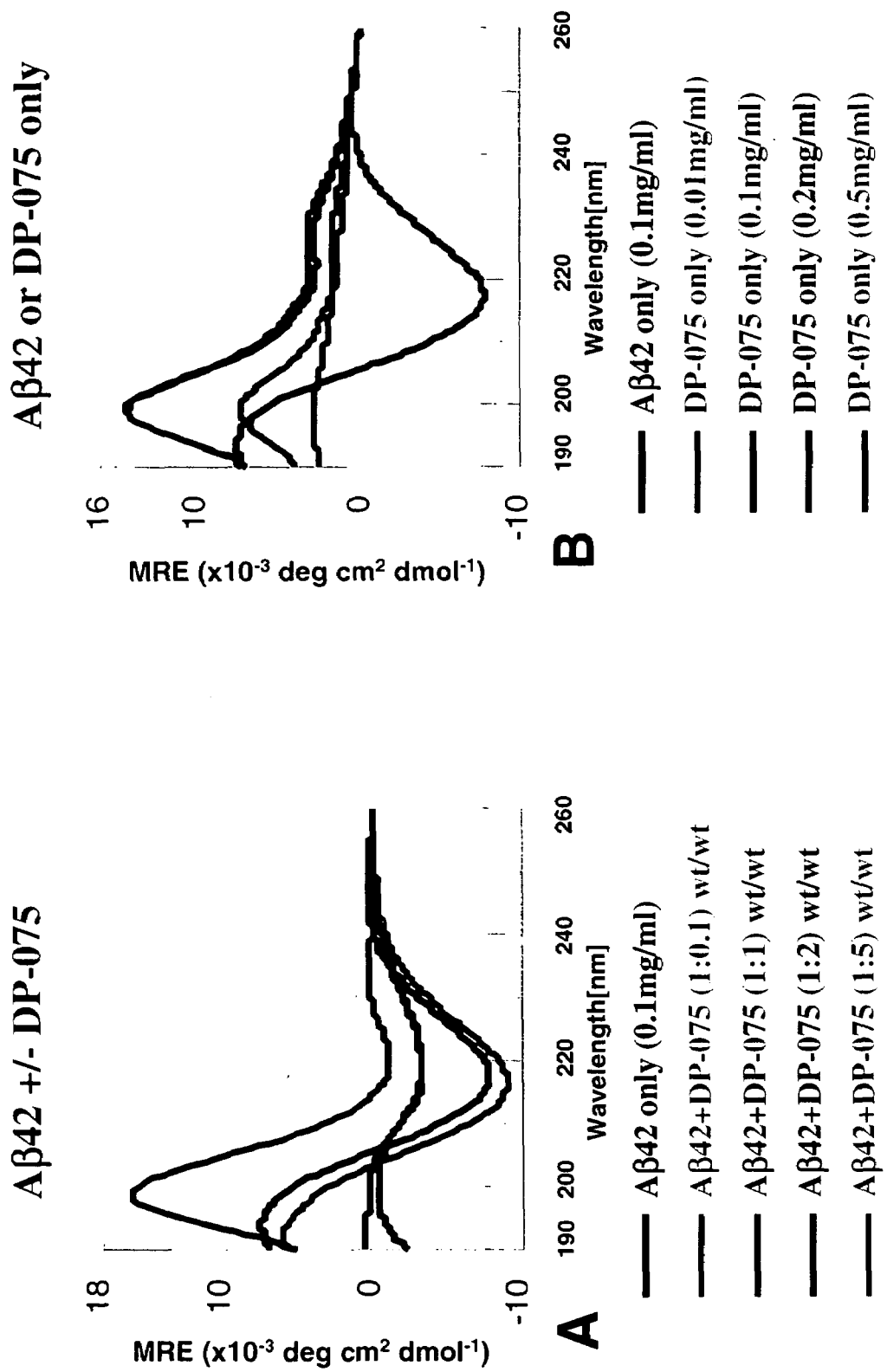
FIG. 65A are CD spectra showing the dose-dependent effects of peptide DP-075 on beta-sheet secondary structure of Aβ42 amyloid fibrils (i.e. Aβ 42+/−DP-075).
FIG. 65B shows the CD spectra of Aβ 42 or DP-075 only.
Figure 66:
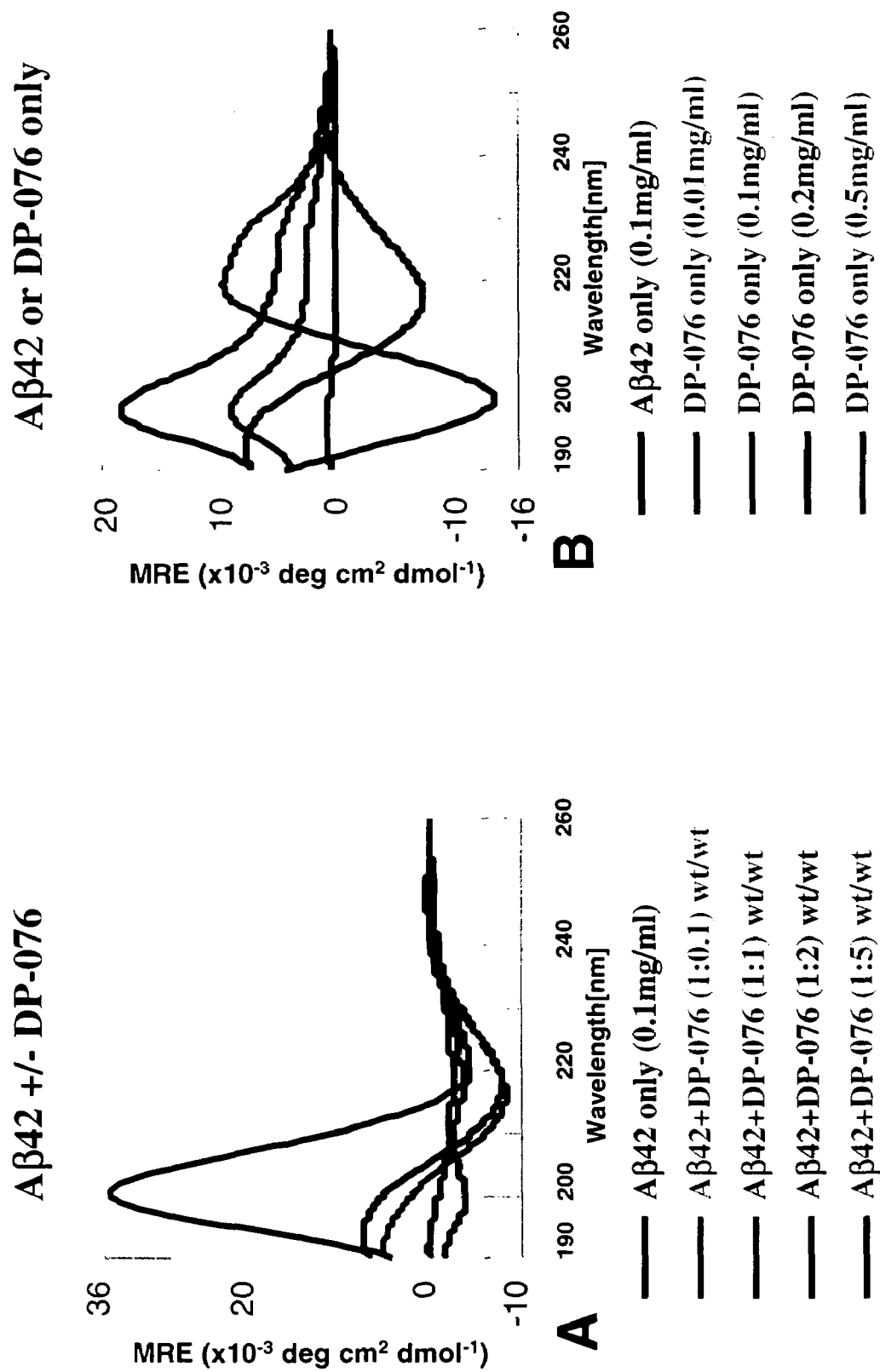
FIG. 66A are CD spectra showing the dose-dependent effects of peptide DP-076 on beta-sheet secondary structure of Aβ42 amyloid fibrils (i.e. Aβ 42+/−DP-076).
FIG. 66B shows the CD spectra of Aβ 42 or DP-076 only.
Figure 67:
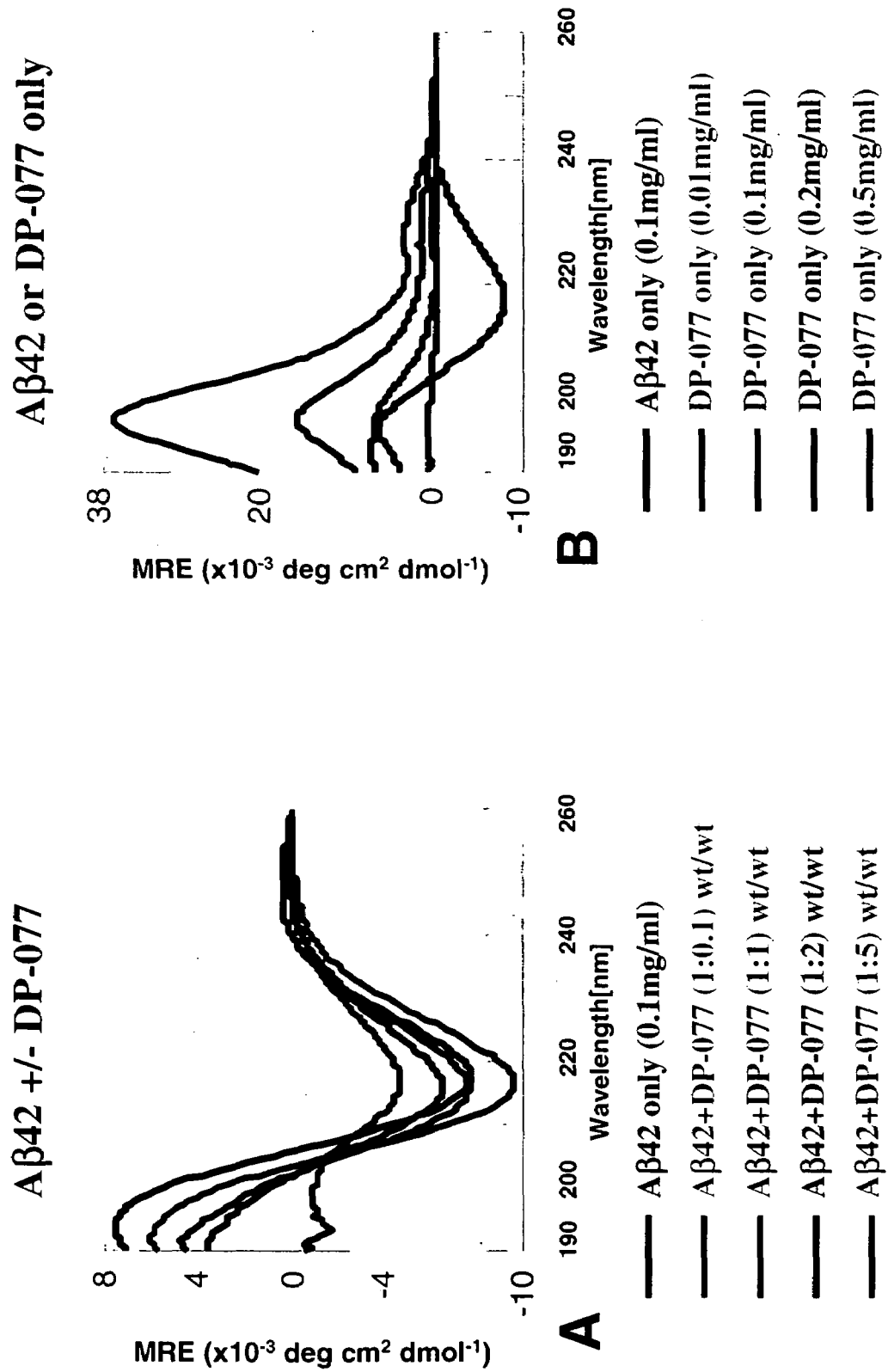
FIG. 67A are CD spectra showing the dose-dependent effects of peptide DP-077 on beta-sheet secondary structure of Aβ42 amyloid fibrils (i.e. Aβ 42+/−DP-077).
FIG. 67B shows the CD spectra of Aβ 42 or DP-077 only.
Figure 68:
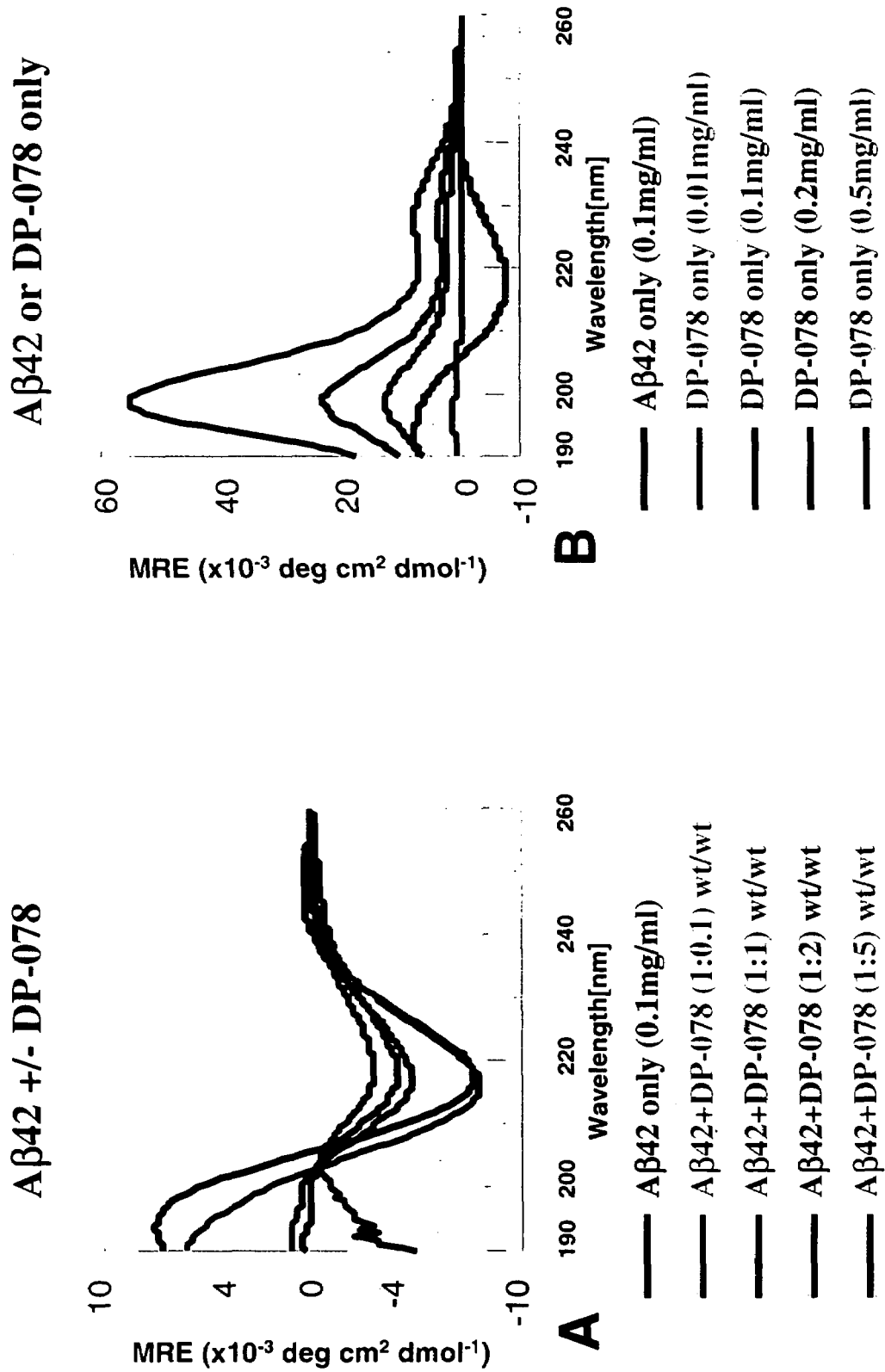
FIG. 68A are CD spectra showing the dose-dependent effects of peptide DP-078 on beta-sheet secondary structure of Aβ42 amyloid fibrils (i.e. Aβ 42+/−DP-078).
FIG. 68B shows the CD spectra of Aβ 42 or DP-078 only.
Figure 69:
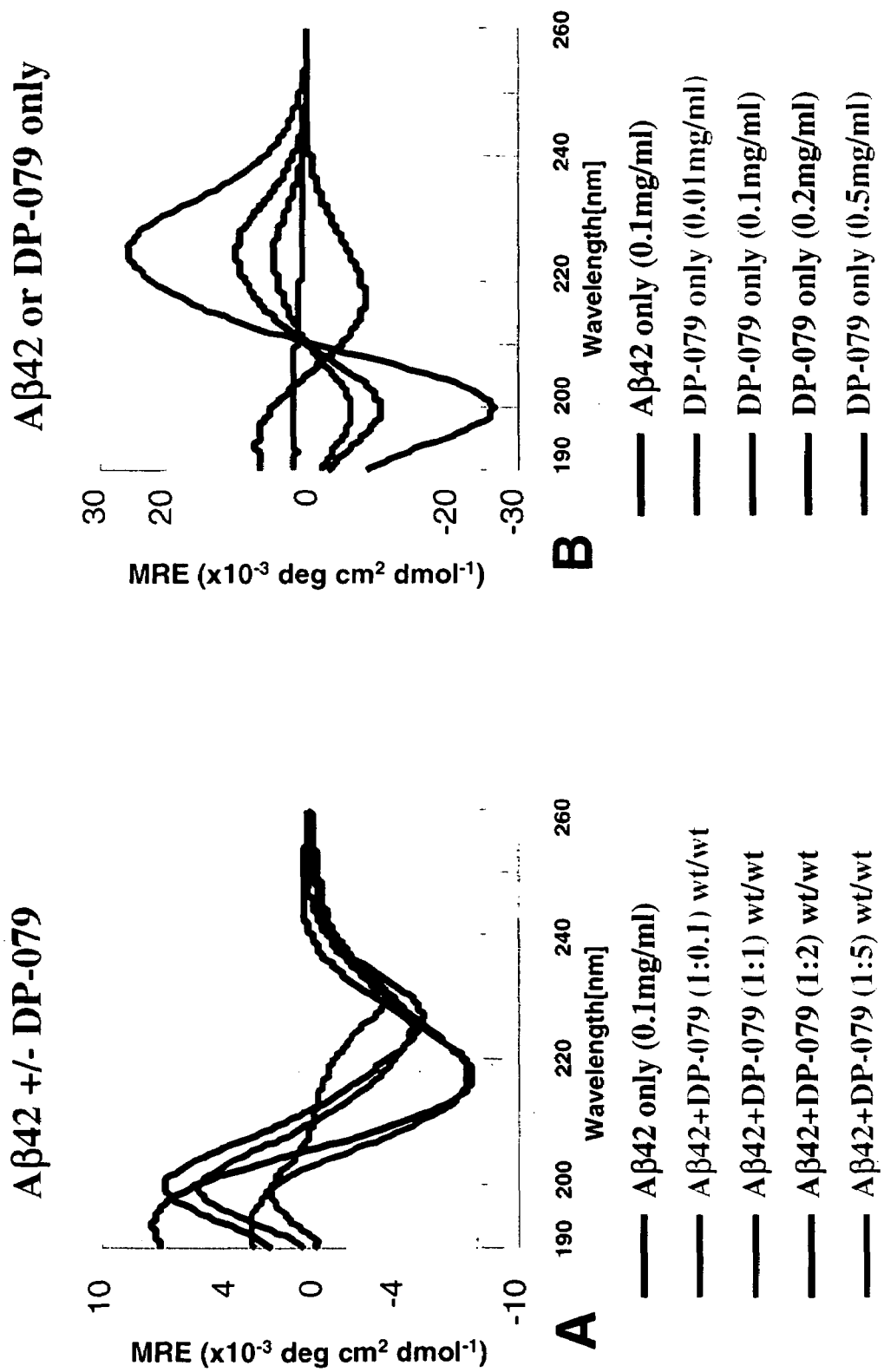
FIG. 69A are CD spectra showing the dose-dependent effects of peptide DP-079 on beta-sheet secondary structure of Aβ42 amyloid fibrils (i.e. Aβ 42+/−DP-079).
FIG. 69B shows the CD spectra of Aβ 42 or DP-079 only.
Figure 71:
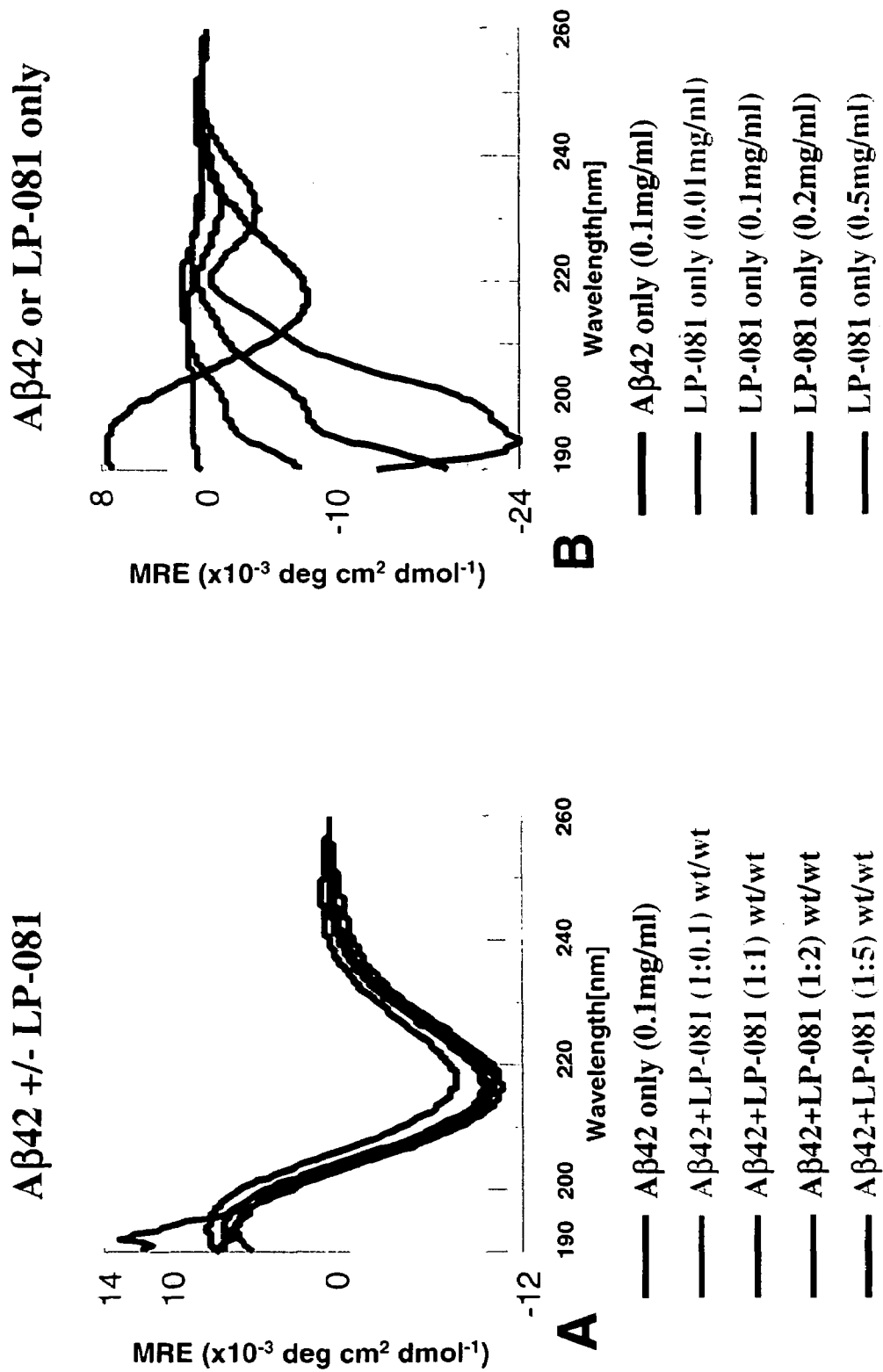
FIG. 71A are CD spectra showing the dose-dependent effects of peptide LP-081 on beta-sheet secondary structure of Aβ42 amyloid fibrils (i.e. Aβ 42+/−LP-081).
FIG. 71B shows the CD spectra of Aβ 42 or LP-081 only.

The CD spectra of Aβ42 alone, Aβ42 plus 6-9mer peptide, and 6-9mer peptide alone, are presented in FIGS. 53 to 61, with an overall summary in FIG. 62.

FIG. 53A shows the CD spectrum of 0.1 mg/ml of Aβ42 after 3 days of incubation (solid line). Both the negative ellipticity at 218 nm and the positive ellipticity at 195 nm indicate the presence of beta-sheet secondary structure. Also in FIG. 53A is the CD spectrum of 0.1 mg/ml of Aβ42 in the presence of 0.2 mg/ml of DP-073 after 3 days of incubation (dotted line), with correction for the spectrum of peptide DP-073. The significant loss of negative ellipticity at 218 nm in the presence of DP-073 indicates a loss of beta-sheet structure in Aβ42. FIG. 53B shows the CD spectrum of 0.2 mg/ml of DP-073 alone (dotted line) with positive ellipticities and maxima at 200 nm indicating an inverted random coil consistent with a amino acid peptide, containing very little beta sheet structure. Also shown in FIG. 53B for comparison is the CD spectrum of 0.1 mg/ml of Aβ42 after 3 days of incubation (solid line)

FIG. 54A shows the CD spectrum of 0.1 mg/ml of Aβ42 after 3 days of incubation (solid line). Both the negative ellipticity at 218 nm and the positive ellipticity at 195 nm indicate the presence of beta-sheet secondary structure. Also in FIG. 54A is the CD spectrum of 0.1 mg/ml of Aβ42 in the presence of 0.2 mg/ml of DP-074 after 3 days of incubation (dotted line), with correction for the spectrum of peptide DP-074. The significant loss of negative ellipticity at 218 nm in the presence of DP-074 indicates a loss of beta-sheet structure in Aβ42. FIG. 54B shows the CD spectrum of 0.2 mg/ml of DP-074 alone (dotted line) with positive ellipticities and maxima at around 200 nm indicating an inverted random coil consistent with a amino acid peptide, with very little beta-sheet structure. Also shown in FIG. 53B for comparison is the CD spectrum of 0.1 mg/ml of Aβ42 after 3 days of incubation (solid line) FIG. 55A shows the CD spectrum of 0.1 mg/ml of Aβ42 after 3 days of incubation (solid line). Both the negative ellipticity at 218 nm and the positive ellipticity at 195 nm indicate the presence of beta-sheet secondary structure. Also in FIG. 55A is the CD spectrum of 0.1 mg/ml of Aβ42 in the presence of 0.2 mg/ml of DP-075 after 3 days of incubation (dotted line). The significant loss of negative ellipticity at 218 nm in Aβ42 in the presence of DP-075, indicates a loss of beta-sheet structure in Aβ42. FIG. 55B shows the CD spectrum of 0.2 mg/ml of DP-075 alone (dotted line) with positive ellipticities and maxima at 200 nm indicating an inverted random coil consistent with a amino acid peptide, containing very little beta sheet structure. Also shown in FIG. 55B for comparison is the CD spectrum of 0.1 mg/ml of Aβ42 after 3 days of incubation (solid line).

FIG. 56A shows the CD spectrum of 0.1 mg/ml of Aβ42 after 3 days of incubation (solid line). Both the negative ellipticity at 218 nm and the positive ellipticity at 195 nm indicate the presence of beta-sheet secondary structure in Aβ42. Also in FIG. 56A is the CD spectrum of 0.1 mg/ml of Aβ42 in the presence of 0.2 mg/ml of DP-076 after 3 days of incubation (dotted line). The significant loss of negative ellipticity at 218 nm in the presence of DP-076 indicates a loss of beta-sheet structure in Aβ42. FIG. 56B shows the CD spectrum of 0.2 mg/ml of DP-076 alone (dotted line) with positive ellipticities and maxima at 200 nm indicating an inverted random coil consistent with a amino acid peptide, containing very little beta sheet structure. Also shown in FIG. 56B for comparison is the CD spectrum of 0.1 mg/ml of Aβ42 after 3 days of incubation (solid line).

FIG. 57A shows the CD spectrum of 0.1 mg/ml of Aβ42 after 3 days of incubation (solid line). Both the negative ellipticity at 218 nm and the positive ellipticity at 195 nm indicate the presence of beta-sheet secondary structure in Aβ42. Also in FIG. 57A is the CD spectrum of 0.1 mg/ml of Aβ42 in the presence of 0.2 mg/ml of DP-077 after 3 days of incubation (dotted line). The slight loss of negative ellipticity at 218 nm in the presence of DP-077 indicates only a slight loss of beta-sheet structure in Aβ42. FIG. 57B shows the CD spectrum of 0.2 mg/ml of DP-077 alone (dotted line) with positive ellipticities and maxima at 200 nm indicating an inverted random coil consistent with a amino acid peptide, containing very little beta sheet structure. Also shown in FIG. 57B for comparison is the CD spectrum of 0.1 mg/ml of Aβ42 after 3 days of incubation (solid line).

FIG. 58A shows the CD spectrum of 0.1 mg/ml of Aβ42 after 3 days of incubation (solid line). Both the negative ellipticity at 218 nm and the positive ellipticity at 195 nm indicate the presence of beta-sheet secondary structure in Aβ42. Also in FIG. 58A is the CD spectrum of 0.1 mg/ml of Aβ42 in the presence of 0.2 mg/ml of DP-078 after 3 days of incubation (dotted line). The significant loss of negative ellipticity at 218 nm in the presence of DP-078 indicates a loss of beta-sheet structure in Aβ42. FIG. 58B shows the CD spectrum of 0.2 mg/ml of DP-078 alone (dotted line) with positive ellipticities and maxima at about 200 nm indicating an inverted random coil consistent with a amino acid peptide, containing very little beta sheet structure. Also shown in FIG. 58B for comparison is the CD spectrum of 0.1 mg/ml of Aβ42 after 3 days of incubation (solid line).

FIG. 59A shows the CD spectrum of 0.1 mg/ml of Aβ42 after 3 days of incubation (solid line). Both the negative ellipticity at 218 nm and the positive ellipticity at 195 nm indicate the presence of beta-sheet secondary structure in Aβ42. Also in FIG. 59A is the CD spectrum of 0.1 mg/ml of Aβ42 in the presence of 0.2 mg/ml of DP-079 after 3 days of incubation (dotted line). The significant loss of negative ellipticity at 218 nm in the presence of DP-079 indicates a loss of beta-sheet structure in Aβ42. However, the shift of minima from 218 nm to 225 nm is unexpected, and thus any loss of ellipticity at 218 nm, may not be due to loss of beta-sheet structure alone. FIG. 59B shows the CD spectrum of 0.2 mg/ml of DP-079 alone (dotted line) with positive ellipticities and maxima at 225 nm and a minima at 200 nm indicating an inverted beta sheet consistent with amino acid peptide with beta sheet structure. However, the maximum at 225 nm indicates a structure reminiscent of cross-linking or disulfide binding protein. Also shown in FIG. 59B for comparison is the CD spectrum of 0.1 mg/ml of Aβ42 after 3 days of incubation (solid line).

FIG. 60A shows the CD spectrum of 0.1 mg/ml of Aβ42 after 3 days of incubation (solid line). Both the negative ellipticity at 218 nm and the positive ellipticity at 195 nm indicate the presence of beta-sheet secondary structure in Aβ42. Also in FIG. 60A is the CD spectrum of 0.1 mg/ml of Aβ42 in the presence of 0.2 mg/ml of DP-080 after 3 days of incubation (dotted line). The significant loss of negative ellipticity at 218 nm in the presence of DP-080 indicates a loss of beta-sheet structure in Aβ42. FIG. 60B shows the CD spectrum of 0.2 mg/ml of DP-080 alone (dotted line) with positive ellipticities and maxima at about 195 nm indicating an inverted random coil consistent with a amino acid peptide, containing very little beta sheet structure. Also shown in FIG. 60B for comparison is the CD spectrum of 0.1 mg/ml of Aβ42 after 3 days of incubation (solid line).

FIG. 61A shows the CD spectrum of 0.1 mg/ml of Aβ42 after 3 days of incubation (solid line). Both the negative ellipticity at 218 nm and the positive ellipticity at 195 nm indicate the presence of beta-sheet secondary structure in Aβ42. Also in FIG. 61A is the CD spectrum of 0.1 mg/ml of Aβ42 in the presence of 0.2 mg/ml of LP-081 after 3 days of incubation (dotted line). The significant gain of negative ellipticity at 218 nm in the presence of LP-081 indicates a gain of beta-sheet structure in Aβ42. FIG. 61B shows the CD spectrum of 0.2 mg/ml of LP-081 alone (dotted line) with negative ellipticities and maxima at about 200 nm indicating an random coil structure of L-peptide. Also shown in FIG. 61B for comparison is the CD spectrum of 0.1 mg/ml of Aβ42 after 3 days of incubation (solid line). It should be noted that LP-081 is the beta-sheet breaker peptide previously reported in the literature (Permanne et al, *FASEB J.* Published online Apr. 10, 2002; Soto-Jara et al, U.S. Pat. No. 5,948,763 Sep. 7, 1999; Soto-Jara, PCT WO 01/34631 A2 May 17, 2001).

FIG. 62 shows the CD ellipticites of 0.1 mg/ml of Aβ42 at 218 nm in the presence of 0.2 mg/ml of various 6-9mer peptides after 3 days of incubation, and after correction for the CD ellipticites of various peptides. The peptides tested here are DP-065 to LP-081, and polylysine. It should be noted that peptides DP-065, DP-067, and LP-081 caused an increase in negative ellipticity at 218 nm, indicating that these peptides surprisingly promote formation of beta-sheet structure of Aβ42. Refer to FIG. 73 for the ranking of effectiveness of various 6-9mer peptides.

EXAMPLE 8

Dose-Dependent Disruption of Alzheimer Fibrils β-sheet Secondary Structure by 6-9mer Peptides as Assessed by CD Spectropolarimetry Circular dichroism (CD) spectropolarimetry is another in vitro technique used to determine a given peptide's effectiveness in disrupting the b-sheet secondary structure of Aβ-fibrils. CD spectra of Aβ42 in the presence or absence of synthetic 6-9mer peptides were recorded at 25° C. on a JASCO-810 Spectropolarimeter using a 0.5 mm path length quartz cuvette, and over the range of 190-260 nm. The instrument was calibrated with an aqueous solution of (+)camphorsulfonic acid. The instrument was then set to collect data at a bandwidth of 5 nm, response time of 32 seconds, data pitch of 0.5 nm, and a scan speed of 10 nm/min. Each CD spectrum was an average of 5 spectra, each taken from a separate replicate solution. The CD results were reported as Molar Residue Ellipticity (MRE) of Aβ42, after subtraction of the background solvent spectrum and/or test peptide spectrum. For this study, fibrillar Aβ42 (0.1 mg/ml) in TPBSF (10% TFE, 150 mM NaF, 50 mM HNaPO$_4$, pH 7.4) was incubated for 3 days at 37° C. in the presence and absence of various peptides at Aβ42:peptide wt/wt ratios of 1:0.1, 1:1, 1:2, and 1:10 before recording the CD spectra.

Figure 72:
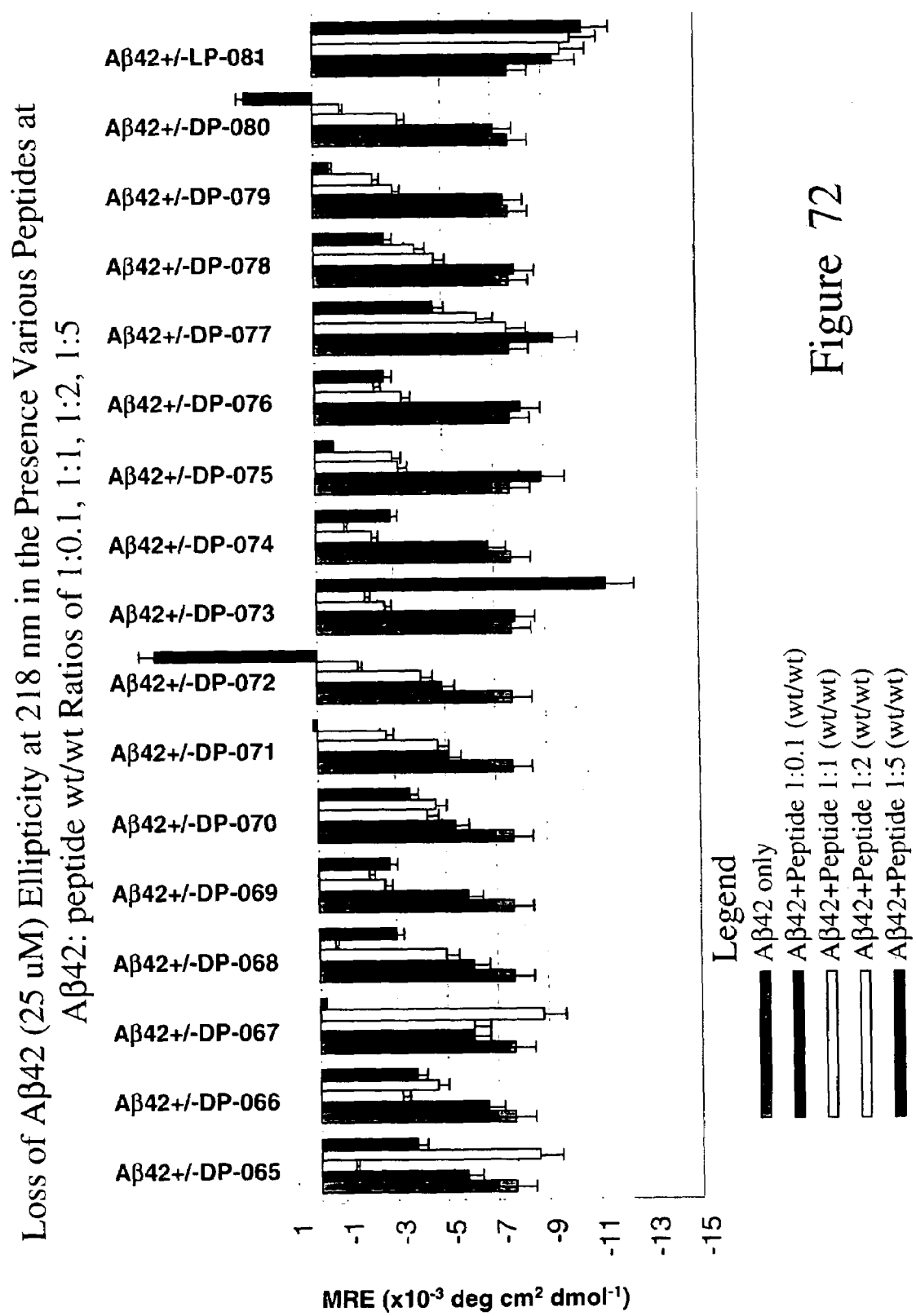
FIG. 72 is a graph showing a summary comparison of the dose-dependent effect of peptides DP-065 to LP-081 on beta-sheet secondary structure of 25 uM Aβ42 amyloid fibrils as assessed by CD. Shown is the molar residue ellipticity of Aβ42 at 218 nm in the y-axis, 45 representing the signal inversely related to the beta-sheet secondary structure.

The CD spectra of Aβ42 alone, Aβ42 plus 6-9mer peptide, and peptide alone were presented in FIGS. 63 to 71, with an overall summary in FIG. 72.

FIG. 63A shows the CD spectrum of 0.1 mg/mi of Aβ42 after 3 days of incubation (blue). Both the negative ellipticity at 218 nm and the positive ellipticity at 195 nm indicate the presence of beta-sheet structure in Aβ42. Also in FIG. 63A is the CD spectrum of 0.1 mg/ml of Aβ42 in the presence of 0.01, 0.1, 0.2, and 0.5 mg/ml of peptide DP-073 after 3 days of incubation (with correction for the spectrum of peptide DP-073). The significant loss of negative ellipticity at 218 nm indicates a loss of beta-sheet structure in Aβ42. The dose-dependent effect is only observed at 0.2 mg/ml and lower. At 0.5 mg/ml of peptide DP-073 the trend stops and reverses course. This is perhaps due to the very high concentration of test peptide causing a significant absorption of the incoming light. FIG. 63B shows the CD spectrum of 0.01, 0.1,0.2, and 0.5 mg/ml of peptide DP-073 alone with positive ellipticities and maxima at 200 nm, indicating an inverted random coil consistent with a D-amino acid peptide with very little beta-sheet structure. However at a high concentration (0.5 mg/ml) an inverted beta-sheet structure is observed. Also shown in FIG. 63B for comparison is the CD spectrum of 0.1 mg/ml of Aβ42 after 3 days of incubation (blue).

FIG. 64A shows the CD spectrum of 0.1 mg/ml of ABβ42 after 3 days of incubation (blue). Both the negative ellipticity at 218 nm and the positive ellipticity at 195 nm indicate the presence of beta-sheet structure in Aβ42. Also in FIG. 63A is the CD spectrum of 0.1 mg/ml of Aβ42 in the presence of 0.01, 0.1, 0.2, and 0.5 mg/ml of peptide DP-074 after 3 days of incubation (with correction for the spectrum of peptide DP-074). The significant loss of negative ellipticity at 218 nm indicates a loss of beta-sheet structure in Aβ42. The dose-dependent effect is only observed at 0.2 mg/ml and lower. At 0.5 mg/ml of peptide DP-074 the trend stops and reverses course. This is perhaps due to the very high concentration of test peptide causing a significant absorption of the incoming light. FIG. 64B shows the CD spectrum of 0.01, 0.1,0.2, and 0.5 mg/ml of peptide DP-074 alone with positive ellipticities and maxima at approximately 200 nm, indicating an inverted random coil consistent with a D-amino acid peptide with very little beta-sheet structure. Also shown in FIG. 64B for comparison is the CD spectrum of 0.1 mg/ml of Aβ42 after 3 days of incubation (blue).

FIG. 65A shows the CD spectrum of 0.1 mg/ml of Aβ42 after 3 days of incubation (blue). Both the negative ellipticity at 218 nm and the positive ellipticity at 195 nm indicate the presence of beta-sheet structure in Aβ42. Also in FIG. 65A is the CD spectrum of 0.1 mg/ml of Aβ42 in the presence of 0.01, 0.1, 0.2, and 0.5 mg/ml of peptide DP-075 after 3 days of incubation (with correction for the spectrum of peptide DP-075). The significant loss of negative ellipticity at 218 nm indicates a loss of beta-sheet structure in Aβ42. The dose-dependent effect is only observed at 0.1 mg/ml and lower. At 0.01 mg/ml of peptide DP-075 the Aβ42 beta-sheet structure is enhanced. FIG. 65B shows the CD spectrum of 0.01, 0.1, 0.2, and 0.5 mg/ml of peptide DP-075 alone with positive ellipticities and maxima at approximately 200 nm, indicating an inverted random coil consistent with a D-amino acid peptide with very little beta-sheet structure. Also shown in FIG. 65B for comparison is the CD spectrum of 0.1 mg/ml of Aβ42 after 3 days of incubation (blue).

FIG. 66A shows the CD spectrum of 0.1 mg/ml of Aβ42 after 3 days of incubation (blue). Both the negative ellipticity at 218 nm and the positive ellipticity at 195 nm indicate the presence of beta-sheet structure in Aβ42. Also in FIG. 66A is the CD spectrum of 0.1 mg/ml of Aβ42 in the presence of 0.01, 0.1, 0.2, and 0.5 mg/ml of peptide DP-076 after 3 days of incubation (with correction for the spectrum of peptide DP-076). The significant loss of negative ellipticity at 218 nm indicates a loss of beta-sheet structure in Aβ42. The dose-dependent effect is only observed at 0.1 mg/ml and lower. At 0.01 mg/ml of peptide DP-076 the Aβ42 beta-sheet structure is enhanced. FIG. 66B shows the CD spectrum of 0.01, 0.1, 0.2, and 0.5 mg/ml of peptide DP-076 alone with positive ellipticities and maxima at approximately 200 nm, indicating an inverted random coil consistent with a D-amino acid peptide with very little beta-sheet structure. However at a concentration of 0.5 mg/ml significant formation of inverted beta-sheet structure is observed Also shown in FIG. 66B for comparison is the CD spectrum of 0.1 mg/ml of Aβ42 after 3 days of incubation (blue).

FIG. 67A shows the CD spectrum of 0.1 mg/ml of Aβ42 after 3 days of incubation (blue). Both the negative ellipticity at 218 nm and the positive ellipticity at 195 nm indicate the presence of beta-sheet structure in Aβ42. Also in FIG. 67A is the CD spectrum of 0.1 mg/ml of Aβ42 in the presence of 0.01, 0.1, 0.2, and 0.5 mg/ml of peptide DP-077 after 3 days of incubation (with correction for the spectrum of peptide DP-077). The loss of negative ellipticity at 218 nm indicates a loss of beta-sheet structure in Aβ42. The dose-dependent effect is only observed at 0.1 mg/ml and higher. FIG. 67B shows the CD spectrum of 0.01, 0.1, 0.2, and 0.5 mg/ml of peptide DP-077 alone with positive ellipticities and maxima at approximately 200 nm, indicating an inverted random coil consistent with a D-amino acid peptide with very little beta-sheet structure. Also shown in FIG. 67B for comparison is the CD spectrum of 0.1 mg/ml of Aβ42 after 3 days of incubation (blue).

FIG. 68A shows the CD spectrum of 0.1 mg/ml of Aβ42 after 3 days of incubation (blue). Both the negative ellipticity at 218 nm and the positive ellipticity at 195 nm indicate the presence of beta-sheet structure in Aβ42. Also in FIG. 68A is the CD spectrum of 0.1 mg/ml of Aβ42 in the presence of 0.01, 0.1, 0.2, and 0.5 mg/ml of peptide DP-078 after 3 days of incubation (with correction for the spectrum of peptide DP-078). The significant loss of negative ellipticity at 218 nm indicates a loss of beta-sheet structure in Aβ42. The dose-dependent effect is observed. FIG. 68B shows the CD spectrum of 0.01, 0.1, 0.2, and 0.5 mg/ml of peptide DP-078 alone with positive ellipticities and maxima at approximately 200 nm, indicating an inverted random coil consistent with a D-amino acid peptide with very little beta-sheet structure. Also shown in FIG. 68B for comparison is the CD spectrum of 0.1 mg/ml of Aβ42 after 3 days of incubation (blue).

FIG. 69A shows the CD spectrum of 0.1 mg/ml of Aβ42 after 3 days of incubation (blue). Both the negative ellipticity at 218 nm and the positive ellipticity at 195 nm indicate the presence of beta-sheet structure in Aβ42. Also in FIG. 69A is the CD spectrum of 0.1 mg/ml of Aβ42 in the presence of 0.01, 0.1, 0.2, and 0.5 mg/ml of peptide DP-079 after 3 days of incubation (with correction for the spectrum of peptide DP-079). The significant loss of negative ellipticity at 218 nm indicates a loss of beta-sheet structure in Aβ42. However, the shift of minima from 218 nm to 225 nm is unexpected, and thus any loss of ellipticity at 218 nm may not be due to loss of beta-sheet structure alone. The loss of ellipticities at 218 nm is however, dose dependent. FIG. 69B shows the CD spectrum of 0.01, 0.1, 0.2, and 0.5 mg/ml of peptide DP-079 alone with positive ellipticities and maxima at approximately 225 nm and a minima at 200 nm indicating an inverted beta-sheet consistent with D-amino acid peptide, with beta-sheet structure. However, the maximum at 225 nm indicates a structure reminiscent of cross-linking or disulfide bonding protein, despite the lack of methionine or cystine. Also shown in FIG. 69B for comparison is the CD spectrum of 0.1 mg/ml of Aβ42 after 3 days of incubation (blue).

FIG. 70A shows the CD spectrum of 0.1 mg/ml of Aβ42 after 3 days of incubation (blue). Both the negative ellipticity at 218 nm and the positive ellipticity at 195 nm indicate the presence of beta-sheet structure in Aβ42. Also in FIG. 70A is the CD spectrum of 0.1 mg/ml of Aβ42 in the presence of 0.01, 0.1, 0.2, and 0.5 mg/ml of peptide DP-080 after 3 days of incubation (with correction for the spectrum of peptide DP-080). There is a dose-dependent loss of negative ellipticity at 218 nm indicating a dose-dependent loss of beta-sheet structure in Aβ42. FIG. 70B shows the CD spectrum of 0.01, 0.1, 0.2, and 0.5 mg/ml of peptide DP-080 alone with positive ellipticities and maxima at approximately 195 nm, indicating an inverted random coil consistent with a D-amino acid peptide with little beta-sheet structure. Also shown in FIG. 70B for comparison is the CD spectrum of 0.1 mg/ml of Aβ42 after 3 days of incubation (blue).

FIG. 71A shows the CD spectrum of 0.1 mg/ml of Aβ42 after 3 days of incubation (blue). Both the negative ellipticity at 218 nm and the positive ellipticity at 195 nm indicate the presence of beta-sheet structure in Aβ42. Also in FIG. 71A is the CD spectrum of 0.1 mg/ml of Aβ42 in the presence of 0.01, 0.1, 0.2, and 0.5 mg/ml of peptide LP-081 after 3 days of incubation (with correction for the spectrum of peptide LP-081). The significant gain of negative ellipticity at 218 nm indicates a gain of beta-sheet structure. However, no dose dependent effect is observed. FIG. 71A shows the CD spectrum of 0.01, 0.1, 0.2, and 0.5 mg/ml of peptide LP-081 alone with positive ellipticities and maxima at approximately 200 nm, indicating a random coil structure of L-peptide. Also shown in FIG. 71B for comparison is the CD spectrum of 0.1 mg/ml of Aβ42 after 3 days of incubation (blue). It should be noted that LP-081 is the beta-sheet breaker peptide previously reported (Permanne et al, *FASEB J.* Published online Apr. 10, 2002; Soto-Jara et al, U.S. Pat. No. 5,948,763 Sep. 7, 1999; Soto-Jara, PCT WO 01/34631 A2 May 17, 2001). FIG. 72 shows the CD spectra and represents a summary of the data of Aβ42 in the presence of increasing amounts of DP-065 to DP-080, and LP-081, as discussed in detail above.

EXAMPLE 9

Stability of Peptides in Human Serum

A desirable characteristic of any potential therapeutic or drug candidate is the ability to resist degradation by enzymes in the blood, to have enough time reach its target. One of the in vitro assays used to determine the stability of peptides in Sequence Group A, B, or C is by incubating these peptides in human serum, and determining the level of the intact peptides (and possible degradation) at various time points. Fifty ul aliquots of various peptides were added to 700 ul of human serum (in triplicate samples). One hundred ul aliquots were then taken at 0, 2, 4, 6, 24, and 32 hrs, followed immediately with the addition of 200 ul of ethanol (or 20 ul of trifluoroacetic acid or 300 ul methanol) and centrifuged at 14,000×g (Eppendorf) for 10 minutes. The level of intact peptides in the supernatant was then determined using LC/MS (Agilent HPLC/MS SL 1100 Series). MS monitored each peptide as it came out of the HPLC using SIM mode positive ion monitoring at masses corresponding to single, double and triple charge peptide ions. The peak in the resulting ion chromatograms were integrated to obtain total ion abundance in each sample. The average of triplicate determinations of total ion abundance for each serum incubation time-point was then plotted as a function of serum incubation time. Most of the peptide degrading enzymes in the body recognizes natural peptides made up of all L-amino acids. As the peptides consist of D-amino acids, their degradation in biological fluids will likely be retarded, as demonstrated in this Example and the following figures.

Figure 76:
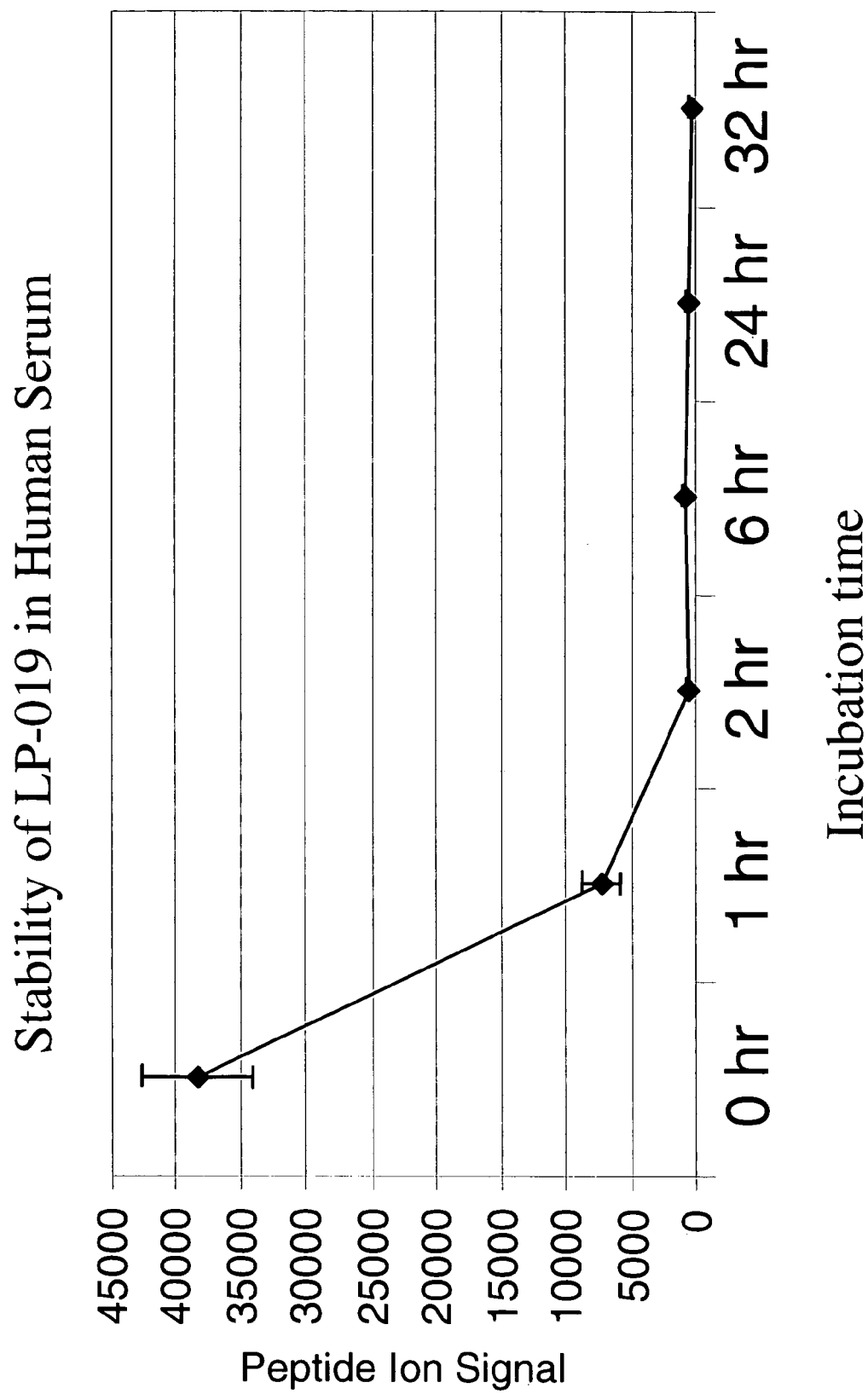
FIG. 76 is a graph demonstrating the lack of stability of peptide LP-019 (negative control) in human serum within a 32-hour incubation period, as assessed by LC/MS.

FIG. 76 shows the level of peptide LP-019 in human serum as a function of time over a 32 hour incubation period The peptide LP-019 consists of all L-amino acids, and as shown in FIG. 76, it is rapidly degraded in serum in less than 1 hr.

Figure 77:
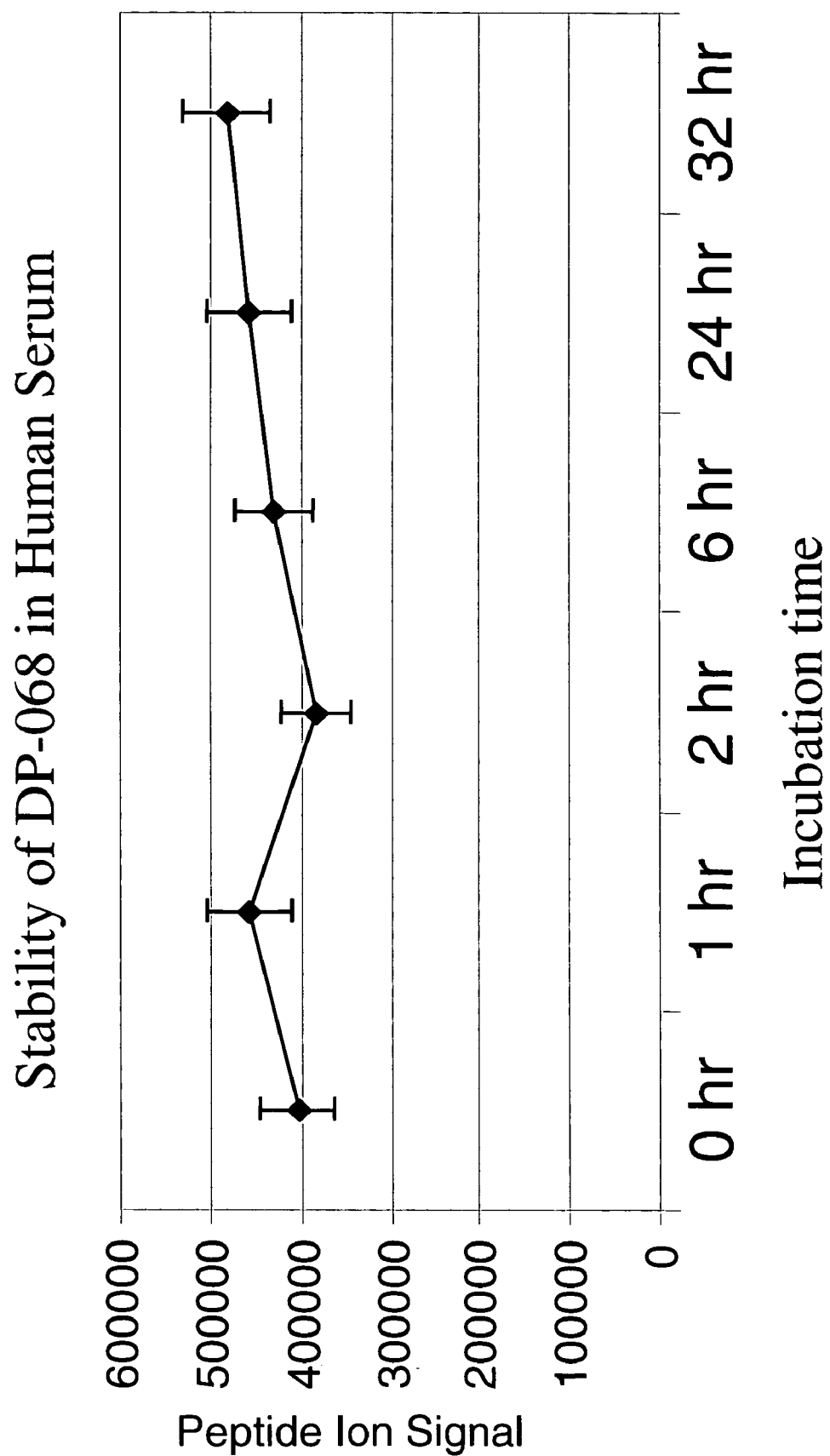
FIG. 77 is a graph demonstrating the stability of peptide DP-068 in human serum within a 32-hour incubation period, as assessed by LC/MS.

FIG. 77 shows the level of peptide DP-068 in human serum as a function of time over a 32 hour incubation period The peptide DP-068 consists of all D-amino acids, and as shown in FIG. 77, it is resistant to degradation in the serum up to and including, 32 hrs.

Figure 78:
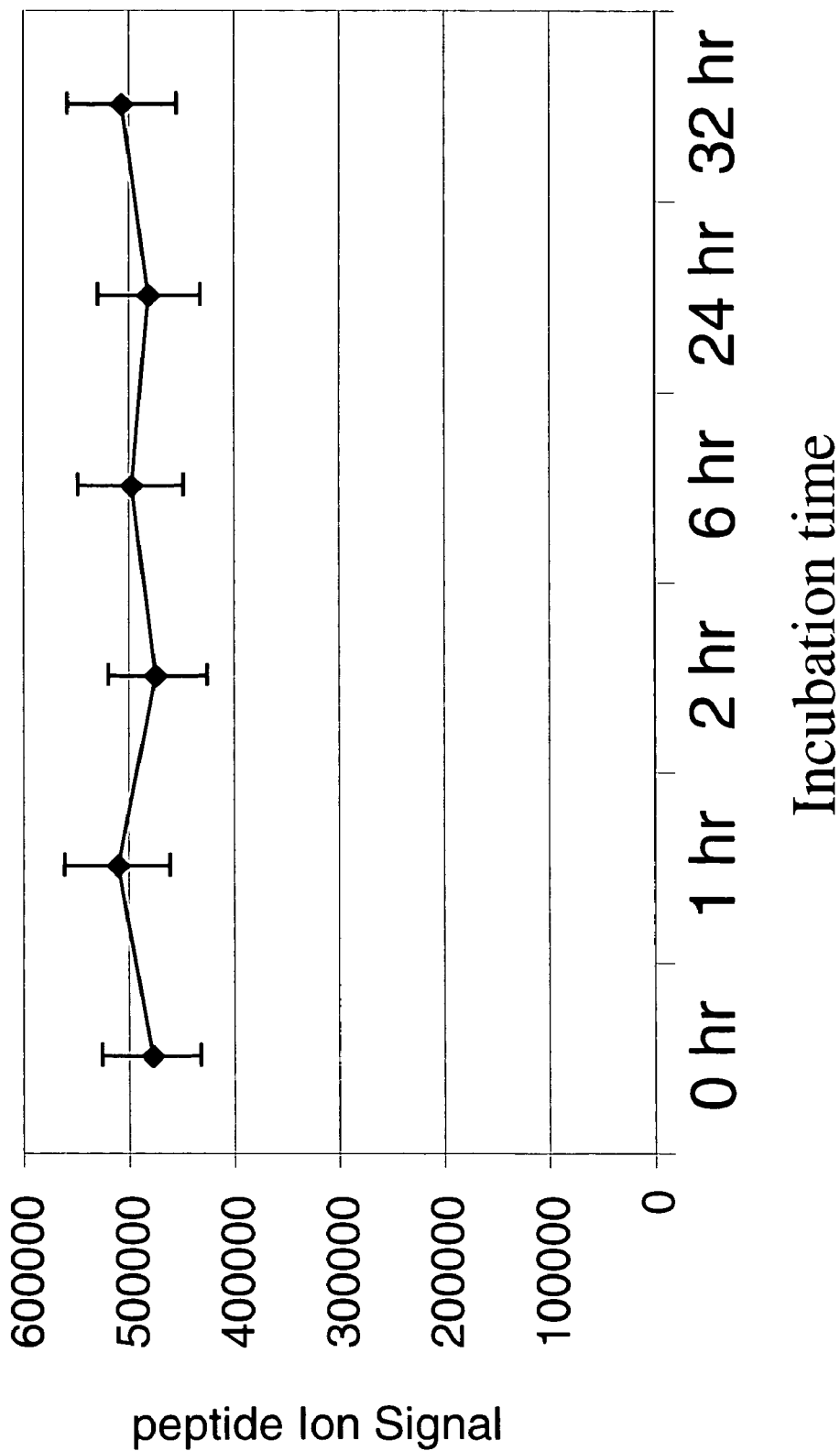
FIG. 78 is a graph demonstrating the stability of peptide DP-069 in human serum within a 32-hour incubation period, as assessed by LC/MS.

FIG. 78 shows the level of peptide DP-069 in human serum as a function of time over a 32 hour incubation period The peptide DP-069 consists of all D-amino acids, and as shown in FIG. 78, it is resistant to degradation in the serum up to and including, 32 hrs.

Figure 79:
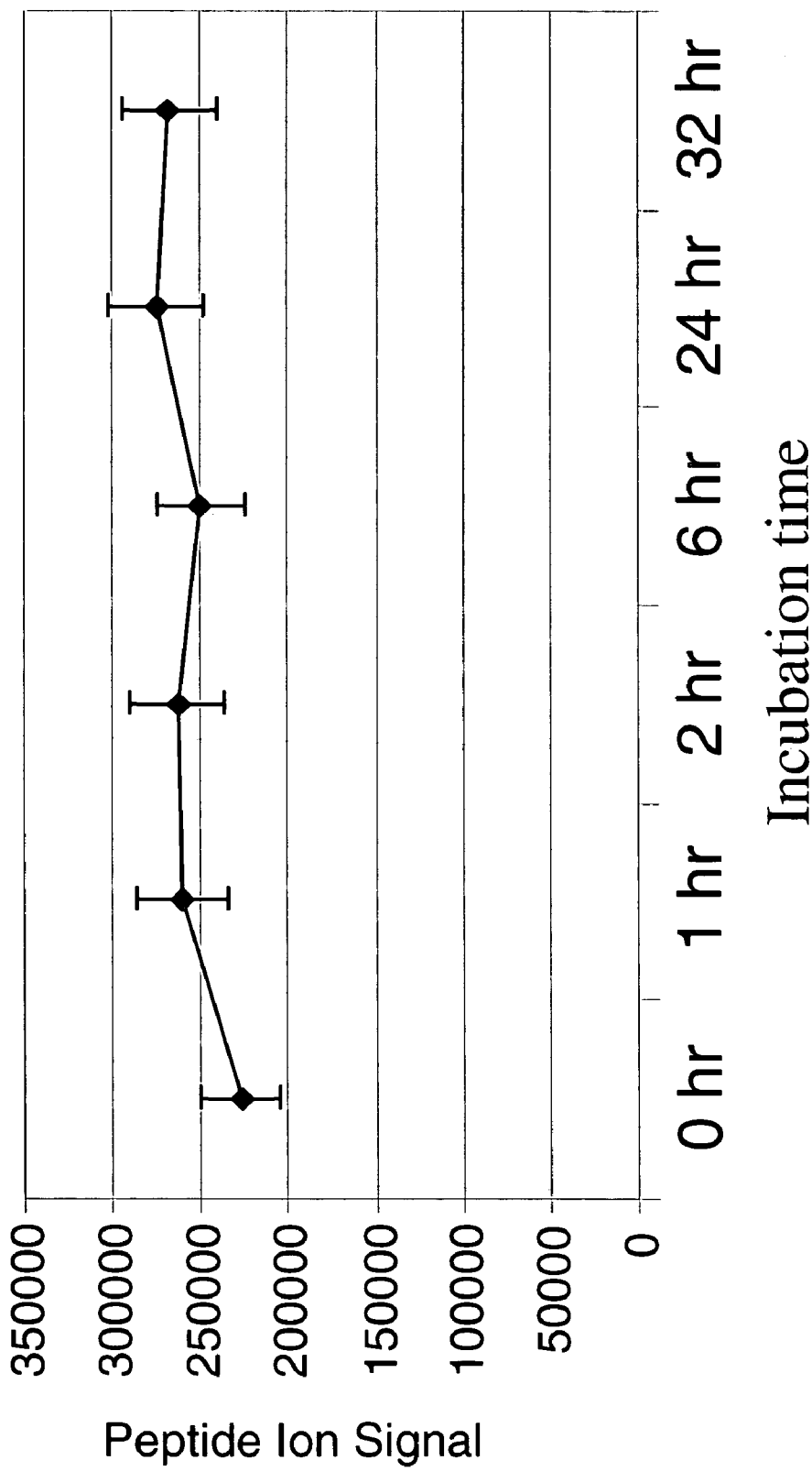
FIG. 79 is a graph demonstrating the stability of peptide DP-074 in human serum within a 32-hour incubation period, as assessed by LC/MS.

FIG. 79 shows the level of peptide DP-074 in human serum as a function of time over a 32 hour incubation period The peptide DP-074 consists of all D-amino acids, and as shown in FIG. 79, it is resistant to degradation in the serum up to and including, 32 hrs.

Figure 80:
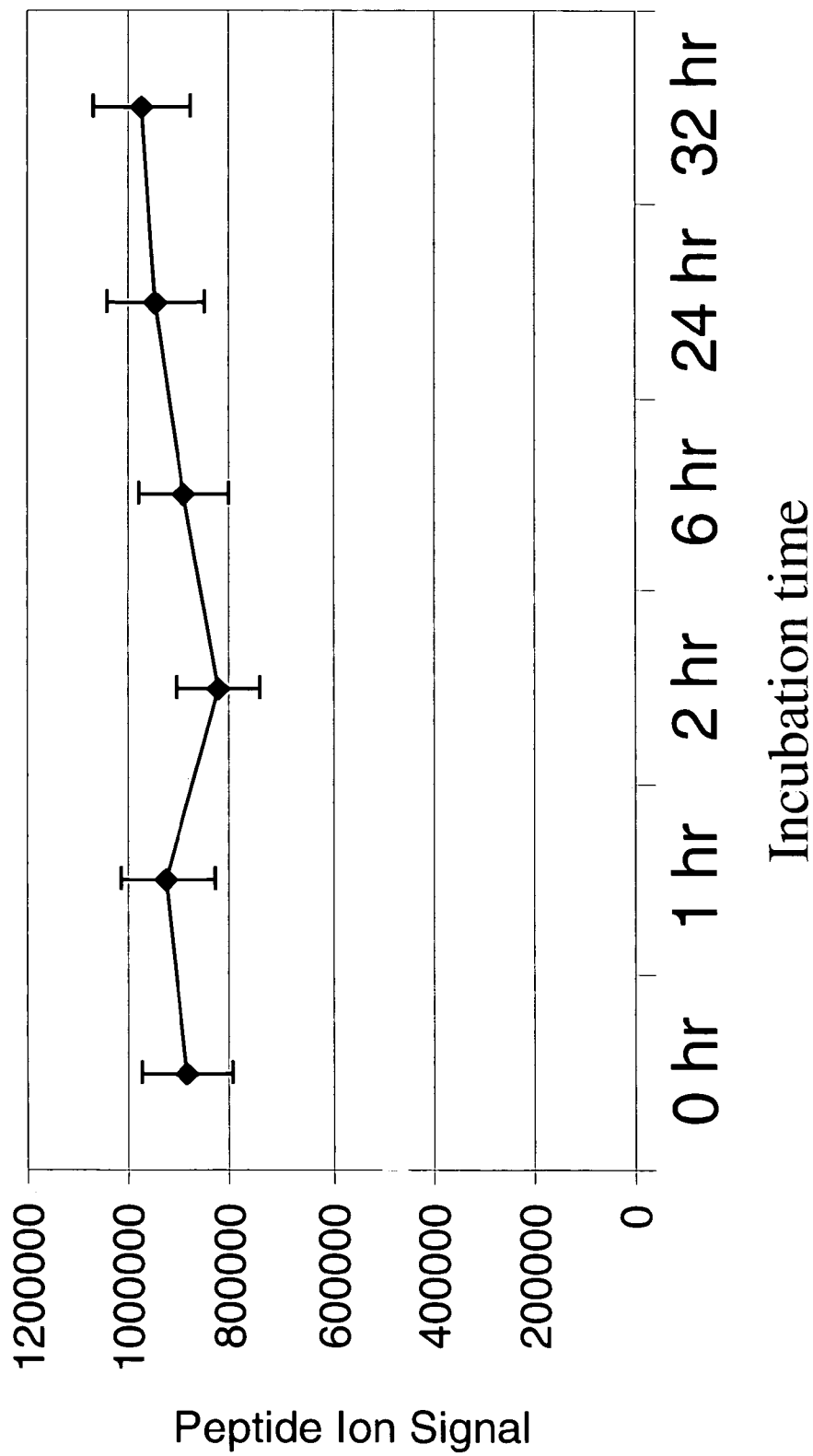
FIG. 80 is a graph demonstrating the stability of peptide DP-076 in human serum within a 32-hour incubation period, as assessed by LC/MS.

FIG. 80 shows the level of peptide DP-076 in human serum as a function of time over a 32 hour incubation period The peptide DP-076 consists of all D-amino acids, and as shown in FIG. 80, it is resistant to degradation in the serum up to and including, 32 hrs.

Figure 81:
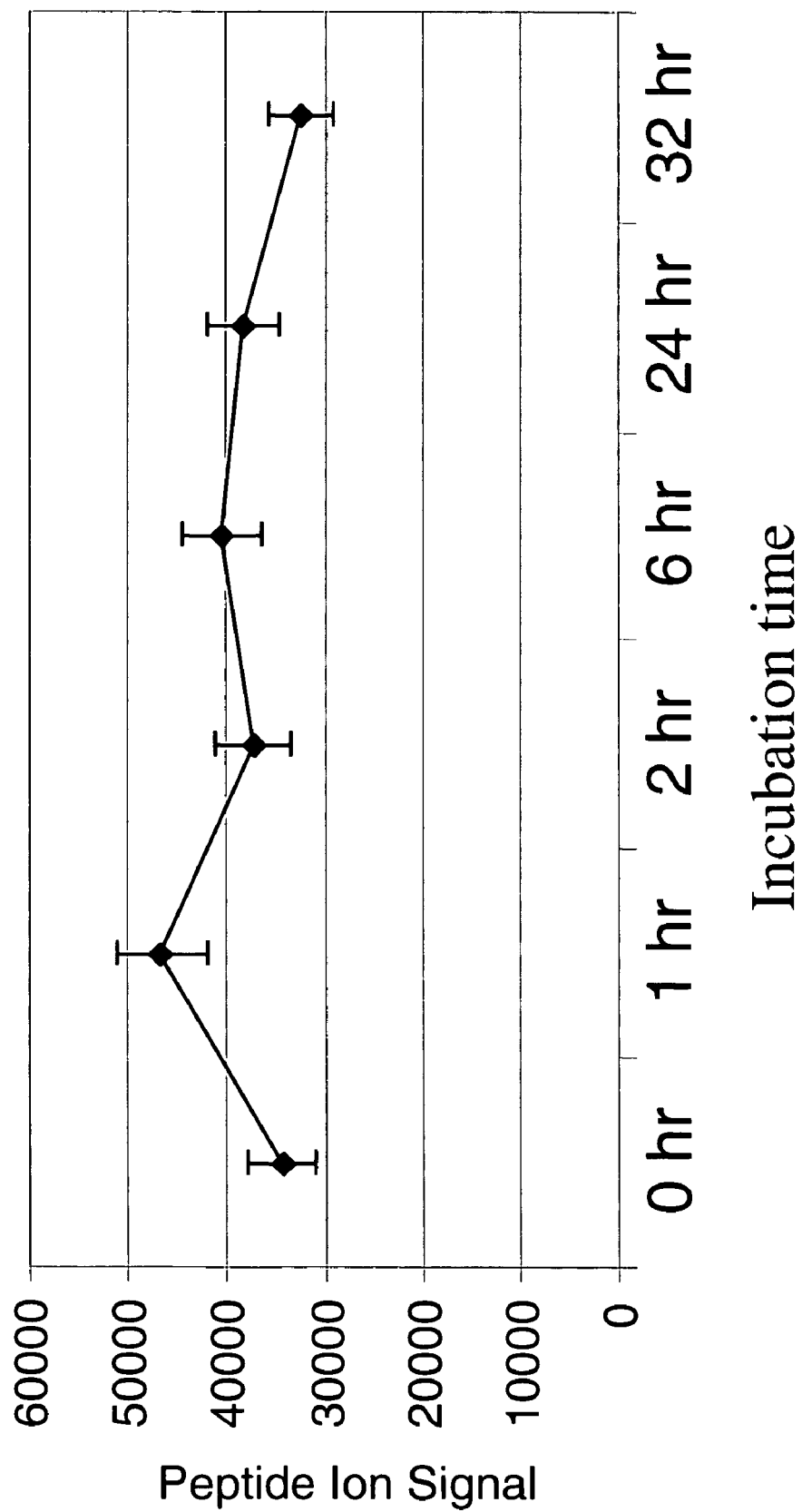
FIG. 81 is a graph demonstrating the stability of peptide DP-080 in human serum within a 32-hour incubation period, as assessed by LC/MS.

FIG. 81 shows the level of peptide DP-080 in human serum as a function of time over a 32 hour incubation period The peptide DP-080 consists of all D-amino acids, and as shown in FIG. 81, it is resistant to degradation in the serum up to and including, 32 hours.

Further data are illustrated as follows:

FIGS. 1*a-k* are peptide sequences and drawings for 5-13 mer peptides DP1-18, LP19-25, DP 26-80 and LP81.

FIG. 2 is a graph showing an ordered summary comparison of the effect of various 12-13mer peptides on beta-sheet secondary structure of 25 μM Aβ42 amyloid fibrils as assessed by circular dichroism (CD) spectropolarimetry. Shown is the percent disruption of Aβ42 fibrils as assessed by loss of ellipticity at 218 nm, representing the signal that is inversely related to beta-sheet secondary structure. FIG. 3 is a graph showing an ordered summary comparison of the effect of 12-13mer peptides on beta-sheet secondary structure of 25 uM Aβ42 amyloid fibrils as assessed by Thioflavin T fluorometry. Shown is the percent disruption of Aβ42 fibrils by various 12-13mer peptides at an Aβ42:12-13mer peptide weight ratio of 1:2.

Figure 4:
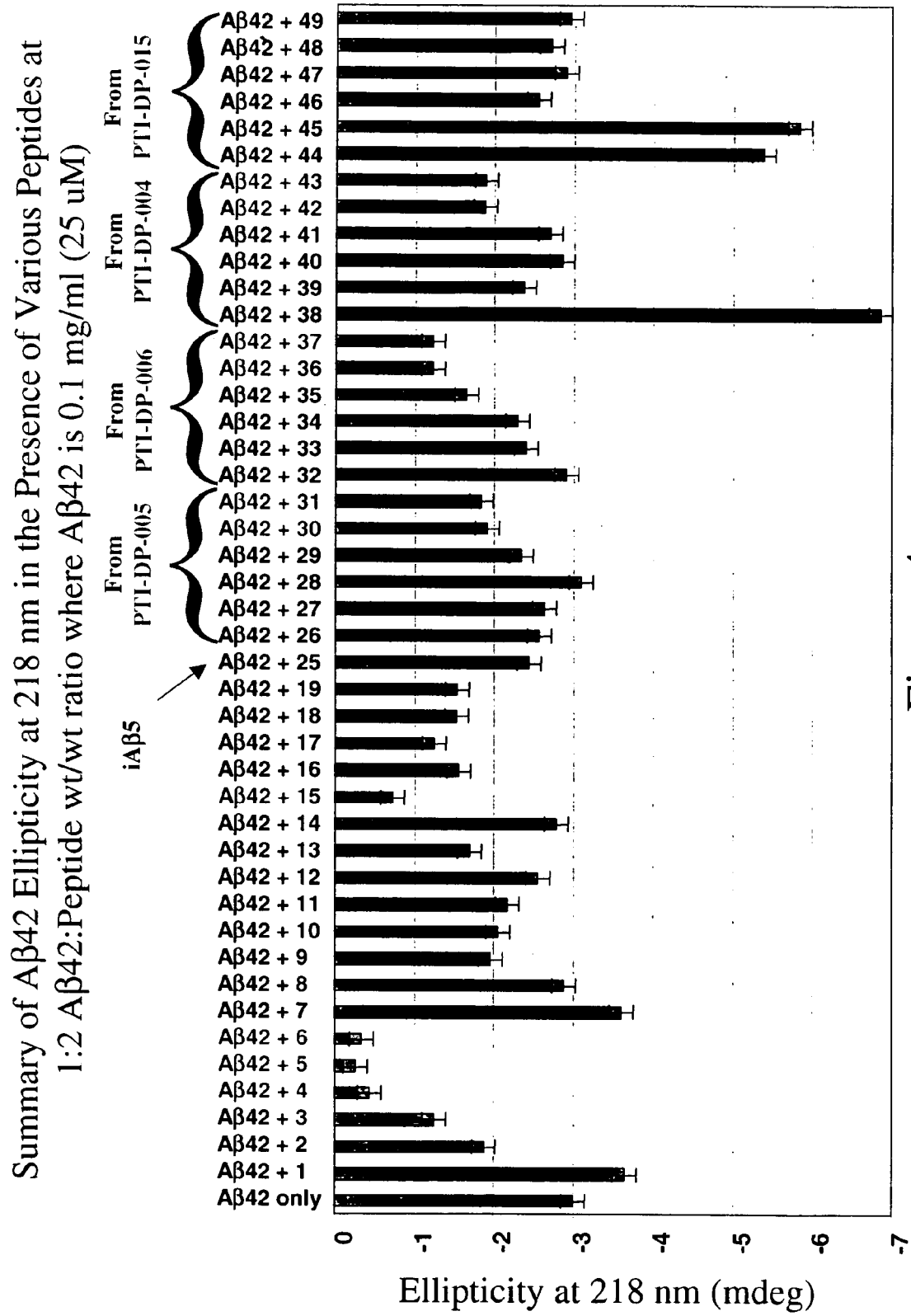
FIG. 4 is a summary of CD spectroscopy results of all peptides up to DP-049.
Figure 5:
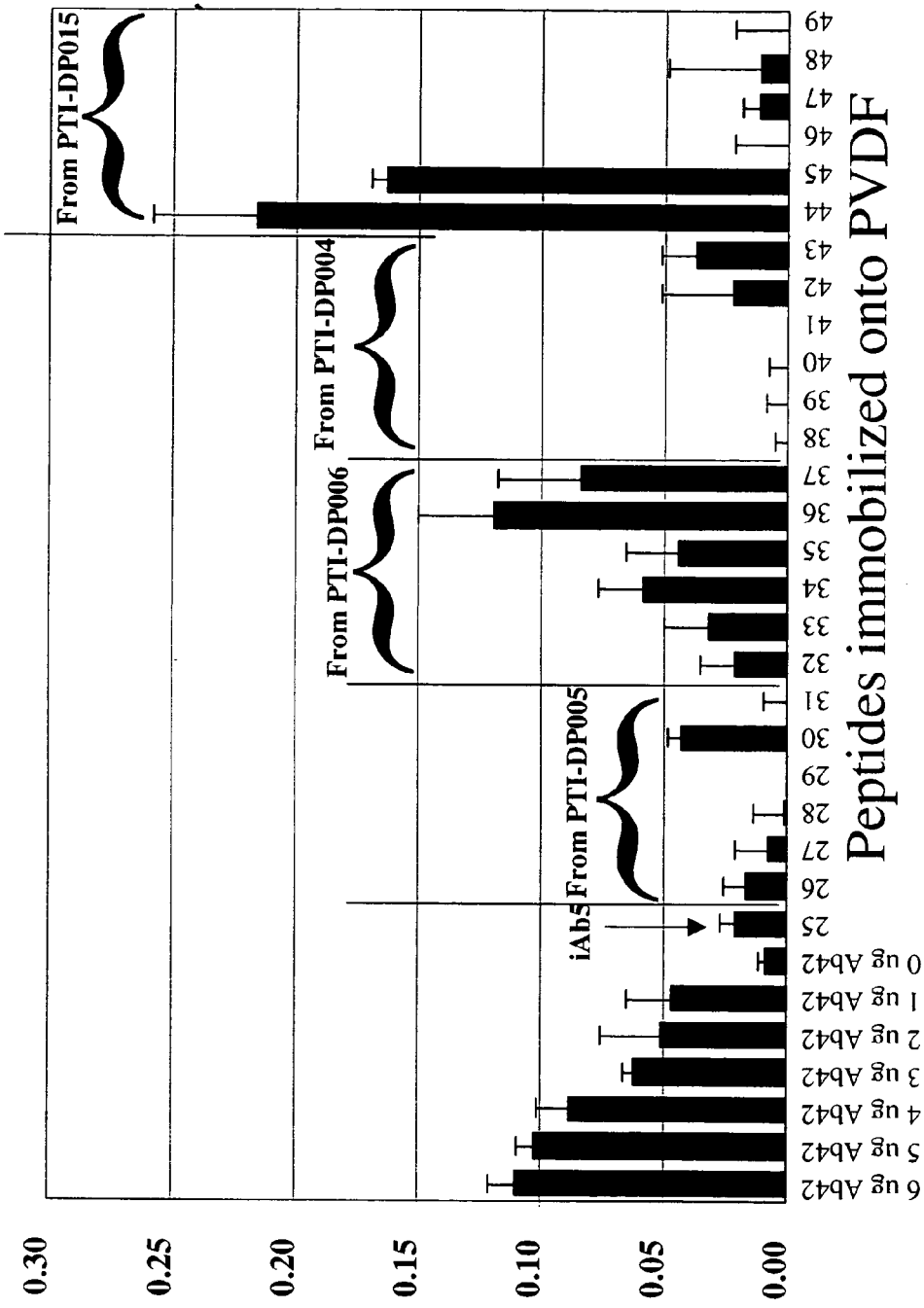
FIG. 5 is a summary of Ab42 binding for peptides LP-025 and DP-026-049.
Figure 6:
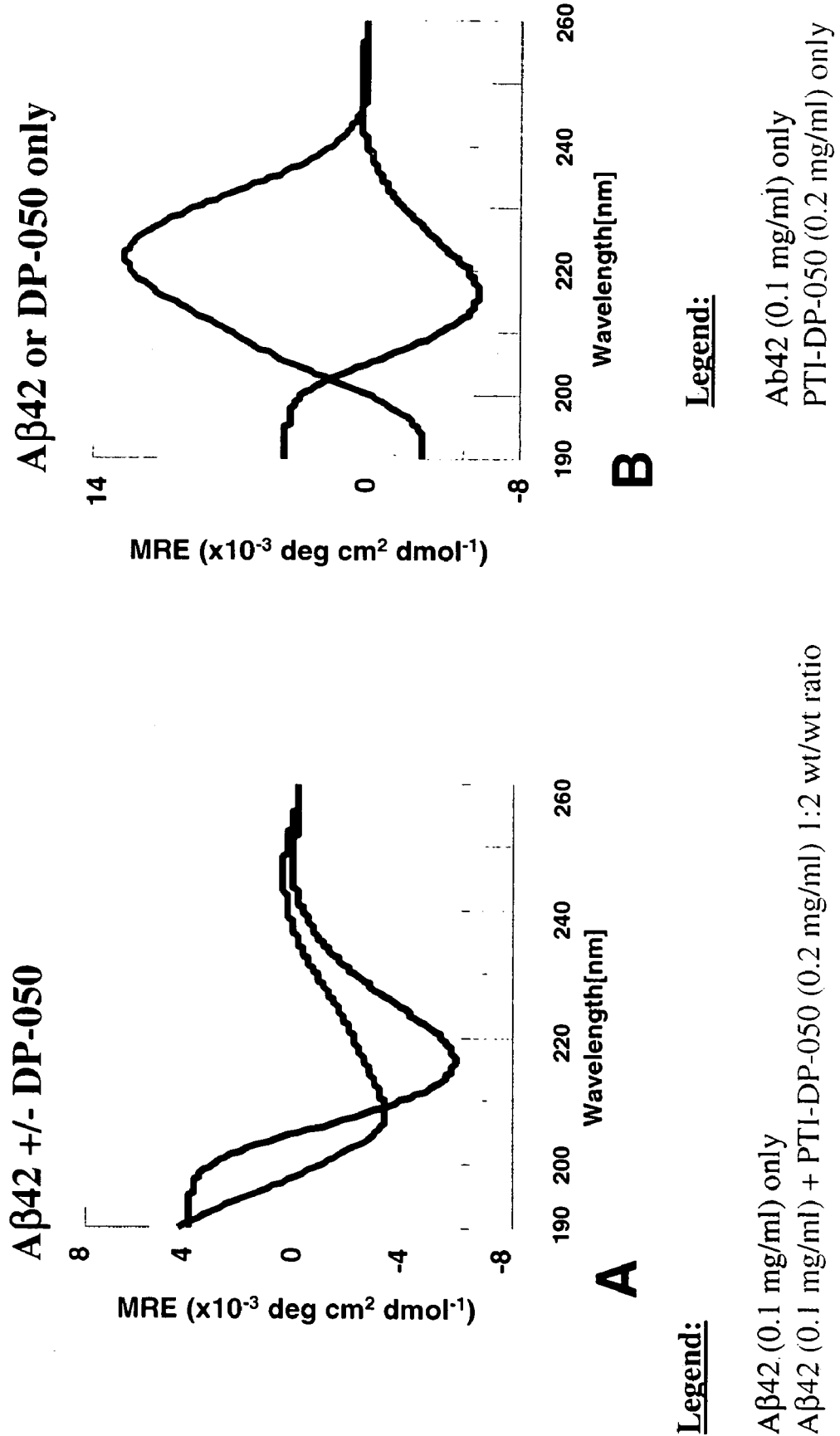
Figure 7:
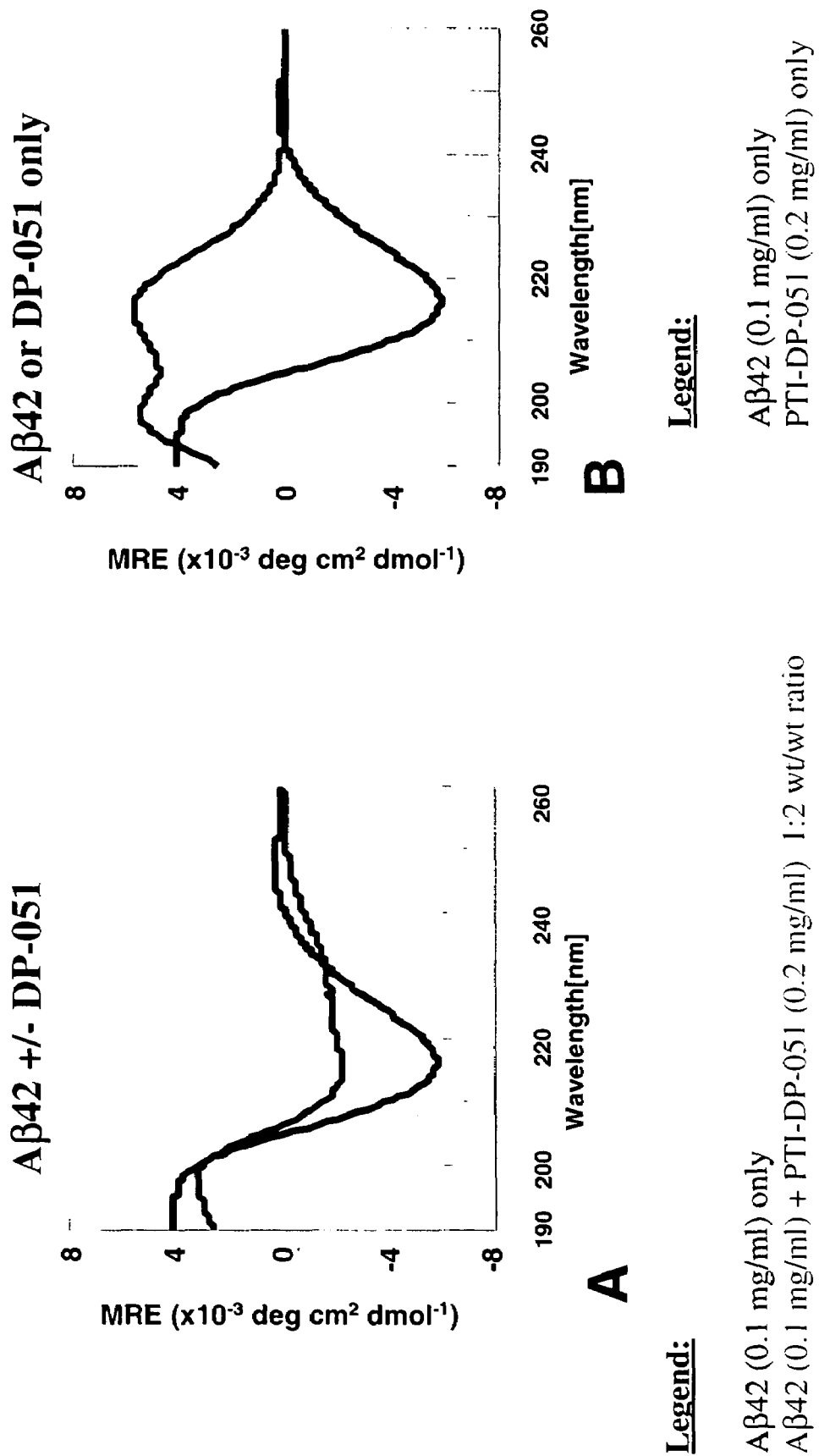
Figure 8:
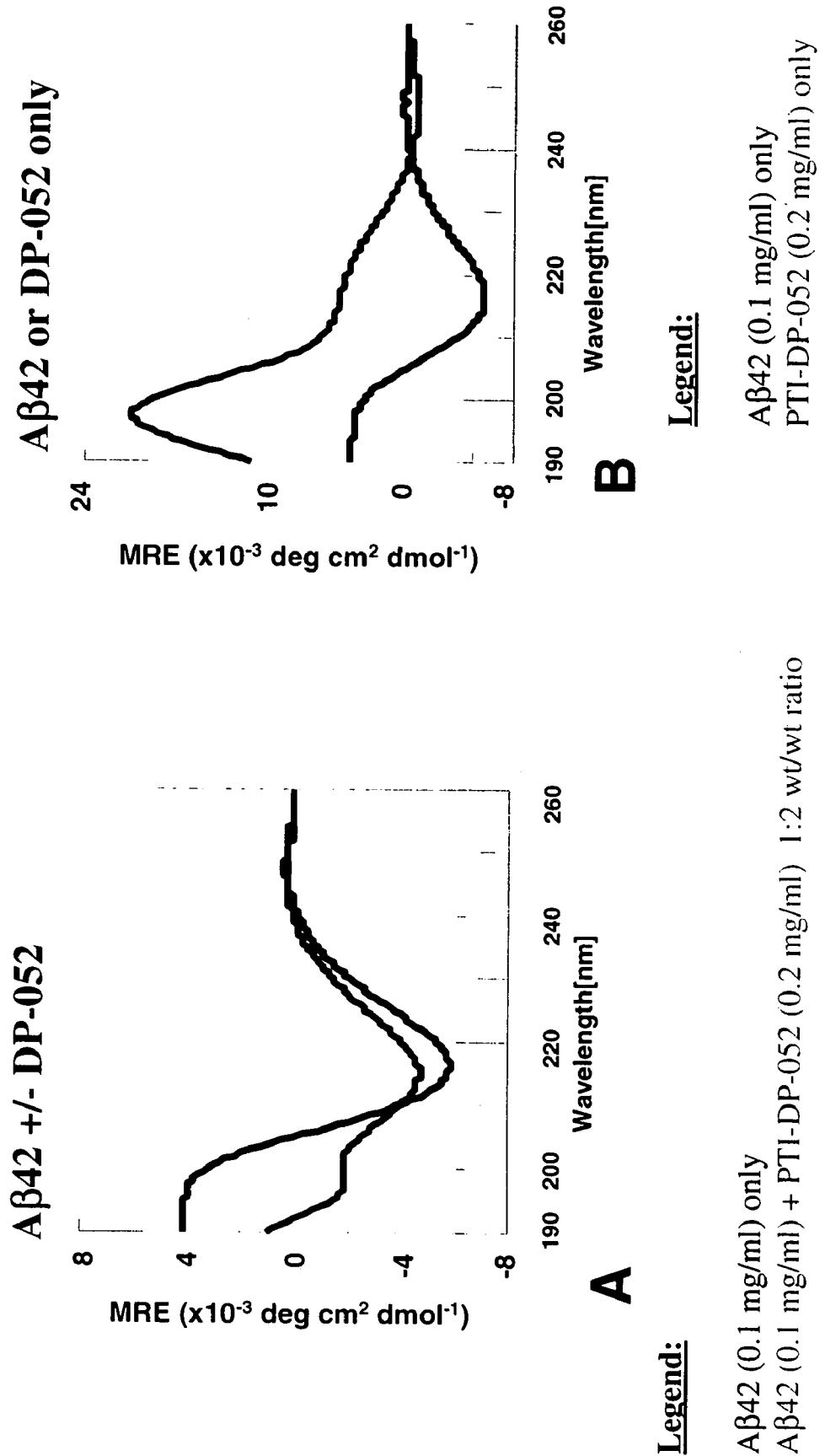
Figure 9:
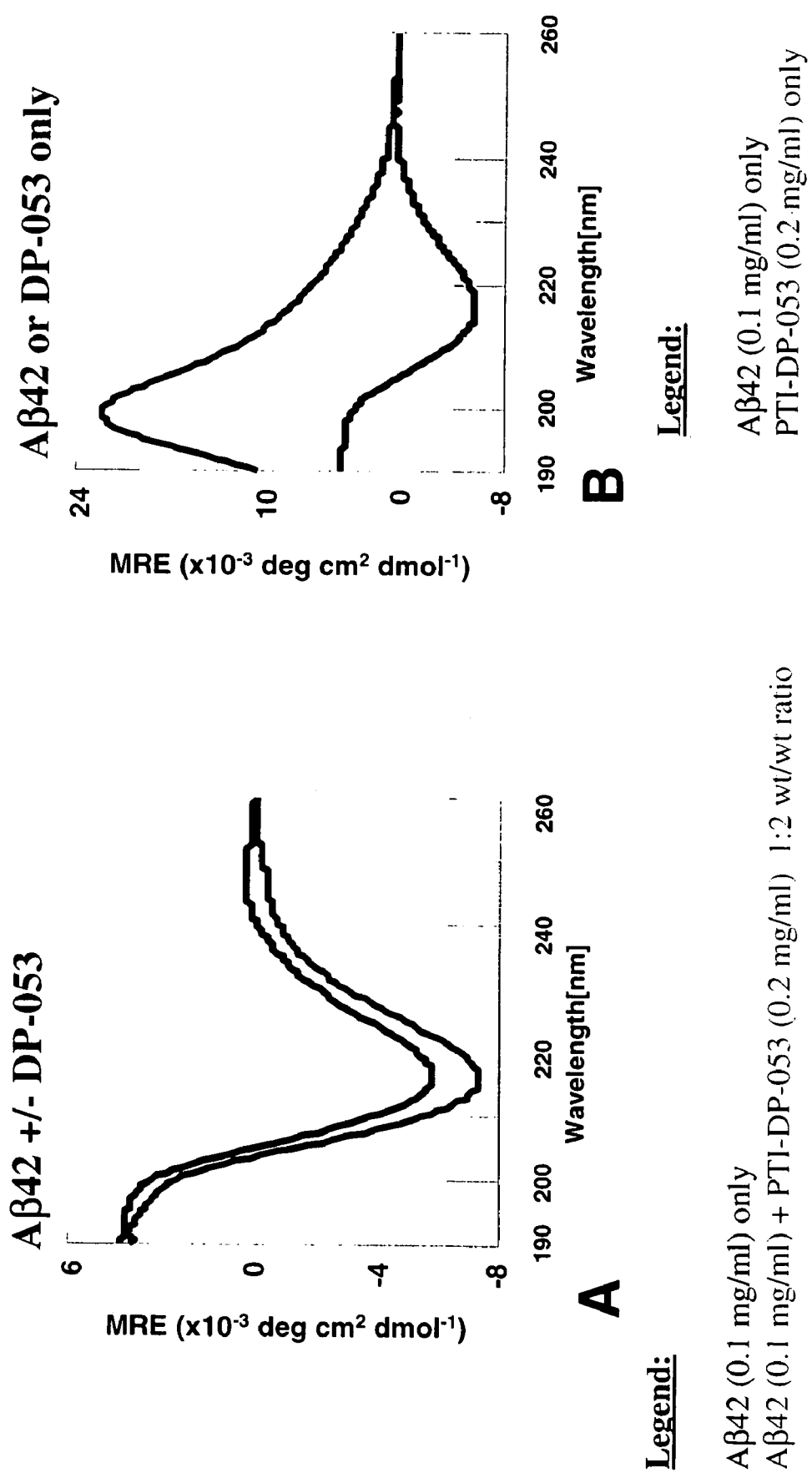
Figure 10:
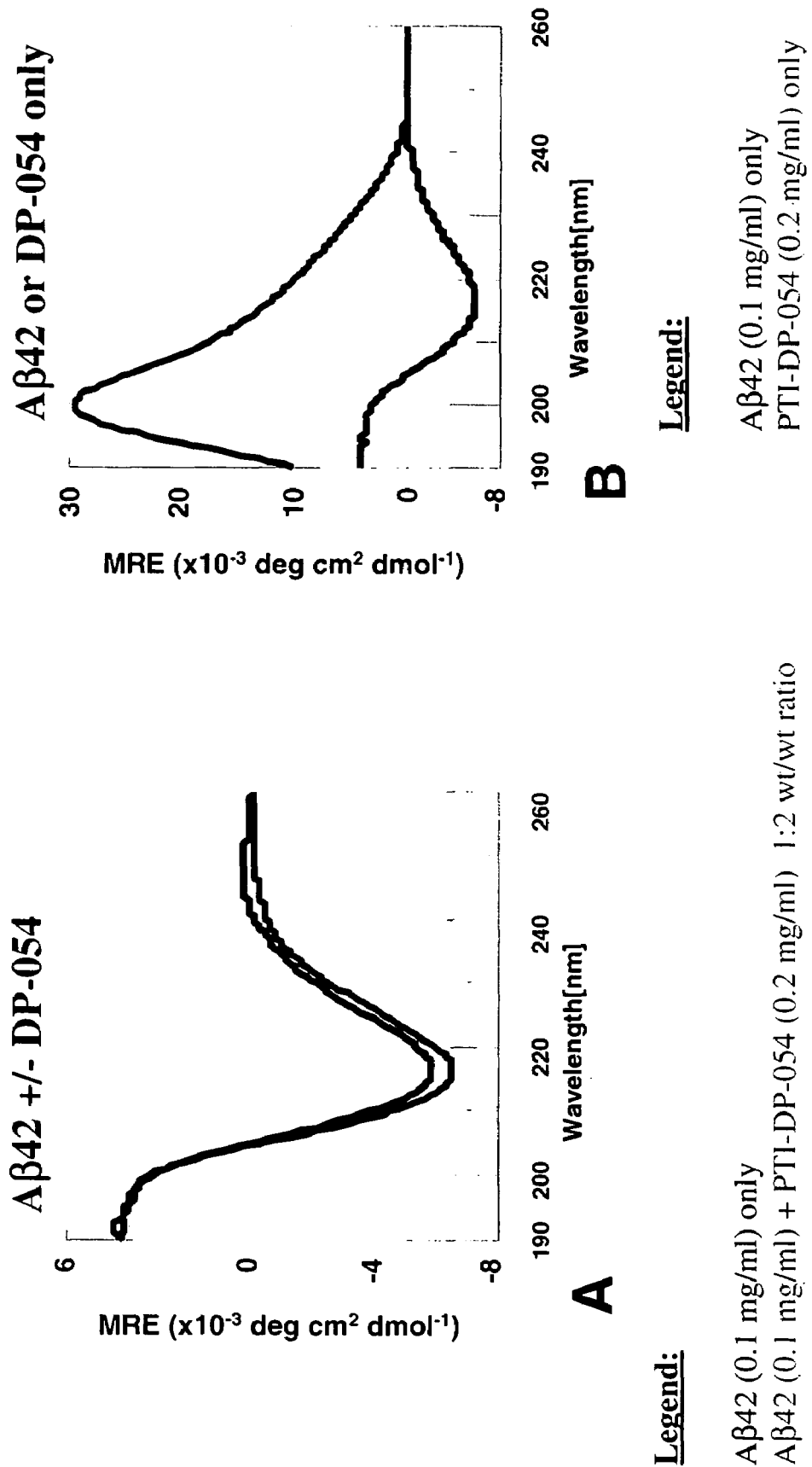
Figure 11:
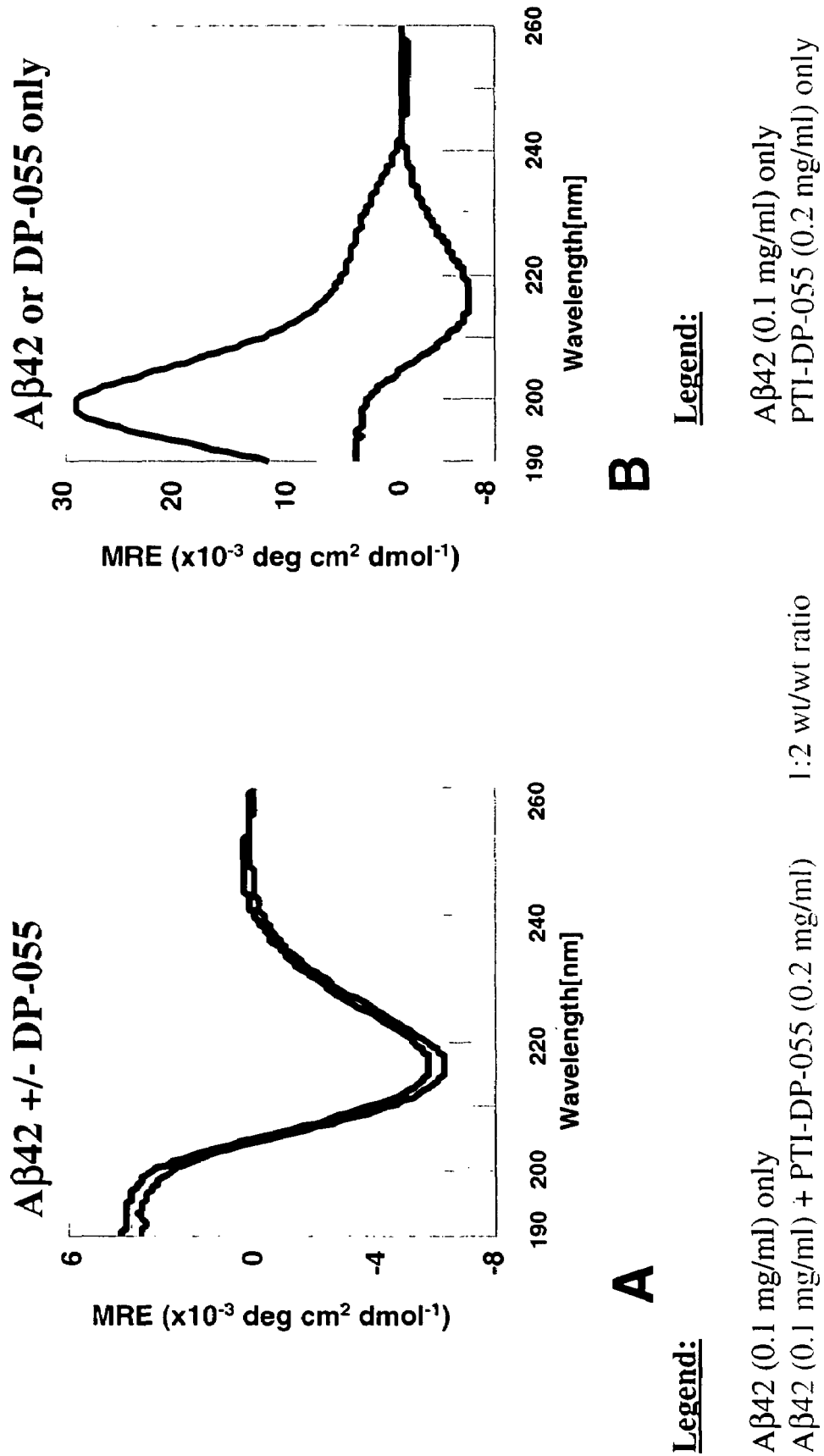
Figure 13:
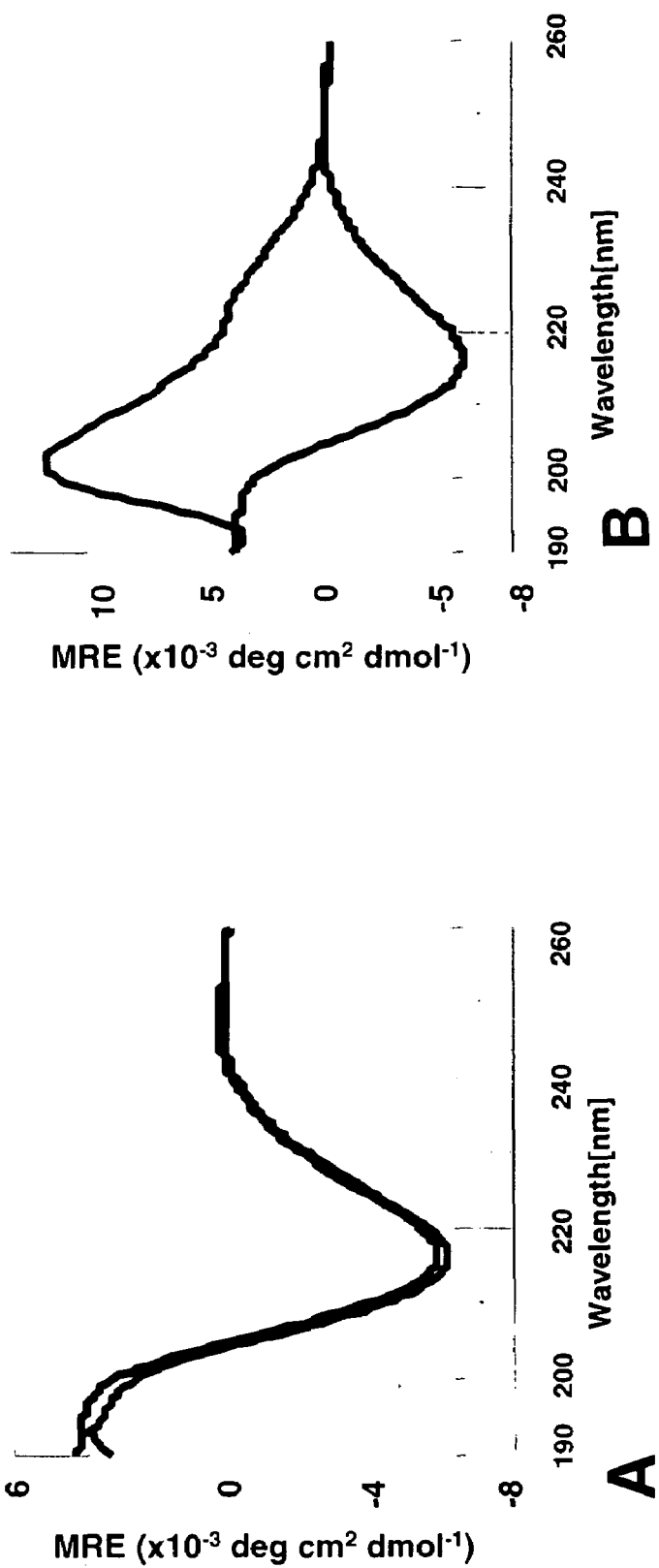
Figure 14:
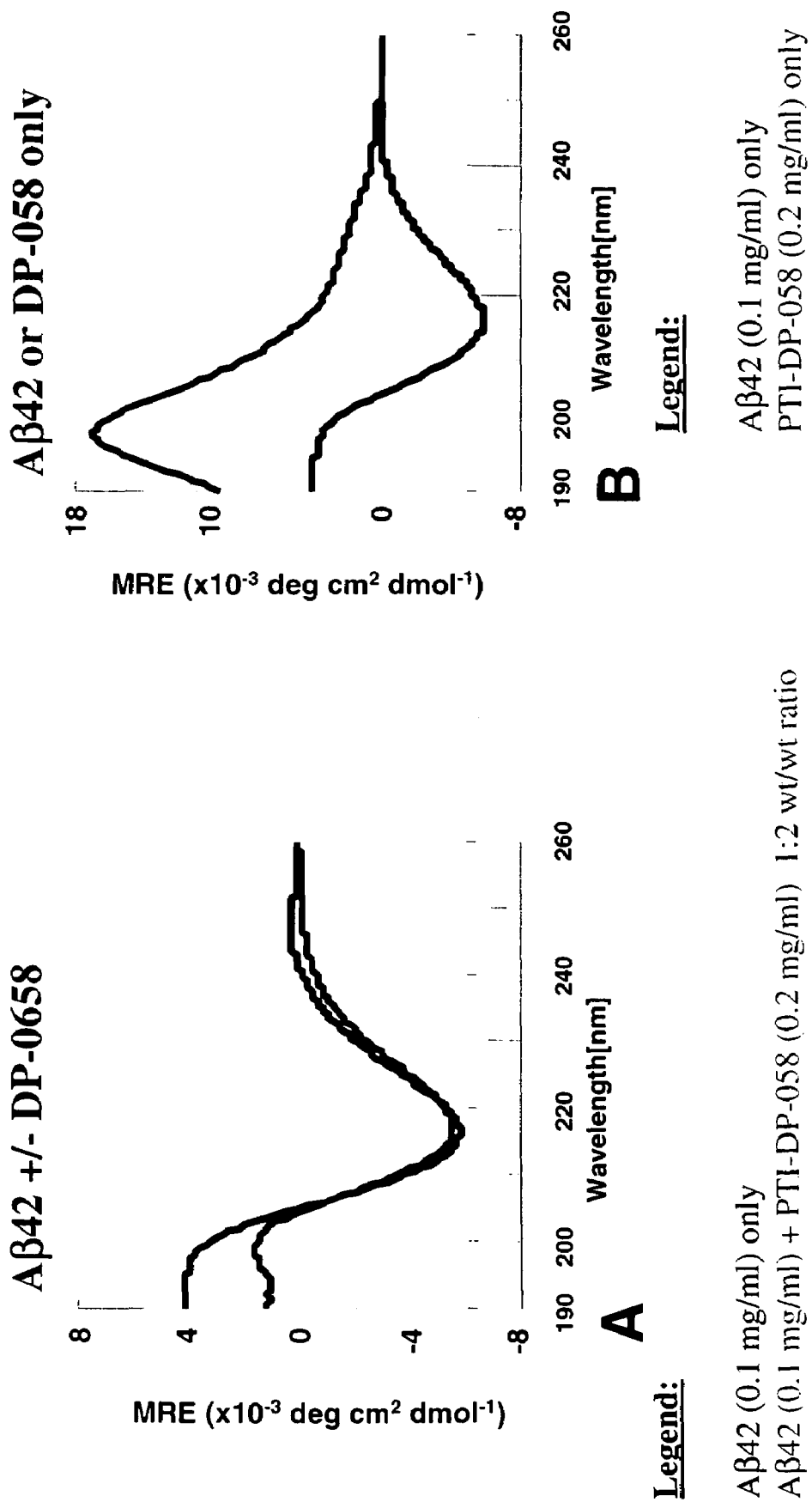
Figure 15:
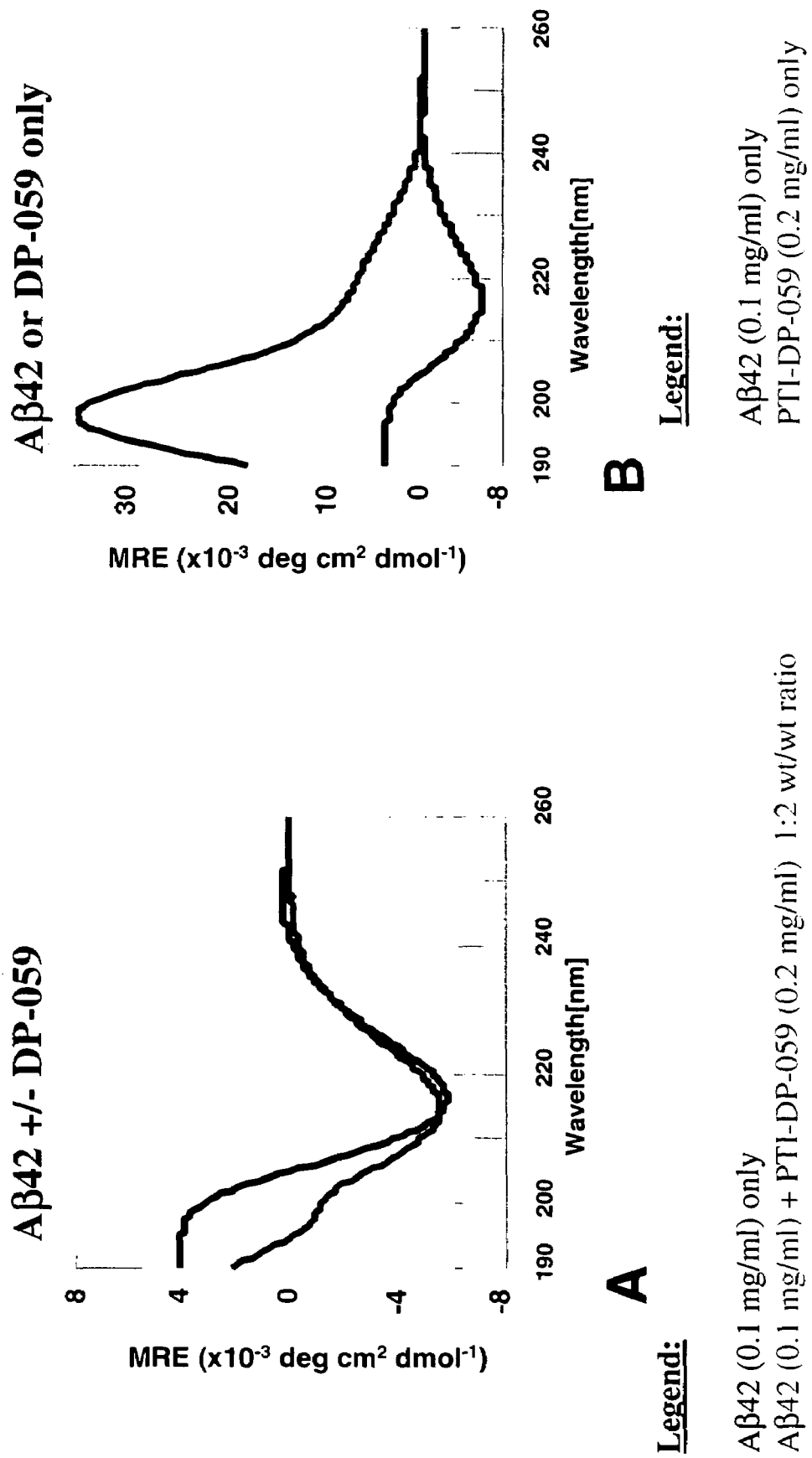
Figure 16:
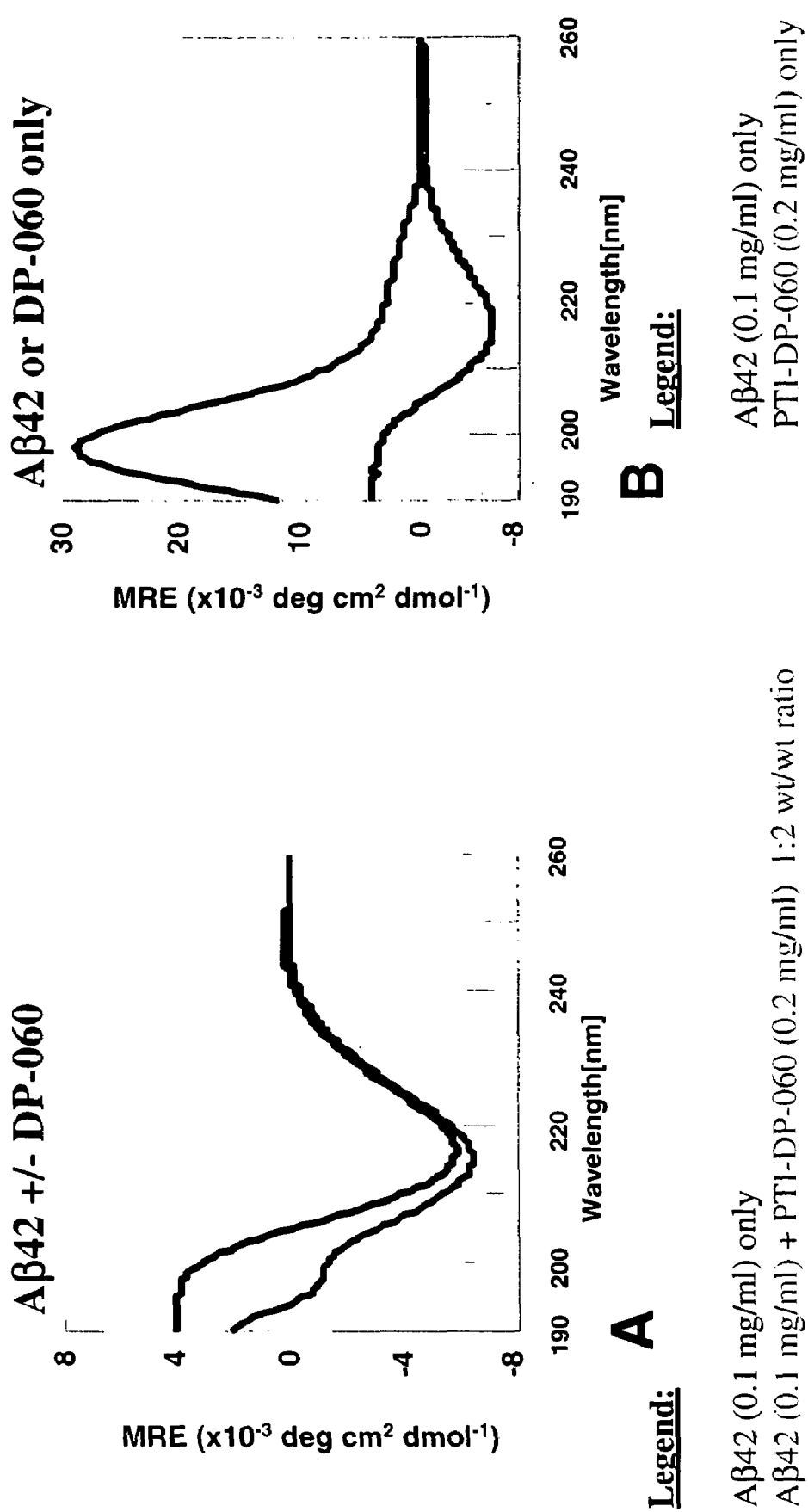
Figure 18:
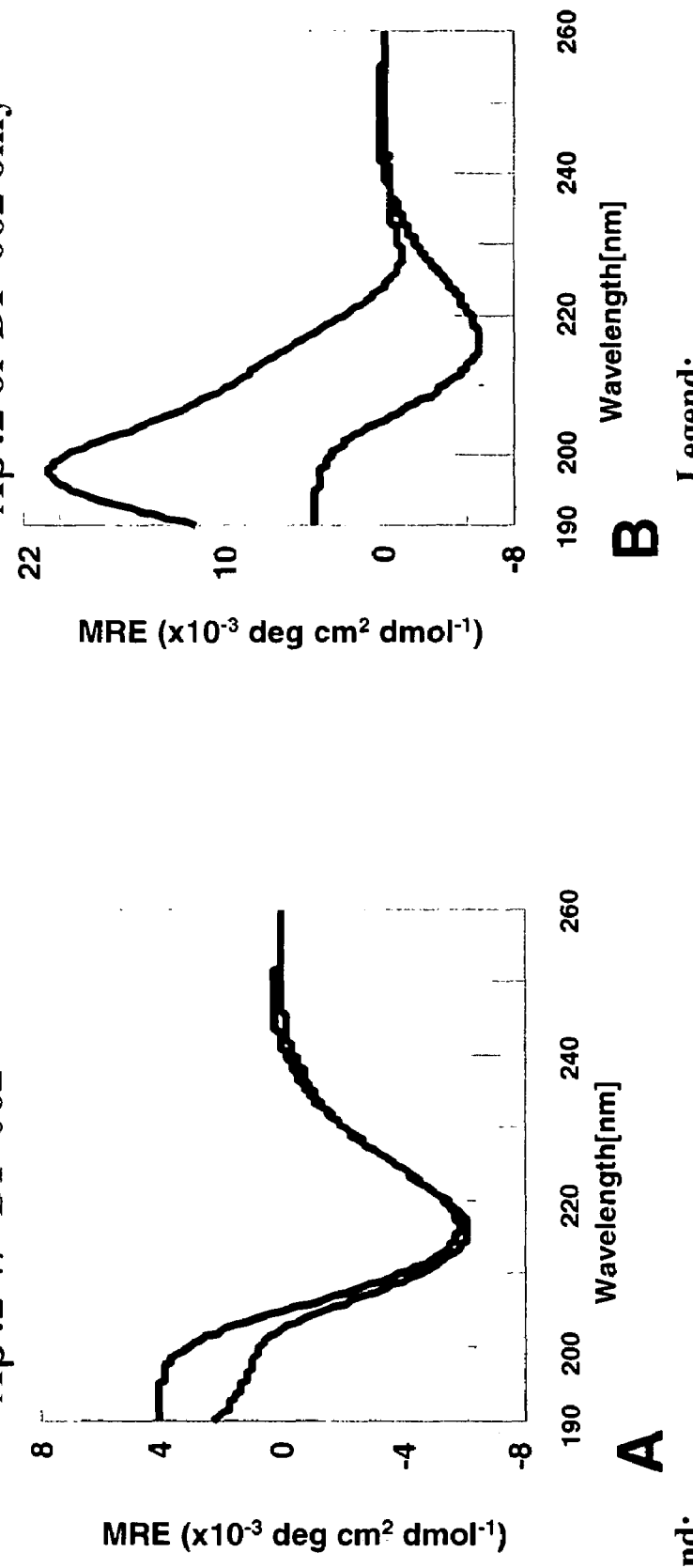
Figure 19:
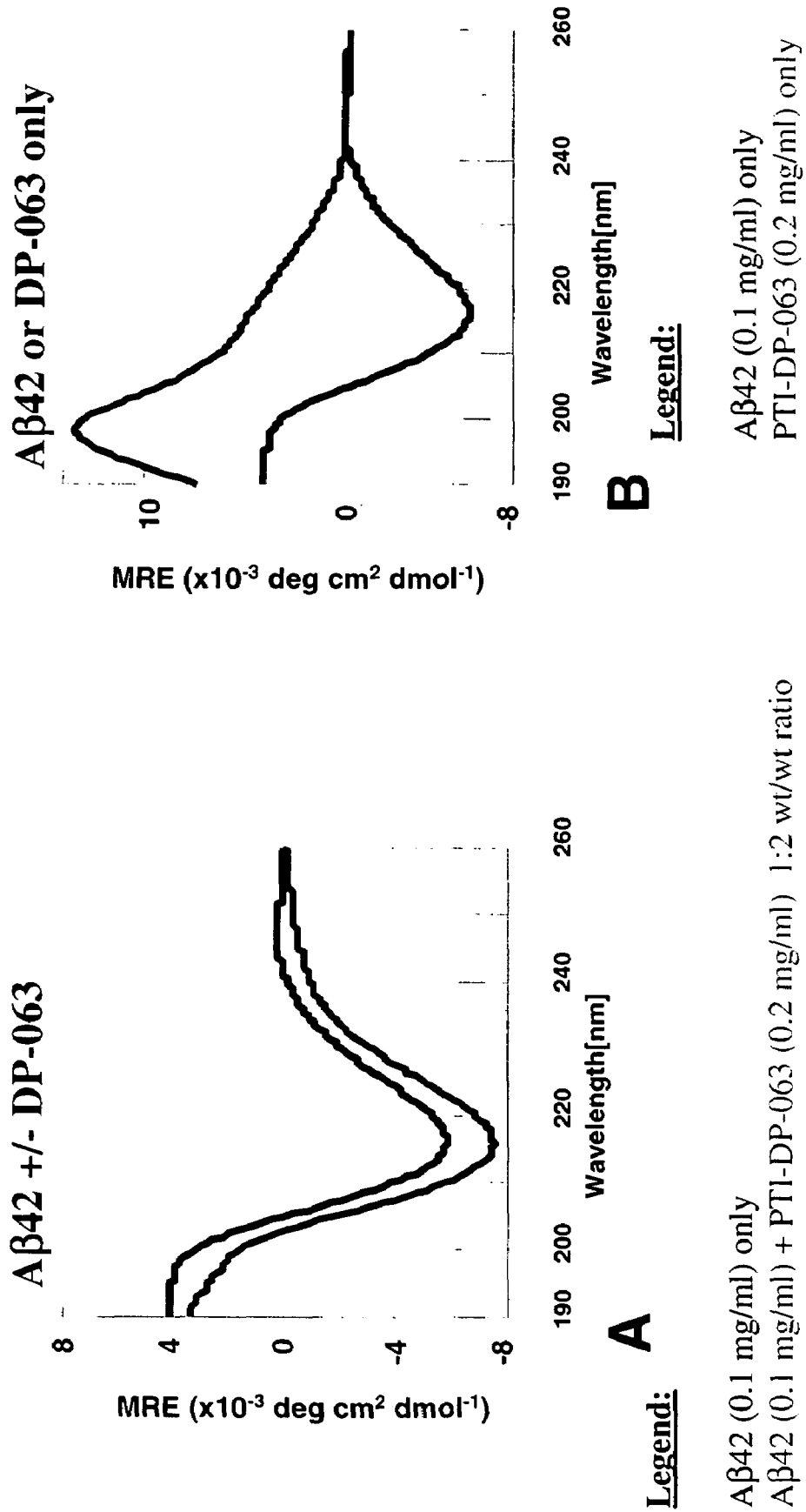
Figure 21:
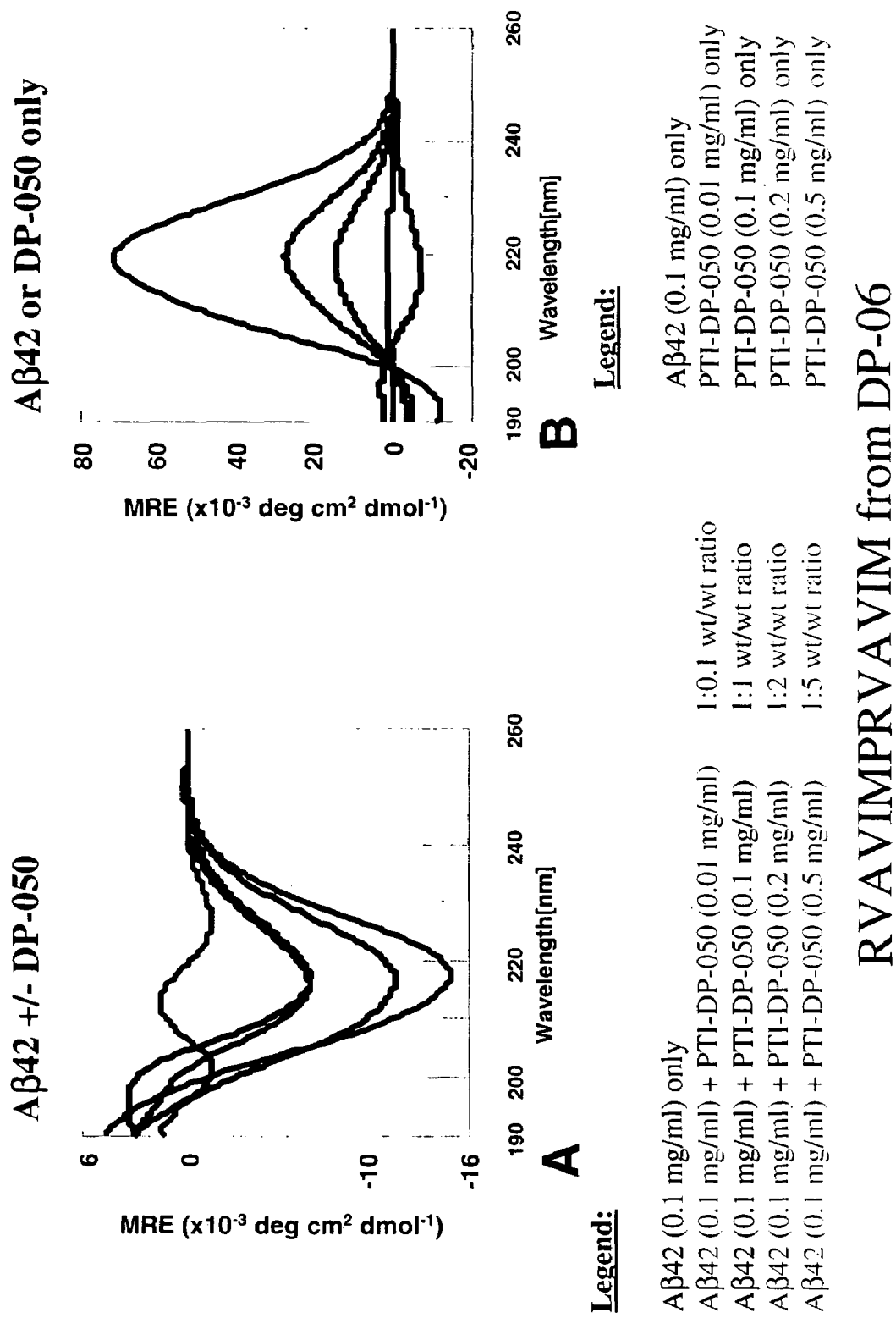
FIGS. 21-30 are CD spectra of Ab42 plus DP-50, 51, 52, 56-61 and DP-064, respectively, at (1:0.1, 1:1, 1:2, 1:5).
Figure 22:
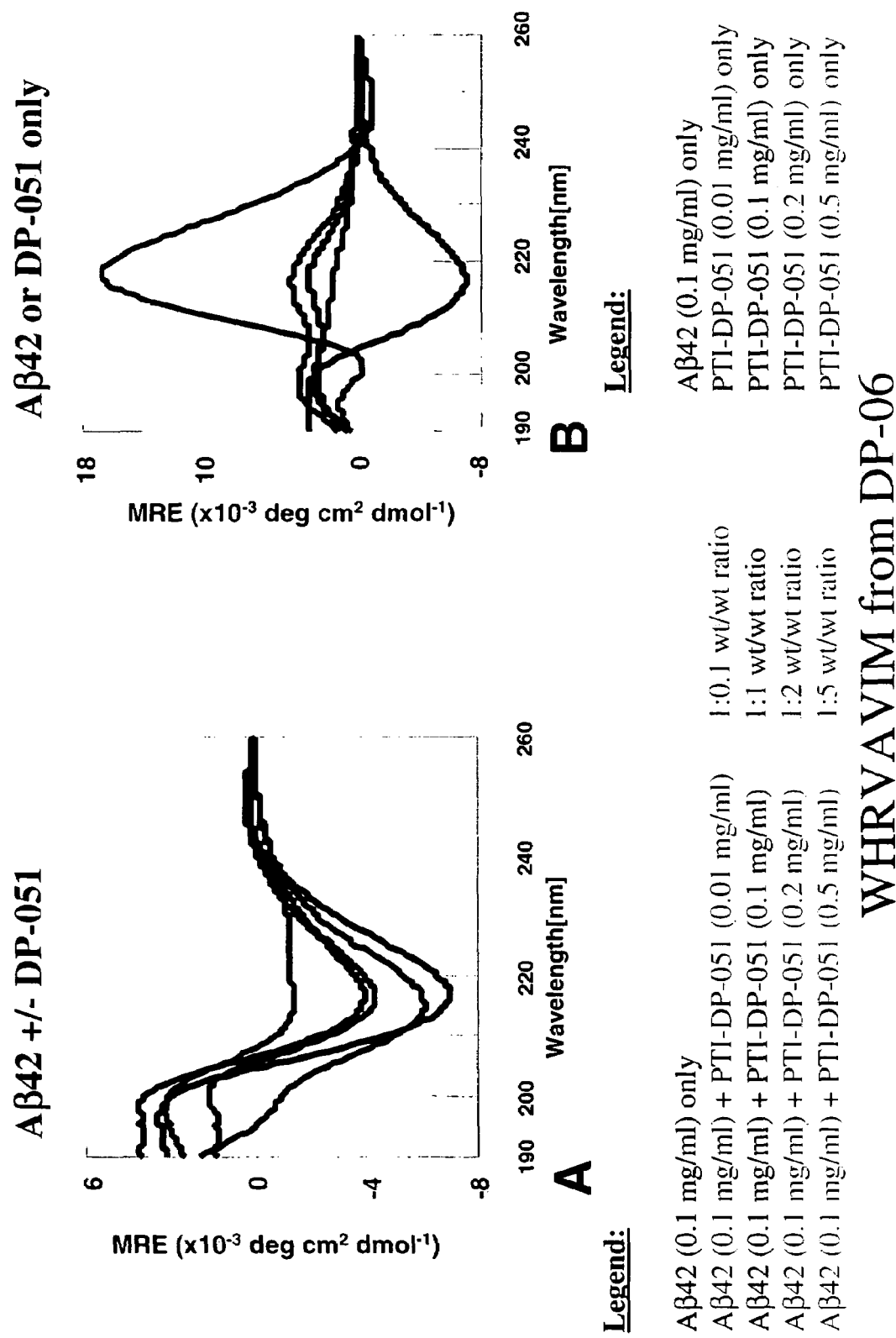
Figure 23:
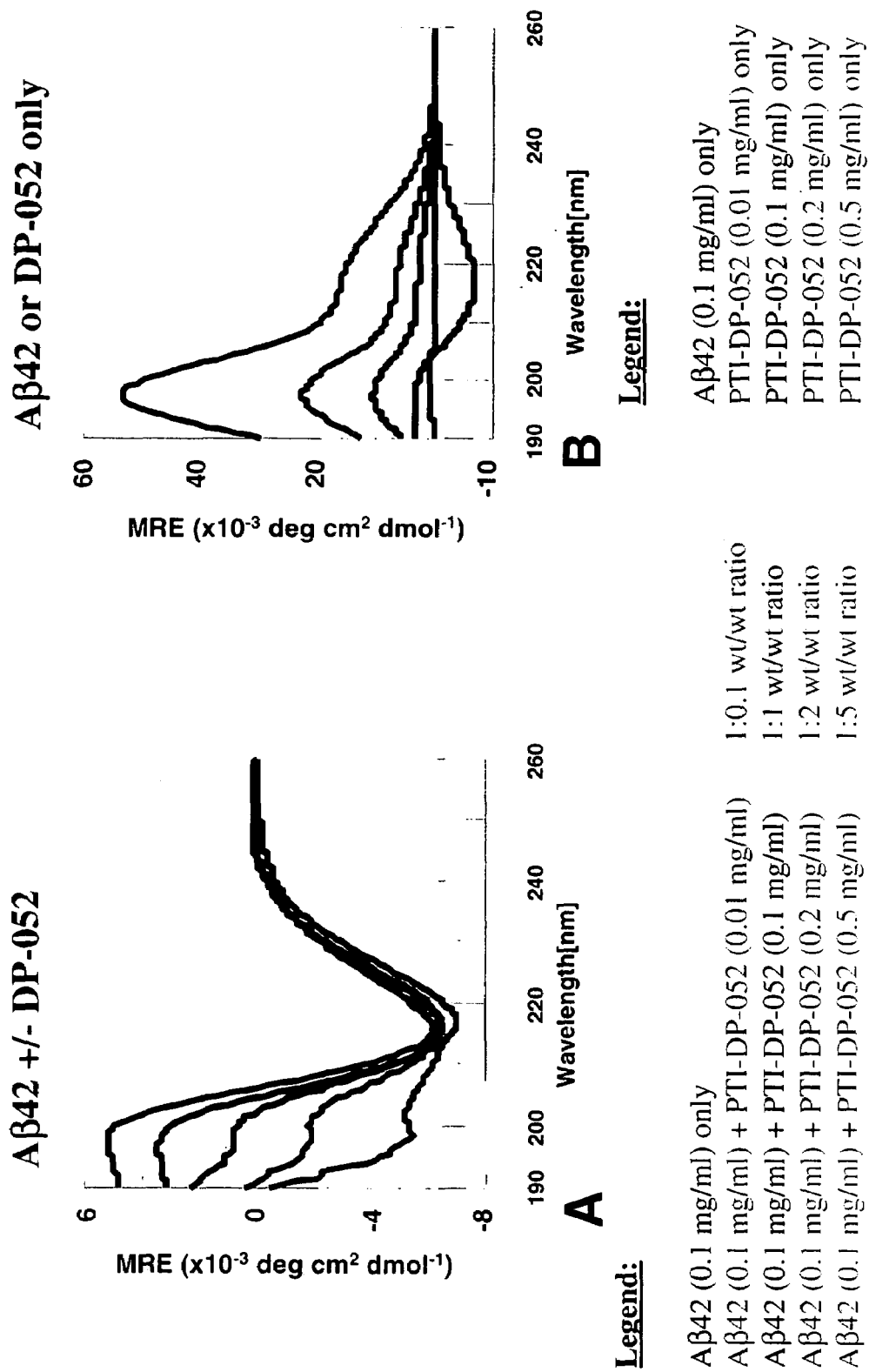
Figure 24:
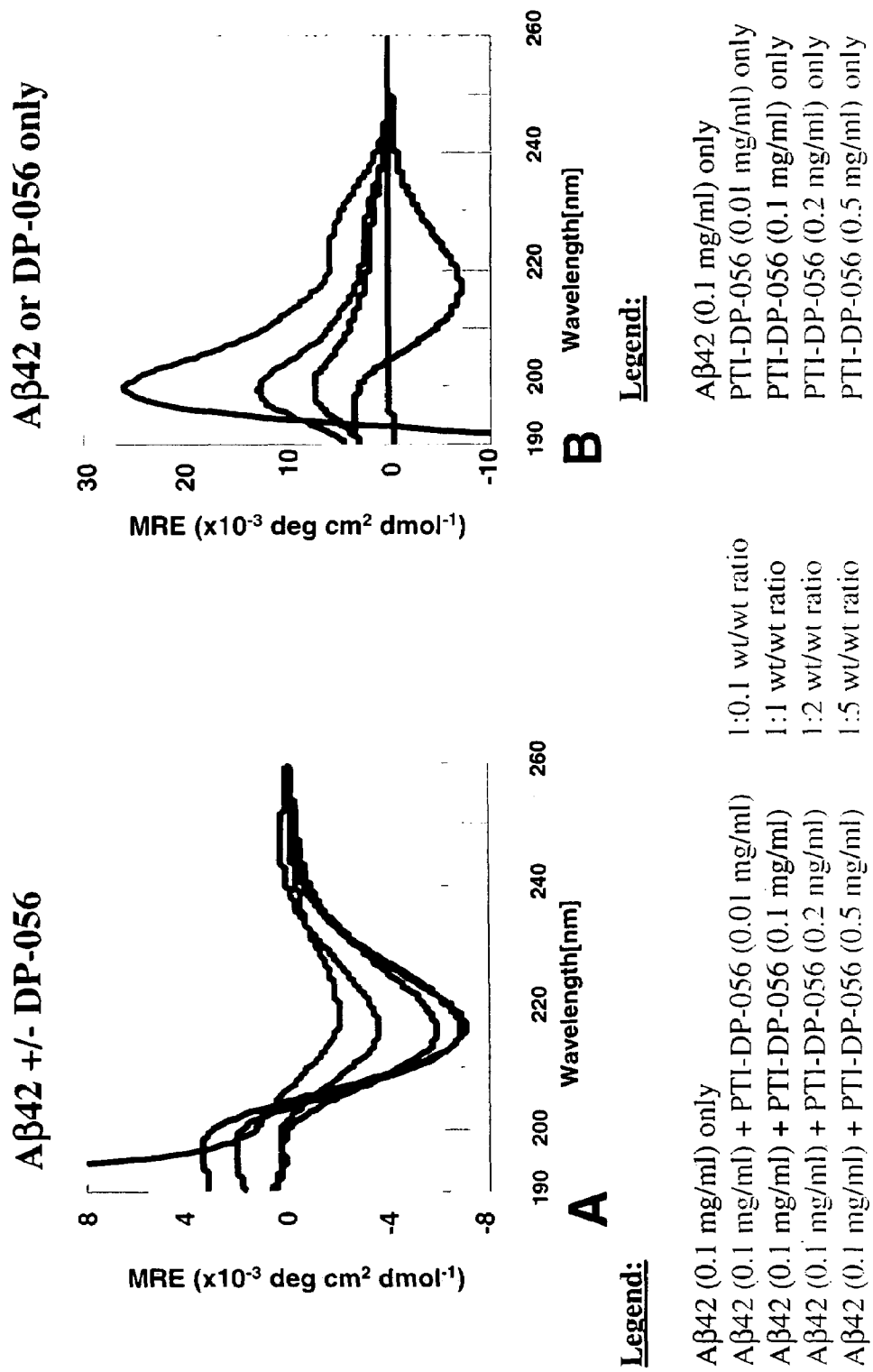
Figure 25:
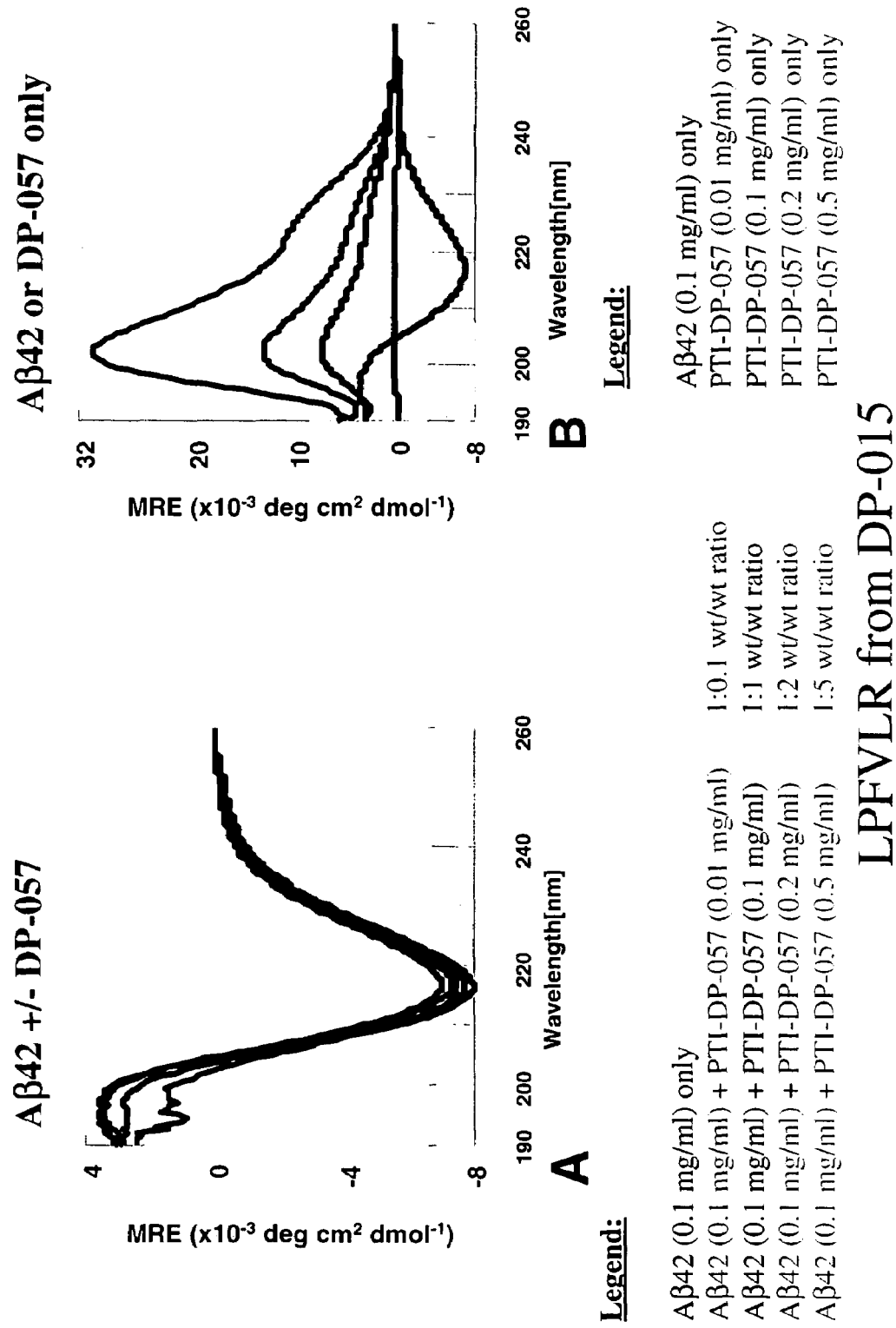
Figure 26:
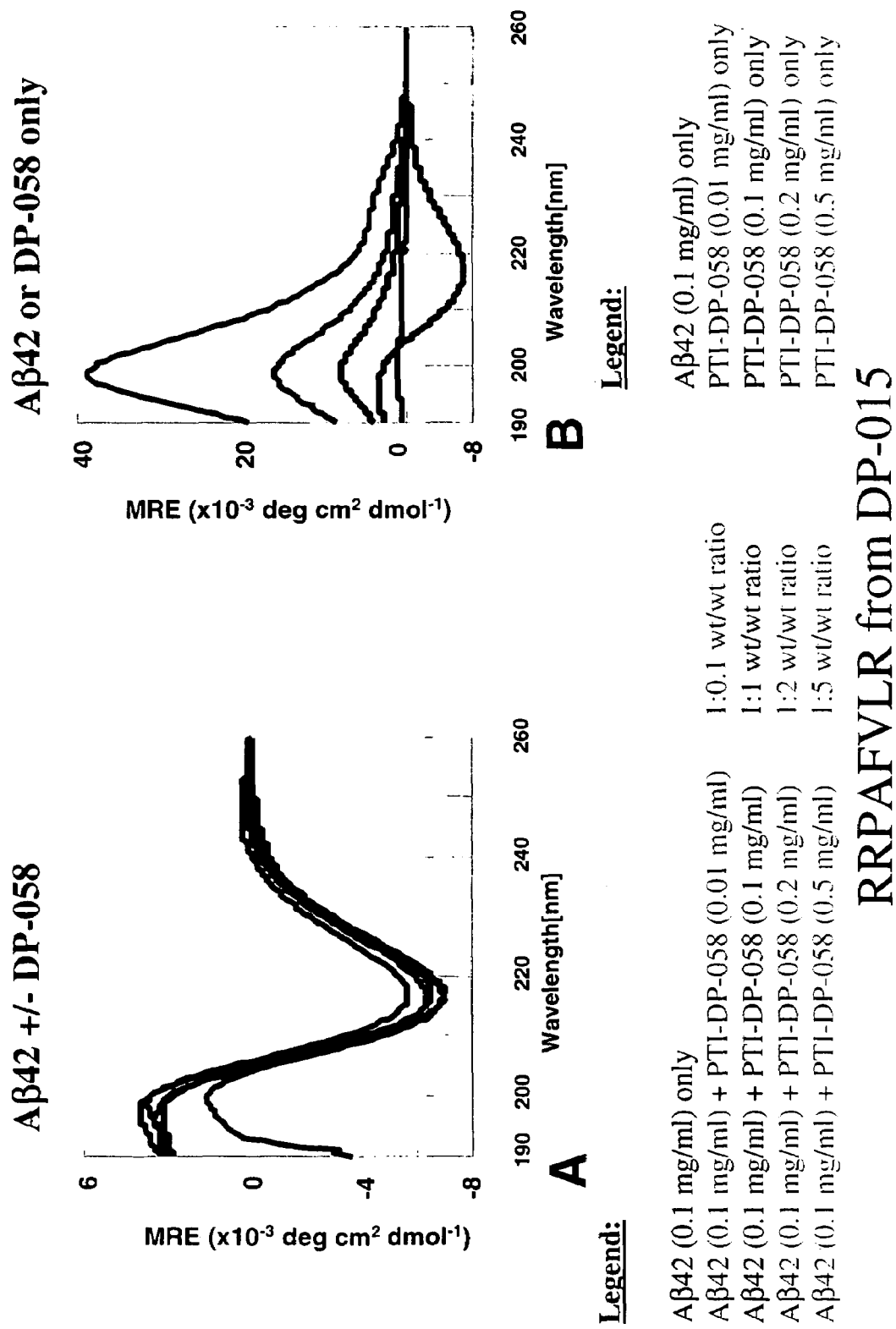
Figure 27:
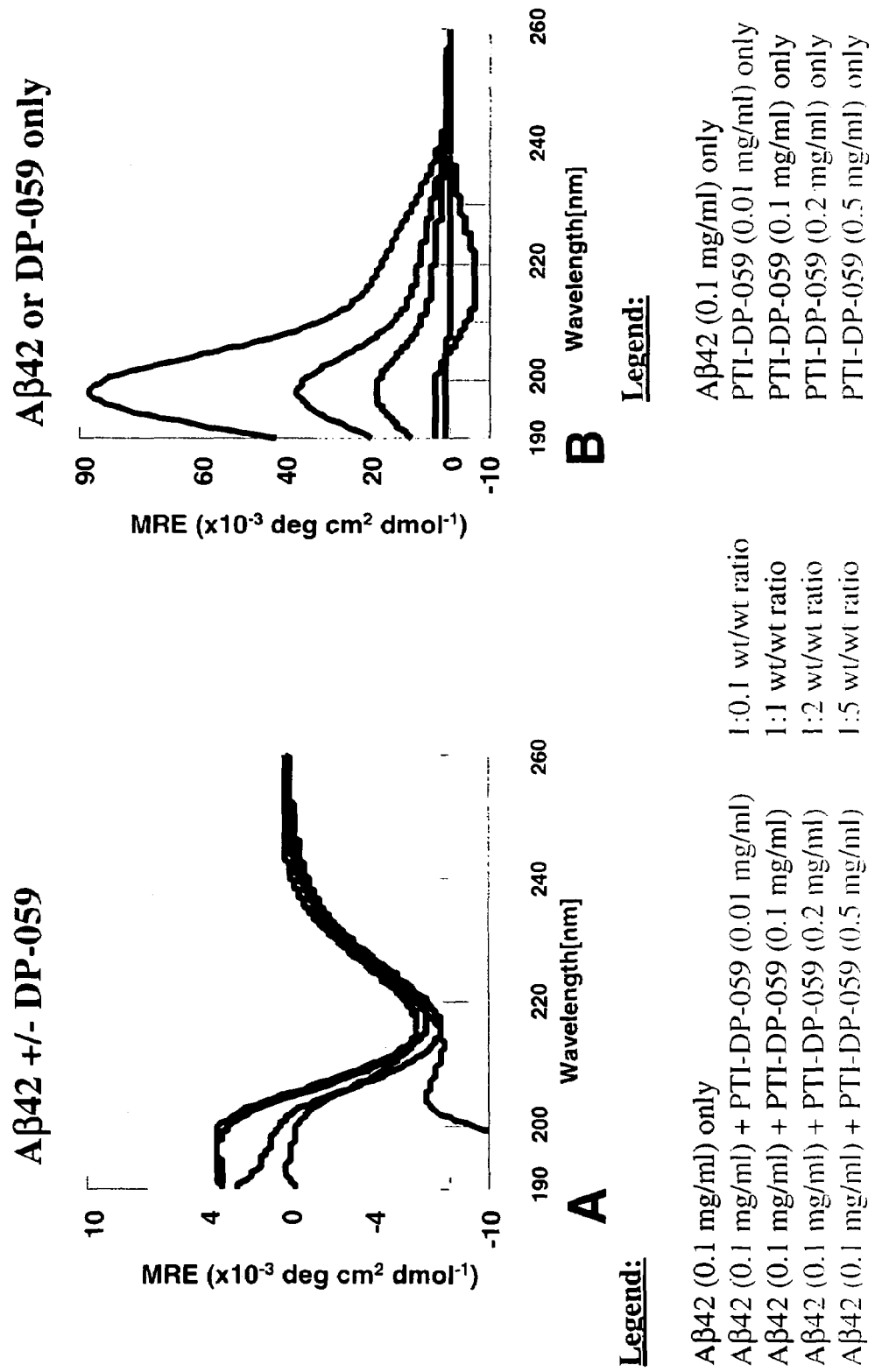
Figure 28:
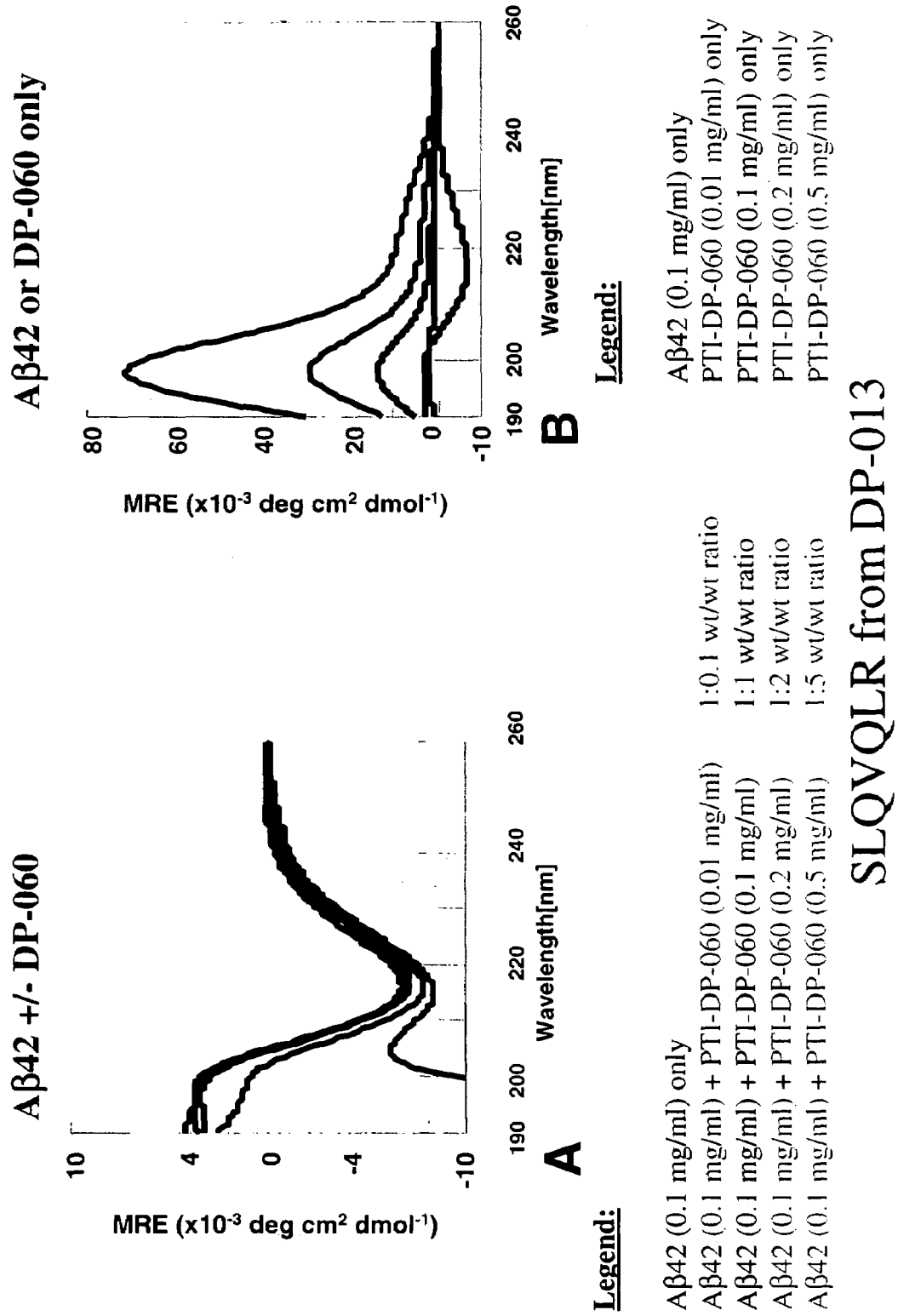
Figure 29:
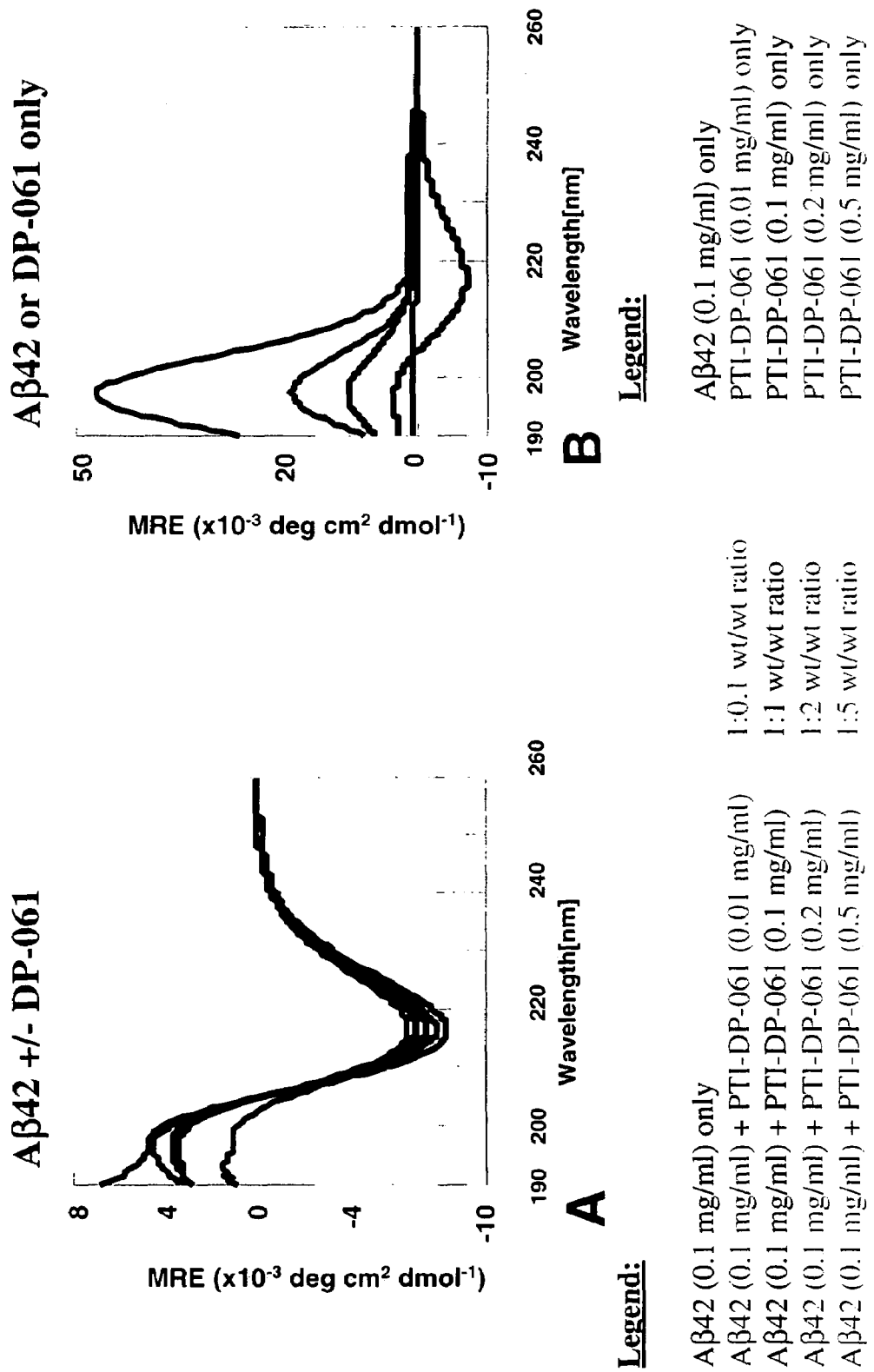
Figure 30:
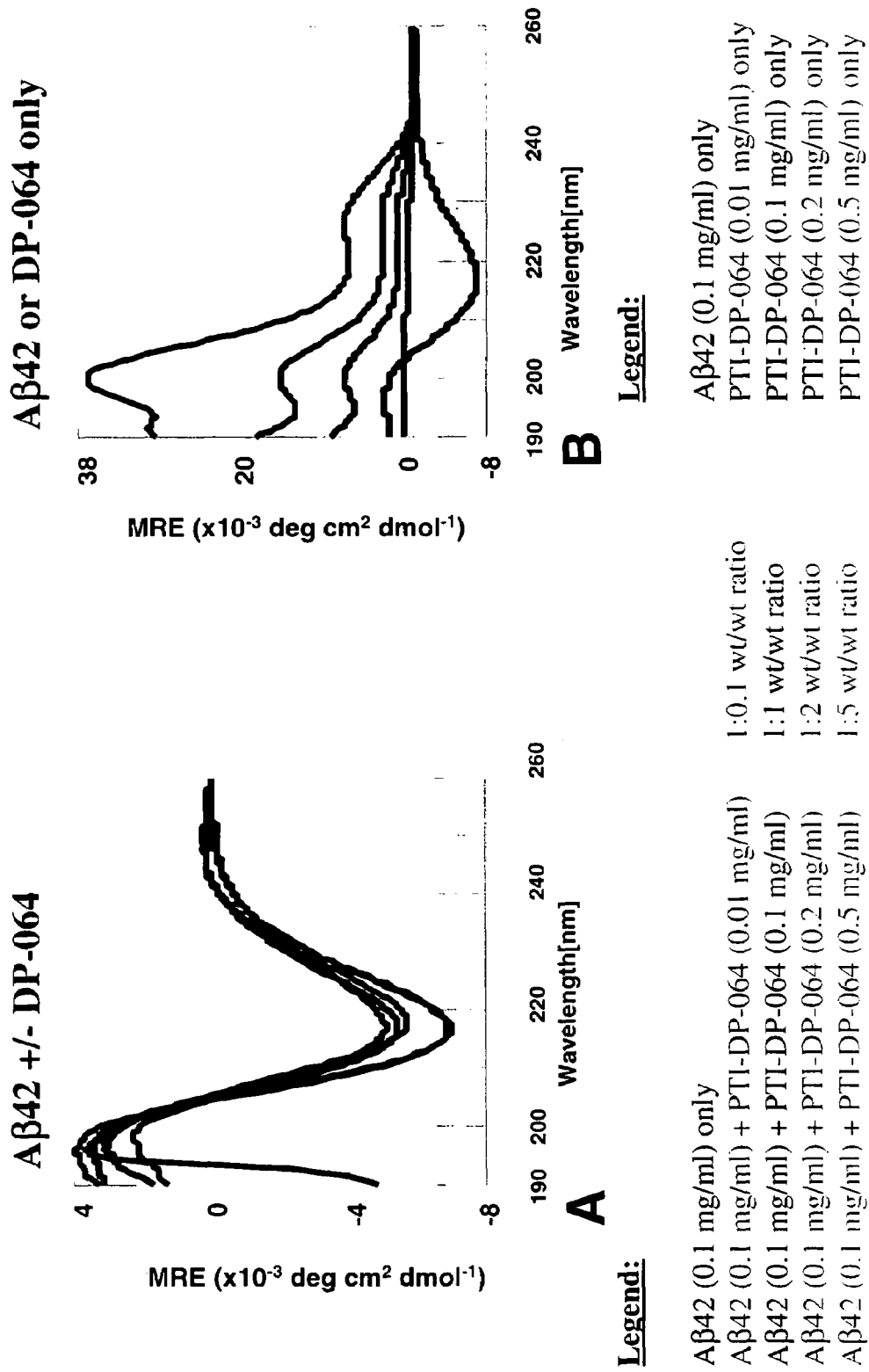

FIG. 4 is a summary of CD spectroscopy results of all peptides up to DP-049. FIG. 5 is a summary of Ab42 binding for peptides LP-025 and DP-026-049.

FIGS. 6-20 are all CD spectra of Ab42 plus DP-50 through DP-064, respectively, at Ab42/peptide wt./wt. concentration of (1:2), showing respective inhibition and disruption efficacies. FIGS. 21-30 are CD spectra of Ab42 plus DP-50, 51, 52, 56-61 and DP-064, respectively, at (1:0.1, 1:1, 1:2, 1:5).

Figure 31:
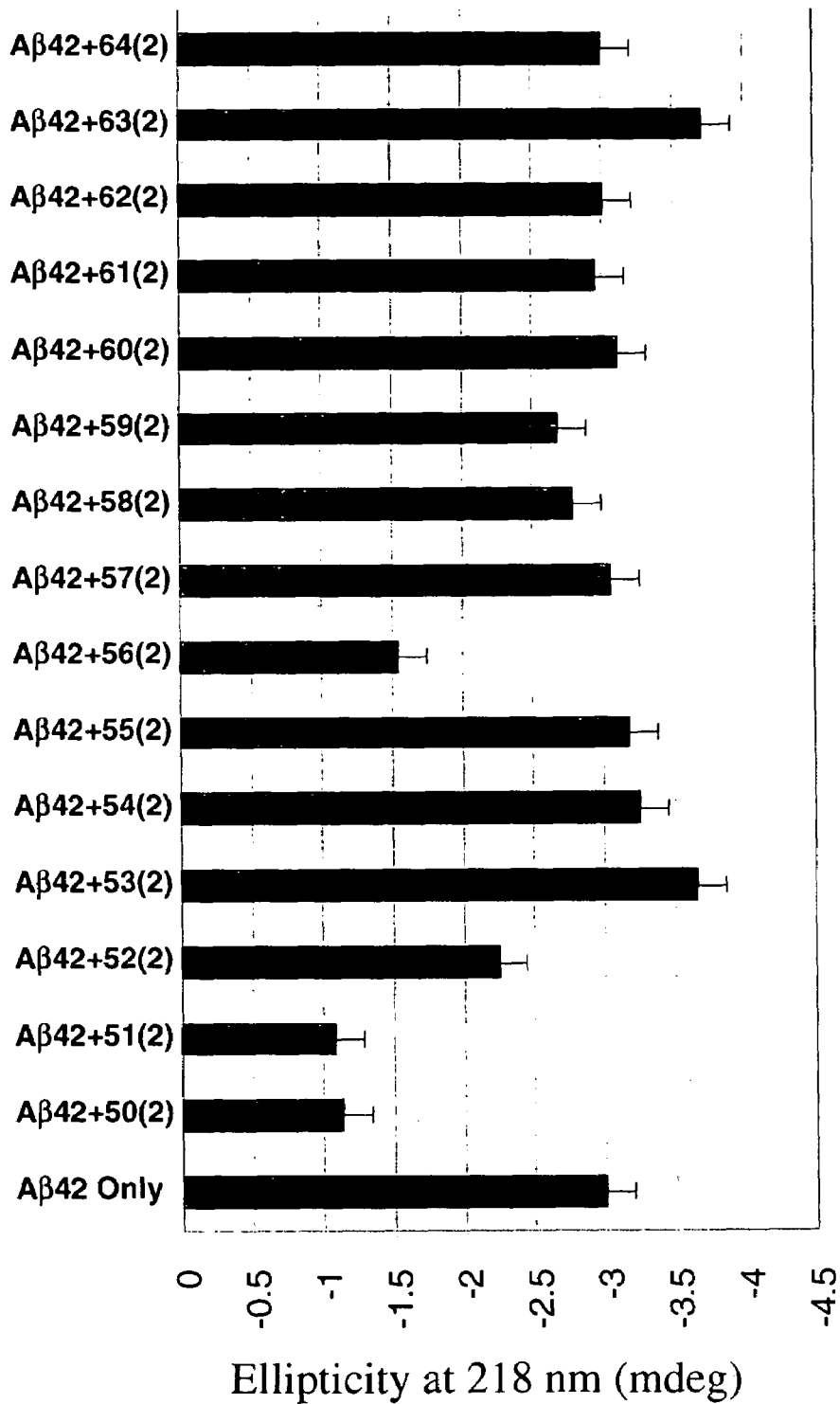
FIG. 31 is a summary of CD spectroscopy results for DP-50 through DP-064 at (1:2).
Figure 32:
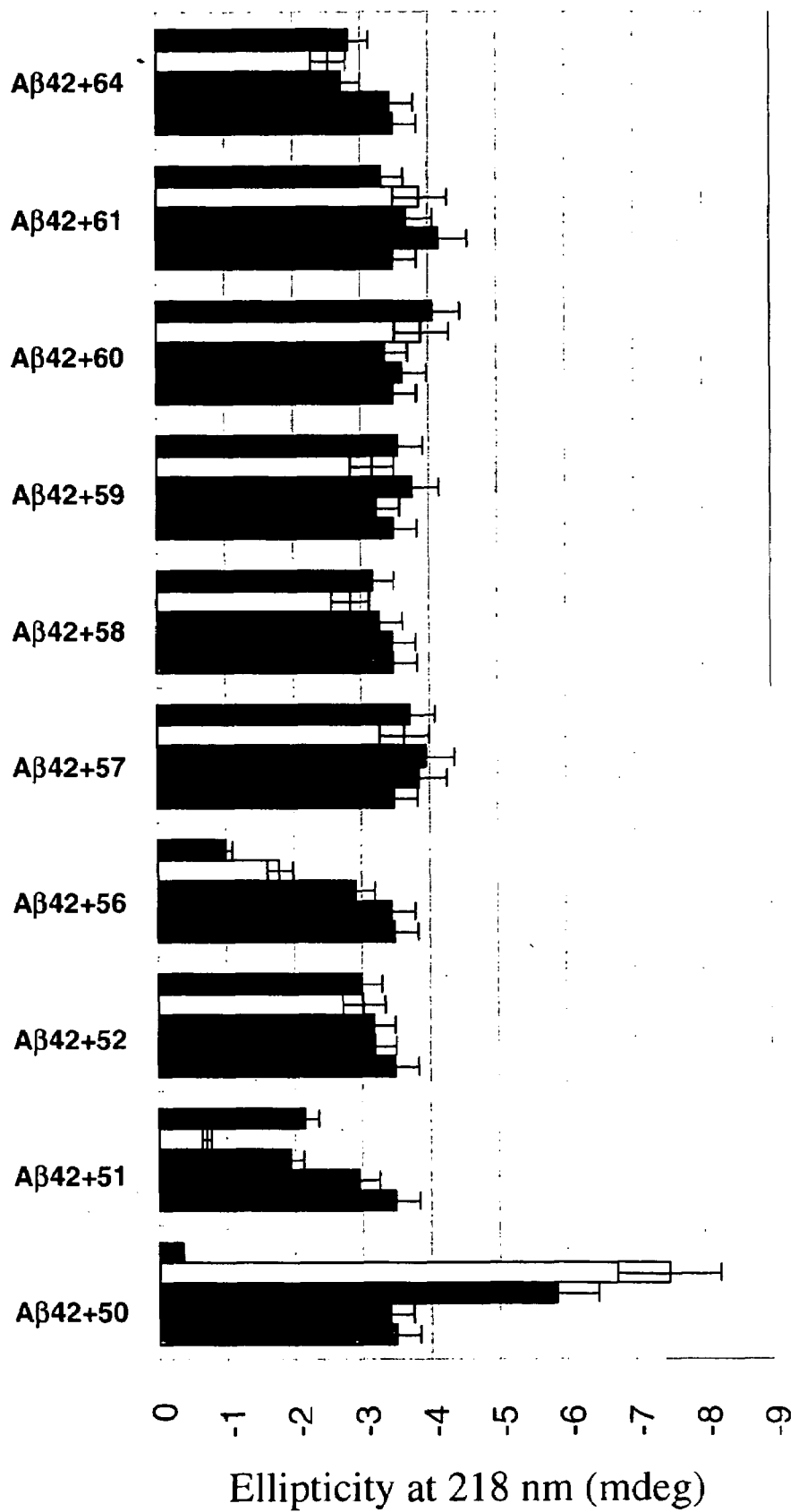
FIG. 32 is a summary of CD spectroscopy results for DP-50, 51, 52, 56-61 and DP-064 at (1:0.1, 1:1, 1:2, 1:5).

FIG. 31 is a summary of CD spectroscopy results for DP-50 through DP-064 at (1:2), while FIG. 32 is a summary of CD spectroscopy results for DP-50, 51, 52, 56-61 and DP-064 at (1:0.1, 1:1, 1:2, 1:5).

Figure 33:
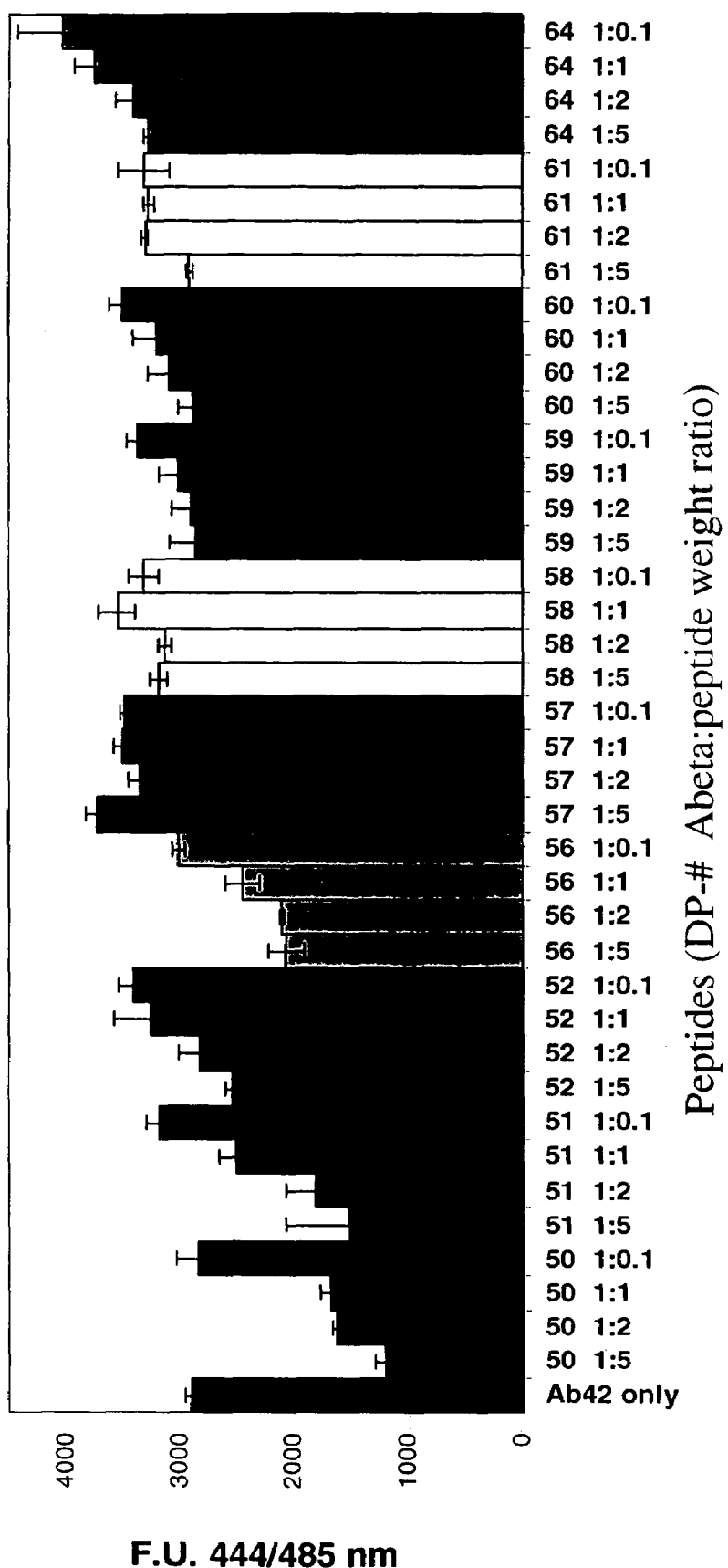
FIG. 33 is a Thio T summary of Ab42+/−DP5O-52, 56-61 and 64.
Figure 34:
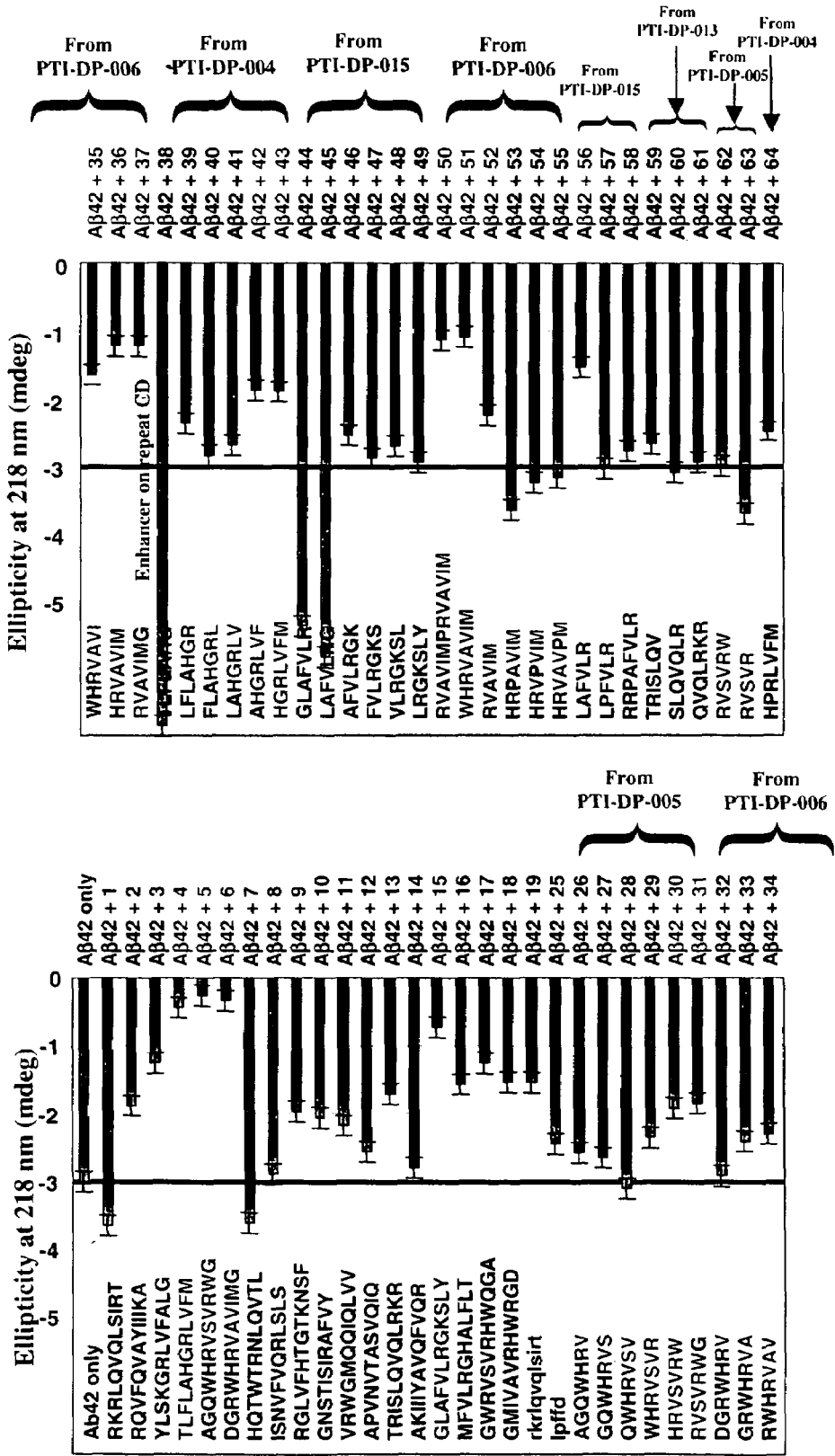
FIG. 34 is a CD summary from DP-01 to DP-064 (1:2).
Figure 35:
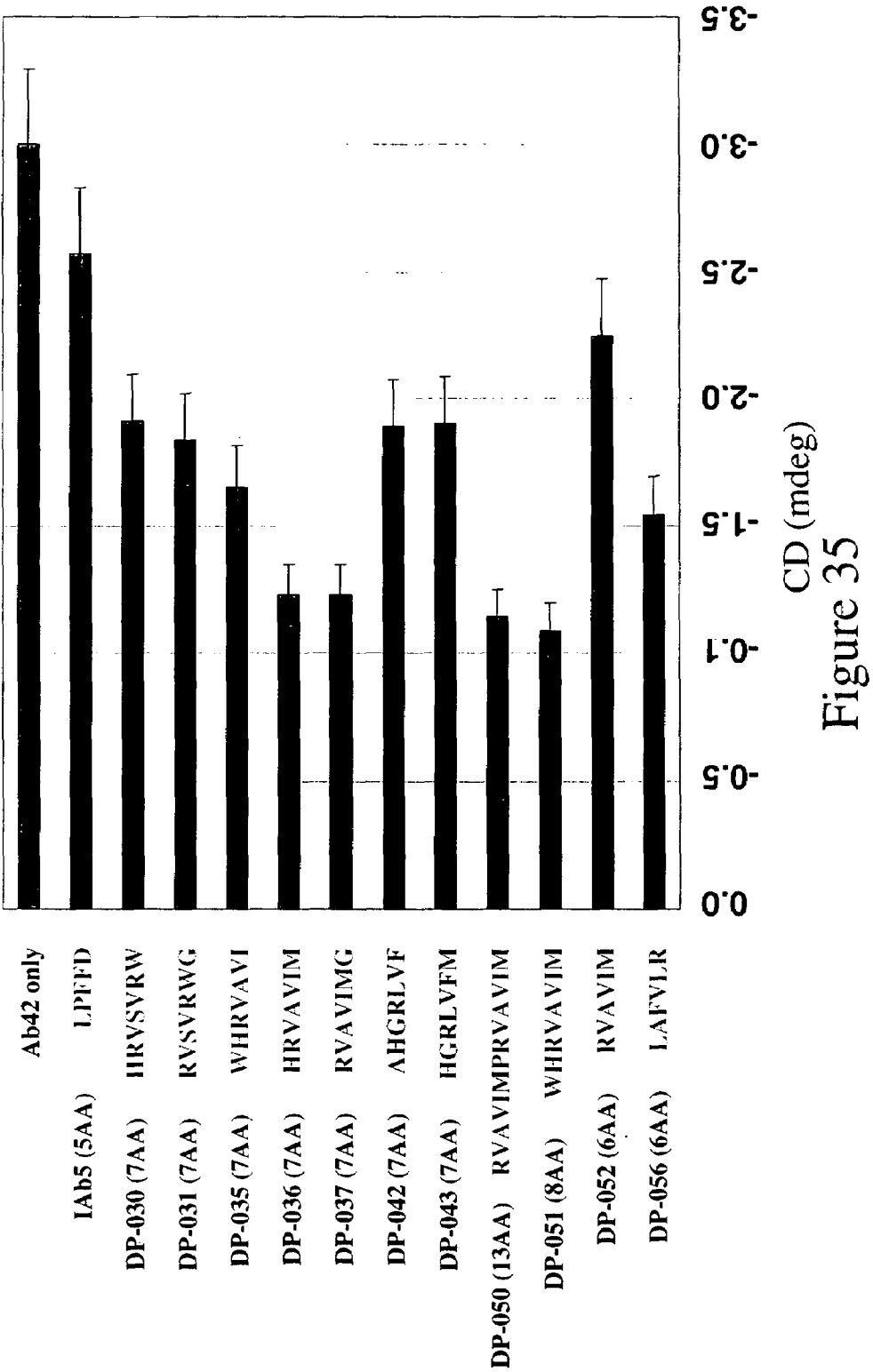
FIG. 35 is a CD summary of selected 11 peptides from DP1-64 compared to IAb5. (LP-025) (1:2).
Figure 36:
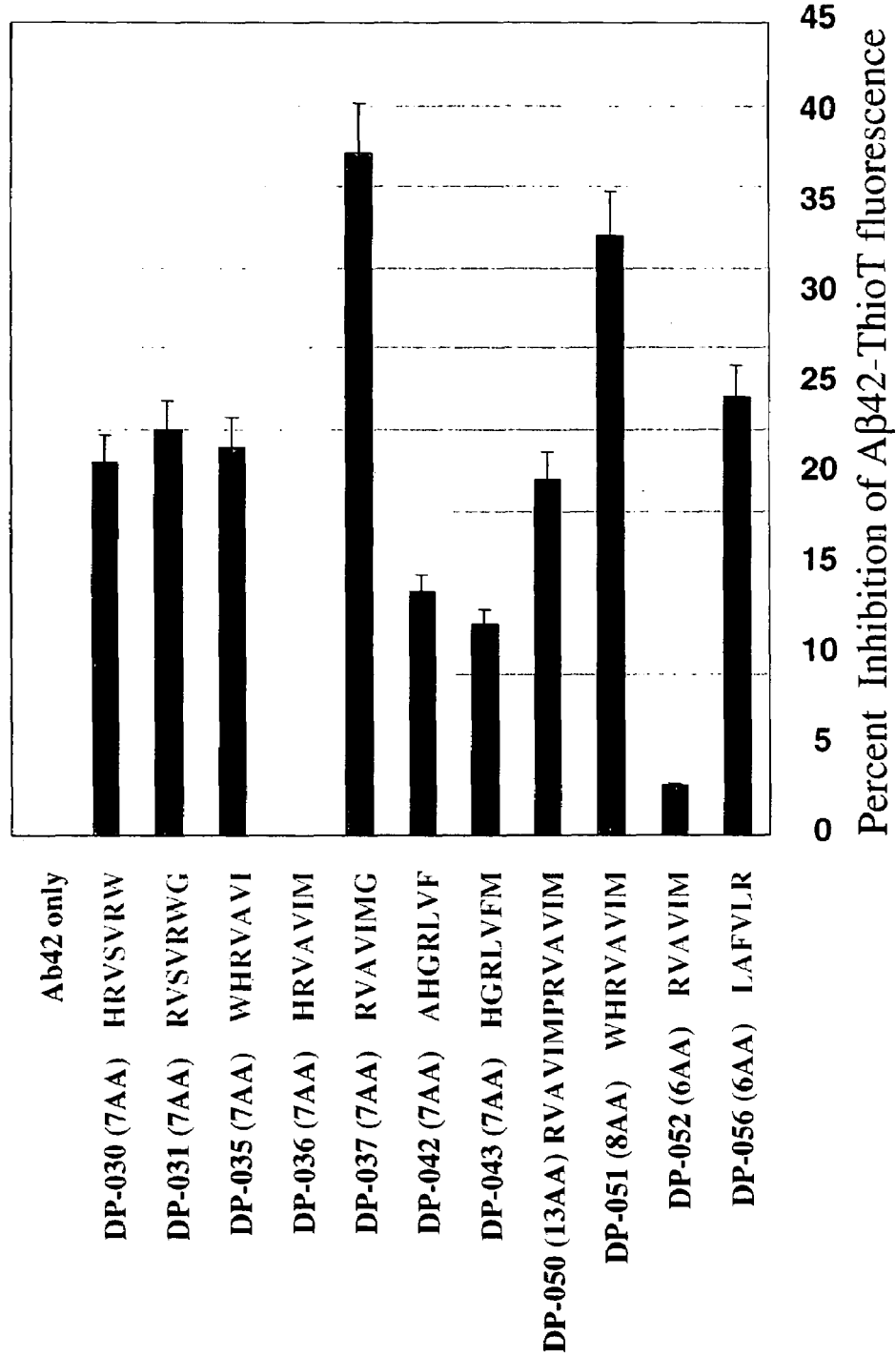
FIG. 36 is a ThioT summary of selected 11 peptides from DP1-64 (1:2).
Figure 38:
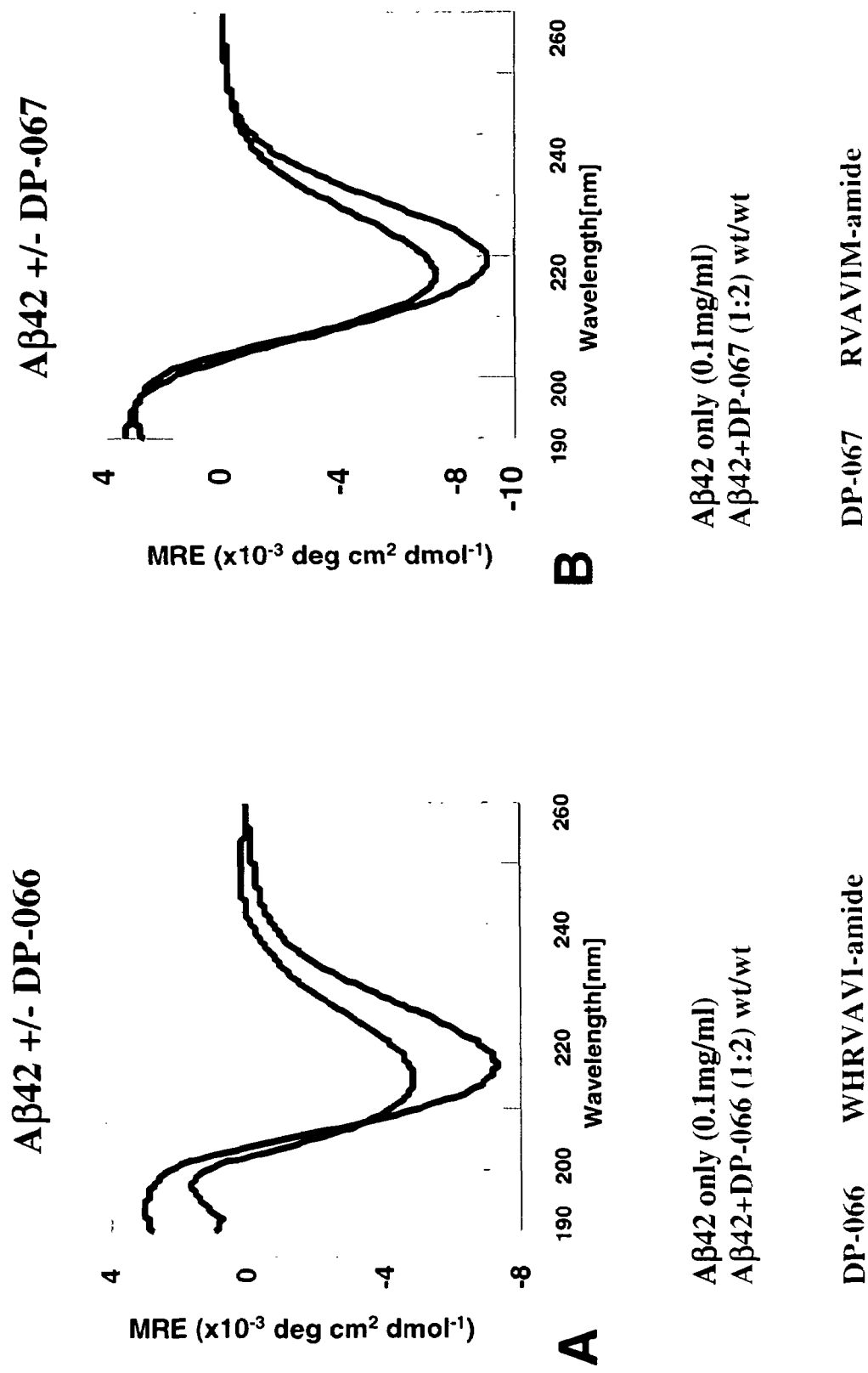
Figure 40:
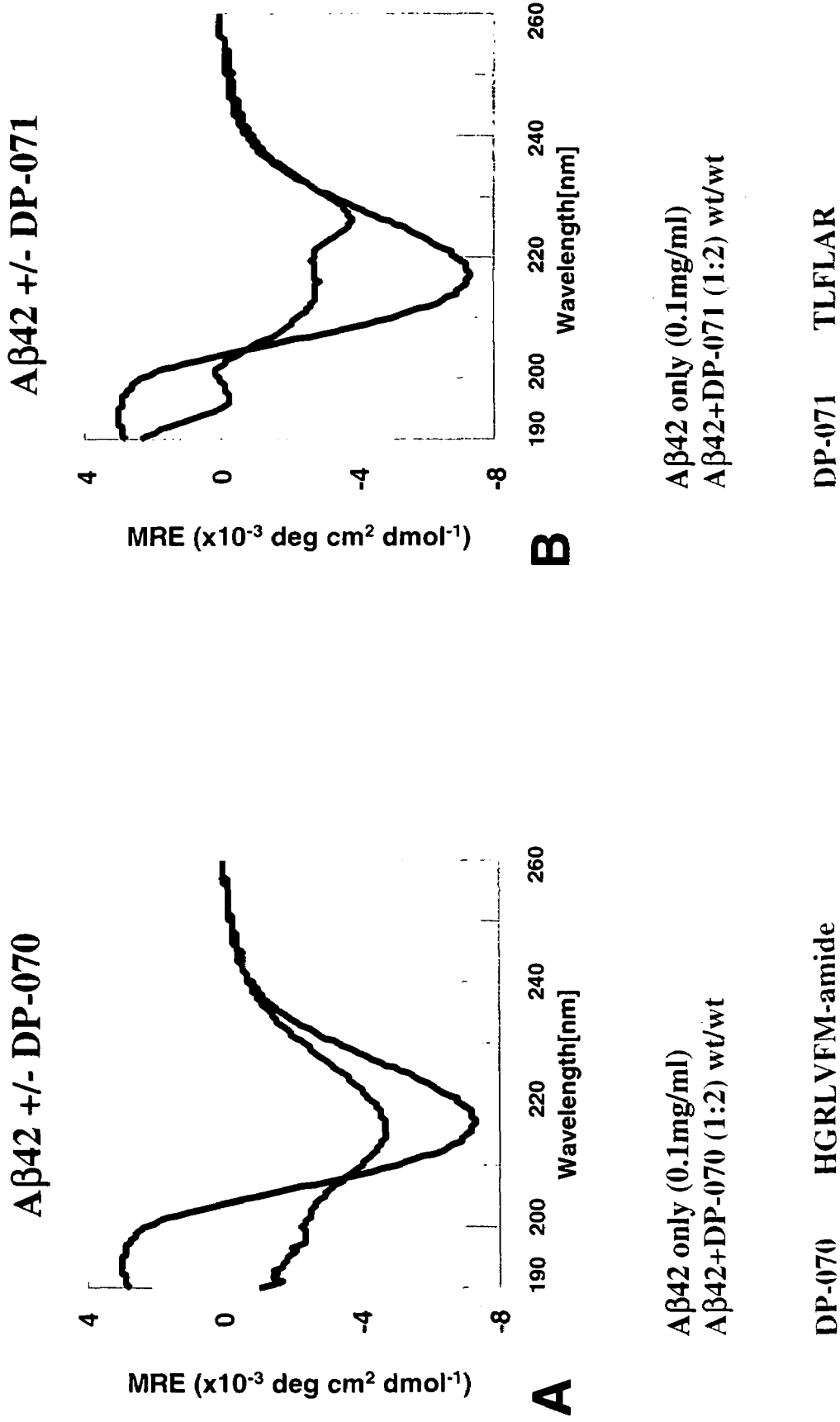
Figure 41:
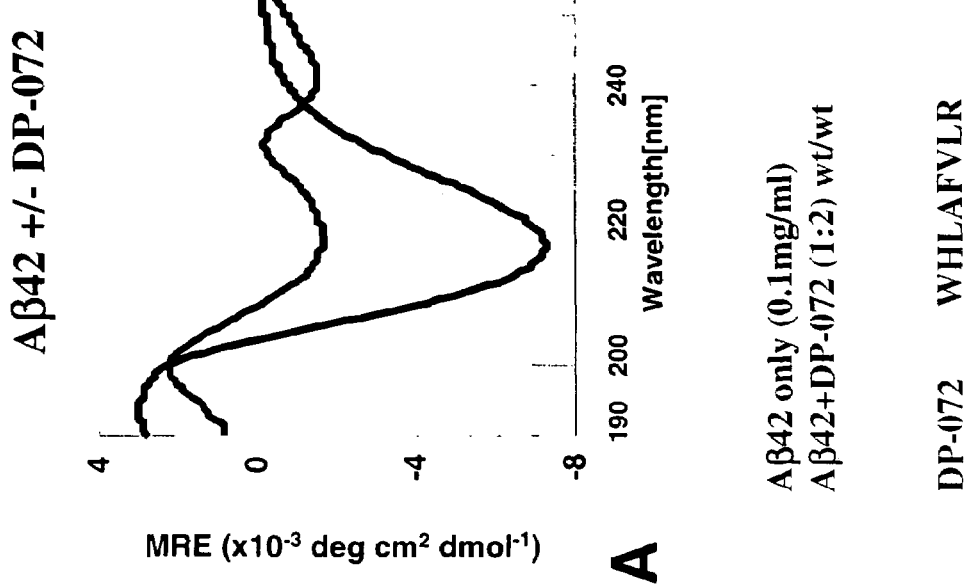
Figure 42:
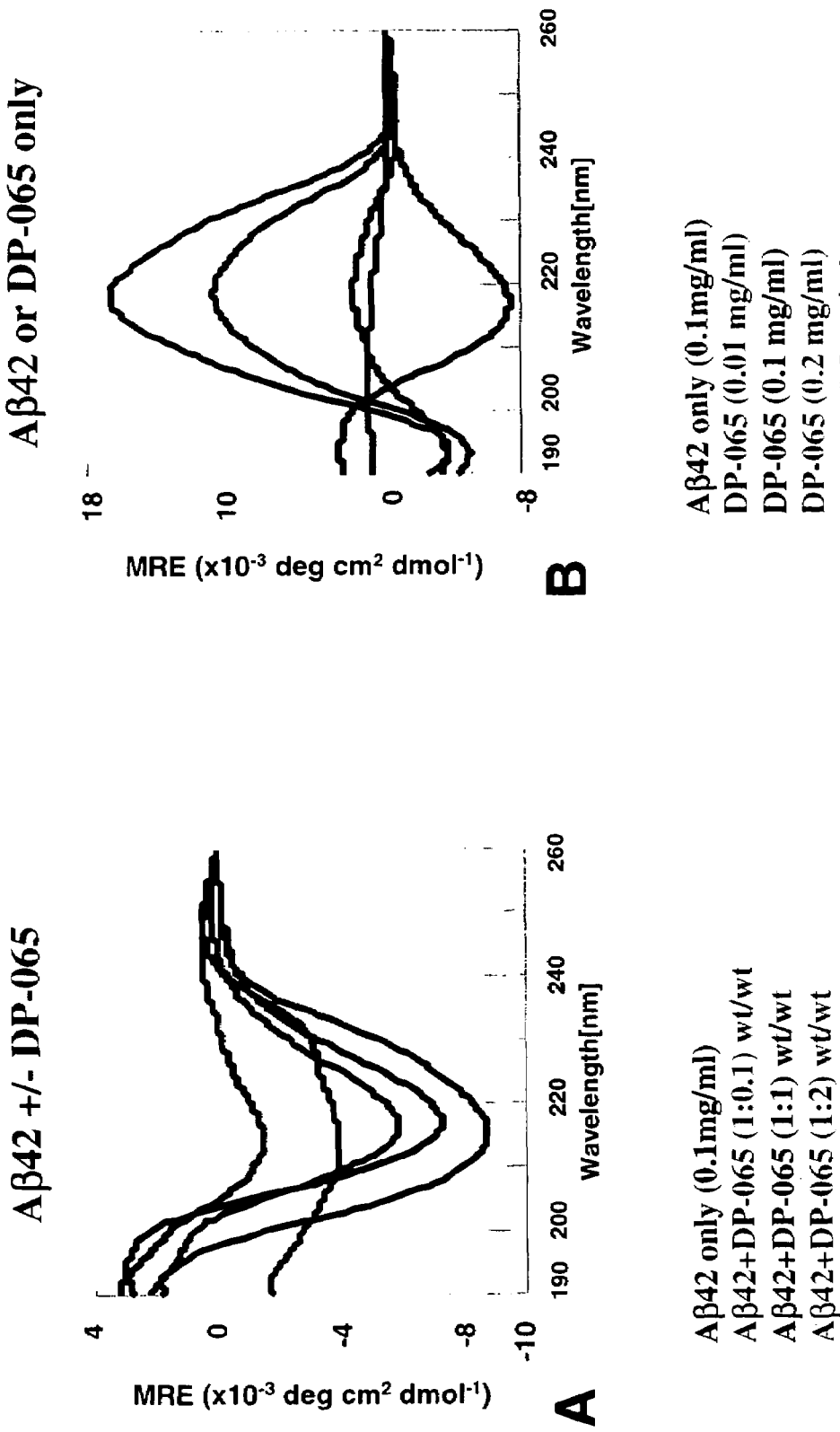
Figure 44:
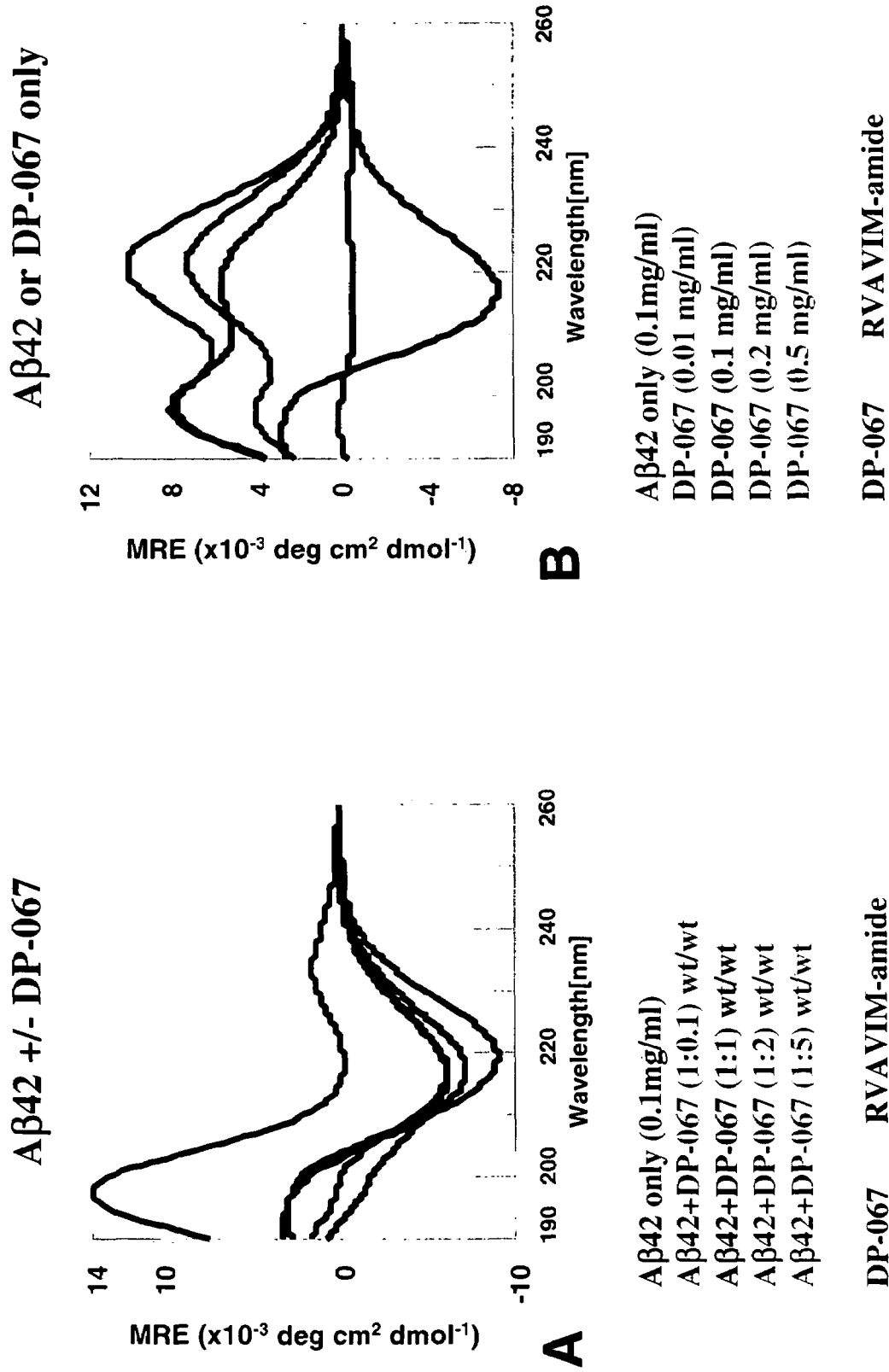
Figure 45:
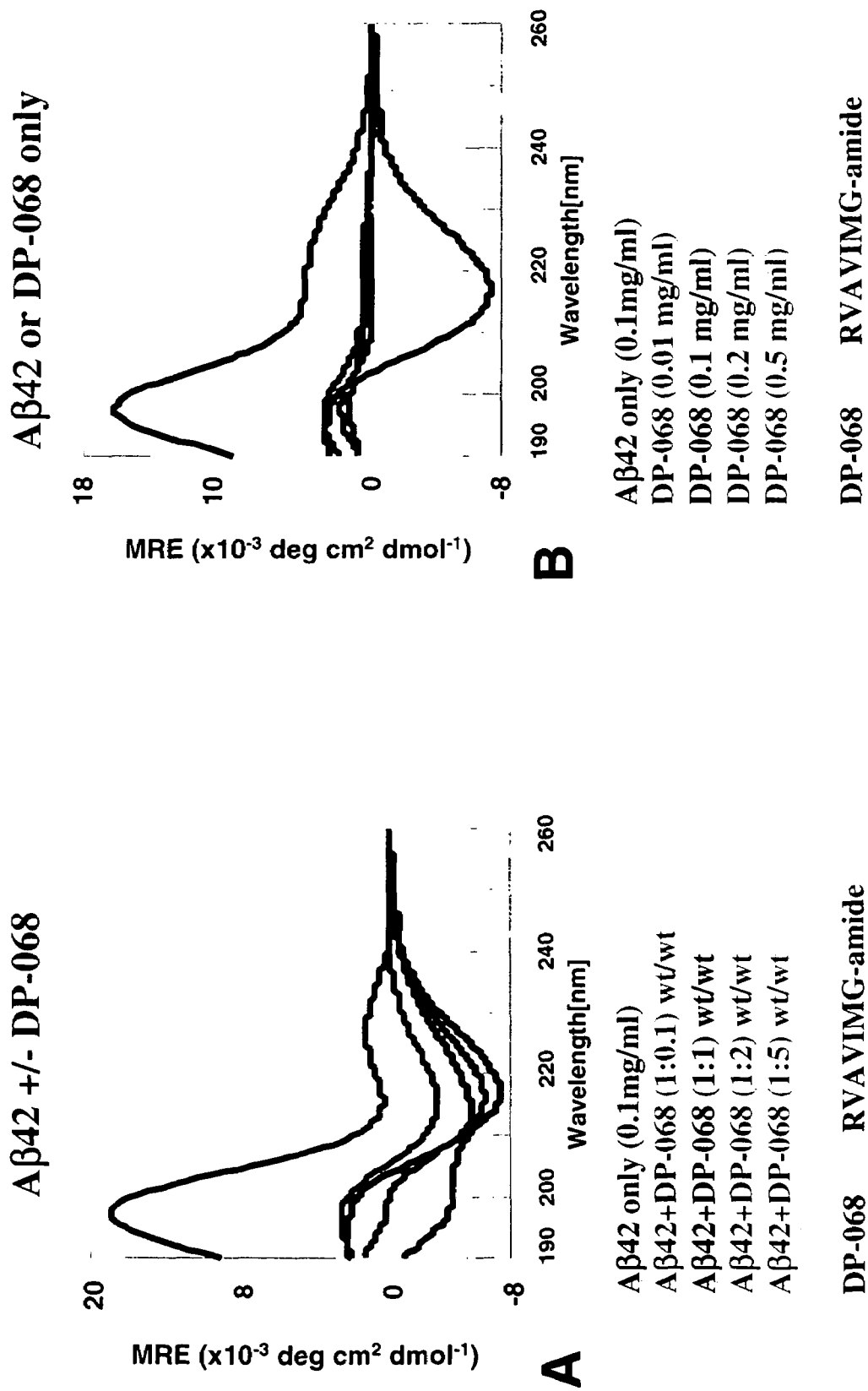
Figure 46:
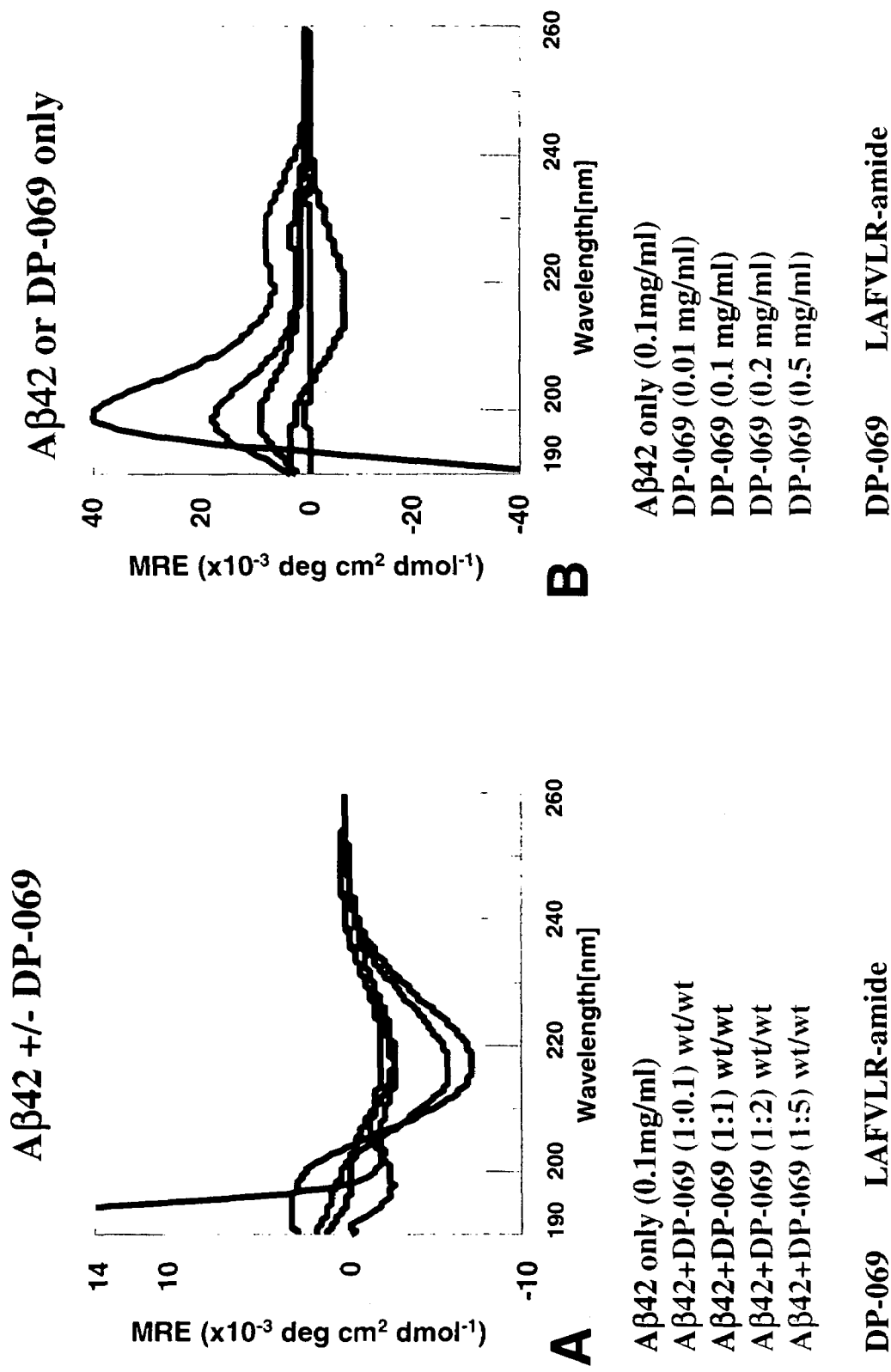
Figure 47:
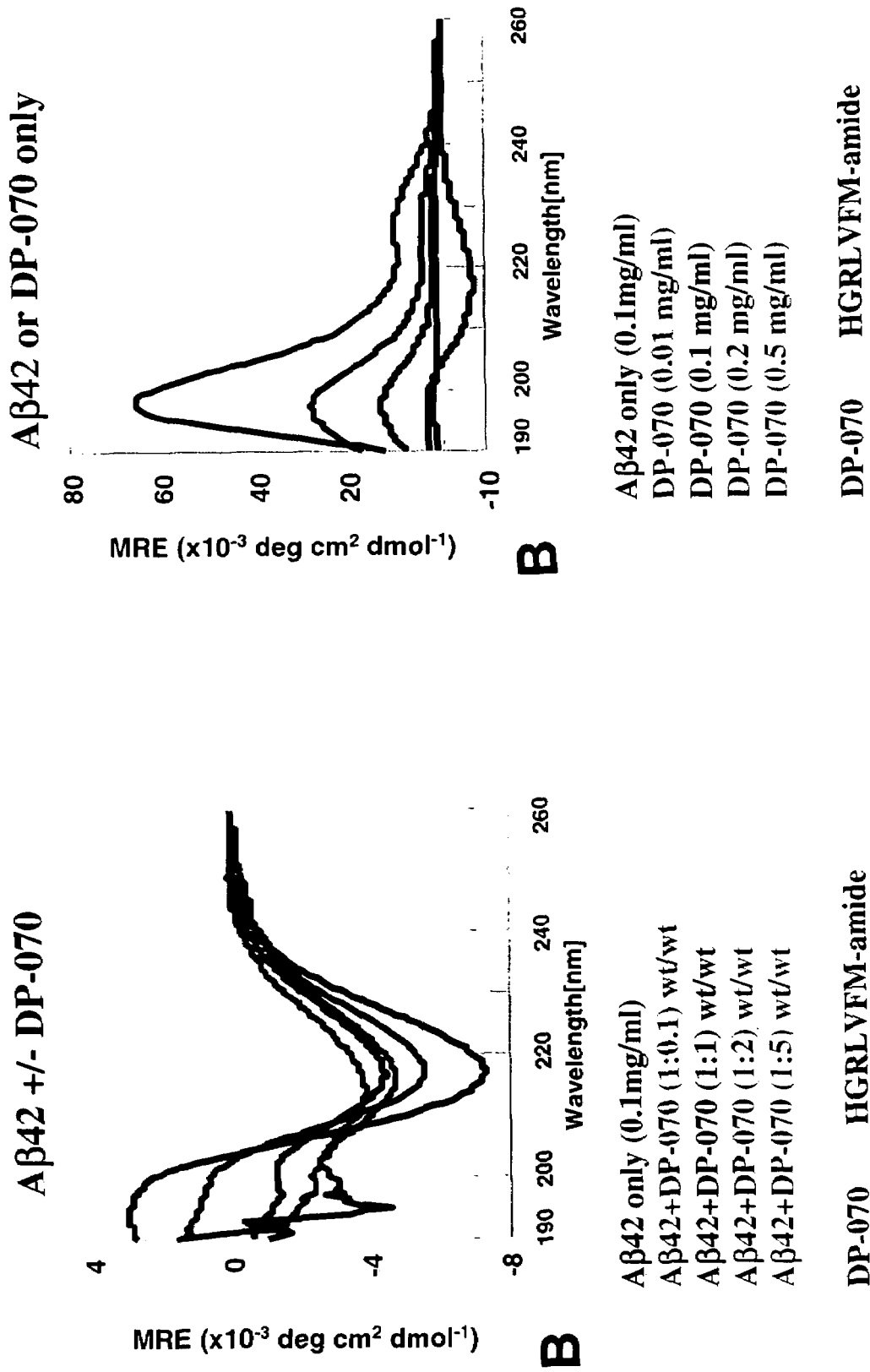
Figure 48:
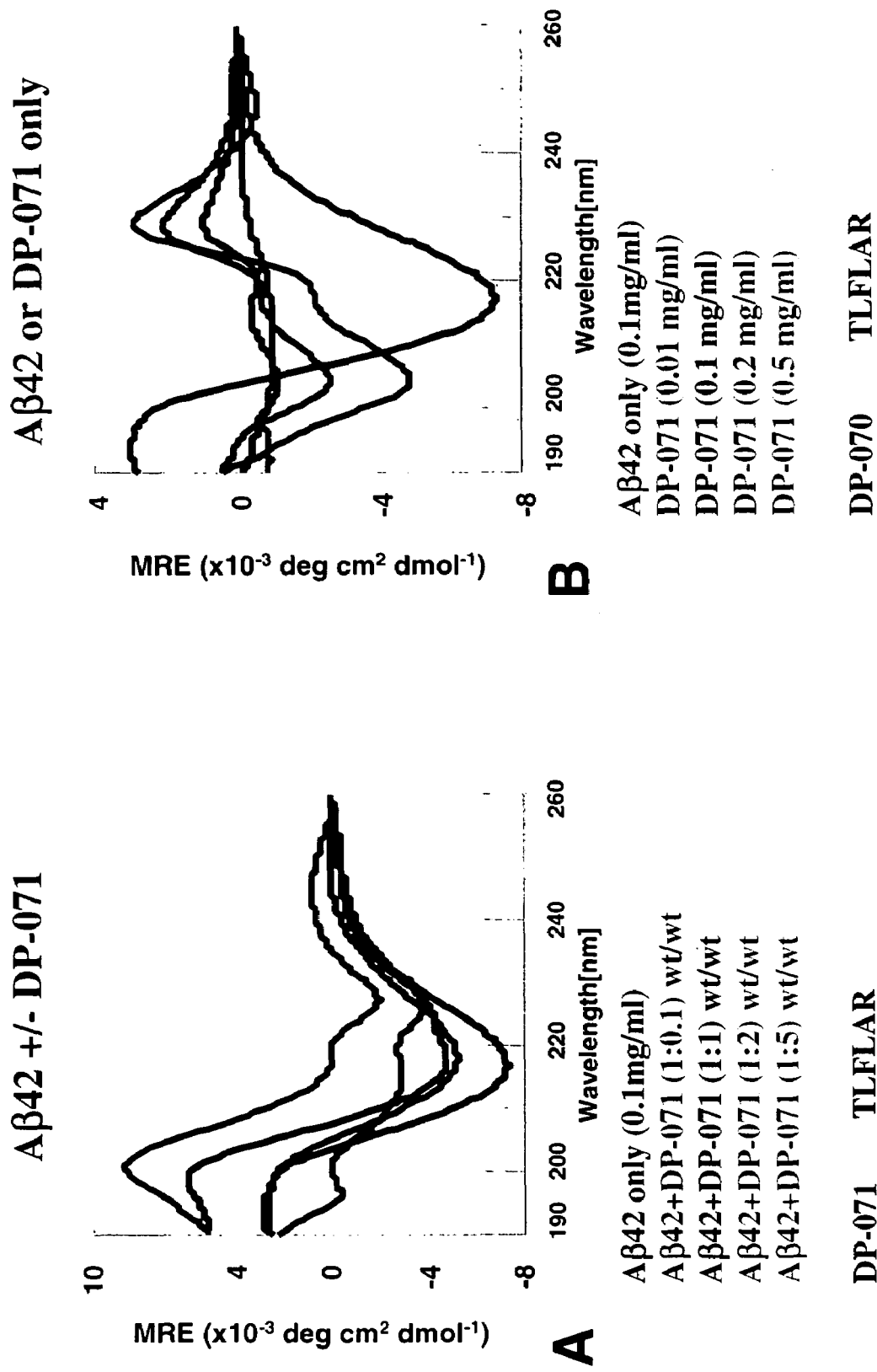

FIG. 33 is a Thio T summary of Ab42+/−DP50-64 at (1:0.1, 1:1, 1:2, 1:5); FIG. 34 is a CD summary from DP-01 to DP-064 (1:2); FIG. 35 is a CD summary of selected 11 peptides from DP1-64 compared to IAb5. (LP-025) at (1:2); FIG. 36 is a ThioT summary of selected 11 peptides from DP1-64 (1:2).

Figure 50:
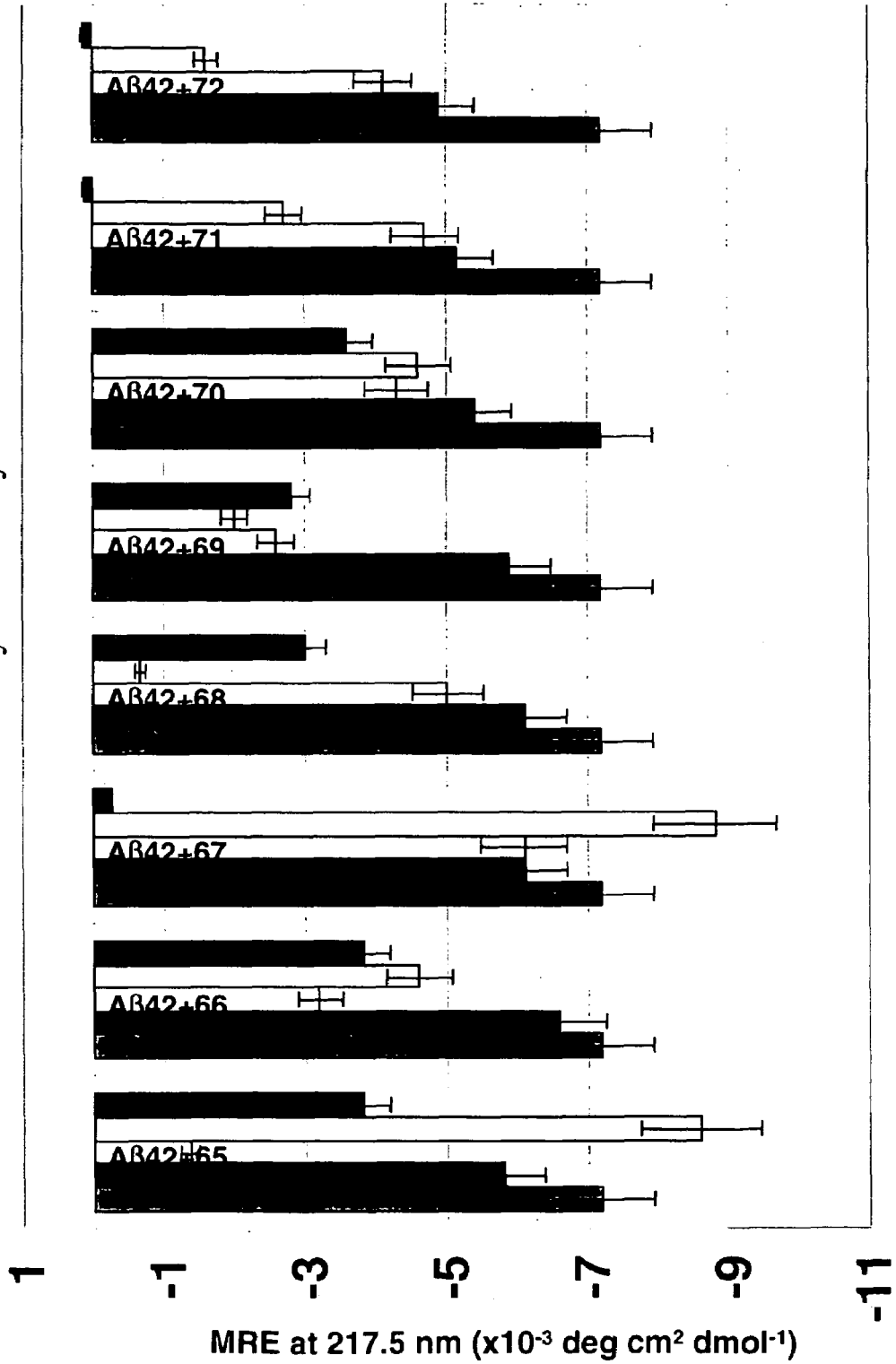
FIG. 50 is a summary of dose response CD of Ab42+/−DP-065 to DP-072.

FIGS. 37-41 are CD spectra of Ab42 plus polylysine and DP-065 through DP-072 at Ab42/peptide wt./wt. concentration of (1:2). FIGS. 42-49 are CD spectra of Ab42 plus DP-065 through DP-072 at (1:0.1, 1:1, 1:2, 1:5), with FIG. 50 as a summary of dose response CD of Ab42+/−DP-065 to DP-072.

Figure 51:
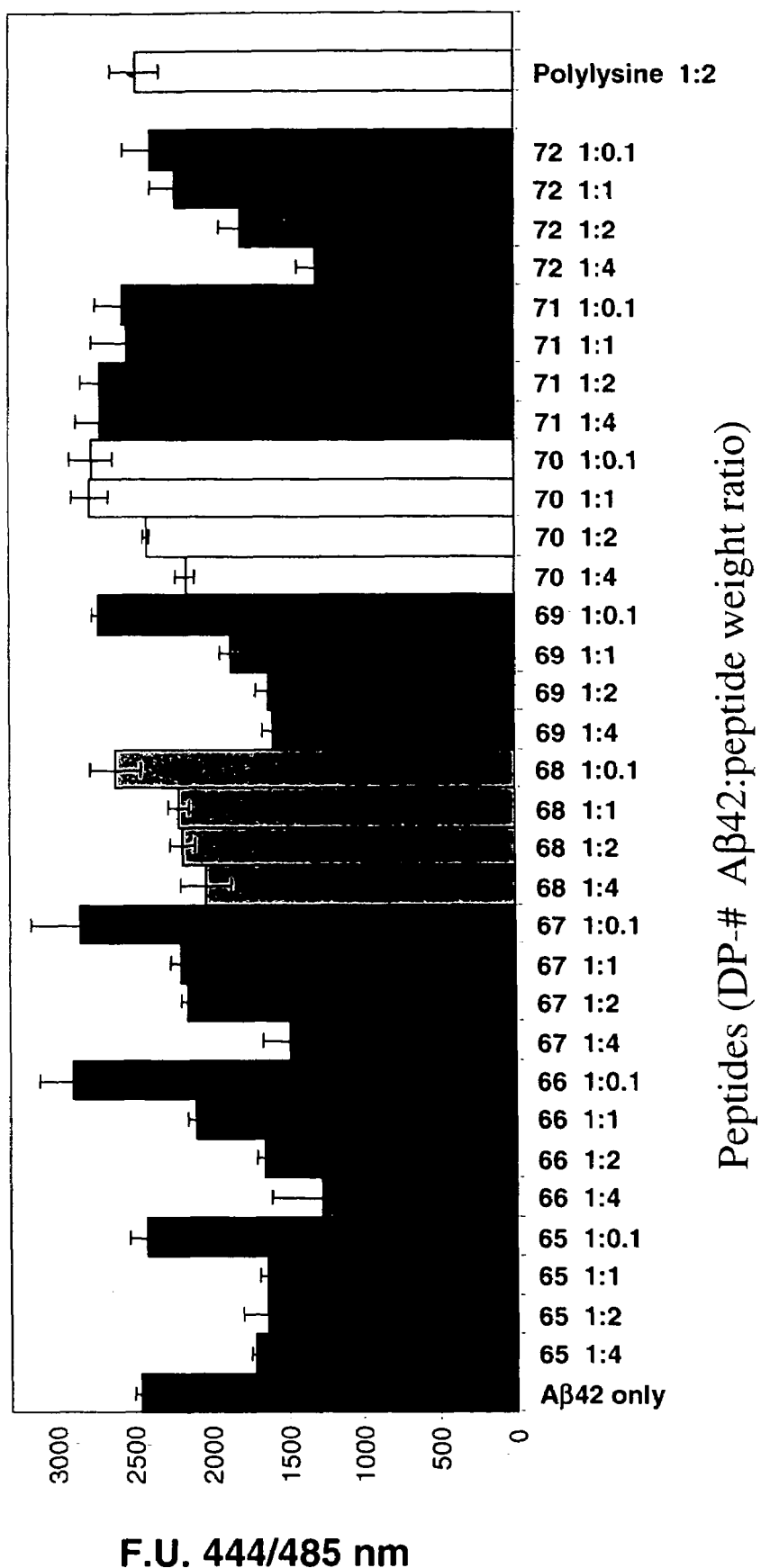
FIG. 51 is a summary of Thio T of Ab42+/−DP65-72 (1:0.1, 1:1, 1:2, 1:4) and polylysine.
Figure 53:
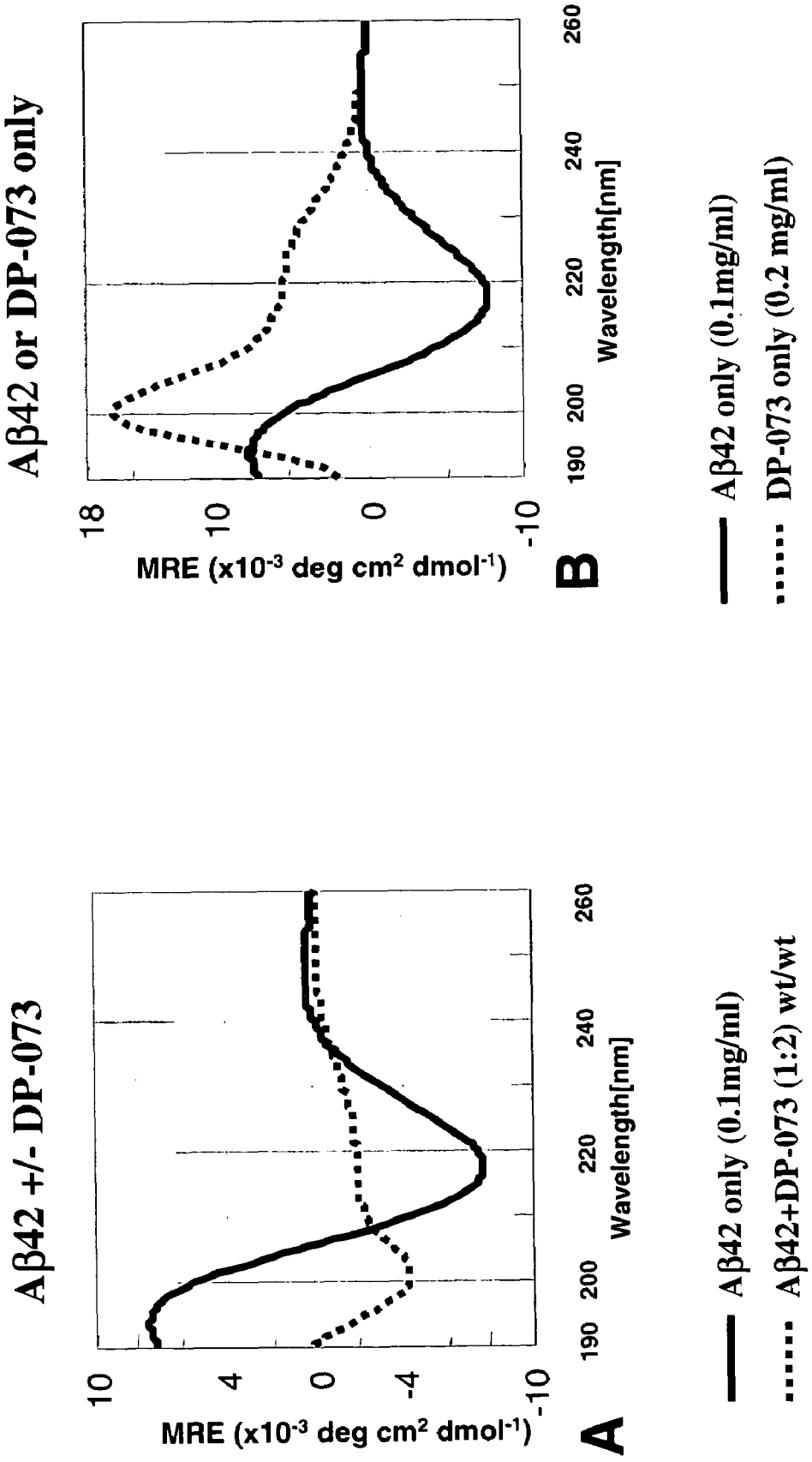
FIG. 53A are CD spectra showing the effects of 0.2 mg/ml of peptide DP-073 on beta-sheet secondary structure of Aβ42 amyloid fibrils (i.e. Aβ 42+/−DP-073).
FIG. 53B shows the CD spectra of Aβ42 or DP-073 only.
Figure 54:
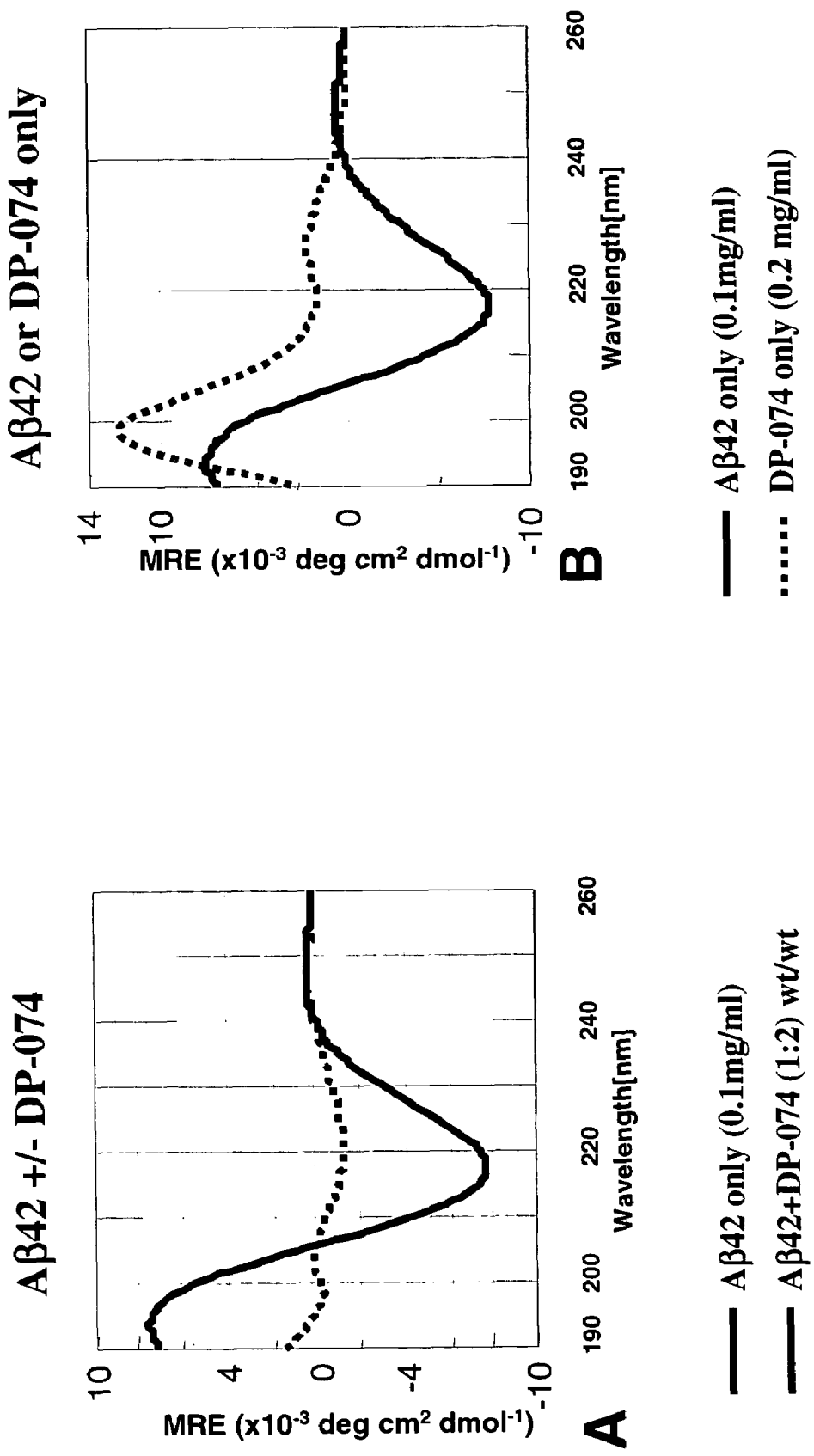
FIG. 54A are CD spectra showing the effects of 0.2 mg/ml of peptide DP-074 on beta-sheet secondary structure of Aβ42 amyloid fibrils (i.e. Aβ 42+/−DP-074).
FIG. 54B shows the CD spectra of Aβ 42 or DP-074 only.
Figure 55:
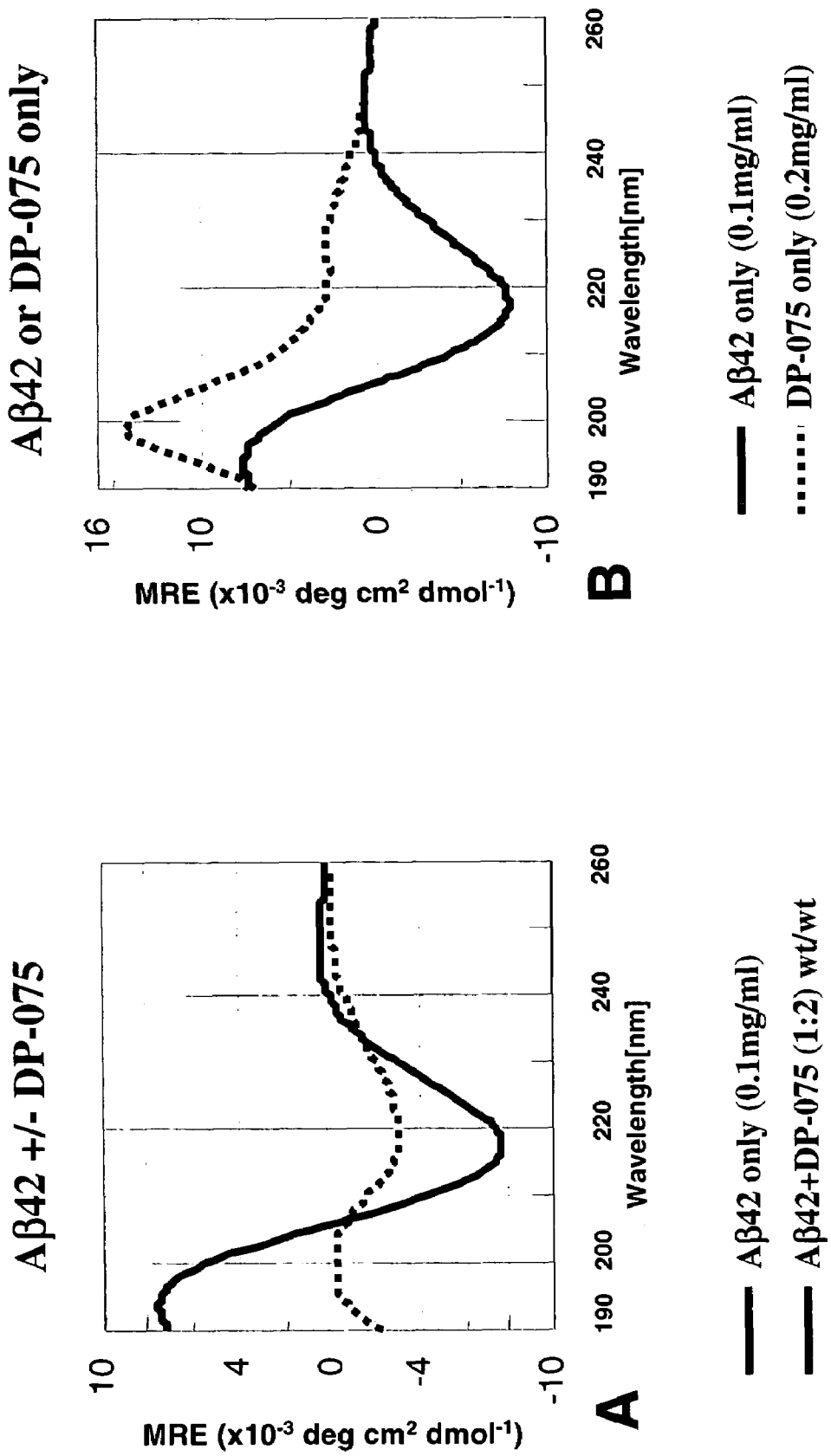
FIG. 55A are CD spectra showing the effects of 0.2 mg/ml of peptide DP-075 on beta-sheet secondary structure of Aβ42 amyloid fibrils (i.e. Aβ 42+/−DP-075).
FIG. 55B shows the CD spectra of Aβ 42 or DP-075 only.
Figure 59:
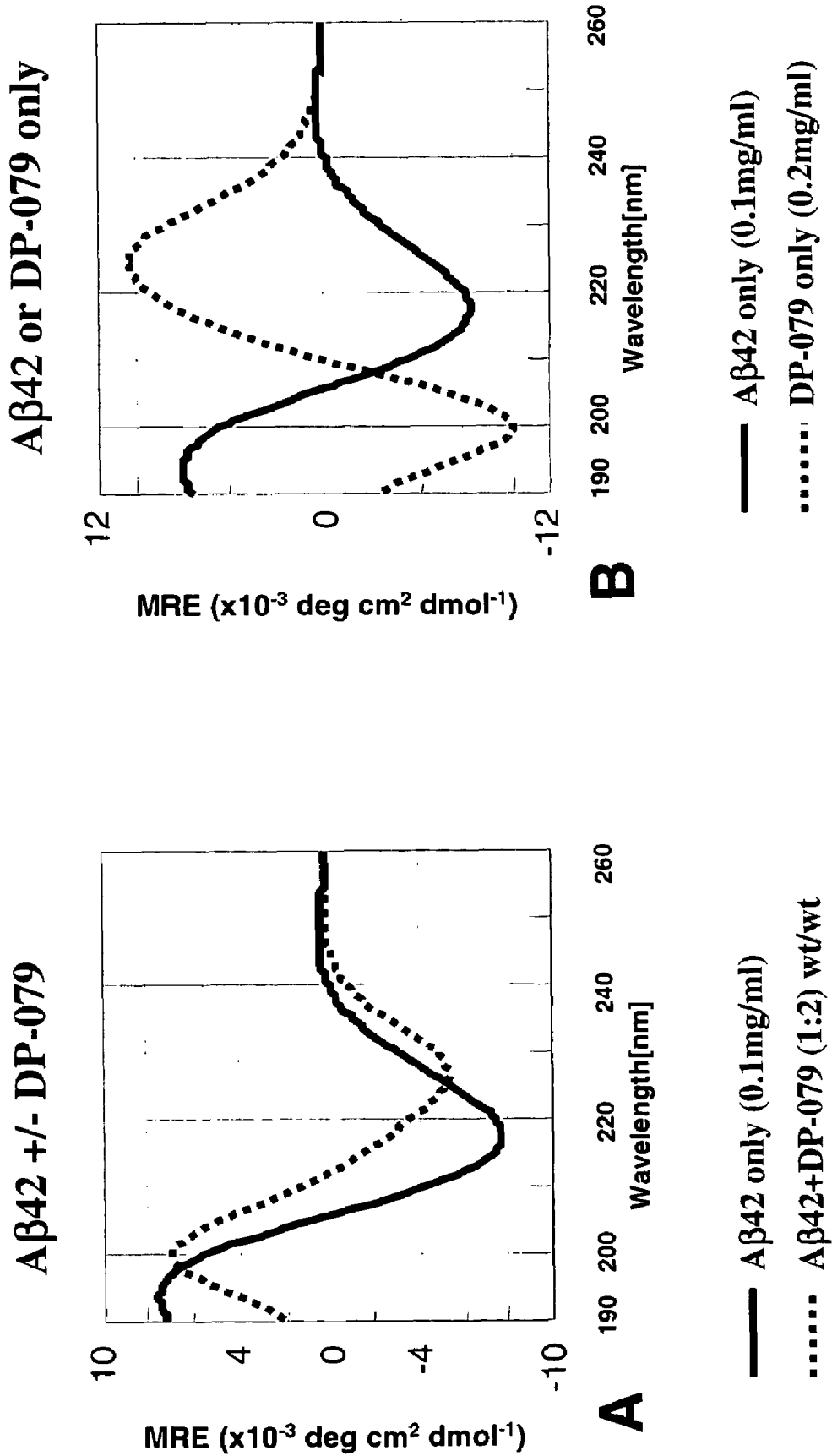
FIG. 59A are CD spectra showing the effects of 0.2 mg/ml of peptide DP-079 on beta-sheet secondary structure of Aβ42 amyloid fibrils (i.e. Aβ 42+/−DP-079).
FIG. 59B shows the CD spectra of Aβ 42 or DP-079 only.
Figure 60:
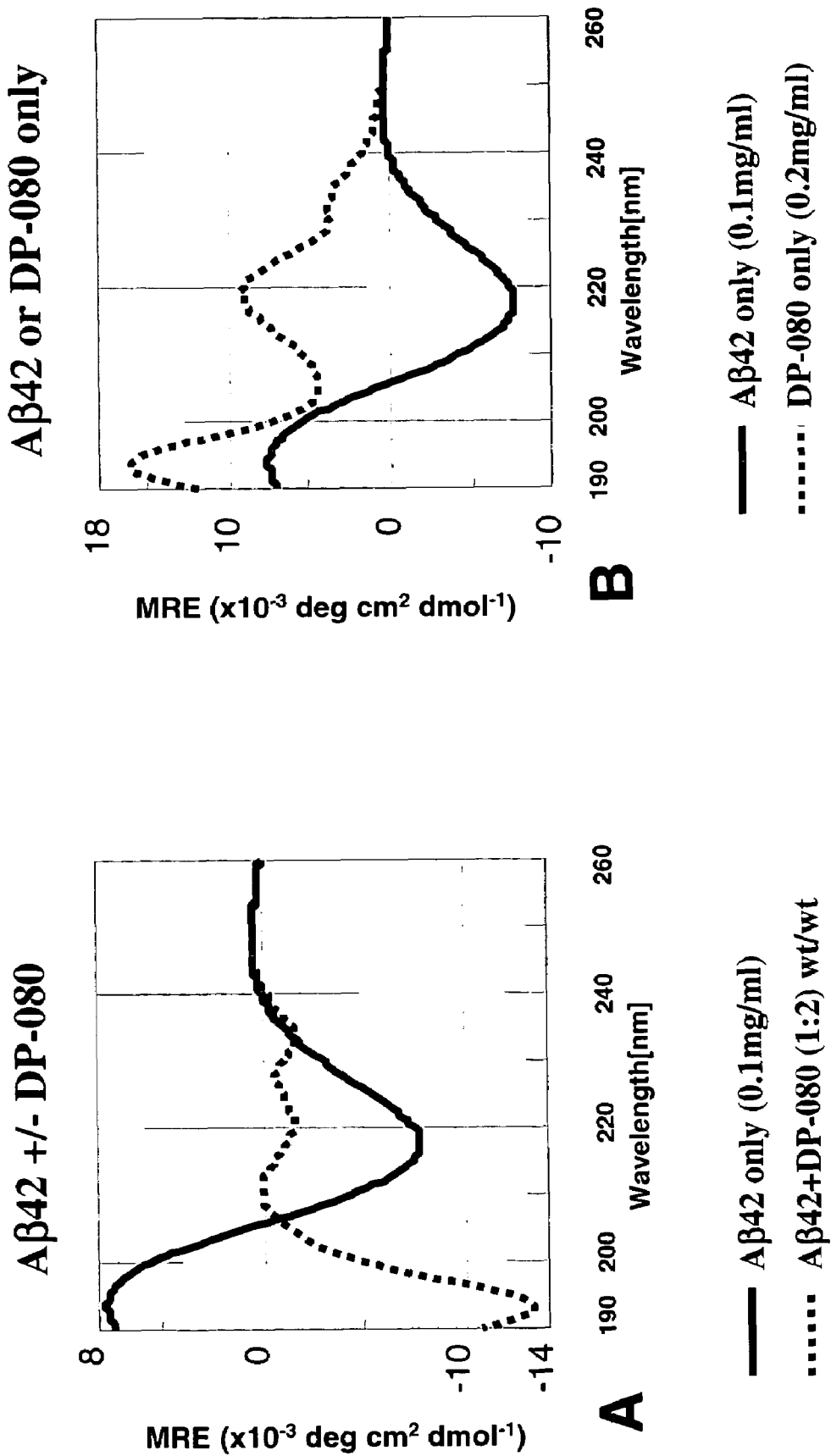
FIG. 60A is a CD spectra showing the effects of 0.2 mg/mi of peptide DP-080 on beta-sheet secondary structure of Aβ42 amyloid fibrils (i.e. Aβ42+/−DP-080).
FIG. 60B shows the CD spectra of Aβ42 or DP-080 only.

FIG. 51 is a summary of Thio T of Ab42+/−-DP65-72 (1:0.1, 1:1, 1:2, 1:4) and lysine, while FIG. 52 is a summary of Thio T ranking 65-72.

Further Aspects and Utilizations

One therapeutic application is to use peptides of Sequence Group A, B, or C as binders or sequesters of Aβ, inhibitors of Aβ amyloid fibril formation, inhibitors of Aβ amyloid fibril deposition, inhibitors of Aβ amyloid fibril accumulation and/or persistence, in Alzheimer's disease, Down's syndrome and other amyloid disorders involving Aβ fibrillogenesis.

"Peptide" refers to two or more amino acids linked together by peptide bonds as known to those skilled in the art. Preferred peptides are those disclosed herein, but may also advantagiously include peptides which have at least a 70%, and more preferably an 80-90% identity to a disclosed peptide. "% Identity" as used herein for peptides means the same amino acids in the same place. Thus, two 10 amino acid peptides are 90% identical if juxtaposition to each other showed that the placement and identity of each amino acid is identical, except for one amino acid. If a ten amino acid peptide is juxtaposed to another ten amino acid peptide and the placement and identity of amino acids is identical, except for two amino acids, then the two 10 amino acid peptides have an 80% identity with each other.

Disclosed peptides are produced by chemical synthetic procedures. Chemical peptide synthesis is a rapidly evolving area in the art, and methods of solid phase peptide synthesis are well-described in the following references, hereby entirely incorporated by reference (Merrifield, *J. Amer. Chem. Soc.* 85:2149-2154, 1963; Merrifield, *Science* 232: 341-347, 1986; Fields, *Int. J. Polypeptide Prot. Res.* 35, 161, 1990). Disclosed peptides may also be utilized as research reagents and materials for discovery of treatments and diagnostics for human diseases.

The route of administration includes oral, intravenous, intra-peritoneal, intra-muscular, subcutaneous, intra-articular, intra-nasal, intra-thecal, intra-dermal, transdermal or by inhalation. An effective dose of each of the peptides disclosed herein as potential therapeutics for use in treating Aβ amyloidosis in Alzheimer's disease and other disorders is from about 1 µg to 500 mg/kg body weight, per single administration, which may readily be determined by one skilled in the art. The dosage depends upon the age, sex, health, and weight of the recipient, kind of concurrent therapy, if any, and frequency of treatment. Other effective dosage range upper limits are 100 mg/kg body weight, 50 mg/kg body weight, 25 mg/kg body weight, and 10 mg/kg body weight.

As used herein polypeptides may consist of -L amino acids, -D amino acids or a mixture of both forms. Amino acids in nature usually consist of -L amino acids. However, substitution with -D amino acids generally demonstrates enhanced bioavailability due to less degradation in biological fluids (such as plasma), and enhanced penetration across the blood-brain-barrier. Polypeptides having an identical amino acid sequence to that found within a disclosed peptide, but in which all or part of the L-amino acids have been substituted with D-amino acids, is a part of the disclosed development of therapeutics to treat Alzheimer's disease and other Aβ amyloidoses.

As used herein "pharmaceutically acceptable carrier" includes any and all solvents, dispersion media, coatings, antibacterial and antifungal agents, isotonic and absorption delaying agents, and the like that are physiologically compatible. In one embodiment, the carrier is suitable for parenteral administration. Preferably, the carrier is suitable for administration into the central nervous system (e.g. intraspinally or intracerebrally). Alternatively, the carrier can be suitable for intravenous, intraperitoneal or intramuscular administration. In another embodiment, the carrier is suitable for oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is compatible with the active compound, use thereof in the pharmaceutical compositions is contemplated. Supplementary active compounds can also be incorporated into the compositions.

As used here in "Aβ amyloidoses" refers to amyloid diseases which involve the formation, deposition, accumulation and/or persistence of Aβ (i.e. beta-amyloid protein), including but not limited to Aβ containing 39-43 amino acids in length, but more preferably, Aβ 1-40, or Aβ 1-42, and mixtures or fragments thereof.

"Aβ amyloidoses" and "Aβ fibrillogenesis diseases" include, but are not limited to Alzheimer's disease, Down's syndrome, forms of familial amyloidosis, cerebrovascular amyloidosis and cerebral hemorrhage, cystatin C amyloid angiopathy, hereditary cerebral hemorrhage with amyloidosis (Dutch type), hereditary cerebral hemorrhage with amyloidosis (Icelandic type), and inclusion body myositis.

Therapeutic Applications

In preferred embodiments, Sequence Group A, B, and C peptides, fragments, analogs, and derivatives thereof are used as amyloid inhibitory therapeutic agents. The Sequence Group A, B, and C peptides, fragments, analogs and derivatives thereof can be synthesized utilizing standard techniques (i.e. using an automated synthesizer). In a preferred embodiment, specific Sequence Group A, B, or C peptides, fragments, analogs or derivatives thereof may be used to bind or sequester Aβ amyloid, inhibit Aβ amyloid formation, deposition, accumulation, and/or persistence in a given patient. Likewise, in another preferred embodiment antiidiotypic antibodies made against Sequence Group A, B, or C peptides, fragments, analogs or derivatives thereof (as described above) may be given to a human patient as potential Aβ binding or sequestering antibodies, that may disrupt or inhibit Aβ amyloid formation, deposition, accumulation and/or persistence in the given patient.

A formulation for use in the treatment of Aβ amyloidoses comprises a pharmaceutically effective amount of a peptide in Sequence Group A, B, or C, fragment, analog or derivative thereof, anti-idiotypic antibody, or anti-idiotypic antibody fragment which includes a pharmaceutically acceptable carrier. The formulations may additionally include other antibodies or conjugates. For parenteral administration, preferred formulations include sterile aqueous or non-aqueous solutions, suspensions, and emulsions, which may contain axillary agents or excipients that are known in the art. The anti-idiotypic antibody formulations can be administered using conventional modes of administration including, but not limited to, topical, intravenous, intra-arterial, intraperitoneal, oral, intralymphatic, intramuscular or intralumbar. Intravenous administration is preferred. Pharmaceutical formulations such as tablets, pills, caplets, soft and hard gelatin capsules, lozenges, sachets, cachets, vegicaps, liquid drops, elixers, suspensions, emulsions, solutions, syrups, tea bags, aerosols (as a solid or in a liquid medium), suppositories, sterile injectable solutions, sterile packaged powders, can be prepared according to routine methods and are known in the art. The administration of such a composition may be by oral or various parenteral routes such as subcutaneous, intravenous, intradermal, intramuscular, intraperitoneal, intranasal, transdermal, anal or buccal routes. Parenteral administration can be by bolus injection or by gradual perfusion over time. Preferred modes of administration of the formulations of Sequence Group A, B, or C, fragments, analogs or derivatives thereof is by oral administration, intravenous, or intranasal application.

Compounds of Sequence Group A, B, or C, fragments, analogs and derivatives thereof, may be administered in the form of a pharmaceutical formulation by any means that achieve their intended purpose, for example, to treat pathologies, such as Alzheimer's disease and other Aβ amyloid diseases, or other related pathologies. The therapeutic formulations can be a variety of dosage forms, with the preferred form depending upon the mode of administration and the therapeutic application. Optimal dosage, frequency, length and modes of administration for an individual patient can readily be determined by conventional protocols, known to those skilled in the art.

It is understood that the dosage of the compound in Sequence Group A, B, or C, fragment, analog and derivative thereof administered in vivo or in vitro will be dependent upon the age, sex, health, and weight of the recipient, type of concurrent treatment (if any), frequency of treatment, and the nature of the effect desired. The most preferred dosage will be tailored to the individual subject, as is understood and determinable by one of skill in the art, without undue experimentation.

A typical regimen for preventing, suppressing or treating pathologies, such as Alzheimer's disease amyloidosis, comprises administration of an effective amount of compound in Sequence Group A, B, or C, fragment, analog or derivative thereof, administered over a period of one to several days, up to and including between one week and about 72 months.

The total dose required for each treatment may be administered in multiple doses or in a single dose. A compound in Sequence Group A, B, or C, fragment, analog and derivative thereof may be administered alone or in conjunction with other therapeutics directed to pathologies, such as Alzheimer's disease or other Aβ amyloid diseases, as described herein.

Effective amounts of a compound in Sequence Group A, B, or C, fragment, analog and derivative thereof, are about 0.01 μg to about 100 mg/kg body weight, and preferably from about 10 μg to about 50 mg/kg body weight, such as 0.05, 0.07, 0.09, 0.1, 0.5, 0.7, 0.9, 1, 2, 5, 10, 20, 25, 30, 40, 45, 50, 55, 60, 65, 70, 75, 80, 85, 90, 95 or 100 mg/kg.

Pharmaceutical compositions comprising at least one Sequence Group A, B, or C compound or anti-idiotypic antibody may also include suitable solutions for administration intravenously, subcutaneously, dermally, nasally, orally, mucosally, rectally or may by injection or orally, and contain from about 0.01 to 99 percent, preferably about 20 to 75 percent of active component (i.e. peptide or antibody) together with the excipient. Pharmaceutical compositions for oral administration include pills, tablets, caplets, soft and hard gelatin capsules, lozenges, sachets, cachets, vegicaps, liquid drops, elixers, suspensions, emulsions, solutions, and syrups.

The Sequence Group A, B, or C compound, fragment, analog and derivative thereof for the treatment of Alzheimer's disease and other central nervous system Aβ amyloidoses may be modified to cross the blood-brain barrier. Various modifications known in the art for increasing transport across the blood-brain-barrier (for reviews of such modifications, see e.g. Pardridge W. M. (1994) Trends in Biotechnol. 12:239-245; Van Bree, J. et al (1993) Pharm World Sci. 15:2-9; and Pardridge W. M. (1992) Pharmacol. Toxicol. 71:3-10). One approach is to increase the lipophilicity (log P) of the peptide by covalent linking of the amino or carboxyl terminal to a fatty acid or acyl group (such as acetyl) as was done in some of Sequence Group A, B, or C peptides. Another approach is to conjugate the peptide to a protein that normally undergoes absorptive mediated transcytosis or receptor mediated transcytosis through the blood-brain-barrier. These proteins include ligands for brain capillary endothelial receptors such as a monoclonal antibody to the transferrin receptor, histones, biotin, folate, niacin, panthothenic acid, or glycopeptides. Another approach is to link the peptide to a highly positively charged compound (as were done in some of the Sequence Group A, B, and C peptides) such as lysine, polylysine, arginine, polyarginine, lysine-arginine peptide, putrescine, spermidine, spermine, etc, all of which are known to facilitate crossing through the blood-brain-barrier presumably by binding to a receptor.

Another approach to enhance blood-brain-barrier transport of peptides is by encapsulation into a carrier vector such as liposome or polymeric microspheres, preferably positively charged for the same reason as described above. The carrier vector can also be modified to target blood-brain-barrier transport receptors, such as the transferrin receptor, by linking the peptide, for example, to an antibody against the transferrin receptor.

Another approach is to co-administer the peptide with agents that permeabilize the blood-brain-barrier, such as bradykinin or a bradykinin agonist.

The blood-brain-barrier permeable drug is a desirable characteristic of central nervous system drugs in general. However, the disclosed embodiments do not necessarily have to fulfill blood-brain-barrier permeability requirements in order to fulfill intended purposes (i.e., effective treatment of Alzheimer's disease and other amyloidosis). Peripheral sequestration of Aβ by Sequence Group A, B, or C compounds, fragments, analogs, derivatives thereof, and anti-idiotypic antibodies will result in movement of Aβ from the brain to the peripheral circulation, depleting brain Aβ, inhibiting brain Aβ amyloid fibril formation, and/or causing dissolution of pre-formed brain Aβ amyloid fibrils. This is due to the fact as demonstrated in the previous studies that Aβ freely crosses the blood-brain-barrier (Poduslo et al., Neurobiol. Dis. 4:27-34, 1997; Ghilardi et al., Neuroreport 17:2607-11, 1996; Pluta et al., Neuroreport. 7:1261-51996, 1996; Zlokovic, Neurobiol Dis. 4:23-6, 1996).

The Sequence Group A, B, or C compound, fragment, analog and derivative thereof for the treatment of Alzheimer's disease and other central nervous system Aβ amyloidoses may be administered in various ways. Methods of administration include but are not limited to systemic administration, parenteral administration i.e., via an intraperitoneal, intravenous, perioral, subcutaneous, intramuscular, intraarterial, intradermal, intramuscular, intranasal, epidural or oral routes. In a preferred embodiment, Sequence Group A, B, or C compound, fragment, analog and derivative thereof may be directly administered to the cerebrospinal fluid by intraventricular injection. In a specific embodiment, it may be desirable to administer Sequence Group A, B, or C compound, fragment, analog and derivative thereof locally to the area or tissue in need of treatment; this may be achieved by, for example, and not by way of limitation, local infusion during surgery, topical application, by injection, by infusion using a cannulae with an osmotic pump, by means of a catheter, by means of a suppository, or by means of an implant.

In yet another embodiment Sequence Group A, B, or C compound, fragment, analog and derivative thereof may be administered in a controlled release system, such as a well-calibrated osmotic pump. In yet another embodiment, a controlled release system can be placed in proximity to the therapeutic target, i.e. the brain, thus requiring only a fraction of the systemic dose.

In yet another aspect, peptidomimetic compounds modeled from Sequence Group A, B, or C peptides identified as binding Aβ or other amyloid proteins, serve as potent inhibitors of amyloid formation, deposition, accumulation and/or persistence in Alzheimer's disease and other Aβ amyloidoses. Peptidomimetic modeling is implemented by standard procedures known to those skilled in the art. These peptidomimetic compounds may be administered with formulations, dosages, frequencies, lengths, and routes as outlined above, for the therapeutic purpose of treating Aβ amyloidosis.

Diagnostic Applications

In disclosed methods, Aβ amyloid can be contacted with a disclosed peptide either in vitro or in vivo. Thus the term "contacted with" is intended to encompass both incubation of the peptide and anti-idiotypic antibodies with Aβ amyloid preparation in vitro and delivery of the peptide and anti-idiotypic antibodies to a site in vivo where Aβ amyloid is present. Since the peptides and anti-idiotypic antibodies interact with Aβ amyloid, they can be used to detect Aβ amyloid, either in vitro or in vivo. Accordingly, the compounds can also be used as diagnostic agents to detect the presence or absence of Aβ amyloid in a biological sample or in vivo in a subject. Furtheremore, detection of Aβ amyloid using the compounds can be used to diagnose Aβ amyloidosis in a subject.

In one embodiment, a compound is used in vitro to detect and quntitate Aβ amyloid in sample (such as cerebrospinal fluid from AD patient, suspected AD patient, a person with a family history of AD, or a normal adult). To aid in detection, the compound can be modified with a detectable substance. The Aβ amyloid in the sample can be immobilized and the compound with the detectable substance is contacted with the immobilized Aβ amyloid or sample, such as in tissue sections. The remaining unbound compound is removed and the compound bound to Aβ can be detected. Alternatively, the unbound compound which is inversely proportional to the bound compound and hence amount of Aβ in the sample can be detected by various means, such as mass spectrometry and other spectrometric determinations including fluoresecence, phosphorescence, and, absorbance of various wavelengths of light from UV to infrared, all the way down to radiowaves such as that for NMR. For example, the detectable substance can be biotin (i.e. an amino-terminally biotinylated Sequence Group A, B, or C peptide) that can be detected using enzyme labeled avidin. The enzyme, in turn, when later exposed to an appropriate substrate, will react with the substrate in such a manner as to produce a chemical moiety which can be detected, for example, by spectrophotometric, fluorometric, or by visual means. Enzymes which can be used detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colometric methods which employ a chromogenic substrate for the enzyme. Detection can be accomplished by colometric methods which employ a chromogenic substrate for the enzyme. Detection can also be accomplished by visual comparison of the extent of enzymatic reaction of a substrate with similarly prepared standards (see Harlow and Lane, *Antibodies: A Laboratory Manual*, Cold Spring Harbor Laboratory 1988; Ausubel et al, eds., *Current Protocols in Molecular Biology*, Wiley Interscience, N.Y. 1987, 1992).

Selected disclosed compounds may also be used to quantitatively or qualitatively detect Aβ amyloid in a biological sample. This can be accomplished by immunofluorescence techniques employing a flourescently labeled disclosed compound coupled with light microscopic, flow cytometric or fluorometric detection.

Detection may be accomplished using any of a variety of other immunoassays. For example, by radiolabeling of the compound. A good description of this assay may be found in *Laboratory Techniques and Biochemistry in Molecular Biology*, by Work et al, North Holland Publishing Company, NY (1978) with particular reference to the chapter entitled "An Introduction to Radioimmune Assay and Related Techniques" by Chard, incorporated entirely by reference herein. The radioactive isotope can be detected by such means as the use of a gamma-counter, a scintillation counter or by autoradiography.

It is also contemplated to label the compound with a fluorescent compound. When the flourescently labeled compound is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine, that are commercially available, e.g., from Molecular Probes, Inc. (Eugene, Oreg., U.S.A.).

Compounds can also be detectably labeled by coupling it to a chemiluminescent compound. The presence of the chemiluminescent-tagged compound is then determined by detecting the presence of luminescence that arises during the course of a chemical reaction. Examples of particularly useful chemiluminescent labeling compounds are luminol, isoluminol, theromatic acridinium ester, imidazole, acridinium salt, and oxalate ester.

Likewise, a bioluminescent compound may be used to label the compound. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, lucifers and aequorin.

Compounds may also be used histologically, as in immunofluorescence or immunoelectron microscopy, for in situ detection of Aβ amyloid. Removing a histological specimen from a patient, and providing the labeled compound to such a specimen may accomplish in situ detection. The compound is preferably provided by applying or by overlaying the labeled compound (or fragment) to a biological sample. Through the use of such a procedure, it is possible to determine not only the presence of Aβ amyloid but also its distribution in the examined tissue. Thus, those of ordinary skill will readily perceive that any of a wide variety of histological methods (such as staining procedures) can be modified in order to achieve such in situ detection.

Compounds which interact with Aβ, or derivatives thereof are also disclosed herein. The compounds can be used for a number of important diagnostic and/or therapeutic applications as described herein. In one aspect, peptides which bind Aβ may be utilized for ligand blot analysis (using standard ligand blotting techniques known to those skilled in the art) to detect the presence of Aβ amyloid protein fragments in human tissues and in tissues of other species. Ligand blot analysis can also be used to determine the apparent size of each amyloid protein fragment. In addition, ligand blotting followed by scanning densitometry (known to those skilled in the art) can be used to quantitate and compare levels of each of the peptides in tissue samples, biological fluids or biopsies obtained from individuals with specific diseases (such as the amyloid diseases) in comparison to tissue samples, biological fluids or biopsies obtained from normal individuals or controls. Biological fluids, include, but are not limited to, blood, plasma, serum, cerebrospinal fluid, sputum, saliva, urine and stool.

In another embodiment, a compound is used in vivo to detect, and if desired, quantitate, Aβ amyloid deposition in a subject, for example, to aid in the diagnosis of Aβ amyloidosis in the subject. To aid in detection, the compound can be modified with a detectable substance, preferably $^{99m}$Tc or radioactive iodine. Methods for labeling peptide compounds with technetium are known in the art. A modifying group can be chosen that provides a site at which a chelation group for $^{99m}$Tc can be introduced, such as a derivative of cholic acid, which has a free amino group. Also provided are Sequence Group A, B, or C peptides labeled with radioactive iodine through their aromatic amino acid, either already present or incorporated, for the purpose of labeling. Any of the various isotopes of radioactive iodine can be incorporated to create a diagnostic agent. Preferably, $^{123}$I (half-life=13.2 hrs) can be used for whole body scintigraphy, $^{124}$I (half-life=4 days) or $^{18}$F for positron emission tomography (PET), $^{125}$I (half-life=60 days) for metabolic turnover studies, and $^{131}$I (half-life=8 days) for whole body counting and delayed low resolution imaging studies.

In compliance with the statute, the invention has been described in language more or less specific as to structural features: It is to be understood, however, that the invention is not limited to the specific features shown, since the means and construction shown comprise preferred forms of putting the invention into effect. The invention is, therefore, claimed in any of its forms or modifications within the legitimate and valid scope of the appended claims, appropriately interpreted in accordance with the doctrine of equivalents.

We claim:

1. A pharmaceutical composition comprising a peptide consisting of Leu-Ala-Phe-Val-Leu-Arg-Lys-amide having at least one D amino acid.

2. The pharmaceutical composition of claim 1 further comprising a pharmaceutically acceptable carrier, diluent or excipient.

3. The pharmaceutical composition of claim 1 wherein each of the amino acids of the peptide are D-amino acids.

* * * * *

UNITED STATES PATENT AND TRADEMARK OFFICE
CERTIFICATE OF CORRECTION

PATENT NO. : 7,384,910 B2  Page 1 of 1
APPLICATION NO. : 11/016706
DATED : June 10, 2008
INVENTOR(S) : Castillo et al.

It is certified that error appears in the above-identified patent and that said Letters Patent is hereby corrected as shown below:

Please insert the following statement in Column 1 after line 15:

This invention was made with Government support under R44 AG017787 awarded by the National Institute on Aging. The Government has certain rights in the invention.

Signed and Sealed this

Twenty-first Day of October, 2008

JON W. DUDAS
*Director of the United States Patent and Trademark Office*